US008993527B2

(12) United States Patent
Mangano

(10) Patent No.: US 8,993,527 B2
(45) Date of Patent: Mar. 31, 2015

(54) METHODS, COMPOSITIONS, AND FORMULATIONS FOR PREVENTING OR REDUCING ADVERSE EFFECTS IN A PATIENT

(75) Inventor: Dennis T. Mangano, Hillsborough, CA (US)

(73) Assignee: Pericor Therapeutics, Inc., New York, NY (US)

(*) Notice: Subject to any disclaimer, the term of this patent is extended or adjusted under 35 U.S.C. 154(b) by 1153 days.

(21) Appl. No.: 11/277,739

(22) Filed: Mar. 28, 2006

(65) Prior Publication Data

US 2006/0293273 A1    Dec. 28, 2006

Related U.S. Application Data

(60) Provisional application No. 60/666,071, filed on Mar. 28, 2005.

(51) Int. Cl.
*A61K 31/7056* (2006.01)
*A61K 31/7052* (2006.01)
*C07H 19/052* (2006.01)
*C07H 19/067* (2006.01)
*A61K 31/7076* (2006.01)

(52) U.S. Cl.
CPC .......... *A61K 31/7056* (2013.01); *A61K 31/7076* (2013.01)
USPC ............................. 514/43; 514/42; 536/28.8

(58) Field of Classification Search
USPC ....................................... 514/43, 42; 536/28.8
See application file for complete search history.

(56) References Cited

U.S. PATENT DOCUMENTS

| | | | |
|---|---|---|---|
| 3,586,604 A | 6/1971 | Yarnanoi et al. | |
| 4,211,771 A | 7/1980 | Witkowski et al. | |
| 4,432,990 A | 2/1984 | Robinson | |
| 4,575,498 A | 3/1986 | Holmes et al. | |
| 4,912,092 A | 3/1990 | Gruber | |
| 5,008,251 A | 4/1991 | Gruber | |
| 5,030,623 A | 7/1991 | Gruber | |
| 5,082,829 A | 1/1992 | Gruber et al. | |
| 5,118,601 A | 6/1992 | Gruber | |
| 5,132,291 A | 7/1992 | Gruber | |
| 5,187,162 A | 2/1993 | Marangos et al. | |
| 5,200,525 A | 4/1993 | Gruber et al. | |
| 5,366,960 A | 11/1994 | Gallagher | |
| 5,629,298 A | 5/1997 | Dobson, Jr. | |
| 5,646,128 A | 7/1997 | Firestein et al. | |
| 5,658,889 A | 8/1997 | Gruber et al. | |
| 5,731,432 A | 3/1998 | Erion et al. | |
| 5,777,100 A | 7/1998 | Bullough et al. | |
| 5,817,640 A | 10/1998 | Gruber et al. | |
| 6,103,702 A | 8/2000 | Law | |
| 6,221,851 B1 | 4/2001 | Feldman | |
| 2001/0018443 A1 | 8/2001 | Varney et al. | |
| 2004/0072138 A1 | 4/2004 | Singh | |
| 2005/0002943 A1 | 1/2005 | Leo et al. | |
| 2005/0233987 A1 | 10/2005 | Lopez Blanco et al. | |
| 2007/0082859 A1 | 4/2007 | Stover et al. | |

FOREIGN PATENT DOCUMENTS

| | | |
|---|---|---|
| EP | 0535884 A1 | 4/1993 |
| EP | 262125 | 3/1996 |
| EP | 301900 | 3/1996 |
| EP | 495091 | 11/1999 |
| GB | 2430882 | 4/2007 |
| WO | WO 92/02213 A | 2/1992 |
| WO | WO 92/02214 | 2/1992 |
| WO | WO 99/26657 A1 | 6/1999 |
| WO | WO 03/037371 A2 | 5/2003 |
| WO | WO 03/037371 A3 | 10/2004 |
| WO | WO 2006/105167 A2 | 10/2006 |
| WO | WO 2006/105167 A3 | 5/2007 |
| WO | 2008086341 | 7/2008 |
| WO | 2009094593 | 7/2009 |

OTHER PUBLICATIONS

Multicenter Study of Perioperative Ischemia (McSPI) Research Group; Anesthesiology, vol. 83, No. 4, Oct. 1995, pp. 658-673.*
Menasche et al. (The Journal of thoracic and cardiovascular surgery, (Oct. 1995) vol. 110, No. 4 Pt 1, pp. 1096-1106) (Abstract Sent).*
Mangano (JAMA: the journal of the American Medical Association, (Jan. 22-29, 1997) vol. 277, No. 4, pp. 325-332) (Abstract Sent).*
Shaw, et al. Purines, pyrimidines, and imidazoles. Part 50. Inhibition of adenylosuccinate AMP-lyase No. 4.3.2.2. By derivatives of N-(5-amino-1-beta-D-ribofuranosylimidazole-4-carbonyl)-L-aspartic acid 5'-phosphate (SAICAR) and virazole 5'-phosphate. J Chem Soc [Perkin 1]. 1979;6:1415-24.*
Kurz et al. (European Journal of Pharmacology 322 (1997) 211-220).*
Ferreira et al. (Rev Port Cardiol. Jan. 1989;8(1):19-26) (Abstract sent).*
Aggarwal, et al. CK-MB release after coronary artery bypass graft surgery in a multicenter population. *Anesthesiology*. 1994; 81: A1291. (Abstract).
Ambrosio, et al. Effects of ATP precursors on ATP and free ADP content and functional recovery of post-ischemic hearts. *Am J Physiol*. 1989; 256:H560-H566. (Abstract).
Antman, et al. A comparison of results of meta-analyses of randomized control trials and recommendations of clinical experts: treatments for myocardial infarction. *JAMA*. 1992; 268:240-248. (Abstract).
CASS Principal Investigators and Their Associates. Myocardial infarction and mortality in the Coronary Artery Surgery Study (CASS) randomized trial. *N Engl J Med*. 1984; 310:750-758. (Abstract).

(Continued)

*Primary Examiner* — Layla Bland
*Assistant Examiner* — Michael C Henry
(74) *Attorney, Agent, or Firm* — Morrison & Foerster LLP

(57) ABSTRACT

The present invention provides methods, compositions, formulations, and kits related to acadesine, or a prodrug, analog, or salt thereof, and/or a blood clotting inhibitor for preventing or reducing adverse side effects in a patient. The type of patient that may benefit includes a patient with decreased left ventricular function, a patient with a prior myocardial infarction, a patient undergoing non-vascular surgery, or a fetus during labor and delivery.

11 Claims, 28 Drawing Sheets

(56) References Cited

OTHER PUBLICATIONS

Clark, R. E. Calculating risk and outcome: the Society of Thoracic Surgeons database. *Ann Thorac Surg*. 1996; 62:S2-5. (Abstract).
Cronstein, et al. Methotrexate inhibits neutrophil function by stimulating adenosine release from connective tissue cells. *Proc Nati Acad Sci U S A*. 1991; 88:2441-2445.
Demeyere, et al. Cardioprotective effects of acadesine inpatients with unstable angina undergoing aortocoronary bypass sugery. *Circulation*.1994; 90(4, pt 2):1-370. (Abstract).
Dersimonian, et al. Meta-analysis in clinical trials. *Control Clin Trials*. 1986; 7:177-188. (Abstract).
Egger, et al. Misleading meta-analysis: lessons from 'an effective, safe, simple' intervention that wasn't. *BMJ*. 1995; 310:752-754. (Abstract).
Ely, et al. Protective effects of adenosine in myocardial ischemia. *Circulation*. 1992; 85:893-904. (Abstract).
Galñanes, et al. Acadesine and myocardial protection: studies of time of administration and dose-response relations in the rat. *Circulation*. 1992; 86:598-608. (Abstract).
Galñanes, et al. Sustained protection by acadesine against ischemia and reperfusion-induced injury: studies in the transplanted rat heart. *Circulation*. 1992; 86:589-597. (Abstract).
Gotzsche, P. C. Reference bias in reports of drug trials. *BMJ*. 1987; 295:654-656. (Abstract).
Gruber, et al. Increased adenosine concentration in blood from ischemic myocardium by AICA riboside: effects on flow, granulocytes, and injury. *Circulation*. 1989; 80:1400-1411.
Haraphongse, et al. The changing clinical profile of coronary artery bypass graft patients, 1970-1989. *Can J Cardiol*. 1994; 10:71-86. (Abstract).
Henry, et al. Adenosine release from red cells mediates inhibition of platelet aggregation by acadesine and delays post-thrombolytic reocclusion in dogs. *Circ Suppl*. 1991; 84:247.
Jain, et al. Incidence of Q wave myocardial infarction during coronary artery bypass graft surgery in the 24-center McSPI population. *Anesthesiology*. 1994; 81:A157.
Jeng, et al. A comparison of meta-analytic results using literature vs individual patient data: paternal cell immunization for recurrent miscarriage. *JAMA*. 1995; 274:830-836. (Abstract).
Jones, et al. Coronary bypass surgery: is the operation different today? *J Thorac Cardiovasc Surg*. 1991; 101:108-115. (Abstract).
Kouchoukos, et al. Report of the ad hoc committee on risk factors for coronary artery bypass surgery. *Ann Thorac Surg*. 1988; 45:348-349. (Abstract).
Lachin, J. Sample size determination for rxc comparative trials. *Biometrics*. 1977; 331:315324. (Abstract).
Lau, et al. Cumulative meta-analysis of therapeutic trials for myocardial infarction. *N Engl J Med*. 1992; 327:248-254. (Abstract).
Mangano, et al. Association of perioperative myocardial ischemia with cardiac morbidity and mortality in men undergoing noncardiac surgery. *N Engl J Med*. 1990; 323:1781-1788. (Abstract).
Mangano, Dennis T. Effects of Acadesine on Myocardial Infarction, Stroke, and Death Following Surgery, A Meta-analysis of the 5 International Randomized Trials. JAMA. 1997; 277(4):325-332.
Mangano, D. T. Myocardial stunning: an overview. *J Cardiac Surg*. 1993; 8:204-213. (Abstract).
Mangano, D. T. Perioperative cardiac morbidity. *Anesthesiology*. 1990; 72:153-184.
Mangano, D. T. Perioperative cardiac morbidity: epidemiology, costs, problems, and solutions. *West J Med*. 1994; 161:87-89.
Martin, et al. Prospective, randomized trial of retrograde warm-blood cardioplegia: myocardial benefit and neurologic threat. *Ann Thorac Surg*. 1994; 57:298-304. (Abstract).
Mazur, et al. Acadesine preserves cardiac function and enhances coronary blood flow in isolated, blood perfused rabbit hearts with repeated ischemia and reperfusion. *J Mol Cell Cardial*. 1991;23:545.
Menasche, et al. Acadesine: a new drug that may improve myocardial protection in coronary artery bypass graft surgery: results of the first international multicenter study. *J Thorac Cardiovasc Surg*. 1995; 110:1096-1106.
Mentzer, et al. The acute effects of AICAR on purine nucleotide metabolism and postischemic cardiac function. *J Thorac Cardiovas Surg*. 1988; 95:286-293. (Abstract).
Molina-Viamonte, et al. AICA-riboside suppresses arrhythmias induced by coronary artery occlusion and reperfusion. *Circulation*. 1990; 82:645.
Mullane, et al. Acadesine: prototype adenosine regulating agent for treating myocardial ischemia-reperfusion injury. *Drug Dev Res*. 1993; 28:336-343. (Abstract).
Mullane, K. The prototype adenosine regulating agent for reducing myocardial ischemic injury. *Cardiovasc Res*. 1993; 27:43-47. (Abstract).
Murphy, et al. Treatment of chronic stable angina: a preliminary report of survival data of the randomized Veterans Administration Cooperative Study. *N. Engl. J. Med*. 1977; 297:621-627. (Abstract).
Oxman, et al. From science to practice: Meta-analyses using individual patient data are needed. JAMA, 1995; 274:845-846.
Rashid, et al. A prospective randomized study of continuous warm versus intermittent cold blood cardioplegia for coronary artery surgery: preliminary report. *Eur J Cardiothorac Surg*. 1994; 8:265-269. (Abstract).
Schaff, et al. Detrimental effect of perioperative myocardial infarction on late survival after coronary artery bypass: report from the Coronary Artery Surgery Study (CASS). *J Thorac Cardiovasc Surg*. 1984; 88:972-981. (Abstract).
Thacker, S. B. Meta-analysis: a quantitative approach to research integration. *JAMA*. 1988; 259:1685-1689. (Abstract).
The Multicenter Study of Perioperative Ischemia (McSPI) Research Group. Effects of acadesine on morbidity and mortality following coronary artery bypass graft surgery. *Anesthesiology*. 1995; 88:658-673.
The Warm Heart Investigators. Randomized trial of normothermic versus hypothermic coronary bypass surgery, *Lancet*. 1994; 343:559-563. (Abstract).
Val, et al. Diagnostic criteria and prognosis of perioperative myocardial infarction following coronary bypass. *J Thorac Cardiovas Surg*. 1983; 86:878 886. (Abstract).
Varnauskas, E. European coronary surgery study. *Z Kardiol*. 1985; 6:73-78. (Abstract).
Vinten-Johansen, et al. Acadesine improves surgical myocardial protection with blood cardioplegia in ischemically injured canine hearts. *Circulation*. 1993; 88:350-358. (Abstract).
Whitehead, et al. A general parametric approach to the meta-analysis of randomized clinical trials. *Stat Med*. 1991; 10:1665-1677. (Abstract).
Young, et al. Inhibition of intracoronary thrombosis by acadesine: an adenosine-mediated, erythrocyte-dependent activity. *Eur Heart J*. 1993;14:31.
Young, et al. Progressive cardiac dysfunction with repeated pacing-induced ischemia: protection by AICA-riboside. *Am J Physiol*. 1991; 261:H1570-H1577. (Abstract).
Yusuf, et al. Magnesium in acute myocardial infarction. *BMJ*. 1995; 310:751-752. (Abstract).
Yusuf, et al. Beta blockade during and after myocardial infarction: an overview of the randomized trials. *Prog Cardiovasc Dis*. 1985; 27:335-371. (Abstract).
Leung, et al. An initial multicenter randomized controlled trial on the safety and efficacy of acadesine in patients undergoing CABG surgery. Anesth Analg. 1994; 78:420434. (Abstract only).
Mitsos, et al. Protective effects of AICAriboside in the globally ischemic isolated cat heart. Pharmacology. 1985; 31(3):121-31. (Abstract only).
Barankiewicz, et al. Alteration of purine metabolism by AICA-riboside in human B lymphoblasts. Arch Biochem Biophys. 1990; 282(2):377-85.
Barankiewicz, et al. Selective adenosine release from human B but not T lymphoid cell line. J Biol Chem. 1990; 265(26):15738-43.
Dixon, et al. AICA-Riboside: Safety, Tolerance, and Pharmacokinetics of a Novel Adenosine-Regulating Agent.*J Clin Pahrmacol*. 1991;31: 342-347.
Greenberg, G. R. Preparation of 5'-Phosphoribosyl-5-Amino-4-Imidazolecarboxamide. *J. Biol. Chem*. 1956;219:423-433.

(56) References Cited

OTHER PUBLICATIONS

Groziak, et al. Nonenzymatic Synthesis of 5-Aminoimidazole Ribonucleoside and Recognition of Its Facile Rearrangements. *Proc. Natl. Acad. Sci. USA*. Oct. 1988;85:7174-7176.

Herchinger, J. The Growing Case for Heart Surgery. The Wall Street Journal online. 2005. 3 pages.

Hsu, et al. Increased Creatine Kinase-MB and Troponin T. Concentrations and Mortality in CABG Patient. *Population Science*. 2000;Abstracts 4159.

Ivanovics, et al. The Synthesis of 2-Substituted Derivatives of 5-Amino-1-.beta.-D-Ribofuranosylimidazole-4-carboxamide. Ring Opening Reactions of 2-Azapurine Nucleosies. *J. Org. Chem.* 1974;39(25):4 pages.

Kikugawa, et al. Platelet Aggregation Inhibitors. *Chem. Pharm. Bull.* 1977;25(8):1959-1969.

Leung, J. M. An Initial Multicenter, Randomized Controlled Trial on the Safety and Efficacy of Acadesine in Patients Undergoing Coronary Artery Bypass Graft Surgery. Anesth. Analg. 1994;78:420-34.

Loh, E. Common Variant in AMPD1 Gene Predicts Improved Clinical Outcome in Patients With Heart Failure. Circulation. 1999;99:1422-1425.

Marumoto, et al. Synthesis and Coronary Vasodilating Activity of 2-Substituted Adenosines, Chem. Pharm. Bull. 1975;23(4):759-774.

Matsumoto, et al. Adenine Nucleotide Degradation during Energy Depletion in Human Lymphoblasts. J. Biol. Chem. Sep. 10, 1979;254(17):8956-8962.

Murakami, et al. Synthesis of 2-Formyladenoise Using Diethoxyacetonitrile As a Synthon. *Heterocycles*. 1981;16(8): 1315-1319.

Novak, et al. Evaluation of the Interaction of Acadesine (ACA) and Allopurinol (Allo). Clinical Pharmacology & Therapeutics. 1993;53(2):161.

Omura, et al. Synthesis of 2-Phenylaminoadenosine From Imidazole Nucleosides. *Chem. Pharm. Bull.* 1981;29(7):1870-1875.

Shaw, E. 5-Amino-4-Imidazolecarboxamide Riboside From Inosine. Ring-opeing Reactions of Purine Nucleosides. *Organic and Biological Chemistry*. Aug. 5, 1958;80:3899-3902.

Smith, et al. ACC/AHA Guidelines for Percutaneous Coronary Intervention (Revision of the 1993 PTCA Guidelines). *Journal of the American College of Cardiology*. 2001;(37)8:2239-22391 xvi.

Smits, et al. Cardioprotective Effects of the Novel Adenosine $A_1/A_2$ Receptor Agonist AMP 579 in a Porcine Model of Myocardial Infarction. *The Journal of Pharmacology and Experimental Therapeutics*. 1998;286:611-618.

Srivastava, et al. Synthesis of 5-Amino-1-(5-deoxy-.beta.-D-Ribofuranosyl) Imidazole-4-Carboxamide and Related 5'-Deoxyimidazole Ribonucleosides, Journal of Medicinal Chemistry. 1975;18(12):1237-1240.

Suggs, et al. Synthesis and Biodistribution of p-Iodophenyl Analogues of a Naturally Occuring Imidazole Ribonucleoside. *J. Heterocyclic Chem*. Sep.-Oct. 1988;25(5):1331-1335.

Extended European Search Report for EP 06739900.6; dated Jul. 15, 2009; 9 pages.

MX Application MX/a/2007/012045 Office Action dated May 4, 2011.

Mullane, K. The Prototype Adenosine Regulating Agent for Reducing Myocardial Ischemic Injury. Cardiovasc Res. 1993; 27:43-47.

American Society of Anesthesiologiests Inc., Oct. 1995, "Effects of Acadesine on the Incidence of Myocardial Infarction and Adverse Cardiac Outcomes after Coronary Artery Bypass Graft Surgery" Multicenter Study of Perioperative Ischemia (McSPI) Research Group, Anesthesiology, v. 83, n. 4, p. 658-673.

Drew, et al., 2008, "Acadesine, an adenosine-regulating agent with the potential for widespread indications" Expert Opin. Pharmacother., v. 9, n. 12, p. 2137-2144.

Dyck, et al., 2006, "AMPK alterations in cardiac physiology and pathology: enemy or ally?" J. Physiol., v. 574.1, p. 95-112.

EP Application EP06739900 Office Action Aug. 5, 2010.

Hardie, D. Grahme, Aug. 2004, "AMP-activated protein kinase: the guardian of cardiac energy status" Journal of Clinical Investigation, v. 114, n. 4, p. 465-468.

Mangano, et al., 2006, "Post-Reperfusion Myocardial Infarction: Long-Term Survival Improvement Using Adenosine Regulation With Acadesine" Journal of the American College of Cardiology, v. 48, n. 1, p. 207-214.

MX Application MX/a/2007/012045 Office Action Sep. 15, 2010.

New Zealand Application 561649 Office Action Aug. 21, 2009.

New Zealand Application 561649 Office Action Sep. 28, 2010.

PCT/US06/011422 International Search Report Jan. 29, 2007.

PCT/US06/011422 IPRP and Written Opinion.

PCT/US09/059454 International Search Report and Written Opinion mailed Dec. 2, 2009.

Philippine Application 12007502139 Office Action dated Feb. 14, 2011.

MX Application MX/a/2007/012045 Office Action Nov. 18, 2010.

Bullough et al., "Adenosine-mediated Inhibition of Platelet Aggregation by Acadesine. A Novel Antithrombotic Mechanism In Vitro and In Vivo," J. Clin. Invest. 94:1524-1532 (1994).

Chen et al., "A sensitive assay for the aminoimidazole-containing drug GP531 in plasma using liquid chromatography with amperometric electrochemical detection: a new class of electroactive compounds," J. Pharm. Biomed. Anal. 14:1535-1538 (1996).

Galinanes et al., "Protection Against Injury During Ischemia and Reperfusion by Acadesine Derivatives GP-1-468 and GP-1-688," J. Thorac. Cardiovasc. Surg. 110:752-761 (1995).

Grettenberger et al., "Spectrophotometric determination of the cardioprotective drug GP531 in human plasma," J. Biochem. Biophys. Methods 33:25-30 (1996).

International Search Report for PCT/US06/11422, mailed 29 Jan. 2007, 1 page.

Mitsos et al., "Protective Effects of AICAriboside in the Globally Ischemic Isolated Cat Heart," *Pharmacology* (1985) 31:121-131.

STN Abstract, Accession No. 86017127, PubMed ID 4048260, from: Mitsos et al. "Protective effects of AICAriboside in the globally ischemic isolated cat heart," *Pharmacology* (1985) 31(3):121-131 (abstract).

\* cited by examiner

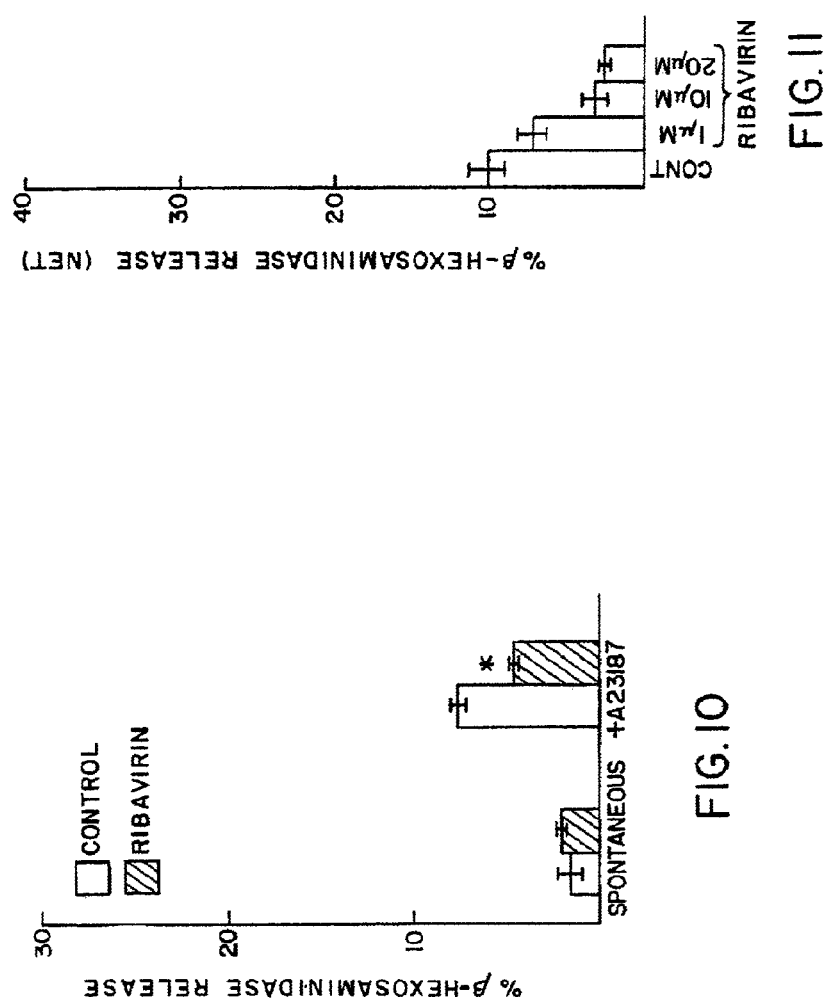

METHODS, COMPOSITIONS, AND FORMULATIONS FOR PREVENTING OR REDUCING ADVERSE EFFECTS IN A PATIENT

CROSS-REFERENCE TO RELATED APPLICATIONS

This application claims priority to U.S. Provisional Application No. 60/666,071, filed Mar. 28, 2005, which is hereby incorporated by reference for all purposes.

BACKGROUND OF THE INVENTION

Gruber (U.S. Pat. No. 4,912,092) described prophylactic administration of AICA riboside compounds, including analogs and prodrugs thereof, to prevent tissue damage associated with undesired decreased blood flow. The AICA riboside compounds are administered in amounts between 0.1 and 500 mg/kg/day. AICA riboside's prodrugs, including those set forth in the commonly assigned U.S. Pat. No. 5,082,829, entitled "AICA Riboside Prodrugs," U.S. application Ser. No. 07/408,107, filed Sep. 15, 1989, entitled "Methods and Compounds for AICA Riboside Delivery and for Lowering Blood Glucose," and U.S. application Ser. No. 07/466,979, filed Jan. 18, 1990, entitled "Method and Compounds for AICA Riboside Delivery and for Lowering Blood Glucose," all of which are incorporated herein in their entireties by this reference, may also be administered. Certain prodrugs of AICA riboside are defined therein, and generally are compounds which, when introduced into the body, will metabolize into AICA riboside or an active metabolite, for example, AICA riboside monophosphate. Other prodrugs include mono-, di- and tri-5' phosphates of AICA riboside.

Adenosine, 9-β-D-ribofuranosyladenine (the nucleoside of the purine adenine), belongs to the class of biochemicals termed purine nucleosides and is a key biochemical cell regulatory molecule, as described by Fox and Kelly in the Annual Reviews of Biochemistry, Vol. 47, p. 635, 1978. It interacts with a wide variety of cell types and is responsible for a myriad of biological effects. For instance, adenosine is a potent vasodilator, an inhibitor of immune cell function, and can at certain levels enhance activation of mast cells, is an inhibitor of granulocyte oxygen-free radial production, is anti-arrhythmic, and is an inhibitory neurotransmitter. Considering its broad spectrum of biological activity, considerable effort has been aimed at establishing practical therapeutic uses for adenosine and its analogs.

Since adenosine is thought to act at the level of the cell plasma membrane by binding to receptors anchored in the membrane, past work has included attempts to increase extracellular levels of adenosine by administration of it into the blood stream. Unfortunately, adenosine is toxic at concentrations that have to be administered to a patient to maintain an efficacious extracellular therapeutic level, and the administration of adenosine alone is therefore of limited therapeutic use. Further, adenosine receptors are subject to negative feedback control following exposure to adenosine, including down-regulation of the receptors.

Other ways of achieving the effect of a high local extracellular level of adenosine exist and have also been studied. They include: (a) interference with the uptake of adenosine with reagents that specifically block adenosine transport, as described by Paterson et al., in the Annals of the New York Academy of Sciences, Vol. 255, p. 402 (1975); (b) prevention of the degradation of adenosine, as described by Carson and Seegmiller in The Journal of Clinical Investigation Vol. 57, p. 274 (1976); and (c) the use of analogs of adenosine constructed to bind to adenosine cell plasma membrane receptors.

There are a large repertoire of chemicals that can inhibit the cellular uptake of adenosine. Some do so specifically and are essentially competitive inhibitors of adenosine uptake, and others inhibit nonspecifically. P-Nitrobenzylthionosine appears to be a competitive inhibitor, while dipyridamole and a variety of other chemicals, including colchicine, phenethylalcohol and papaverine inhibit uptake nonspecifically.

Extracellular levels of adenosine can be increased by the use of chemicals that inhibit enzymatic degradation of adenosine. Previous work has focused on identifying inhibitors of adenosine deaminase, which participates in the conversion of adenosine to inosine. Adenosine deaminase activity is inhibited by coformycin, 2'-deoxycoformycin, and erythro 9-(2-hydroxy-3-nonyl)adenine hydrochloride.

A number of adenosine receptor agonists and antagonists have been generated having structural modifications in the purine ring, alterations in substituent groups attached to the purine ring, and modifications or alterations in the site of attachment of the carbohydrate moiety. Halogenated adenosine derivatives appear to have been the most promising as agonist or antagonist and, as described by Wolff et al. in the Journal of Biological Chemistry, Vol. 252, p. 681, 1977, exert biological effects in experimental systems similar to those caused by adenosine.

Although all three techniques discussed above may have advantages over the use of adenosine alone, they have several disadvantages, the major disadvantages being that they rely on chemicals that have adverse therapeutic side effects, primarily due to the fact that they must be administered in doses that are toxic, and that they affect nonselectively most cell types. As described in Purine Metalolism in Man, (eds. De Bruyn, Simmonds and Muller), Plenum Press, New York, 1984, most cells in the body carry receptors for adenosine. Consequently, the use of techniques that increase adenosine levels generally throughout the body can cause unwanted, dramatic changes in normal cellular physiology.

With respect to post ischemic myocardial tissue and adenosine, it is stated in Swain, J. L., J. J. Hines, R. L. Sabina, and E. W. Holmes, Circulation Research 51:102-105 (1982), and in Holmes et al., U.S. Pat. No. 4,575,498 (issued Mar. 11, 1986), that adenosine concentration and blood flow are not altered in ischemic canine hearts exposed to the purine nucleoside 5-amino-4-imidazolecarboxamide riboside (AICA riboside). They also state that depletion of purine nucleotide pools, especially adenosine triphosphate (ATP), has been postulated to play a role in such dysfunction following, e.g., an ischemic event, and claim to have demonstrated an enhanced nucleotide synthesis and concomitant repletion of ATP pools by treating post-ischemic myocardium with the purine analog AICA riboside, stating that repletion of ATP pools should, in theory, enable the amelioration of tissue damage.

Several other groups of investigators, however, have published studies in which they were unable to demonstrate an enhanced repletion of ATP pools in ischemic tissue by the method of Swain et al., supra. Mentzer, R. M., Ely, S. W., Lasley, R. D., Lee, B. K. and Berne, R. M., Fed. Proc. 43:903 (1984); Mitsos, S. E., S. R. Jolly and B. R. Lucchesi, Pharmacology 31:121-131 (1985); Hoffmeister, H. M., Nienaber, C., Mauser, M. and Schaper, W. E., Basic Research in Cardiology 80:445-458 (1985); Mauser, M., H. M. Hoffmeister, C. Nienaber, and W. E. Schaper, Circul. Res. 56:220-230 (1985). In fact, Hoffmeister et al. demonstrate that ATP repletion by another mechanism does not improve cardiac dysfunction.

Even Holmes and Swain have documented that AICA riboside does not effectively reach ATP because of an inhibition of the conversion of inosine monophosphate (IMP) to adenosine monophosphate (AMP). Sabina, R. L., Kemstine, K. H., Boyd, R. L., Holmes, E. W. and Swain, J. L., J. Biol. Chem. 257:10178 (1982); Amidon, T. M., Brazzamano, S., Swain, J. L., Circ. Suppl. 72:357 (1985); Swain, J. L., Hines, J. J., Sabina, R. L., Harburg, O. L. and Holmes, E. W., J. Clin. Invest. 74:1422-1427 (1984). Amidon et al., supra, state that "These results indicate that adenylosuccinate synthetase and/ or lyase activities are limiting in isolated hearts and suggest that interventions designed to bypass IMP in AN (Adenine Nucleotide) synthesis might be more advantageous for increasing AN pool size." Swain et al., supra., (J. Biol. Chem.), also demonstrated that AICA riboside does not consistently alter ATP levels in non-ischemic myocardium.

While Mitsos et al., supra claimed that their study demonstrated that AICA riboside infused intracoronary in high doses protected globally ischemic hearts from the mechanical dysfunction associated with an ischemic insult, Hoffineister et al., Basic Res. Cardiol. 80:445-458 (1985), showed that on producing a reversible ischemia in dogs by coronary artery occlusion, AICA riboside application did not improve postischemic function and, in fact, worsened it. Swain et al., supra (J. Clin. Invest.) confirms the detrimental effects of high doses of AICA riboside on muscle contractility. Thus, the proposal that the administration of AICA riboside would be of benefit to patients after an ischemic event for repletion of ATP pools does not appear to be valid.

It will be appreciated from the foregoing discussion that a technique that would increase extracellular levels of adenosine or adenosine analogs at specific times during a pathologic event, that would increase these compounds without complex side effects, and which would permit increased adenosine levels to be selectively targeted to cells that would benefit most from them would be of considerable therapeutic use. By way of example, such a technique would be especially useful in the prevention of, or response during, an ischemic event, such as heart attack or stroke, or other event involving an undesired, restricted or decreased blood flow, such as atherosclerosis, for adenosine is a vasodilator and prevents the production of superoxide radicals by granulocytes. Such a technique would also be useful in the prophylactic or affirmative treatment of pathologic states involving increased cellular excitation, such as (1) seizures or epilepsy, (2) arrhythmias, and (3) inflammation due to, for example, arthritis, autoimmune disease, Adult Respiratory Distress Syndrome (ARDS), and granulocyte activation by complement from blood contact with artificial membranes as occurs during dialysis or with heart-lung machines. It would further be useful in the treatment of patients who might have chronic low adenosine such as those suffering from autism, cerebral palsy, insomnia and other neuropsychiatric symptoms, including schizophrenia. The compounds useful in the invention, which include AICA riboside, may be used to accomplish these ends.

Another area of medical importance is the treatment of allergic diseases, which can be accomplished by either preventing mast cells from activating, or by interfering with the mediators of allergic responses which are secreted by mast cells. Mast cell activation can be down-regulated by immunotherapy (allergy shots) or by mast cell stabilizers such as cromalyn sodium, corticosteroids and aminophylline. There are also therapeutic agents which interfere with the products of mast cells such as anti-histamines and adrenergic agents. The mechanism of action of mast cell stabilization is not clearly understood. In the case of aminophylline, it is possible that it acts as an adenosine receptor antagonist. However, agents such as cromalyn sodium and the corticosteroids are not as well understood.

It will be appreciated, therefore, that effective allergy treatment with compounds which will not show any of the side effects of the above-noted compounds, such as drowsiness in the case of the anti-histamines, agitation in the case of adrenergic agents, and Cushing disease symptoms in the case of the corticosteroids, would be of great significance and utility. In contrast to compounds useful in the invention, such as AICA riboside and ribavirin, none of the three known mast cell stabilizers are known or believed to be metabolized in the cell to purine nucleoside triphosphates or purine nucleoside monophosphates.

Gruber (U.S. Pat. No. 5,817,640) described particular therapeutic concentrations of AICA riboside for the prevention of tissue damage associated with decreased blood flow in humans, and the determination of dosages which achieve efficacy while avoiding undesirable side effects. In one aspect, the AICA riboside or a prodrug thereof is administered to a person in an amount, which maintains a blood plasma concentration of AICA riboside for a sufficient time so that the risk of tissue damage is reduced in that person, of from about 1 ug/ml to about 20 ug/ml. In another aspect, the AICA riboside is administered to a person at a dosage of from about 0.01 mg/kg/min to about 2.0 mg/kg/min to reduce the risk of tissue damage. Another aspect features the prevention of tissue damage by administering a total dosage of AICA riboside of from 10 mg/kg to 200 mg/kg.

AICA riboside enters cells and is phosphorylated to AICA riboside monophosphate ("ZMP"), a naturally occurring intermediate in purine biosynthesis. AICA riboside increases extracellular adenosine levels under conditions of net ATP breakdown and, therefore, in light of the cardioprotective and neuroprotective properties of adenosine it may have potential therapeutic uses. However, AICA riboside has a relatively low potency and short half life. Also, we have found that AICA riboside does not cross the blood-brain barrier well and is inefficiently absorbed from the gastrointestinal tract. These characteristics of limited potency, limited oral bioavailability and limited brain penetration decrease its potential for use as a therapeutic agent.

AICA riboside treatment has been reported to have beneficial effects in a number of experimental models of myocardial ischemia. In a dog model, in which pacing induced a profound progressive decline in wall thickening and endocardial blood flow and an increase in ST segment deviation of the intramyocardial EKG, AICA riboside markedly attenuated these changes to maintain contractile function> Young and Mullane, Am. J. Physio., in press (1991)!. In another dog model, in which ischemia was induced by coronary artery occlusion, AICA riboside was reported to be beneficial by significantly decreasing ischemia-induced arrhythmias and improving blood flow to the ischemic region of the myocardium (Gruber et al, Circulation 80 (5): 1400-1410 (1990)). An effect of AICA riboside to increase regional blood flow and maintain contractile function was also reported in a dog model of coronary embolization in which ischemia was induced by administration of microspheres directly into the coronary circulation (Takashima et al, Heart and Vessels 5 (Supplement 4): 41 (1990)). A potential consequence of this reported redistribution in blood flow by AICA riboside was said to be a reduction of infarct size (McAllister et al, Clinical Research 35: 303A (1987)). Treatment with AICA riboside has been reported to have favorable consequences in other experimental models of myocardial ischemia. For instance, Mitsos et al (Pharmacology 31: 121-131 (1985)) reported that AICA riboside improved the recovery of post-ischemic function in the isolated blood-perfused cat heart and Bullough et al. (Jap. J. Pharmacol 52: 85p (1990)) reported improved recovery in an isolated buffer-perfused guinea pig heart. Thus, AICA riboside has been reported to alleviate ischemia-induced injury to the heart in various experimental models.

AICA riboside has also been reported to protect brain tissue from damage in two different experimental models of cerebral ischemia. In a gerbil model of global ischemia, AICA riboside was reported to prevent the degeneration of hippocampal CA-1 cells, which in control animals were virtually completely destroyed (Phillis and Clough-Helfman, Heart and Vessels 5 (Supplement 4): 36 (1990)). In a rat model of focal ischemia, AICA riboside treatment was reported to provide a significant reduction in infarct size. The protective effects of AICA riboside have also been reported in other models of ischemia, including rat skin flap survival (Qadir et al, Fed Proc. A626 (1988); Salemo et al in Proceedings of 35th Annual Meeting of the Plastic Surgery Research Council, pp. 117-120 (1990)) and gastro-intestinal ischemia-reperfusion injury (Kaminski & Proctor, Circulation Res. 66 (6): 1713-1729 (1990)).

A number of studies suggest that the beneficial effects of AICA riboside can be ascribed, at least in part, to an increase in local levels of adenosine, which has similar cardioprotective (Olafsson et al, Circulation 76: 1135-1145 (1987)) and neuroprotective properties (Dragunow & Faull, Trends in Pharmacol. Sci. 7: 194 (1988); Marangos, Medical Hypothesis 32: 45 (1990)). Evidence for AICA riboside-induced enhancement of adenosine levels is both direct i.e. a consequence of measurement of adenosine itself in both animal and cell culture models (Gruber et al, Circulation 80(5): 1400-1410 (1990); Barankiewicz et al, Arch. Biochem. Biophys., 283: 377-385, (1990)) and indirect i.e. implicated by reversal of the anti-ischemic properties of AICA riboside by removal of exogenous adenosine using adenosine deaminase (Young & Mullane, Am. J. Physio., in press (1991)). In hearts subjected to ischemia and reperfusion, cellular damage has been, in part, attributed to plugging of the microvessels by neutrophils. Adenosine has been reported to inhibit neutrophil adhesion to coronary endothelial cells and hence neutrophil accumulation (Cronstein et al., J. Clin. Invest. 78: 760-770 (1986)). Consequently, another feature of the adenosine-mediated protective effects of AICA riboside in the heart can be through prevention of neutrophil-dependent tissue injury in some models of ischemia and reperfusion. This is supported by evidence for decreased accumulation of neutrophils in the ischemic region of the heart by AICA riboside (Gruber et al, Circulation 80: 1400-1410 (1990)).

A recognition of the cardioprotective and neuroprotective properties of adenosine have led to attempts to explore the therapeutic use of exogenously administered adenosine itself. However the short half life of adenosine in blood (<10 secs) necessitates the use of high doses and continuous infusions to maintain levels appropriate for most treatments. Adenosine itself causes hypotension, i.e. reduces blood pressure; it is also a negative chronotropic and dromotropic agent, i.e. reduces heart rate and electrical conduction in the heart, respectively. Adenosine would therefore exert marked systemic hemodynamic effects at concentrations that would be required to elicit cardioprotective or neuroprotective properties. These systemic cardiovascular actions are frequently contraindicated in most clinical conditions where adenosine could be useful. In contrast, as a result of its local effects on adenosine levels, AICA riboside administration does not produce such side-effects, even at doses considerably higher than the expected therapeutic levels (Gruber et al; Circulation 80: 1400-1410, (1990); Young & Mullane, Am. J. Physio., in press, (1991)).

Adenosine receptor agonists have also been studied and effects similar to adenosine have been reported in a number of experimental models. (Daly, J. Med. Chem. 25(3): 197 (1982). Again, because most cell types have adenosine receptors, exogenously administered adenosine agonists exhibit profound actions on a variety of tissues and organs, outside of the target organ, thereby limiting their therapeutic potential.

Other ways of potentially achieving the effect of a high local extracellular level of adenosine have been studied. They include: a) interference with the uptake of adenosine with reagents that specifically block adenosine transport, as described by Paterson et al., in the Annals of the New York Academy of Sciences, Vol. 255, p. 402 (1975); b) prevention of the degradation of adenosine, as described by Carson and Seegmiller in The Journal of Clinical Investigation, Vol. 57, p. 274 (1976); and c) the use of analogs of adenosine constructed to bind to adenosine cell plasma membrane receptors.

There are a repertoire of chemicals that reportedly can inhibit the cellular uptake of adenosine. Some have been reported to do so specifically, and are believed to be essentially competitive inhibitors of adenosine uptake, and others are believed to inhibit nonspecifically. p-nitrobenzylthioinosine appears to be a competitive inhibitor, while dipyridamole and a variety of other chemicals, including colchicine, phenethylalcohol and papaverine appear to inhibit uptake nonspecifically.

U.S. Pat. No. 4,115,641 to Fischer et al. is directed to certain ribofuranosyl derivatives which are said to have cardiac and circulatory-dynamic properties. In particular, Fischer et al. are directed to certain compounds which are said to have intrinsic adenosine-like modes of action as determined by measuring decreased heart rate and blood pressure.

In contrast, AICA riboside and AICA riboside-like compounds lead to enhanced adenosine levels at the specific time and location of a pathological event and thus permit increased adenosine levels to be selectively targeted without the detrimental side effects.

The present invention is directed to AICA riboside analogs which exhibit and, in many cases, improve upon, the positive biological effects of AICA riboside. The novel compounds typically exhibit one or more of the following improvements over AICA riboside 1) functional benefits at lower doses; 2) more potent adenosine regulating actions; 3) increased half-lives or; 4) increased oral bioavailability and/or brain penetration.

Post-surgical complications are a significant source of morbidity and mortality, and healthcare expenditure.

For cardiac surgery, approximately one million patients undergo such every year, and approximately one in six develops a serious major organ complication relating to the heart, brain, kidney, GI tract and lung (Mangano, et al., 1997, *J. Intensive Care Med.* 12:148-160). Yet despite numerous advances in monitoring and technique, no drug has been shown to reduce or prevent these complications. The preoccupation has been with bleeding, and drugs are now used to prevent such. However, drugs which inhibit bleeding generally cause thrombosis, and therefore may induce ischemia and irreversible organ injury (Cosgrove, et al., 1992, *Ann. Thorac. Surg.* 54:1031-36).

For noncardiac surgery, approximately 250 million patients undergo such every year, and approximately four percent develop a serious major organ complication relating to the heart (Mangano, et al., 1990, *Anesthesiology* 2:153-84;

Mangano, et al., 1990 *NEJM* 323:1781-88). Only one drug has been shown to mitigate injury-atenolol (Mangano, et al., 1996, *NEJM* 335:1713-20). As well, concerns for bleeding predominate, and drugs preventing thrombosis (anti-platelet, anti-clotting) are virtually contraindicated (Eagle, et al., 1999, *JACC* 34:1262-1347; Pearson, et al, 1994, *Circulation* 90:3125-33; Baumgartner, et al., 1994, *Johns Hopkins Manual of Surgical Care*, Mosby Yearbook, St. Louis).

However, for both cardiac and noncardiac surgery, marked excitotoxic and inflammatory responses occur for days after surgery, if not months after surgery (Silicano and Mangano, 1990, Mechanisms and Therapies. In: *Estafanous, ed. Opioids in Anesthesia* Butterworth Publishers, pp. 164-178). Such markedly exaggerated responses are associated with platelet and clotting factor activation, which may precipitate thrombosis.

Although recognized as a possibility, such agents are relatively—and in some cases (fibrinolytics), absolutely-contraindicated because of fear of excessive hemorrhage at the surgical site, as well as at other sites (Eagle, et al., 1999, *JACC* 34:1262-1347; Pearson, et al., 1994, *Circulation* 90:3125-3133; Baumgartner, et al., 1994, *Johns Hopkins Manual of Surgical Care*, Mosby Yearbook, St. Louis). Further, some believe—especially after cardiac surgery—that platelet and clotting factor function are depressed after surgery, so that thrombosis is not an issue (Kestin, et al., 1993, *Blood* 82:107-117; Khuri, et al., 1992, *J. Thorac. Cardiovasc. Surg.* 104:94-107). Thus, no effort has been made to investigate the use of anti-clotting agents immediately following surgery.

Finally, Applicants have shown that perioperative events manifest over six to eight months or longer (Mangano, et al. 1992, *JAMA* 268:233-39); thus, continuation of use of such anti-clotting agents throughout the in-hospital, and then post-discharge course, is rational.

Surgery patients—now numbering 40 million per year in the U.S. alone—are aging nearly twice as rapidly as the overall population. (See, Mangano, et al., 1997, *J. Intensive Care Med.* 12:148-160).

The current standards of care are unsatisfactory to address this critical problem, and novel approaches are desperately needed to prevent post-surgical complications in our aging population.

The electronic monitoring of the fetal heart rate is an important part of the labor and delivery process for women. In some cases, a deceleration in fetal heart rate, including persistent late decelerations with loss of beat-to-beat variability, nonreassuring variable decelerations associated with loss of beat-to-beat variability, prolonged severe bradycardia, sinusoidal pattern, confirmed loss of beat-to-beat variability not associated with fetal quiescence, medications or severe prematurity, can require emergency intrauterine fetal resuscitation and immediate delivery. (Sweha, et al., 1999. *American Family Physician* 59(9):2487-2507; Kripke 1999, *American Family Physician* 59(9):2416). There is a need for methods to prevent or reduce adverse effects from these events for the health of the fetus.

SUMMARY OF THE INVENTION

The present invention relates to methods of preventing or reducing adverse effects in a patient, including by administering acadesine or a prodrug, analog, or salt thereof; or acadesine or a prodrug, analog, or salt thereof and a blood clotting inhibitor. In addition, the invention includes pharmaceutical formulations, compositions, cardioplegic solutions, and kits related to preventing or reducing adverse effects in a patient. The invention may benefit several types of patients, including a patient with decreased left ventricular function, a patient with a prior myocardial infarction, a patient undergoing non-vascular surgery, or a fetus during labor and delivery.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 10. β-hexosaminidase release from control and ribavirin-treated mast cells. Mouse bone marrow-derived mast cells cultured for three to seven days in media alone (open) or 10 µM ribavirin (hatched) were challenged with the calcium ionophore A23187. The percentages of β-hexosaminidase release from resting and stimulated cells are shown as means+/−SE of duplicate values from seven experiments. The asterisks (*) identify data significantly different from control cells ($p<0.05$). Similar results were obtained with DNP-BSA antigen stimulation of anti-DNP IgE-sensitized mast cells.

FIG. 11. Dose-response effects of ribavirin on mast cell β-hexosaminidase release. Mast cells were cultured in media alone (controls) or 1, 10, or 20 µM ribavirin for six days, washed, challenged with A23187, and net β-hexosaminidase release was quantitated. Ribavirin-treated cells at all concentrations tested released significantly less-hexosaminidase when challenged with A23187. Mediator content and spontaneous release were no different in control and ribavirin-exposed cells. Depicted are means+/−SE of duplicate determination from three experiments.

DETAILED DESCRIPTION OF THE INVENTION

Figure 1:
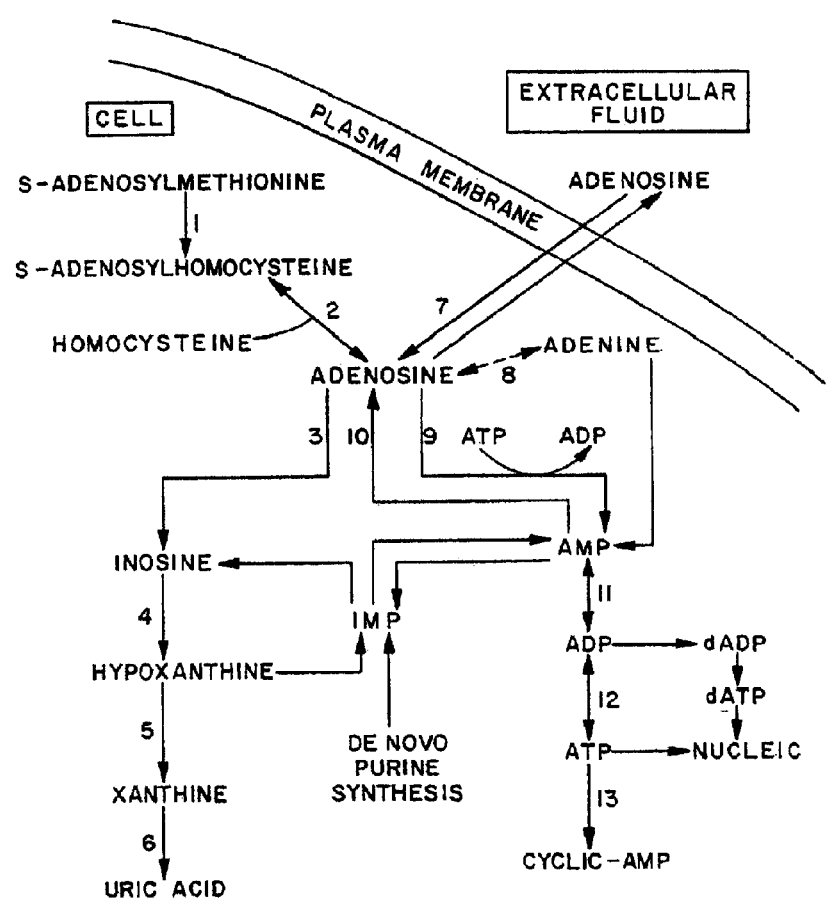
FIG. 1. Metabolic pathways of adenosine.

"Ejection fraction" refers to a measure of the function of the left ventricle, also called left ventricular ejection fraction (LVEF). The ejection fraction is the percentage of blood ejected from the left ventricle with each heart beat. An LVEF of 50% indicates that the left ventricle ejects half its volume each time it contracts. A normal ejection fraction is 50% or higher. A reduced ejection fraction indicates that cardiomyopathy is present.

In one aspect, the invention provides a method of preventing or reducing adverse effects in a patient with decreased left ventricular function having an ejection fraction of less than 30% by administering an effective amount of acadesine, or a prodrug, analog or salt thereof. Another embodiment provides a method where the patient is female and/or or between the age of 65 and 95.

Another aspect of the invention provides a method of decreasing tissue damage associated with decreased blood flow in a patient by administering an effective amount of acadesine, or a prodrug, analog, or salt thereof, wherein the patient is a fetus during labor and delivery. In one embodiment, an effective amount of acadesine, or a prodrug, analog, or salt thereof is administered to the woman delivering the fetus.

In one aspect, the invention provides a pharmaceutical embodiment, the invention provides a pharmaceutical formulation comprising acadesine, or a prodrug, analog, or salt thereof for use in administration to a fetus during labor and delivery to prevent or reduce tissue damage associated with decreased blood flow in the fetus.

Novel methods are described for enhancing adenosine release, especially during net ATP catabolism, i.e., during a time of a decreasing or decreased ratio of ATP synthesis to ATP breakdown in cells or cellular compartments.

Novel methods are also described for stabilizing mast cells.

Also included within the scope of the invention is a method of screening purine nucleoside compounds or analogs for the ability to enhance the cellular synthesis and release of adenosine comprising administering to cultured cells a first composition comprising a purine nucleoside compound or analog to be screened, administering to said cultured cells a second composition comprising a compound which promotes net catabolism of adenosine triphosphate, and determining the level or amount of adenosine released by said cultured cells.

This last method may further comprise a first control set of cultured cells to which neither said first composition nor said second composition is added, a second control set of cultured cells to which said first composition is added, and a third control set of cultured cells to which said second composition is added. The cultured cells may be derived from a human malignant cell line, such as Epstein-Barr virus transformed B lymphocytes, or the W1-L2 human splenic lymphoblast cell line, such as that used in Example II herein. Compounds used to create compositions for the promotion of net catabolism of adenosine triphosphate include calcium ionophores and 2-deoxyglucose.

Methods for enhancing adenosine release utilize the administration of compounds which are believed to alter one or more of the biochemical pathways of adenosine metabolism so that the net result is an enhanced extracellular concentration of adenosine (resulting from one or more processes, including enhanced intracellular production and/or release of adenosine). Examples of compounds useful in the invention include compounds broadly classified as purine nucleosides and related analogs, such as AICA riboside, AICA ribotide, 1-β-D-ribofuranosyl-1H-1,2,4-triazole-3-carboxamide (ribavirin), ribavirin monophosphate, and various pro-forms of the above compounds. The compounds are taken up by cells and, if necessary, are believed to be converted to their monophosphate and, to a lesser extent, their triphosphate forms. Also included are (1) agents that can enhance endogenous synthesis of AICA ribotide or metabolites, such as purine intermediary metabolites or compounds that can form these metabolites, e.g., succinylaminoimidazole carboxamide (SAICA) riboside, (2) agents that cause a buildup of AICA-ribotide or its metabolites, including methotrexate, and (3) agents that cause bacterial flora to increase AICA riboside production, such as sulfonamides. These compounds can be administered to a patient either prophylactically, in some cases, and/or in direct response to a bodily condition in others. Purine nucleosides that enhance the excretion of cellular adenosine and/or adenosine analogs may be administered to a living system over the concentration range of 0.5 micromolar to 0.5 molar and, typically, are administered in concentrations up to 0.5 molar.

Adenosine or inosine are generated from adenosine triphosphate n the course of rapid cellular energy utilization, such as during seizure activity, arrhythmias, or a condition resulting in decreased blood flow (ischemia), such as a stroke, heart attack, or angina. Normally, during such an event, the production of inosine is greater than that of adenosine. In the area of low flow during coronary occlusion, for example, the ratio of venous inosine to adenosine is approximately 100 to 1. A certain percentage of inosine and adenosine exit the cell and are present in the immediate extracellular environment. The compounds useful in the methods described and claimed herein have been shown to enhance the extracellular concentration of adenosine, and the production of inosine has been shown to be decreased. Adenosine levels are not altered significantly throughout the patient because alterations in adenosine production only occur in areas of, and at the time of, net ATP use and because adenosine is rapidly degraded. Thus, the methods described and claimed herein will cause a localized increased concentration of extracellular adenosine instead of a systemic or generalized adenosine enhancement.

Oxidation of low density lipoprotein (LDL) is one of the first, if not the first, steps in the process of atherosclerosis, a process believed to involve inflammation and to be due to mononuclear cell and/or granulocyte activation. The oxidized lipids are taken up by macrophages to form the atherosclerotic plaque. Because adenosine prevents the production of superoxide radicals by granulocytes, the compounds of the invention which enhance adenosine release should slow, prevent, or reverse the development of atherosclerosis.

Patients that are suffering from (1) autoimmune disease, (2) arthritis, (3) psoriasis, (4) organ transplant rejection, (5) complement-mediated granulocyte activation after exposure to heart-lung or dialysis membranes, (6) ARDS, or other inflammatory conditions, Whether due to granulocyte activation (as (1)-(6) above can be) or mononuclear cell activation, should also experience relief on treatment With the compounds useful in the invention because ATP catabolism is expected during an inflammatory response.

Patients suffering from diseases which may be associated with chronic low adenosine, such as insomnia, autism, schizophrenia and cerebral palsy, will also benefit from the use of the invention to increase adenosine concentrations.

Further, treatment with compounds of the invention will benefit patients suffering from a variety of illnesses relating to mast cell degranulation. They include individuals suffering from allergies, particularly asthma, hay fever, chronic urticaria, urticaria pigmentosa and eczema. Both AICA riboside and ribavirin, for example, suppress mast cell activation, including the prevention of mast cell degranulation. Decreased mast cell activity will also benefit patients with reduced blood flow because agents released from mast cells can increase damage during ischemia through processes such as arrhythmias or vessel spasm.

It is anticipated that compounds useful in the invention will be effectively administered in amounts ranging from about 0.1 mg/kg/day to about 500 mg/kg/day, preferably from about 15 mg/kg/day to about 200 mg/kg/day. That range of dosages should be especially suitable for compounds useful in the invention as prophylactics for the prevention of tissue damage associated with undesired restricted or decreased blood flow. The use of at least about 0.1 mg/kg/day of AICA riboside or AICA ribotide, preferably from about 1.0 mg/kg/day to about 500 mg/kg/day for said prophylaxis and, more preferably, from about 20 mg/kg/day to about 100 mg/kg/day, is further anticipated. Also contemplated for said prophylaxis is the administration of ribavirin or ribavirin monophosphate in an amount of at least about 0.1 mg/kg/day, preferably from about 1.0 mg/kg/day to about 20 mg/kg/day. In the case of treatment of brain diseases, such as stroke, seizures, epilepsy, transient ischemic attack, autism, schizophrenia, cerebral palsy and insomnia, a dosage of more than 200-500 mg/kg/day may be needed because of the blood/brain barrier. The use of brain-directed pro-drugs may, however, enable a lower dosage.

FIG. 1 illustrates the pathways by which adenosine is formed and degraded within cells. Adenosine may be transported into cells or released from cells. The metabolism of adenosine may utilize some of these pathways: 1, S-adenosylmethionine methyltransferase; 2, S-adenosylhomocysteine hydrolase; 3, adenosine deaminase; 4, purine nucleoside phosphorylase; 5 & 6, xanthine oxidase; 7, transport mechanisms; 8, adenosine phosphorylase (not established in humans); 9, adenosine kinase: 10, 5' nucleotidase and non-specific phosphatase; 11, adenylate kinase; 12, nucleoside diphosphokinase; 13, adenylate cyclase; 14, AMP deaminase; and 15, adenylosuccinate synthetase and adenylosuccinate lyase.

As described in more detail below, the effects of the use of the compounds described, including the purine nucleosides ribavirin and AICA riboside, on extracellular adenosine concentration have been demonstrated both in vitro and in vivo. To deliver these molecules to patients, it is anticipated that they will most often be administered orally, since the compounds of the invention are not readily degraded by extracellular enzymes in the body or by exposure to low pH present in the stomach. These drugs can also be administered intravenously, by direct intramuscular injection, subcutaneously, topically to skin or mucous membranes, rectally, or by inhalation. Compositions acceptable for pharmaceutical use are well known. Pro-drugs may also be utilized, i.e., those which, when introduced into the body, metabolize to the active forms of the claimed compounds.

Because the purine nucleoside AICA riboside can be metabolized to uric acid, this agent may b used with allopurinol or other drugs that prevent uric acid synthesis, or with a uricosuric agent such as probenicid. Certain agents, such as methotrexate and ribavirin, whose metabolites inhibit AICA ribotide transformylase, may cause an elevation of endogenously synthesized AICA ribotide and create effects similar to administering the purine nucleoside. Concomitant administration of AICA riboside or AICA ribotide with an inhibitor of AICA ribotide transformylase should have at least additive effects. In addition, any one of the de novo purine nucleotide synthesis intermediates (after the first committed step for purine synthesis) or their nucleosides or bases can be assumed to be rapidly converted to AICA ribotide. An example is SAICA ribotide or its nucleoside or base.

The compounds can be used to enhance extracellular concentrations of adenosine and, therefore, to treat diseases that arise from, or are aggravated by, insufficient blood flow through a particular organ or portion thereof. For example, heart attacks or strokes, the microvascular disease of diabetes mellitus (which can affect the brain, the kidney, the heart, the skin, the retina, and the peripheral nerves and their associated microvasculatures), or events resulting in a less prolonged loss of blood flow, such as angina pectoris, transient ischemic attacks, bowel ischemia, kidney ischemia, intermittent claudication of skeletal muscle, migraine headaches, and Raynaud's phenomenon can be treated by administering the compounds of the invention. Adenosine is known to be both a potent vasodilator, which acts by reducing vascular smooth muscle contraction, and an inhibitor of granulocyte free radical production, a process involved in ischemic injury. As noted, it should also be useful in the treatment of atherosclerosis.

Upon contact with cells, it is believed that the compounds useful in the invention enter the cell where they can be phosphorylated by adenosine kinase or, in the case of administration of base, they can be converted to a nucleotide by a phosphoribosyl transferase enzyme to yield a purine nucleotide monophosphate, and eventually also the nucleoside triphosphate. The triphosphate form may comprise a pool for breakdown to the monophosphate form.

While not wishing to be bound by the following proposed mode of action, it is postulated that the compounds of the invention, or their metabolites, inhibit one or more enzymes in the adenosine biologic pathway, including AMP deaminase, thus shunting ATP more toward the cellular production, release, and less re-uptake of adenosine, and shunting it away from, concomitantly, the cellular production and release of inosine.

It is important to note that ribavirin cannot be metabolized into normal purines, i.e., it does not become AMP, ADP, ATP, IMP, or the guanosine phosphates GMP, GDP, or GTP. In other words, the compounds useful in the invention can enhance adenosine release without being directly metabolized into adenosine. AICA riboside has biochemical properties similar to ribavirin and appears to enhance adenosine release by a similar mechanism rather than by a circuitous conversion to adenosine. The compounds have been shown not to act by the repletion of ATP pools.

FIG. 1 shows that adenosine is primarily metabolized in either of two ways. First, as shown by pathway 3, adenosine may be catabolized by the enzyme adenosine deaminase to form inosine. Inosine is then, for the most part, either further degraded by the enzymes represented in pathways 4, 5 and 6, or shunted out of the cell across the plasma membrane. Transport mechanisms 7 are shown, which enable the transport of adenosine across the cellular plasma membrane in both directions.

Adenosine may also be anabolized by the enzyme adenosine kinase, represented by 9, to adenosine monophosphate (AMP) or to S-adenosylhomocysteine by S-adenosylhomocysteine hydrolase, represented by 2 (depending on homocysteine availability). The former is an energy-requiring reaction. AMP is then either acted on by the enzyme AMP deaminase (14) to form inosine monophosphate (IMP), or further anabo by various enzymatic reactions to form adenosine triphosphate (ATP) or cyclic-AMP. Inhibition of adenosine kinase or S-adenosylhomocysteine hydrolase can indirectly lead to a decrease in uptake of adenosine.

Referring to Examples I-III on the release of adenosine, it is shown by the results in FIGS. 2, 3, 7-9, and Table 1, that the presence of AICA riboside during net ATP catabolism increases cellular release of adenosine and, concomitantly, decreases cellular release of inosine (see Example IV and FIG. 5), suggesting that there is an inhibition of the conversion of AMP to IMP, or that there is an inhibition of the conversion of adenosine to inosine.

Figure 6:
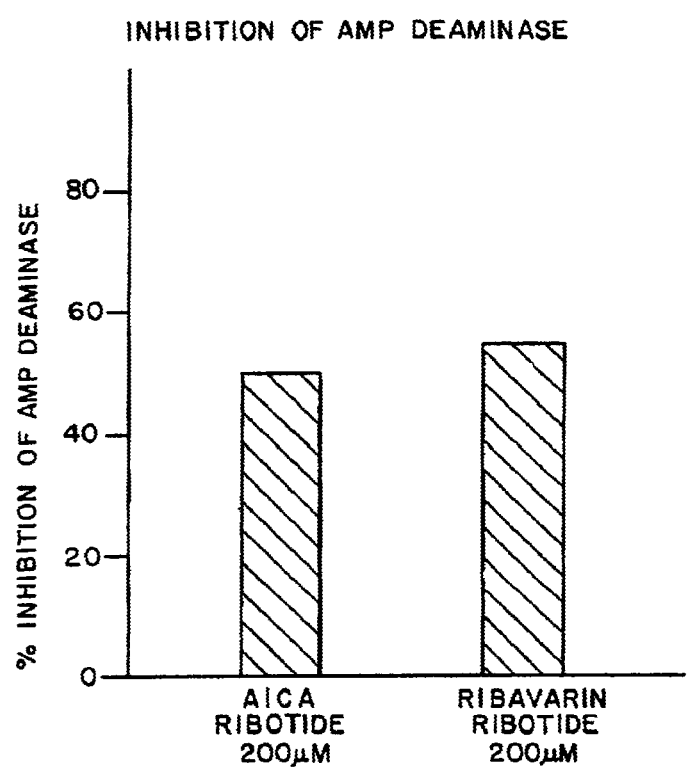
FIG. 6. Effects of AICA ribotide and ribavirin ribotide on inhibition of the enzyme AMP deaminase.

The cell culture experiments of Examples I and II show that AICA riboside increases the cellular release of adenosine even in the presence of 2-deoxycoformycin, a potent inhibitor of the enzyme adenosine deaminase. Thus, it appears that the compounds of the invention have their effect at a point in the adenosine pathway other than or in addition to the reaction catalyzed by adenosine deaminase. They are believed to inhibit the conversion of AMP to IMP by interfering with the action of the enzyme AMP deaminase. The ability of metabolites of the compounds of the invention to inhibit the enzyme AMP deaminase was evaluated in Example VII, and the results are shown in FIG. 6. AICA ribotide and a structurally similar compound, ribavirin monophosphate, were shown to have similar inhibitory effects on AMP deaminase.

It is also possible, however, that the compounds of the invention inhibit the enzymatic conversion of IMP to inosine by 5' nucleotidase, thus decreasing the breakdown of IMP, the result being an increase in the amount of cellular release of adenosine. Further, the compounds of the invention may act to inhibit, directly or indirectly, cellular re-uptake, phosphorylation, or deamination of adenosine.

In summary, a suggested pathway enabling the beneficial effect seen with compounds useful in the invention is the entry of such compounds into the cell, where they become ribosylated (if the sugar ring is not yet present) and phosphorylated (if not yet phosphorylated) to their monophosphate form. The monophosphate forms of the claimed compounds inhibit AMP deaminase. During ATP catabolism, the AMP pool increases more in treated cells than in untreated cells because AMP is no longer able to move as readily to IMP. Cleavage of the purine monophosphates results in a higher cellular release of adenosine with a concomitant lower cellular release of inosine. Because adenosine appears to be a natural beneficial mediator during certain pathological events, enhancement of its release by channeling ATP to adenosine instead of inosine is a novel and extremely important method of treatment.

During a heart attack, adenosine is normally released and it assists in maintaining the patency of ischemic vessels through vasodilation and inhibition of granulocyte free radical production and concomitant microvascular plugging, as described below. The compounds useful in the invention enhance adenosine release and, therefore, enhance the normal protective effect of adenosine during such an ischemic event.

While the release of adenosine is at times a beneficial event, high levels of adenosine in areas where it is not required can be detrimental. One virtue of the invention described and claimed herein is that the patient is not treated with adenosine itself and the compounds useful in the invention selectively increase adenosine release from cells in which there is a net ATP breakdown. Thus, only cells in the vicinity are treated. Treatment of patients with compounds useful in the invention allows the targeting of enhanced adenosine release specifically to tissue undergoing net ATP catabolism, i.e., to tissue which is in need of adenosine release. The systemic effects of adenosine administration are avoided. Further, adenosine is released only at the specific time it is needed. All diseases and pathologic states described or disclosed herein involve or are believed to involve localized net ATP catabolism.

Additionally, cells that would respond beneficially to adenosine are more responsive than they would be if they were continually bathed in higher concentrations of adenosine. Because adenosine is available only instantaneously when it is needed, receptors on the surfaces of cells, such as granulocytes and smooth muscle cells, are not continually exposed and, therefore, have a much larger response, as their adenosine receptors have not been down-regulated by continual adenosine exposure.

In addition to acting to cause vasodilation through the release of adenosine, the compounds of the invention can increase collateral blood flow by a second mechanism. Studies have shown that in the region of restricted blood flow, granulocytes become activated, release oxygen-free radicals, and subsequently stick in and damage microvasculature. Drugs useful in the invention through enhanced adenosine release prevent granulocytes from producing the free radicals and, therefore, granulocytes stick less in the microvessels (see Example VIII), which allows blood flow from collateral vessels into the blocked area. As shown by Example IX, indium-labelled granulocytes are washed out of AICA riboside-treated dog hearts at one hour of ischemia significantly more than in saline-treated dogs, leading to increased collateral blood flow. Thus, the uptake of the compounds of the invention by muscle and/or endothelial cells, followed by subsequent release of adenosine during ischemia, should cause vasodilation and/or suppression of granulocyte activation and inhibit concomitant clogging and damage of the microvasculature, thereby leading to a reduction in damage to the cardiac muscle.

As shown by Examples I-VI, IX, XIII, and XIV, an important aspect of the compounds of the invention is that they can be administered as prophylactic agents. When the drug is present in advance of an ischemic event, seizure activity, or other bodily state targeted for treatment, the net breakdown of ATP can be directed in larger measure to adenosine rather than inosine.

If the drug is introduced into a patient to reach an ischemic region after or during an event causing that ischemia, there is little or no ability to direct ATP to adenosine at that site because the target ATP pools are depleted relatively quickly. Also, because many of the damaging events during ischemia occur rapidly, the drug should ideally be present at the earliest possible moment. With the drug present as a prophylactic agent, there is also the possibility that the process sought to be interrupted can be slowed early enough to prevent any permanent damage. For example, the increased microvascular blood flow from vasodilation and decreased white cell sticking could maintain microvascular patency, as well as in a sense help wash away clots, clot-promoting material, or other deleterious agents from the proximal atherosclerotic regions.

Other factors make it important to administer the drug before or during an ischemic event. If a drug is administered after a blockage, it is less able to reach the tissue involved because there is little or no blood flow to this area. See Example III and FIG. 4. It is also believed that, for example, AICA riboside is metabolized to AICA ribotide and that this is the active form of the molecule. This is an energy-requiring reaction utilizing ATP. If ATP is not available because of high metabolic activity and/or increased ATP destruction, then the AICA riboside or a similar drug cannot be made into its active form. In addition, during rapid ATP breakdown, the inosine in the cell may be significantly competing with the drug for entry into the cell, both compounds being purine nucleoside analogs.

Further, compounds of the invention are envisioned to be beneficial in combination with certain other treatment modalities, as described below. As compounds of the invention, when taken prophylactically, enhance adenosine release during an acute ischemic event, a heart-attack patient undergoing such treatment would have a greater chance of not dying of a sudden arrhythmia before entry to a hospital. In addition, the microvascular bed would be protected during the time the patient is in transit to the hospital and before additional therapy can be instituted.

Often, an acute ischemic event is silent for some time, and there is an additional delay before the patient realizes what is happening and help is sought. When medical help reaches the patient, of course, as when an ambulance arrives or when the patient reaches a hospital, the patient can be given thrombolytic therapy. Thrombolytic therapy, such as the infusion of tissue plasminogen activator (t-PA), streptokinase, urokinase, or anticoagulants such as heparin or Coumadin, are all aimed at opening up a proximal occlusion, such as occurs during a heart attack or stroke. Currently, the patient needs to receive this treatment within about four hours of an acute ischemic event. After several hours, there is irreversible damage to the tissues, especially the microvascular bed. If the patient is prophylactically taking AICA riboside or another compound of the invention, the patient's microvascular bed will be protected longer because of the presence of enhanced adenosine.

The enhanced adenosine release prevents superoxide free radical production and/or granulocyte plugging and damage to the microvessels. Therefore, the patient should be protected for a longer period of time after the acute ischemic event. For example, for perhaps 8-16 hours after a cardiovascular occlusion, it would still be possible to institute one of these thrombolytic therapies in order to open a proximal lesion. Again, opening a proximal lesion is only beneficial if the downstream microvessels are able to be perfused.

Compounds useful in the invention will also be beneficial in combination with thrombolytic agents, such as tissue plasminogen activator, as well as with other agents which are either free radical scavengers or prevent the production of free radicals. Examples of free radical scavengers are superoxide dismutase, a protein which is infused after an ischemic event, or materials which have less proven efficacy, such as catalase, acetylcysteine (mucomyst), vitamin E, gluthathione, and selenium. Examples of compounds which are thought to prevent free radical production are allopurinol by its inhibition of xanthine oxidase, and icosopentanoic acid by its down regulation of prostaglandin metabolites and, finally, antibodies against certain receptors on activated granulocytes which prevent their sticking in microvessels. Compounds useful in the invention, through elevated adenosine, inhibit the NADPH oxidase free radical-generating system of granulocytes and should, therefore, also be useful when combined with agents such as allopurinol, which inhibits free radical production from xanthine oxidase.

Another disease caused by or able to cause restricted blood flow is myocardial arrhythmia. Although restricted blood flow can initiate the onset of arrhythmia, the precise cause is unknown. However, it is known that lipid peroxidation by oxygen radicals is arrhythmogenic. Since the latter are produced by granulocytes, the inhibition of granulocyte superoxide production by the method of the invention can be expected to control arrhythmia. In addition, mast cells are in higher concentration in areas of atherosclerosis. Suppression of their activation might reduce the release of other mediators of arrhythmias. Adenosine also has direct anti-arrhythmic effects on myocytes. The prophylactic effect of AICA riboside treatment on arrhythmias was demonstrated by Examples VI and XIV, the results showing a decreased number of premature ventricular depolarizations and ventricular tachycardia episodes. Rapid firing of cells during arrhythmia causes increased net ATP catabolism and adenosine release.

The adenosine released from neuronal cells when they are stimulated and break down ATP during seizure (epileptic) activity normally will feedback and suppress this seizure (epileptic) activity. In the presence of compounds useful in the invention, the amount of suppression of a seizure event should be significantly increased. Example XIII demonstrates that AICA riboside causes a decreased incidence and prolonged latency to pentylene tetrazol-induced seizures.

Patients that are suffering from autoimmune diseases, arthritis, or other inflammatory conditions should also experience relief if treated with purine nucleosides or analogs useful in the invention because ATP catabolism is expected during the increased cellular excitation associated with an inflammatory response. Inflammatory diseases occur naturally in man and appear to involve an immune reaction to an individual's own tissues. For an autoimmune response to be mounted, it is required that different immune cells interact to support the response. Thus, chemicals that interfere with the requisite cell-cell interactions can be expected to interfere with the course of the disease. One immune cell type necessary for the generation of an autoimmune response is the lymphocyte. Because adenosine is well known to be suppressive to lymphocytes, administering compounds useful in the invention, such as AICA riboside or ribavirin, should inhibit or deplete this population of immune cells during an inflammatory episode, and thus be of considerable therapeutic benefit to inflammatory disease sufferers. Also, as noted, adenosine inhibits granulocyte production of oxygen-free radicals and adherence to endothelial cells, both of which appear to be important factors in many inflammatory processes, such as autoimmune diseases.

Conditions potentially associated with chronic low adenosine may also be treated by compounds of the invention. These pathologic states include autism, insomnia, cerebral palsy, schizophrenia, and other neuropsychiatric symptoms. It is anticipated that doses ranging from 0.1 mg/kg/day up to about 200 mg/kg/day will be beneficial. The results of therapeutic trials with AICA riboside in patients with adenylosuccinase deficiency (autism) are shown in Example X. The oral administration of AICA riboside at a single dose of 5 mg/kg/day, increased to 2×5 mg/kg/day and, finally, to 2×10 mg/kg/day, showed a clear-cut improvement in one of two patients, both patients being described as "more pleasantly active and more easy to handle during therapy" by the father, thereby prompting his request for resumption of the trial. No clinical or biochemical side effects were observed, which suggests that higher doses may be administered with additional beneficial effects.

With respect to mast cell degranulation, treatment with, for example, AICA riboside or ribavirin will benefit patients suffering from a variety of illnesses. For example, individuals suffering from allergies, particularly asthma, hay fever (including allergic conjunctivitis and allergic rhinitis), chronic urticaria, urticaria pigmentosa and eczema, can be expected to benefit from purine nucleoside and purine nucleoside analog treatment. As discussed in B. Benacerra and A. Unanue in Textbook of Immunology (Williams & Williams Baltimore/London, 1979), a key to suppressing allergic responses is to prevent the release of pharmacologically active substances by mast cells. Mast cells are large basophilic staining cells with extensive granules that contain substances, such as histamines, that are liberated by the mast cell during an allergic reaction and are required to support the allergic response. The release of these pharmacologically active substances present in mast cells is termed "degranulation." Thus, chemicals that prevent degranulation should have a beneficial effect on reducing the severity of the allergic response. As such, patients experiencing allergies can be successfully treated with AICA riboside or ribavirin, as these molecules prevent mast cell degranulation. Mast cell activation also causes the release of prostaglandins and leukotrienses (non-preformed mediators) such as slow reactive substance of anaphylaxis. The purine nucleosides and analogs useful in the invention also prevent release of these mediators of inflammation. As shown by Example XI, prophylactic treatment of mast cells with ribavirin exhibited a marked attenuation of hexosaminidase release, the results being set forth in FIGS. 10 and 11. The results from Example XII, similarly, showed that AICA riboside inhibits activation (leukotriene $C_4$ release) and degranulation (β-hexosaminidase release) of mast cells.

Applicant's invention relates to the discovery of particularly therapeutive concentrations of AICA riboside for the prevention of tissue damage associated with decreased blood flow in humans, and the determination of dosages which achieve efficacy while avoiding undesirable side effects. Applicant's invention also relates to the discovery of particularly therapeutic concentrations and dosages of AICA riboside which prevent or reduce the severity of adverse clinical outcomes, including adverse cardiovascular and/or cerebrovascular events in patients at risk for such events. Applicant has discovered that it is preferable to maintain an intravascular concentration of AICA riboside of from about 1 µg/ml to about 20 µg/ml, to obtain the beneficial effects of AICA riboside, and to prevent side effects which may occur at higher dosages. Applicant has discovered that the ideal range is about 3 to about 6 µg/ml, and especially about 5 µg/ml.

Thus, in a first aspect, the invention features a method of preventing tissue damage associated with decreased blood flow in humans by administering AICA riboside to a person in an amount, which maintains a blood plasma concentration of AICA riboside for a sufficient time so that the risk of such tissue damage is reduced in that person, of from about 1 µg/ml to about 20 µg/ml, preferably a concentration of about 3 µg/ml to about 6 µg/ml, and more preferably at about 5 µg/ml. It is desirable that the concentration of AICA riboside in the person results in an elevation of serum uric acid to a level of no greater than about 16.0 mg/dl, and more preferably no greater than about 9.0 mg/dl.

By "preventing tissue damage" is meant lessening the frequency, duration and/or severity of ischemic events and/or reducing the deleterious effects of undesired decreased blood flow on the tissue. The incidence, duration and severity of ischemic events may be measured by methods known in the art. For example, in the use of AICA riboside during coronary artery bypass graft (CABG) surgery, the following methods may be employed: (1) comparison of ST segment changes on continuous Holter electrocardiographic recordings; (2) assessment of regional wall motion by transesophageal echocardiography; (3) serial measurement of creatinine phosphokinase MB; and (4) serial 12-lead electrocardiographic analyses. Methods for measurement of deleterious effects of undesired decreased blood flow are also known in the art. Deleterious effects of tissue damage may include adverse clinical outcomes, such as adverse cardiovascular and/or cerebrovascular events including those observed in connection with CABG surgery. Such adverse events include cardiac death (i.e., death due to primarily a heart-related cause), transmural and/or non-transmural myocardial infarction, cerebrovascular accident, congestive heart failure, and life-threatening dysrhythmia, which may occur during and/or following such surgery. Other adverse clinical outcomes which may be prevented by administration of AICA riboside include hepatic injury (documented by enzyme elevation), pancreatic injury (documented by enzyme elevation), disseminated intravascular coagulation (including that due to bowel ischemia) and death (from non-cardiac causes). By reducing the risk of tissue damage is meant diminishing the opportunity for tissue damage as compared to the opportunity which existed without the administration of AICA riboside. The use of AICA riboside or prodrugs thereof may also protect brain tissue from injury due to decreased blood flow.

By AICA riboside is meant 5-amino-1-β-D-ribofuranosyl-imidazole-4-carboxamide (also known as acadesine).

In a second aspect, the invention features a method of preventing tissue damage associated with decreased blood flow in humans by administering AICA riboside for a sufficient time to reduce the risk of such tissue damage, in a dosage of from about 0.01 mg/kg/min to about 2.0 mg/kg/min; preferably, from about 0.05 mg/kg/min to about 0.2 mg/kg/min; and more preferably of about 0.1 mg/kg/min for anesthetized patients and about 0.125 mg/kg/ruin for non-anesthetized patients or those patients anesthetized for a short period of time.

In certain embodiments, the tissue to which damage is prevented is cardiac muscle or cardiac microvasculature. In other embodiments, the tissue to which damage is prevented is brain tissue or brain microvasculature.

In certain embodiments, the tissue damage which is prevented is that tissue damage which occurs as a result of undesired decreased blood flow occurring during surgery, such as during cardiac surgery (for example, CABG surgery) or during vascular surgery. In these embodiments, the compound may be administered beginning shortly before the induction of anesthesia, and continue through the duration of the surgery, and for about one hour following completion of surgery, or for at least about seven hours following completion of surgery, or longer, depending on factors such as duration of the surgery.

In another embodiment, the AICA riboside is administered both to a patient undergoing cardiac surgery and in the perfusate solution used to perfuse the patient's heart during such surgery. Preferably, the AICA riboside concentration in the perfusate solution is in the range of about 5 µM to about 100 µM, more preferably about 20 µM.

In another embodiment, AICA riboside is administered in combination or conjunction with allopurinol, preferably in an amount of between about 100 mg/day to about 1200 mg/day, and more preferably in an amount of about 300 mg/day. Allopurinol reduces uric acid levels and thus, may be administered in combination with, or in conjunction with, AICA riboside (or a prodrug of AICA riboside) to allow administration of a larger dosage of AICA riboside or prodrug while avoiding adverse side effects of increased uric acid levels. As noted above, it is desirable for uric acid levels not to exceed about 16 mg/dl, and preferable for them not to exceed about 9 mg/dl.

In another embodiment, the invention further involves the identification of a person in need of prevention of such decreased blood flow, prior to administering AICA riboside (or a prodrug thereof). Those skilled in the art will recognize that by "identification" is meant determination of patients at risk for tissue damage, e.g., those patients undergoing surgery or other procedures. Risk factors for those patients undergoing cardiac surgery include elevated age (for example, above 70 years of age); emergency or urgent surgery, which may be complicated by unstable angina; failed percutaneous transluminal coronary angioplasty; decreased left ventricular function (as determined by an ejection fraction of less than about 40%); chronic or acute renal failure; dysrhythmia (under treatment); or MI within the past several years. See, e.g., Mangano, Anesthesiology 72:153-184 (1990). Risk factors for those patients undergoing non-cardiac surgery include elevated age (for example, above 65-70 years of age); atherosclerotic heart disease, i.e., coronary artery disease, as evidenced by peripheral vascular disease or carotid artery disease; diabetes; renal failure; heart failure currently under therapy; left ventricular hypertrophy and hypertension; hypertension for over 5 years; emergency or urgent surgery; MI within 6 months to a year prior to surgery; angina; arrhythmia or hypercholesterolemia. The invention also includes identification of patients who are in need of prophylactic administration of AICA riboside because of a chronic, genetic, or similar condition, or due to angina, transient ischemic attack, evolving or recent MI, or evolving or recent stroke. Thus, those not undergoing surgery may face an increased risk for tissue damage, as well.

In another aspect, the invention features a method of preventing tissue damage associated with decreased blood flow in a human by administering a total dose of AICA riboside in an amount of from 10 mg/kg to 200 mg/kg; preferably in an amount between 30 mg/kg and 160 mg/kg. For cardiac surgery, a preferred amount is about 40 mg/kg. For other indications, such as non-cardiac surgery, a preferred amount is about 120 mg/kg. Those skilled in the art will recognize that such total doses can be achieved by varying the concentration of AICA riboside administered, the rate of administration and/or the duration of administration.

In another aspect, the invention features a method of prevention of tissue damage associated with undesired decreased blood flow in humans by administering a prodrug of AICA riboside in an amount effective to provide a blood plasma level of AICA riboside from about 1 µg/ml to about 20 µg/ml, preferably about 3 µg/ml to about 6 µ/ml and more preferably about 5 µg/ml. The amount of prodrug necessary to achieve these levels is readily determined by one skilled in the art using standard methodologies. A prodrug may be administered in combination with, or in conjunction with, allopurinol, preferably with allopurinol being administered in an amount of from about 100 mg/day to about 1200 mg/day, and preferably in an amount of about 300 mg/day. Such administration will avoid adverse side effects of high uric acid levels. A prodrug may be administered as described above for AICA riboside itself.

In another aspect, the invention features a method of preventing adverse clinical outcomes, including adverse cardiovascular and/or cerebrovascular events, in those at risk for such outcomes, which comprises administering AICA riboside, or a prodrug thereof, in an amount which provides a blood plasma concentration of AICA riboside of between about 1 µg/ml and about 20 µg/ml, preferably between about 3 µg/ml and about 6 µg/ml and more preferably about 5 µg/ml. By "adverse clinical outcome" is meant an event which has a clinically detrimental effect on a patient. By "adverse cardiovascular event" is meant an event pertaining to the heart or blood vessels which is detrimental to a patient. By "adverse cerebrovascular event" is meant an event pertaining to blood vessels affecting the brain which is detrimental to a patient.

The invention further involves the identification of patients at risk for adverse clinical outcomes, including adverse cardiovascular and adverse cerebrovascular events. Risk factors for those patients undergoing cardiac surgery include elevated age (for example, above 70 years of age); emergency or urgent surgery, which may be complicated by unstable angina; failed percutaneous transluminal coronary angioplasty; decreased left ventricular function (as determined by an ejection fraction of less than about 40%); chronic or acute renal failure; dysrhythmia (under treatment); or MI within the past several years. See, e.g., Mangano, Anesthesiology 72:153-184 (1990). Risk factors for those patients undergoing non-cardiac surgery include elevated age (for example, above 65-70 years of age); atherosclerotic heart disease, i.e., coronary artery disease, as evidenced by peripheral vascular disease or carotid artery disease; diabetes; renal failure; heart failure under therapy; left ventricular hypertrophy and hypertension; hypertension for over 5 years; emergency or urgent surgery; MI within 6 months to a year prior to surgery; angina; arrhythmia or hypercholesterolemia. The invention also includes identification of patients who are in need of prophylactic administration of AICA riboside because of a chronic, genetic, or similar condition, or due to angina, transient ischemic attack, evolving or recent MI, or evolving or recent stroke. Thus, those not undergoing surgery may face an increased risk for tissue damage, as well.

In another aspect, the invention features a method of preventing adverse clinical outcomes, including adverse cardiovascular and/or cerebrovascular events in those at risk for such events by administering AICA riboside for a sufficient time to reduce the risk of such events, in a dosage of from about 0.01 mg/kg/min to about 2.0 mg/kg/min; preferably from about 0.05 mg/kg/min to about 0.2 mg/kg/min; and more preferably of about 0.1 mg/kg/min or 0.125 mg/kg/min, depending on anesthesia.

In certain embodiments, the adverse cardiovascular event which is prevented is myocardial infarction. "Myocardial infarction" includes transmural and non-transmural myocardial infarction. In the case of CABG surgery, transmural MI is evidenced by the presence of a new Q wave in ECG testing and an elevated CK-MB concentration, and non-transmural MI is evidenced by elevated CK-MB concentration without a new Q wave. In other embodiments, the cardiovascular event which is prevented is cardiac death. By "cardiac death" is meant death of a patient from a primary cardiac cause, for example, from myocardial infarction, dysrhythmia or ventricle dysfunction.

Another aspect of the invention provides a method of preventing or reducing adverse effects in a patient who has had a myocardial infarction by administering an effective amount of acadesine, or a prodrug, analog, or salt thereof. In one embodiment, the myocardial infarction occurred within the last 24, 36, or 48 hours. Another embodiment provides a method where the patient is female and/or or between the age of 65 and 95.

In certain embodiments, the cerebrovascular event which is prevented is cerebrovascular accident. By "cerebrovascular accident" is meant injury to the brain associated with decreased blood flow, e.g., stroke.

In certain embodiments, the risk for adverse cardiovascular or cerebrovascular event occurs as a result of indications such as angina or transient ischemic attack. In other embodiments, the risk of adverse cardiovascular or cerebrovascular &vents occurs as a result of cardiac surgery, for example, CABG surgery, or as a result of non-cardiac surgery, for example, vascular surgery. In the case of surgery, the AICA riboside may be administered beginning shortly before the induction of anesthesia, and continued through the duration of surgery, for about 1 hour following completion of surgery, or for about 7 hours total. Administration may continue for a longer time, for example, 24 hours or more following surgery. Prolonged administration is especially effective for non-cardiac surgery because adverse events tend to occur later. For example, it has been observed that in cardiac surgery, MI tends to occur mainly in the first day following surgery, however, in non-cardiac surgery, MI tends to occur mainly in the second or third day following surgery. Thus, in the case of non-cardiac surgery, AICA riboside (or a prodrug) is administered for a more prolonged period after surgery, for example, for 7-48 hours.

Another aspect of the invention provides a method of preventing or reducing adverse effects in a patient undergoing non-vascular surgery by administering an effective amount of acadesine, or a prodrug, analog, or salt thereof. Non-vascular surgery includes abdominal, neurological, gynecological, orthopedic, urological, and otolaryngological surgery. More specifically, the non-vascular surgery includes, small and large bowel resection, appendectomy, laparoscopy, paracentesis, transurethral resection of the prostate (TTRP), hysterectomy, tuba ligation, vasectomy, salpingo-oophorectomy, Cesarean section, hemorthoidectomy, tonsillectomy, myringodectomy, placement of myringotomy tubes, removal of polyp(s) from the colon and rectum, repair of rectal prolapse, removal and treatment of neoplasms of the bowel, curettage, thoracentesis, thoracotomy, rhinoplasty, liposuction and the like.

In another embodiment, the AICA riboside is administered both to a patient undergoing cardiac surgery, and in the perfusate solution used to perfuse the patient's heart during such surgery. Preferably, the AICA riboside concentration in the perfusate solution is in the range of about 5 µM to about 100 µM, more preferably about 20 µM.

In another embodiment, AICA riboside is administered in combination or conjunction with allopurinol, preferably in an amount of between about 100 mg/day and about 1200 mg/day, and more preferably in an amount of between about 300 mg/day.

In another embodiment, the invention provides a method for preventing or reducing the occurrence of an adverse cardiovascular or cerebrovascular event in a patient undergoing CABG surgery, which method comprises the steps of: (a) administering to said patient 0.1 mg/kg/min AICA riboside intravenously for about 7 hours perioperatively; and (b) perfusing the heart of said patient with a perfusate solution of 20 µM AICA riboside.

Yet another aspect of the invention provides a method of preventing stroke in a patient undergoing CABG by administering an effective amount of acadesine, or a prodrug, analog, or salt thereof.

In another aspect, the invention features a method of preventing, or reducing the severity of, myocardial infarction in a human at risk for myocardial infarction, which method comprises administering AICA riboside or a prodrug thereof to said human in an amount which provides a blood plasma concentration of AICA riboside in said human of between about 3 µg/ml and about 6 µg/ml, for a sufficient time to reduce the risk of said myocardial infarction. Increased risk of myocardial infarction may result from surgery, either cardiac surgery, such as CABG surgery, or non-cardiac surgery, such as vascular surgery, or from factors other than surgery, e.g., indications of reversible ischemia, such as angina or silent ischemia, or of evolving or recent MI or stroke.

In another aspect, the invention features a method of preventing, or reducing the severity of, cerebrovascular accident in a human at risk for cerebrovascular accident; which method comprises administering AICA riboside or a prodrug thereof to said human in an amount which provides a blood plasma concentration of AICA riboside in said human of between about 3 µg/ml and about 6 µg/ml, for a sufficient time to reduce the risk of said cerebrovascular accident. Increased risk of cerebrovascular accident may result from surgery, either cardiac (such as CABG surgery) or non-cardiac (such as vascular surgery) or from non-surgical risks such as transient ischemic attack.

In another embodiment, the invention features a method of preventing, or reducing the severity of, cardiac death, which method comprises administering AICA riboside or a prodrug thereof to said human in an amount which provides a blood plasma concentration of AICA riboside in said human of between about 3 µg/ml and about 6 µg/ml, preferably about 5 mg/ml, for a sufficient time to reduce the risk of said cardiac death. Increased risk of cardiac death may result from the surgery, cardiac or non-cardiac. For example, the risk may result from CABG surgery.

The AICA riboside may be administered continuously or in a plurality of doses. To reduce the risk of tissue damage, the AICA riboside may be administered for a period of at least about 15 minutes. It may be administered for a duration of greater than about 4 hours and preferably for a duration of about 7 hours. In other cases, the AICA riboside may be administered for a duration of greater than about 10, 12, 16, 24, or even about 48 hours.

The AICA riboside may be administered intravenously, by intracoronary or intraarterial infusion, orally, or by any other methods known in the art, including introduction into the patient's blood in an extracorporeal circuit, for example, using a heart-lung machine or dialysis. AICA riboside may be administered prophylactically, or in response to a known bodily condition.

In one embodiment, AICA riboside is prepared as a therapeutic solution from a lyophilized form to prevent variable discoloration of a liquid formulation observable during storage. Preferably, the AICA riboside is non-pyrogenic.

Another aspect provides a pharmaceutical formulation comprising acadesine, or a prodrug, analog, or salt thereof and a pharmaceutically acceptable carrier, diluent or excipient, wherein the formulation provides a patient in need with a blood plasma concentration of acadesine, or a prodrug, analog, or salt thereof between about 1 µg/ml to about 20 µg/ml for a sufficient amount of time, and the formulation is lipophilic. In one embodiment, the amount of time is about seven hours. In another embodiment, the pharmaceutical formulation is in a micelle form.

In another aspect, the invention features a kit for use in administering AICA riboside to a patient undergoing cardiac surgery, e.g., CABG surgery, which comprises lyophilized AICA riboside for use in preparing an AICA riboside solution for intravenous infusion into a patient undergoing cardiac surgery and AICA riboside in solution for use in preparing a cardioplegic perfusate solution to be used to perfuse the heart of a patient undergoing cardiac surgery. Preferably, the AICA riboside is non-pyrogenic. Preferably, the lyophilized AICA riboside is provided in an amount of from 100 mg to 2,000 mg; more preferably in an amount of 500 mg. Preferably, the AICA riboside in solution is provided in a volume of from 1 ml to 20 ml; more preferably 5 ml. Preferably, the concentration of the AICA riboside in solution is about 1 mg/ml.

The lyophilized AICA riboside may be combined with a suitable diluent, such as water or saline solution to put it in a form suitable for infusion into the patient.

The AICA riboside in solution may be in a solution of water, saline solution, or cardioplegic solution. The AICA riboside in solution is of a concentration suitable for adding to cardioplegic perfusate solution such that the final concentration of AICA riboside in the cardioplegic solution is from 5 µM to 100 µM, preferably 20 µM. For example, if 5 ml of 1 mg/ml AICA riboside is added to one liter of cardioplegic perfusate solution, the resulting concentrate will be approximately 5 µg/ml or 20 µM.

One of the advantages of applicant's discovery of the particularly useful therapeutic concentrations and dosages of AICA riboside is that efficacy can be obtained at dosages at which the side effects of elevated serum or urinary uric acid levels and/or crystalluria are lessened, if not avoided altogether, and which avoid decreased blood glucose levels.

Applicant also discovered that lower doses of AICA riboside were needed to achieve the desired blood concentration levels in anesthetized patients than in non-anesthetized patients. It appears that the dose needed in anesthetized patients may be about 20-50% less than the dose needed in non-anesthetized patients. Thus, a preferred dosage of AICA riboside (or prodrug) in a non-anesthetized patient or a patient anesthetized for a short time is larger than the preferred dosage for an anesthetized patient. Accordingly, dosages of from about 0.075 mg/kg/min to about 0.30 mg/kg/min are preferred in such cases, more preferably between about 0.10 mg/kg/min and about 0.15 mg/kg/min, and most preferably about 0.125 mg/kg/min.

Definitions

As used herein, the following terms have the following meanings, unless expressly stated to the contrary.

The term "hydrocarbyl" refers to an organic radical comprised of primarily carbon and hydrogen and includes alkyl, alkenyl and alkynyl groups, as well as aromatic groups including aryl and aralkyl groups and groups which have a mixture of saturated and unsaturated bonds, alicyclic (carbocyclic or cycloalkyl) groups or such groups substituted with aryl (aromatic) groups or combinations thereof and may refer to straight-chain, branched-chain or cyclic structures or to radicals having a combination thereof.

The term "alkyl" refers to saturated aliphatic groups, including straight, branched and carbocyclic groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "aryl" refers to aromatic groups having from about 6 to 14 carbon atoms and includes cyclic aromatic systems such as phenyl and naphthyl.

The term "aralkyl" refers to an alkyl group of about 1 to 4 carbon atoms substituted with an aryl group of from 6 to 10 carbon atoms and includes, for example, benzyl, p-chlorobenzyl, p-methylbenzyl and 2-phenylethyl.

The term "alkenyl" refers to unsaturated alkyl groups having at least one double bond [e.g. $CH_3 CH=CH(CH_2)_2-$] and includes both straight and branched-chain alkenyl groups.

The term "alkynyl" refers to unsaturated groups having at least one triple bond [e.g. $CH_3 C\equiv C(CH_2)_2$]— and includes both straight chain and branched-chain groups.

The term "halo" or "halogen" refers to fluorine, chlorine, bromine and iodine.

The term "acyl" refers to the group

wherein $R^1$ is hydrocarbyl.

The term "alkylene" refers to straight, branched-chain and carbocyclic alkylene groups which are biradicals, and includes, for example, groups such as ethylene, propylene, 2-methylpropylene (e.g.

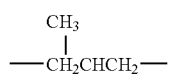

1,6-n-hexylene, 3-methylpentylene (e.g.

1,4-cyclohexylene, and the like.

The term "amide" or "amido" refers to the group

wherein each R" is independently hydrogen or hydrocarbyl, or to compounds having at least one such group.

The term "carboxaride" refers to the group

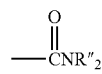

wherein each R" is independently hydrogen or hydrocarbyl. The term "unsubstituted carboxamide" refers to the group

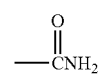

The term "acylamino" refers to the group

wherein each R' is hydrocarbyl. The term "lower acylamino" refers to acylamino groups wherein R' is alkyl of 1 to 6 carbon atoms.

The term "carbonate ester" refers to the group

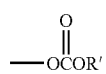

wherein each R' is hydrocarbyl or to compounds having at least one such group.

The term "acyl ester" refers to the group

wherein each R' is hydrocarbyl or to compounds having at least one such group.

The term "phosphate ester" refers to the group

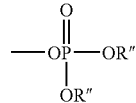

wherein each R" is independently hydrogen or hydrocarbyl and/or to compounds having at least one such group, and includes salts thereof.

The term "mixed ester" refers to compounds having at least one carbonate ester group and at least one acyl ester group or to compounds having combinations of different acyl ester or carbonate ester groups.

The term "carboxylic acid ester" or "carboxy ester" refers to the group

wherein each R' is hydrocarbyl or to compounds having at least one such group.

The term "carbocyclic AICA riboside" refers to an analog of AICA riboside wherein the oxygen atom in the ribosyl ring has been replaced by a methylene (—CH$_2$).

The term "hydrocarbyloxy" refers to the group R'O— wherein R' is hydrocarbyl.

The term "alkoxy" refers to the group R'O— wherein R' is alkyl.

The term "hydrocarbylthio" refers to the group having the formula R'S— wherein R' is hydrocarbyl.

The term "hydrocarbylamino" refers to the groups —NHR' or —NR'$_2$ where R' is an independently selected hydrocarbyl group.

The term "hydrocarbylimidate" refers to the group

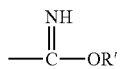

wherein each R" is hydrocarbyl.

The term "carboxamideoxime" refers to the group

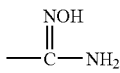

The term "hydrocarbyloxyamidine" refers to the group

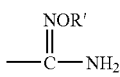

wherein each R' is hydrocarbyl.

The term "hydrocarbyloxycarbonyl" refers to the group

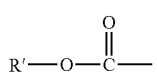

wherein each R' is hydrocarbyl.

The term "hydrocarbyloxycarboxy" refers to the group

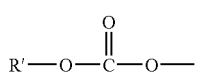

wherein R' is hydrocarbyl.

The term "thioester" refers to the group

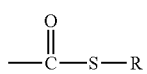

wherein each R' is hydrocarbyl.

Preferred AICA Riboside Analogs

According to the present invention, preferred analogs of AICA riboside include compounds of the formula I

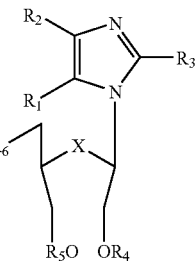

or a pharmaceutically acceptable salt thereof wherein X is —O— or —CH$_2$—; R$_1$ is hydrogen, amino, hydrocarbylamino, acylamino, or dihydrocarbylaminoalkyleneimino; R$_2$ is hydrogen, cyano, hydrocarbylimidate, carboxamideoxime, hydrocarbyloxyamidine, carboxamide, or carboxylic acid or an amide, ester, thioester or salt thereof; R$_3$ is hydrogen, hydrocarbyl, amino, hydrocarbylamino, halogen, hydroxy (including tautomeric 2-imidazolone), hydrocarbyloxy, sulfhydryl (including tautomeric 2-imidazolthione), or hydrocarbylthio; R$_4$ and R$_5$ are independently hydrogen, alkyl, acyl or hydrocarbyloxycarbonyl; R$_6$ is hydrogen, hydrocarbyl, halogen, hydroxy, hydrocarbyloxy, sulfhydryl, hydrocarbylthio, sulfamyloxy, amino, hydrocarbylamino, azido, acyloxy or hydrocarbyloxycarboxy or phosphate ester group or salts thereof; provided that when R$_1$ is amino, R$_2$ is unsubstituted carboxamide, R$_3$ is hydrogen; R$_4$ and R$_5$ are hydrogen, acyl or hydrocarboxycarbonyl; then R$_6$ is not hydroxy, acyloxy or hydrocarbyloxycarboxy.

Alternatively R$_2$ may be a group of the formula:

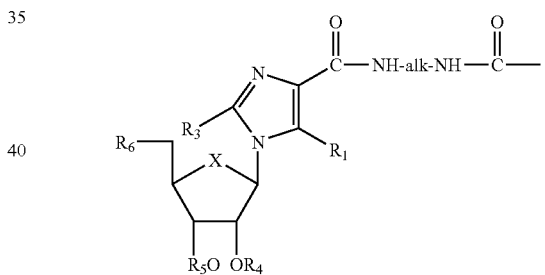

wherein R$_1$, R$_3$, R$_4$, and R$_5$ and R$_6$ are as previously defined in conjunction with formula (I) and alk is an alkylene group of from 2 to 8 carbon atoms. Suitable alk groups include n-hexylene and 1,4-cyclohexylene. Since compounds of the above formula wherein R$_3$ is hydroxy or sulfhydryl may exist in their isomeric (tautomeric) imidazole-2-one and imidazole-2-thione forms, these isomers are intended to be included in the ambit of Formula I.

Preferred compounds include those wherein (i) R$_1$ is amino, R$_2$ is carboxamide wherein one of the amide hydrogens is replaced by a hydrocarbyl group, more preferably an aralkyl group (such hydrocarbyl or aralkyl group is optionally substituted, suitable substituents include those set forth below); R$_3$ is hydrogen, R$_4$ and R$_5$ are hydrogen or hydrocarbyloxycarbonyl, more preferably and R$_6$ is hydroxy or amino (Series I); (ii) R$_1$ is amino, R$_2$ is carboxamide, R$_3$ is halogen or sulfhydryl, R$_4$ is hydrogen, R$_5$ is hydrogen and R$_6$ is hydroxy (Series II); (iii) R$_1$ is amino, R$_2$ is carboxamide; R$_3$, R$_4$ and R$_5$ are hydrogen and R$_6$ is amino (Series III) and (iv) R$_1$ is amino, R$_2$ is carboxamide, R$_3$ is hydrogen, R$_4$ is alkyl, R$_5$ is hydrogen and R$_6$ is hydroxy (Series IV).

In particular, in view of their demonstration of activity in various experimental models, preferred compounds include Compound Nos. 10, 23, 25, 29, 47, 52, 53 (Series I), 27, 43 (Series II), 21, 66 (Series III) and 20, 34 (GP-1-250) and 32 (GP-1-262) (Series IV) of Tables XII and XIII.

Preferred Novel AICA Riboside Analogs

One preferred group of compounds of formula I include certain novel AICA riboside analogs wherein X is —O— or —CH$_2$—; R$_1$ is amino, hydrocarbylamino or dihydrocarbylaminoalkyleneimino, R$_2$ is carboxamide wherein one of the amide hydrogens (attached to the nitrogen atom) is optionally replaced by alkyl, cycloalkyl, or aryl or aralkyl, optionally substituted with 1 to 3 substituents independently selected from halogen, alkyl, aryl, nitro, amino, hydrocarbylamino, sulfhydryl, hydrocarbylthio, hydroxy, hydrocarbyloxy, trifluoromethyl, or sulfonamide; R$_2$ is carboxamide wherein both amide hydrogens are replaced by alkyl or together by an alkylene or aralkylene group to form a ring; or R$_2$ is —C(O)—S—R$_7$ wherein R$_7$ is alkyl, cycloalkyl, aryl or aralkyl optionally substituted with 1 to 3 substituents independently selected from halogen, alkyl, aryl, nitro, amino, hydrocarbylamino, sulfhydryl, hydrocarbylthio, hydroxy, hydrocarbyloxy, trifluoromethyl or sulfonamide; or further, R$_2$ is a group of formula II wherein R$_1$, R$_3$, R$_4$, R$_5$ and R$_6$ are as defined with formula I and alk is alkylene of 2 to 8 carbon atoms; R$_3$ is hydrogen, amino, hydrocarbylamino, halogen, hydroxy (including tautomeric imidazolone), hydrocarbyl, sulfhydryl (including tautomeric 2-imidazolthione) or hydrocarbylthio; R$_4$ and R$_5$ are independently hydrogen, hydrocarbyl (of 1 to about 18 carbon atoms), acyl or hydrocarbyloxycarbonyl; and R$_6$ is hydroxy, hydrogen, hydrocarbyl, halogen, hydrocarbyloxy, sulfhydryl, hydrocarbylthio, sulfamyloxy, amino, hydrocarbylamino, azido, acyloxy, hydrocarbyloxycarboxy or phosphate ester or salt thereof; provided that when —X— is —O— or —CH$_2$—, R$_1$ is amino, R$_2$ is unsubstituted carboxamide, R$_3$ is hydrogen, R$_4$ and R$_5$ independently are hydrogen, acyl or hydrocarbyloxycarbonyl, then R$_6$ is not hydrogen, hydroxy, acyloxy or hydrocarbyloxycarboxy or when R$_4$ and R$_5$ are both hydrogen, then R$_6$ is not a phosphate ester; when X is oxygen, R$_1$ is amino, R$_2$ is unsubstituted carboxamide, R$_3$ is sulfhydryl, and R$_4$ and R$_5$ are both hydrogen, then R$_6$ is not acetoxy; when X is oxygen, R$_1$ is amino, R$_2$ is unsubstituted carboxamide and R$_3$ is chloro, bromo, amino or methoxy, and R$_4$ and R$_5$ both hydrogen, then R$_6$ is not hydroxy or when R$_4$ and R$_5$ are both acetyl, then R$_6$ is not acetoxy; and provided further that when X is oxygen, R$_1$ is amino, R$_2$ is benzylcarboxamide or p-iodophenylcarboxamide, R$_3$ is hydrogen, then R$_4$ and R$_5$ are not both hydrogen and R$_6$ is not hydroxy; or when R$_2$ is p-iodophenylcarboxamide, then R$_4$ and R$_5$ are not both acetyl and R$_6$ is not acetoxy.

Preferred compounds include those wherein R$_1$ is amino, R$_2$ is carboxamide substituted with an aralkyl group, more preferably a benzyl group, having from 1 to 3 ring substitutions as described above, or cycloalkyl. In view of their activity in various experimental models, preferred compounds include Compound Nos. 23, 25, 29, 47, 52 and 53.

One example of an especially preferred compound is a compound where X is oxygen, R$_1$ is amino, R$_2$ is p-chlorobenzylcarboxamide, R$_3$, R$_4$ and R$_5$ are hydrogen and R$_6$ is amino and salts thereof. One particularly preferred salt is the hydrochloride salt. Other particularly preferred salts are sodium and potassium salts, especially disodium and mono potassium.

A preferred AICA riboside analog is a compound represented by the formula (Ia)

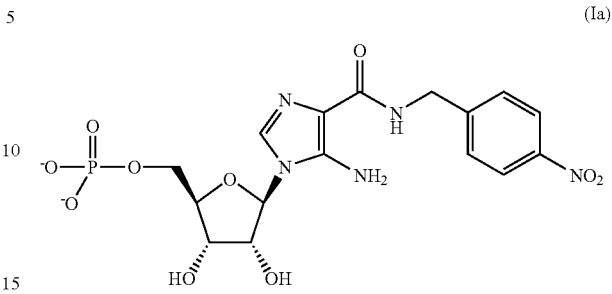

(Ia)

In one embodiment, the invention provides a prodrug, analog, or salt of the compound of formula Ia.

In one aspect, the invention provides a kit for use in administering the compound of formula Ia, or a prodrug, analog, or salt thereof to a patient undergoing cardiac surgery comprising a lyophilized form of the compound of formula Ia, or a prodrug, analog, or salt thereof for infusion into the patient and the compound of formula Ia, or a prodrug, analog, or salt thereof in solution for perfusion into the heart of the patient. In another aspect, the invention provides a kit for administering the compound of formula Ia, a prodrug, analog, or salt thereof to a patient comprising a sterile container of lyophilized compound represented by formula Ia, or a prodrug, analog, or salt thereof.

In one embodiment, the invention provides a cardioplegic solution comprising a composition comprising the compound of formula Ia.

In another embodiment, the invention provides a method of preventing or reducing adverse effects in a patient undergoing CABG surgery comprising administering perioperatively to the patient an effective amount of a composition comprising the compound of formula Ia, or a prodrug, analog, or salt thereof.

In another embodiment, the invention provides a pharmaceutical formulation comprising the compound of formula Ia, or a prodrug, analog, or salt thereof and at least one pharmaceutically acceptable carrier, diluent, or excipient. In one embodiment, the formulation provides a patient in need thereof with a blood plasma concentration of between about 1 µg/ml and about 20 µg/ml over a sufficient period of time. In another embodiment the period of time is about seven hours. In another embodiment, the formulation is adapted for oral administration. In another embodiment, the formulation is adapted for oral administration in a solid dosage form.

In another aspect, the invention provides a cardioplegic solution comprising a composition comprising a compound represented by the formula (IIa)

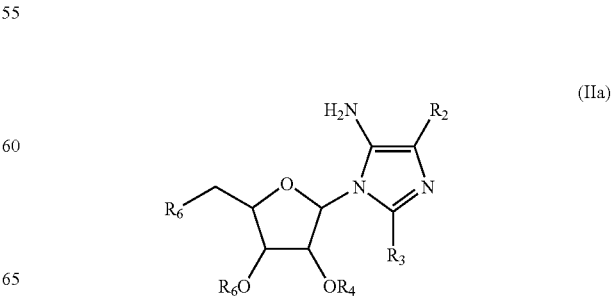

(IIa)

wherein $R_2$ is selected from the group consisting of hydrogen, —CN and the group

where T is selected from oxygen, sulfur, NOH, NH, and $NO(CH_2)_n CH_3$ where n is from 0 to 2) and U is selected from lower alkoxy, amino, a 3 to 6 member heterocyclic ring optionally fused to a 3 to 6 member aryl ring, and the group

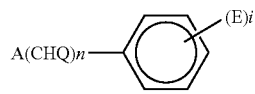

wherein A is one of NH and S, n is from 0 to 3, i is from 0 to 2, Q is one of hydrogen and hydroxy, and E represents a nitro or hydroxy group, provided that where U is amino, T is not one of sulfuer, NOH, NH, and $NOCH_3$; where T is amino, U is not lower alkoxy; and where A is amino and n is 1, Q is not hydroxy;

$R_3$ is selected from hydrogen, halogen, and S—W, where W is phenyl, or substituted phenyl, or hydrogen when T is not oxygen and U is not amino;

$R_4$ and $R_5$ are each independently selected from hydrogen, —$COCH_3$ and lower alkyl, or together form a cyclic carbonate; and $R_6$ is selected from, hydroxy, phosphate ester, —$OSO_2NH_2$, sulfhydryl, halogen, —$OCOCH_3$, —$SCH_3$, —$SOCH_3$, $NH_2$ and $N_3$;

and pharmaceutically acceptable salts thereof;

provided that when $R_2$ is $CONH_2$, CONH-para-iodophenyl, hydrogen, CN, or $CONHCH_2$-φ and $R_3$ is hydrogen or halogen, and $R_4$ and $R_5$ are hydrogen, acyl, or together form a cyclic carbonate, then $R_6$ is not halogen, phosphate ester, OH, or —O-acyl wherein said compound, a prodrug, analaog, or salt thereof is at a concentration of between 5 µM to 100 µM.

In one embodiment, a kit for use in administering an acadesine analog to a patient undergoing cardiac surgery may comprise a lyophilized form of the compound of formula Ia or Ia, a prodrug, analog, or salt thereof for infusion into the patient and/or a solution form of the compound of formula Ia or Ia, a prodrug, analog, or salt thereof for perfusion into the heart of the patient.

A preferred AICA riboside analog is 5-amino-1-β-D-(5-benzylamino-5-deoxy-1-β-D-ribofuranosyl)imidazole-4-carboxamide, having the chemical structure of formula (IIa)

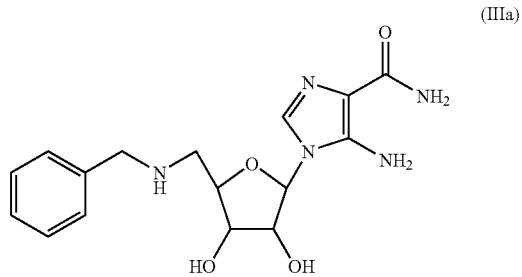 [SMILES: NC(=O)c1ncn(C2OC(CNCc3ccccc3)C(O)C2O)c1N]

Another preferred AICA riboside analog is 5-amino-1-(5-amino-5-deoxy-β-D-ribofuranosyl)imidazole-4-N-[(4-chlorophenyl)methyl]carboximide having the chemical structure of formula (IVa):

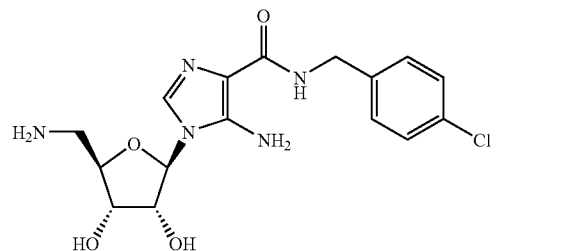

In one embodiment, the prodrug, analog, or salt of compound of formula IIIa or formula IVa is provided.

In one aspect, the invention provides a cardioplegic solution comprising the compound of formula IIIa or formula IVa in a concentration of between about 5 µM to about 100 µM. In another aspect, a kit is provided for administering the compound of formula IIIa or formula IVa to a patient undergoing cardiac surgery, comprising a lyophilized form of the compound of formula IIIa or formula IVa, or a prodrug, analog, or salt thereof for infusion into the patient and a solution comprising the compound of formula IIIa or formula IVa, a prodrug, analog, or salt thereof for perfusion into the heart of the patient.

In another aspect, the invention provides a kit for administering to a patient the compound of forumula IIIa or IVa, or a prodrug, analog, or salt thereof comprising a sterile container of lyophilized compound of formula IIIa of formula IVa, or a prodrug, analog, or salt thereof.

In another aspect, the invention provides a method of preventing or reducing adverse effects in a patient with decreased left ventricular function having an ejection fractoin that is about less than 30% comprising administering to the patient an effective amount of the compound of formula Ia, IIa, IIIa or formula IVa, or a prodrug, analog, or salt thereof. In another aspect, the invention provides a method of preventing for reducing adverse effects in a patient by administering an effective amount of the compound of formula Ia, IIa, IIIa or formula IVa, a prodrug, analog, or salt thereof, wherein the patient has had one, two, three, or more than three past myocardial infarctions. In one embodiment, the most recent myocardial infarction occured within the last 24, 36 or 48 months. In another embodiment of the two methods described above, the patient is female and/or is between the age of 65 and 95. In another embodiment, the compound of formula Ia, IIa, IIIa or IVa, or a prodrug, analog, or salt thereof is administered at a concentration which provides a blood plasma concentration in a patient of between about 1 µg/ml to about 20 µg/ml over a sufficient period of time. In one embodiment, the blood plasma concentration is maintained over a period of about seven hours. In another embodiment, the compound of formula IIIa or formula IVa, or a prodrug, analog, or salt thereof is administered at 0.1 mg/kg/minute. In another embodiment, the compound of formula IIIa or formula IVa is administered to a patient over about seven hours.

Another aspect of the invention provides a method of preventing or reducing adverse effects in a patient undergoing a non-vascular surgery comprising administering to the patient an effective amount of the compound of formula Ia, IIa, IIIa or formula IVa, or a prodrug, analog, or salt thereof. In one embodiment, the invention can be used on a wide variety of non-vascular surgeries, including, but not limited to, cardiac, abdominal, neurological, gynecological, orthopedic, urological, vascular, and surgery related to otolaryngology. More specifically, non-vascular surgery includes, small and large bowel resection, appendectomy, laparoscopy, paracentesis, transurethral resection of the prostate (TURP), hysterectomy, tuba ligation, vasectomy, salpingo-oophorectomy, Cesarean section, hemorrhoidectomy, tonsillectomy, myringodectomy, placement of myringotomy tubes, removal of polyp(s) from the colon and rectum, repair of rectal prolapse, removal and treatment of neoplasms of the bowel, curettage, thoracentesis, thoracotomy, rhinoplasty, liposuction and the like.

Another aspect provides a pharmaceutical formulation comprising a compound of formula IIIa or formula IVa, or a prodrug, analog, or salt thereof and a pharmaceutically acceptable carrier, diluent or excipient, wherein the formulation provides a patient in need with a blood plasma concentration of a compound of formula IIIa or formula IVa, or a prodrug, analog, or salt thereof between about 1 µg/ml to about 20 µg/ml for a sufficient amount of time. In another embodiment, the amount of time is about seven hours. In another embodiment, the pharmaceutical formulation is in a micelle form. In one embodiment, the formulation is lipophilic.

In another aspect, the invention provides a pharmaceutical formulation for use in administering acadesine, or the compound of formula Ia, IIa, IIIa or IVa, or a prodrug, analog, or salt thereof to a patient in need thereof, wherein the formulation is adapted for application as a spray or an aerosol.

In another aspect, a kit is provided for use in administering acadesine, or the compound of formula Ia, IIa, IIIa or IVa, or a prodrug, analog, or salt thereof to a patient undergoing cardiac surgery, comprising acadesine or the compound of formula Ia, IIa, IIIa or IVa, or a prodrug, analog, or salt thereof in a lyophilized form for use in preparing a solution containing the acadesine, or the compound of formula Ia, IIa, IIIa or IVa, or a prodrug, analog, or salt thereof for infusion into a patient and acadesine or the compound of formula Ia, IIa, IIIa or IVa, or a prodrug, analog, or salt thereof in an aerosol or sprayable form for application directly to the heart of the patient. In another embodiment, the solution for infusion is adapted for application as a spray or as an aerosol.

Preparation of Preferred Novel AICA Riboside Analogs

The novel substituted imidazole analogs of the present invention can be synthesized by well known chemical reactions as demonstrated in the examples which follow. In general, compounds of formula (I) can be prepared from 4-methyl-5-nitro-1H-imidazole by the route described by Baker et al (Baker D., J. Org. Chem. 47: 3457 (1982)) to prepare 1-benzyl-5-nitro-1H-imidazole-4-carboxylic acid, followed by the additional step of reducing the nitro group to give the desired amino group at $R_1$. Alternatively, the elegant synthesis of AICA riboside reported by Ferris et al. (Ferris, J. P., J. Org. Chem. 50: 747 (1985), allows a versatile route to 4-substituted 5-aminoimidazoles starting with the appropriately protected riboside and diaminomaleonitrile. This route also allows for the introduction of the desired $R_3$ alkyl, hydrocarbyl and aryl groups by selection of the appropriate ortho ester in the cyclization reaction of the maleonitrile to the imidazole. Other desired $R_3$ substituents can be introduced by the methods described by Miyoshi et al. (Miyoshi T., Chem. Pharm. Bull. 24(9): 2089 (1976) for the preparation of 2-bromo and 5-amino-2-thio-1-(2,3-O-isopropylidene-β-D-ribofuranosyl)-4-imidazole carboxamide or the method of Ivanovics et al. (Ivanovics, G. A. et al., J. Org. Chem. 25: 3631 (1974)) for the preparation of 2-alkoxy, 3-amino, and 2-hydroxy (as the tautomeric 2-imidazolones) substituted 5-amino imidazole-4-carboxamides. Compounds where the desired $R_1$ substituent is acylamino can be prepared by acylation of the corresponding appropriately protected $R_1$ amino compound with the desired acyl anhydride followed by de-O-acylation with ammonia or sodium methoxide. Compounds where $R_1$ is alkylamino or arylamino can be prepared by reductive alkylation of the corresponding appropriately protected $R_1$ amino compound with the desired hydrocarbyl amine as described by Sato et al. (Chem. Pharm. Bull. 37: 1604 (1989)).

Preparation of compounds where $R_6$ is acyloxy or hydrocarbyloxycarboxy can be prepared selectively by reaction of the appropriate hydrocarbyl acid anhydride or hydrocarbyl chloro carbonate with the 2',3'-O-isopropylidene protected riboside followed by removal of the isopropylidene group with dilute aqueous acid as described by Miyoshi et al. (vide supra). Compounds where $R_6$ is hydrocarbyloxy can be prepared from the protected 5-substituted pentoses (Snyder J. R., Carbonhydr. Res. 163: 169 (1987)), using the method of Ferris et al. (vide supra). Compounds according to formula (I) where $R_6$ is sulfhydryl, hydrocarbylthio or hydrocarbylamino can be prepared from the 5'-deoxy-5'-iodo-2,3'-isopropylidene imidazole riboside (Srivastava P. C., J. Med. Chem. 18: 1237 (1975)) by nucleophilic displacement of the halogen with the desired amine or mercaptan. Compounds according to formula (I) where $R_6$ is alkylamido or arylamido can be prepared from the corresponding 5-amino-5'-deoxyimidazole riboside by acylation with the desired alkyl or aryl acid anhydride followed by de-O-acylation with ammonia or sodium methoxide. Compounds according to formula (I) where $R_6$ is hydrocarbyl can be prepared from the 1-(2,3-O-isopropylidene-β-D-ribo-pento-1,5-dialdo-1,4-furanosyl) imidazoles by the Wittig reaction modification of nucleosides described by Montgomery et al. (J. Het. Chem. 11: 211 (1974)). Compounds according to formula (I) where $R_6$ is phosphate or a phosphate ester can be prepared by the general method of Khwaja et al. (Tetrahedron 27: 6189 (1971)) for nucleoside phosphates.

Utility

The AICA riboside analog compounds of this invention will be particularly useful in the reduction of injury during or prevention of ischemia-related events i.e. conditions that arise because of restriction of blood supply. This includes heart attack, or myocardial infarction, a situation that follows from obstruction of one or more of the coronary arteries supplying blood to the heart muscle, or myocardium, and which, if prolonged, leads to irreversible tissue damage. Compounds which, like AICA riboside, lead to increased local levels of adenosine, and thereby increasing blood flow to the ischemia myocardium, will ameliorate this tissue damage.

One current treatment for a heart attack is thrombolytic therapy, which involves administering a clot dissolving agent such as streptokinase or tissue plasminogen activator factor (tPA). However, these drugs must be used within a few hours (1-3) of the heart attack and their effectiveness decreases dramatically with longer delay. The compounds of the present invention, which can be administered prophylactically (i.e, before the event) to achieve a benefit, would therefore clearly be useful.

Angina pectoris is a condition in which the blood supply is sufficient to meet the normal needs of the heart but insufficient when the needs of the heart increase (e.g. during exercise), and/or when the blood supply becomes more limited (e.g. during coronary artery spasm). Patients with angina pectoris or with related conditions such as transient ischemic episodes or silent ischemia could similarly benefit from such an adenosinergic intervention.

In advanced coronary artery disease or persistent chest pain at rest, a number of clinical procedures are currently used to improve blood supply to the heart. These include percutaneous transluminal coronary angioplasty (PTCA), also known as angioplasty; percutaneous transluminal directional coronary atherectomy, laser atherectomy, intravascular stents and coronary artery bypass graft surgery. The compounds of this invention will also be useful as adjunctive therapies to these techniques.

Another factor lending to cardiovascular problems is abnormal heart rhythm, or arrhythmias, which lead to deficiencies in the ability of the heart to supply blood. The ability of these compounds, like AICA riboside, to reduce arrhythmias will also make them useful in suppressing this condition.

Stroke and central nervous system (CNS) trauma conditions resulting from reduced blood supply to the CNS and is thus amenable to an intervention that provides increased levels of adenosine to the compromised tissue to facilitate tissue survival. Other indications ameliorated by agents effecting regional blood flow include organ transplantation, skin flap grafting in reconstructive surgery, peripheral vascular disease, endotoxemia, hemorrhagic shock, pulmonary edema, pulmonary injury secondary to burns (thermal injury) or septicemia, pulmonary hypertension, microembolization, impotence, glomerulonephritis or progressive glomerulosclerosis, artherosclerosis, myocarditis, vasculitis and cardiomyopathies and cardiopulmonary arrest.

It is now clear that a significant component of the neurodegeneration resulting from stroke or CNS trauma is caused by increased excitatory amino acid release, which results in neurons being stimulated to death. Adenosine has been reported to inhibit excitatory amino acid release (Burke and Nadler J. Neurochem. 51: 1541 (1988)). The compounds of this invention which increase adenosine levels, therefore would also be useful in conditions where excitatory amino acids are implicated such as Huntington's chorea or Alzheimer's disease (Marangos et al. Trends Neurosci. 10: 65 (1987)) and Parkinson's disease (Sonsella et al. Science 243: 398 (1989)). These studies, together with results from experimental models of memory (Harris et al. Brain Res. 323: 132 (1984)) suggest additional utility of these compounds in treatment of disorders related to the effects of the aging process on CNS function.

Adenosine has been reported to be an endogenous modulator of inflammation by virtue of its effects on stimulated granulocyte function (Cronstein et al., J. Clin. Invest. 78: 760-770 (1986)) and on macrophage, lymphocyte and platelet function. The compounds of this invention will therefore be useful in conditions in which inflammatory processes are prevalent such as arthritis, osteoarthritis, autoimmune disease, adult respiratory distress syndrome (ARDS), inflammatory bowel disease, necrotizing enterocolitis, chronic obstructive pulmonary disease (COPD) and other inflammatory disorders.

Adenosine has been proposed to serve as a natural anticonvulsant (Lee et al., Brain Res. 321: 1650-1654 (1984); Dunwiddie, Int. Rev. Neurobiol. 27: 63-139 (1985)). Agents that enhance adenosine levels will therefore be useful in the treatment of seizure disorders. In a recent study, Marangos et al., Epilepsia 31: 239-246 (1990) reported that AICA riboside was an inhibitor of seizures in an experimental animal model.

AICA riboside analogs will also be useful in the treatment of patients who might have chronic low adenosine levels or who might benefit from enhanced adenosine, such as those suffering from autism, cerebral palsy, insomnia, anxiety, or other neuropsychiatric symptoms or those suffering from irritable bowel syndrome. Indeed, a number of studies (Komhuber and Fischer Neurosci. Lett. 34: 32 (1982); Kim et al. Eur. Neurol. 22: 367 (1983)) have linked excitatory amino acids with the pathophysiology of schizophrenia.

The compounds of this invention may also be useful in treating other conditions in which AICA riboside itself has beneficial effects. For instance, since AICA riboside has been reported to have anti-allergic actions in a guinea pig model of bronchospasm induced by antigen sensitization (Bergren et al., submitted to J. of Allergy and Clinical Immunology (1990)), AICA riboside analogs may have therapeutic benefit in the treatment of asthma, hayfever or allergic diseases.

The AICA riboside analogs of the present invention are therefore useful in the treatment of a variety of clinical situations where increasing extracellular adenosine levels and in some cases, at the same time, providing free radical scavenging and/or antioxidant activity are beneficial.

Compounds of the invention are administered to the affected tissue at the rate of from 0.01 to 3.0 µmole/min/kg, preferably from 0.1 to 1.0 µmol/min/kg. Under circumstances where longer infusions are desirable, the compounds may be administered at lower rates, e.g. 0.003 to 0.3 µmole/kg/min, preferably 0.01 to 0.1 µmole/kg/min. Such rates are easily maintained when these compounds are intravenously administered as discussed below. When other methods are used (e.g., oral administration), use of time-release preparations to control the rate of release of the active ingredient may be preferred. These compounds are administered in a dose of about 0.01 mg/kg/day to about 200 mg/kg/day, preferably from about 0.5 mg/kg/day to about 100 mg/kg/day. Exemplary preferred doses for oral administration are 0.3 to 30 mg/kg/day, most preferably 1 to 10 mg/kg/day.

For the purposes of this invention, the compounds of the invention may be administered by a variety of means including orally, parenterally, by inhalation spray, topically, or rectally in formulations containing conventional non-toxic pharmaceutically acceptable carriers, adjuvants and vehicles. The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including those from the group consisting of sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium carbonate, sodium carbohate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophylized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 200 µmoles of active material compounded with an appropriate and convenient amount of carrier material which may vary from about 5 to about 95% of the total compositions. It is preferred that pharmaceutical composition be prepared which provides easily measurable amounts for administration. For example, an aqueous solution intended for intravenous infusion should contain from about 20 to about 50 µmoles of the active ingredient per milliliter of solution in order that infusion of a suitable volume at a rate of about 30 ml/hr can occur.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Examples of use of the method of the invention includes the following. It will be understood that these examples are exemplary and that the method of the invention is not limited solely to these examples.

The method may be used following thrombolysis for coronary occlusion. The compound would be given as a sterile injectable preparation with water or isotonic sodium chloride as the solvent. The solution can be administered intravenously or directly into the coronary artery at the time of left heart catheterization or into a carotid artery. The rate of administration could vary from 0.2 to 1 µmole/min/kg with, for example, an infusion volume of 30 ml/hr. Duration of therapy would typically be about 96 hours.

Angina and early myocardial infarcts can be treated by intravenous administration using a sterile injectable preparation using the rates discussed above.

Compounds of the invention can also be administered to patients intravenously during cardiac bypass surgery or to other surgical patients at risk for a myocardial infarct. The compound can be added directly to the solution administered by the membrane oxygenation, or to the cardiac preservation solution, at the rates discussed above.

Organs can be preserved using the method of the invention by perfusing the organ with a solution containing a compound of the invention. The dosage administered would vary with the rate of perfusion of the organ, as is well understood to those skilled in the art. This method is particularly applicable to organs and tissues used in organ transplantation.

DESCRIPTION OF PREFERRED EMBODIMENTS

We have identified a number of analogs of AICA riboside that improve the recovery of post-ischemic function in experimental models of ischemia. As shown in Table I, the benefit that results from treatment with the preferred analogs is at least equal to AICA riboside (Compounds Nos. 11, 40 (Series I), and 19 (Series III)), and in many examples achieved at lower concentrations than AICA riboside (e.g. Compound Nos. 10, 23, 25, 29, 47, 52, 53 (Series I), 27 (Series II), 21, and 66 (Series III)). Preferred compounds include prodrugs, such as carboxylic acid esters of the 2' and 3' hydroxyls. For example, preferred prodrugs of Series IIII are those where $R^4$ and $R_5$ (Formula I) together form a cyclic carbonate. In functional assays, which specifically evaluate compounds for their ability to increase extracellular adenosine levels, many of these preferred analogs show markedly enhanced potency compared to AICA riboside. The results of evaluating the compounds for their ability to inhibit stimulated contraction in the isolated ileum, an adenosine-mediated functional response, showed that these compounds in each of the preferred series were more effective than AICA riboside (Table II). In addition, the N-4 substituted AICA riboside analogs (Series I) enhanced both tissue adenosine levels in ischemic rat hearts (Table III) and inhibited adenosine utilization in coronary endothelial cells (Table IV) to a significantly greater degree than AICA riboside. A number of compounds from this preferred series (I) also bind with greater affinity to the NBTI-specific adenosine transport site (Table V). These data suggest that the improved functional benefit of this preferred analog series compared to AICA riboside arises, at least in part, from their ability to increase extracellular adenosine levels and that this ability may be accounted for by inhibition of adenosine transport. (See Table V and FIGS. 22 and 23). The C-2 substituted AICA riboside analogs (Series II) also appear to augment adenosine release as exemplified by the effects of Compound No. 13 on adenosine production in cell culture (Table VI). Moreover, certain of these compounds are inhibitors of the adenosine metabolizing enzyme, adenosine kinase (see Table VII). The 2'-C substituted AICA riboside analogs (Series IV) profoundly modulate adenosine utilization in a cell culture model (FIGS. 2A, 2B and 2C). In this preferred series (IV), each of the test compounds is also an effective inhibitor of adenosine deaminase, another important adenosine-metabolizing enzyme (Table VII). Thus, these compounds increase extracellular adenosine levels more effectively than AICA riboside and this can be explained by enhanced inhibition of adenosine deaminase.

AICA riboside analogs have also been evaluated for their effects on platelet function. As shown in Table IX, certain compounds inhibit platelet aggregation in human whole blood. Inhibition of platelet aggregation by many of the test compounds is enhanced in the presence of a non-inhibitory concentration of adenosine. Adenosine has been reported to be a potent antiplatelet agent, but with a short half life in blood. Accordingly, the inhibition of platelet aggregation observed in the presence of these AICA riboside analogs may be due to the adenosine regulating activity of these compounds.

Figure 21:
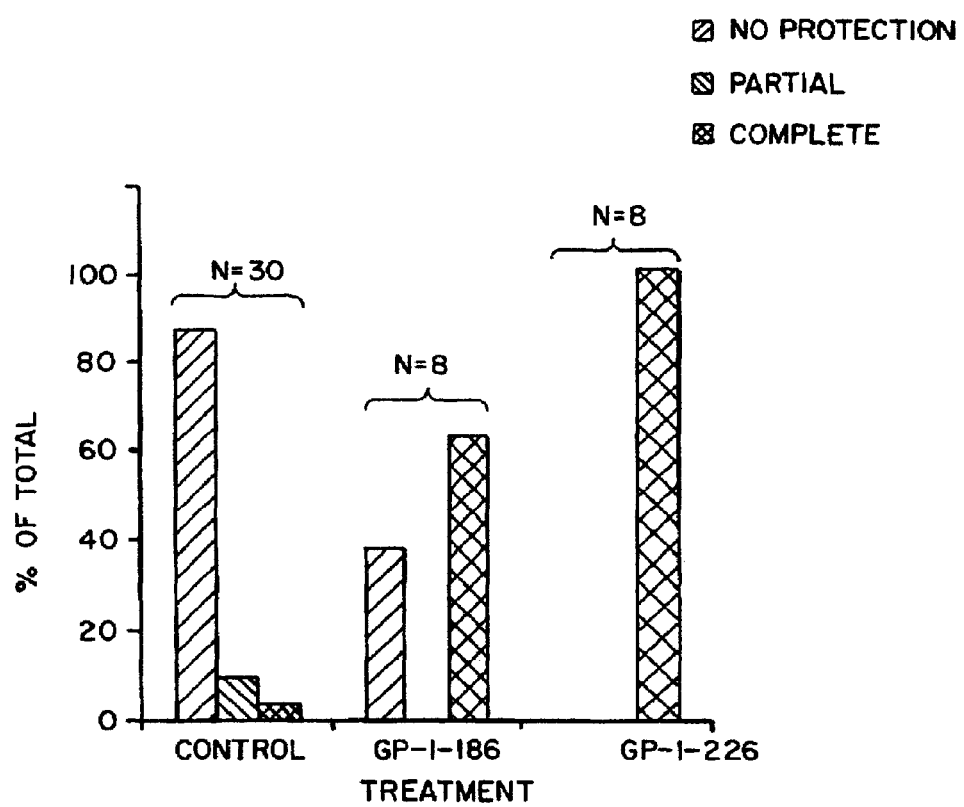
FIG. 21 depicts the effects of N-4 (Series I) substituted AICA riboside analogs (Compound Nos. 10(1-186) and 11(1-226)) in a gerbil brain ischemia model.

Certain preferred AICA riboside analogs (Compound No. 53 (1-468), Compound No. 21 (1-227)) are also orally bioavailable in the dog (see Table X). Furthermore, treatment with the AICA riboside analog Compound No. 53 (1-468), provided functional benefits in a canine model of stable angina (see Table XI). In addition to their cardiovascular benefits, certain AICA riboside analogs (Compound Nos. 10 (1-186) and 11 (1-226) (Series I)) also have demonstrated protective effects in a gerbil model of brain ischemia (FIG. 21).

To assist in understanding the invention, the results of a series of experiments are presented that demonstrate the benefit of these preferred analogs in models of ischemia and, moreover, provide a rationale for these analogs exhibiting enhanced potency compared to AICA riboside. Also presented are a series of Examples which exemplify the synthesis of these compounds. These examples should not, of course, be construed as specifically limiting the invention and such variations of the invention, now known or later developed, which would be within the purview of one skilled in the art are considered to fall within the scope of the invention as described herein and hereinafter claimed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein rnay be employed in practicing the invention. It is intended that the following claims define the scope of the invention and that methods and structures within the scope of these claims and their equivalents be covered thereby.

Definitions

"Administered" or "administration" refers to the introduction of the blood clotting inhibitor to the patient. Administration refers to the giving of a dose by a person, including, for example, a health care provider or the patient himself.

"Blood clotting inhibitor" refers to any drug, agent or pharmaceutical composition that can block, prevent or inhibit the formation of blood clots or dissolves or breaks down a blood clot. A blood clotting inhibitor can be any blood clotting inhibitor currently known to those of skill in the art or one later developed. The blood clotting inhibitor can be from any drug class of blood clotting inhibitors known to those of skill in the art including, but not limited to, antiplatelet agents, thrombolytic enzymes, aggregation inhibitors, glycoprotein IIb/IIIa inhibitors, glycosaminoglycans, thrombin inhibitors, anticoagulants, heparin, low molecular weight heparins, coumarins, indandione derivatives, tissue plasminogen activators and combinations thereof. The blood clotting inhibitors can be in any pharmaceutical dosage form and administered by any route known to those of skill in the art.

"Perioperative" refers to the time period before surgery (pre-operative), after surgery (post-operative), during surgery (intra-operative), and/or any combination as described herein. For example, the blood clotting inhibitor can be administered 48 hours perioperatively; that is, the blood clotting inhibitor can be administered 48 hours before surgery (pre-operatively), 48 hours after surgery (post-operative), during surgery (intra-operative) or any combination of these administration times. The administration during the perioperative period can be a single dose or multiple doses within the perioperative time period. It will be appreciated by those of skill in the art that 'pre-operative' refers to the time period before surgery, 'post-operative' refers to the time period after surgery and 'intra-operative' refers to the time period during surgery.

"Long-termi" refers to the time period after hospital discharge, and extending for 6 months or longer. For example, the blood clotting inhibitor can be administered at the time of discharge as one dose, and then may be continued for 6 months, one year or longer, after the perioperative period.

"Surgery" or "surgical" refers to any manual or operative methods or manipulations for the treatment or prevention of disease, injury or deformity. Surgery includes methods or manipulations conducted while a patient is under anesthesia, including local or general anesthesia. Surgery can be performed by a doctor, surgeon or dentist, generally in a hospital or other health care facility. Patients undergoing surgery can be hospitalized or ambulatory, e.g., out-patient surgery. Surgery does not include percutaneous intervention (PTI) or percutaneous transluminal coronary angioplasty (PTCA).

"Coronary artery bypass graft" or "CABG" refers to cardiac surgery wherein one or more bypass grafts are implanted between the aorta and the coronary blood vessel, commonly using saphenous veins or internal mammary arteries as grafts. "Vein graft CABG" refers to CABG surgery wherein a saphenous vein(s) is used for grafting. "Artery graft CABG" refers to CABG surgery wherein an internal mammary artery (arteries) is used for grafting.

Timing of Administration

The blood clotting inhibitor can be administered perioperatively; that is, before surgery, after surgery and/or during surgery, or any combination as described herein. For example, if the half-life of the drug is long (24-48 hours), the blood clotting inhibitor can be administered as one dose within 48 (or 24) hours prior to surgery with repeated doses during or after surgery. Drugs with shorter half-lives can be given sooner before surgery and then be administered during or after surgery. In some patients, and some circumstances, the treating physician may decide to suspend preoperative treatment, and only start administration postoperatively, e.g., 48 hours after surgery, after wound closure to assure that no bleeding has occurred in the field (no open blood vessels) before starting anti-clotting therapy. Such immediate postoperative administration of a blood clotting inhibitor is within the scope of the invention.

Perioperative administration includes the time period before surgery (pre-operative), after surgery (post-operative), during surgery (intra-operative), and/or any combination as described herein. For example, the blood clotting inhibitor can be administered 6 months, 3 months, 1 month, 1 week, 96 hours, 48 hours or less perioperatively; that is, the blood clotting inhibitor can be administered 6 months, 3 months, 1 month, 1 week, 96 hours, 48 hours or less before surgery, 6 months, 3 months, 1 month, 1 week, 96 hours, 48 hours or less after surgery, or both 6 months, 3 months, 1 month, 1 week, 96 hours, 48 hours or less before and after surgery. In addition, the blood clotting inhibitor can be administered, for example, 36, 24, 12, 8, 6, 4, 2 or 1 hour perioperatively; that is the blood clotting inhibitor can be administered, for example, 36, 24, 12, 8, 6, 4, 2 or 1 hour before surgery and/or 36, 24, 12, 8, 6, 4, 2 or 1 hour after surgery and/or during surgery. One can administer the blood clotting inhibitor for an equal number of hours pre and post surgery. For example, one can administer the blood clotting inhibitor 48 hours prior to surgery and 48 hours after surgery. One can administer the blood clotting inhibitor for an unequal number of hours pre and post surgery. For example, one can administer the blood clotting inhibitor 48 hours prior to surgery and 24 hours after surgery. One can administer the blood clotting inhibitor, for example, 36 hours prior to surgery and 36 hours after surgery. One can administer the blood clotting inhibitor 36 hours prior to surgery and 12 hours after surgery. One can administer the blood clotting inhibitor, for example, 12 hours prior to surgery and 12 hours after surgery. One can administer the blood clotting inhibitor, for example, 8 hours prior to surgery and 8 hours after surgery. One can administer the blood clotting inhibitor, for example, 6 hours prior to surgery and 8 hours after surgery. One can administer the blood clotting inhibitor, for example, 6 hours prior to surgery and 6 hours after surgery. One can administer the blood clotting inhibitor, for example, 8 hours prior to surgery and 4 hours after surgery. One can administer the blood clotting inhibitor 4 hours prior to surgery and 4 hours after surgery. One can administer the blood clotting inhibitor 2 hours prior to surgery and 8 hours after surgery. One can administer the blood clotting inhibitor 4 hours prior to surgery and 1 hour after surgery. One can administer the blood clotting inhibitor, for example, 24 hours prior to surgery and during surgery. One can administer the blood clotting inhibitor, for example, during surgery and 6 hours after surgery.

Administration in the perioperative period can be a single, one time dose or multiple doses of the blood clotting inhibitor. In certain embodiments, perioperative administration can be continuous, uninterrupted administration of the blood clotting inhibitor (e.g. a continuous infusion or transdermal delivery). In another embodiment, perioperative administration is single or multiple discreet administration(s) within the perioperative time frame (e.g. a single dose given within the perioperative period or multiple doses given within the perioperative period). In one embodiment, the blood clotting inhibitor can be administered within 6 days, 5 days, 4 days, 3 days, 2 days or 1 day perioperatively. In another embodiment, the blood clotting inhibitor can be administered within 48 hours, 36 hours, 24 hours, 12 hours, 8 hours, 6 hours or 1 hour perioperatively.

The blood clotting inhibitor can be administered during surgery, for example, contemporaneously with the use or discontinuation of cardiopulmonary bypass or contemporaneously with reperfusion of an ischeric area. Administration can be continued long term for example, after surgery, following discharge from hospital and for six months, one year or longer post-operatively.

In certain embodiments, when the patient is on chronic blood clotting inhibitor therapy prior to surgery, the blood clotting inhibitor is not discontinued pre-operatively, in contrast to standard practice.

Perioperatively, the patient need not be conscious for administration of the blood clotting inhibitor. For example, the blood clotting inhibitor can be given during surgery while the patient is under anesthesia. During some ambulatory or outpatient surgeries, the patient remains conscious and in such a situation, the blood clotting inhibitor can be given during surgery when the patient is conscious.

Such therapy can be continued after discharge. In the course of long-term treatment, as described above, the formulation and dosage can be continued or adjusted, or the type of blood clotting inhibitor can be changed to another blood clotting inhibitor.

Surgery and Surgical Complications

The present invention provides methods of preventing or reducing post-surgical morbidity and mortality. In certain aspects the methods comprise the perioperative administration of a blood clotting inhibitor to prevent or reduce post-surgical complications. The blood clotting inhibitor can be administered perioperatively; that is prior to, during and/or after surgery, and after hospital discharge. Significantly, the prevention or reduction of post-surgical morbidity and mortality extends beyond hospitalization.

Surgery refers to any manual or operative methods or manipulations for the treatment or prevention of disease, injury or deformity. Surgery includes methods conducted while a patient is under anesthesia, including local or general anesthesia. Surgery can be performed by a doctor, surgeon or dentist, generally in a hospital or other health care facility. Patients undergoing surgery can be hospitalized or ambulatory, e.g., out-patient surgery. For purposes of this invention surgery includes, but is not limited to abdominal surgery (e.g. surgery of the abdominal viscera), bench surgery, (e.g. surgery performed on an organ that has been removed from the body, after which it can be reimplanted), cardiac (e.g. surgery of the heart), cerebral (e.g. surgery upon the brain), cineplastic (e.g. surgery to create a tunnel through a muscle adjacent to the stump of an amputated limb, to permit use of the muscle in operating a prosthesis), cosmetic (e.g. surgery to improve a patient's appearance by plastic restoration, correction or removal of blemishes), dentofacial (e.g. surgery involving defects of the face and structures of the mouth), neurological (e.g. surgery involving the peripheral or central nervous system), oral (e.g. surgery involving defects of the mouth, jaws and associated structures), orthopedic (e.g. surgery dealing with bones and bony structures), pelvic (e.g. surgery involving the pelvis, predominately obstetrical and gynecological), plastic (e.g. surgery involving the restoration, reconstruction, correction or improvement in the shape and appearance of body structures that are defective, damaged or misshapened by injury, disease, or growth and development) or rectal (e.g. surgery of the rectum), urological (e.g. surgery related to the genitourinary system, predominately in males), vascular (e.g. surgery of the blood vessels), and surgery related to otolaryngology (e.g. surgery of the ears, nose, throat or related structures). The surgery can be conservative (e.g. surgery to preserve or remove with minimal risk, diseased or injured organs, tissues, or extremities) or radical (e.g. surgery designed to extirpate all areas of locally extensive disease and adjacent zones of lymphatic drainage). In certain embodiments, the surgery can be cardiac surgery, including cardiac valve replacement, heart and heart-lung transplant, and implantation of artificial heart devices and defibrillators, valve replacement or valve repair and congenital surgery.

In certain embodiments, when the cardiac surgery is CABG, the surgery can be coronary artery bypass grafting using saphenous veins or internal mammary arteries, referred to herein as vein graft CABG or artery graft CABG, respectively. In one embodiment, when the surgery is vein graft CABG, the blood clotting inhibitor is not aspirin administered from the time beginning 12 hours pre-operatively through seven hours post-operatively. In another embodiment, when the surgery is vein graft CABG, the blood clotting inhibitor is not dipyridamole administered from the time beginning 48 hours pre-operatively through 24 hours post-operatively. See, Goldman, et al., 1988, *Circulation* 77:1324-32; Chesebro, et al., 1982, *NEJM* 307:73-8; Chesebro, et al., 1984, *NEJM* 310:209-14. In another embodiment, when the surgery is vein graft CABG, the blood clotting inhibitor is not ticlopidine or aprotinin. See, *Drug Facts and Comparisons*, updated monthly, September, 2002, Facts and Comparisons, Wolters Kluwer Company, St. Louis, Mo.

In certain embodiments, when the cardiac surgery is artery graft CABG, the blood clotting inhibitor is not aprotinin.

The invention can be used on a wide variety of surgeries, including, but not limited to, cardiac, abdominal, neurological, gynecological, orthopedic, urological, vascular, and surgery related to otolaryngology. More specifically, surgery includes, small and large bowel resection, appendectomy, laparoscopy, paracentesis, transurethral resection of the prostate (TURP), hysterectomy, tuba ligation, vasectomy, salpingo-oophorectomy, Cesarean section, hemorrhoidectomy, tonsillectomy, myringodectomy, placement of myringotomy tubes, removal of polyp(s) from the colon and rectum, repair of rectal prolapse, removal and treatment of neoplasms of the bowel, curettage, thoracentesis, thoracotomy, rhinoplasty, liposuction and the like.

Ambulatory or outpatient surgery includes surgery for which hospitalization and/or general anesthesia is generally not required. Such surgeries include placement of myringotomy tubes, hemorrhoidectomy and the like.

The invention can reduce post-surgical morbidity and mortality during the post-surgical hospitalization recovery period and after discharge from hospital. The post-surgical morbidity and mortality can be from any surgical complication. Complications of surgery can be cardiac (myocardial infarction, congestive heart failure, serious cardiac dysrhythmias, ischemia) neurological (stroke, encephalopathy, cognitive dysfunction, transient ischemic attacks, seizures), renal (failure, dysfunction or renal death), gastrointestinal (infarction, ileus, ischemia, mesenteric thrombosis or GI death), pulmonary (failure, respiratory distress syndrome, edema), and the like.

Blood Clotting Inhibitor

The present invention provides methods of preventing or reducing post-surgical morbidity and mortality. In certain aspects the methods comprise the perioperative administration of a blood clotting inhibitor to prevent or reduce post-surgical complications. The blood clotting inhibitor can be administered perioperatively; that is prior to, during and/or after surgery, and after hospital discharge.

The blood clotting inhibitor of the present invention can be any drug, agent or pharmaceutical composition that prevents or inhibits blood clotting. The inhibitor can act by preventing or inhibiting blood clot formation by any of a variety of mechanisms including reduction of blood clotting factors or reducing platelet activation or aggregation, or mitigating the effects of instigating factors, such as inflammation or stress. The blood clotting inhibitor can also act by breaking down or dissolving a blood clot after formation. It will be apparent to those of skill in the art that there are several classes of blood clotting inhibitor, including antiplatelet agents, thrombolytic enzymes, aggregation inhibitors, glycoprotein IIb/IIIa inhibitors, glycosaminoglycans, thrombin inhibitors, anticoagulants, heparins, low molecular weight heparins, coumarins, indandione derivatives and tissue plasminogen activators. See, *The Physicians' Desk Reference* (56$^{th}$ ed., 2002) Medical Economics; *Mosby's Drug Consult*, 2002, Elsevier Science; Goodman and Gilman's *The Pharmacologic Basis of Therapeutics*, (9$^{th}$ ed. 1996) Pergamon Press; *Drug Facts and Comparisons*, updated monthly, September, 2002, Facts and Comparisons, Wolters Kluwer Company, St. Louis, Mo.

For the purposes of this invention, any drug, agent or pharmaceutical composition that prevents or inhibits the formation of blood clots or dissolves or breaks down a blood clot is suitable for use in the present invention. Such a blood clotting inhibitor can be, for example, cilostazol (PLETAL®, Otsuka), clopidogrel (PLAVIX®, Sanofi), ticlopidine (TICLID®, Syntex), tirofiban (AGGRASTAT®, Merck), eptifibatide (INTEGRILIN®, COR Therapeutics), abciximab (REOPRO®, Eli Lill y), anagrelide (AGRYLIN®, Roberts), dipyridamole (PERSANTIN®, Boehringer Ingelheim), aspirin (ECOTR®, and others), dipyridamole/aspirin (AGGRENOX®, Boehringer Ingelheim), dalteparin (FRAGMIN®, Pharmacia), enoxaparin (LOVENOX®, Aventis), tinzaparin (INNOHE®, DuPont), heparin (various), danaparoid (ORGANON®, Organon), antithrombin III (THROMBATE®, Bayer), lepirudin (REFLUDAN®, Hoechst-Marion Roussel), argatroban (ACOVA®, SmithKlineBeecham), bivalirudin (ANGIOMAX®g, Medicines Company), warfarin (COUMADIN®, DuPont) anisidione (MIRADON®, Schering), alteplase (ACTIVASE®, Genetech), reteplase (RETAVASE®, Boehringer Mannheim), tenecteplase (TNKASE®, Genentech), drotrecogin (XIGRIS®, Eli Lilly), anistreplase (EMINASE®, Roberts), streptokinase (STREPTASE®, Astra), urokinase (ABBOKINASE®, Abbott) and combinations thereof.

It will be appreciated by those of skill in the art that blood clotting inhibitors are used for the treatment of occluded catheters and for the maintenance of patency of vascular access devices. Heparin, urokinase, streptokinase and alteplace are generally employed for such uses. The use of blood clotting inhibitors for the treatment of occluded catheters and for the maintenance of patency of vascular access devices is not within the scope of the invention.

In certain embodiments where the blood clotting inhibitor is a low molecular weight heparin, the surgery is preferably not hip replacement, knee replacement or abdominal surgery. When the drug is dalteparin, the dose is preferably not 2500 IU subcutaneously once daily, starting 1 to 2 hours preoperatively and repeating once daily for 5-10 post-operatively or 5000 IU subcutaneously the evening before surgery and repeated once daily for 5-10 days postoperatively. When the drug is enoxaparin, the dose is preferably not 40 mg once daily subcutaneously given initially 9 to 15 hours prior to surgery and continued for 21 days or 40 mg once daily subcutaneously starting 2 hours prior to surgery and continued for 7 to 10 days; 12 days if tolerated.

In certain embodiments where the blood clotting inhibitor is heparin, the surgery is preferably not abdominothoracic or cardiac surgery. When the drug is heparin, the dose is preferably not 5000 Units subcutaneously 2 hours before surgery and 5000 Units every 8 to 12 hours thereafter for 7 days or until the patient is fully ambulatory. When the drug is heparin, the dose is preferably not 150 Units/kg for patients undergoing total body perfusion for open heart surgery. When the drug is heparin, the dose is preferably not 300 Units/kg for procedures less than 60 minutes or 400 Units/kg for procedures longer than 60 minutes.

In certain embodiments where the blood clotting inhibitor is danaparoid, the surgery is not elective hip replacement surgery. When the drug is danaparoid, the dose is preferably not 750 anit-Xa units twice daily subcutaneously beginning 1 to 4 hours preoperatively and then not sooner than 2 hours after surgery continued for 7-10 days postoperatively.

In certain embodiments where the blood clotting inhibitor is warfarin, the surgery is preferably not cardiac valve replacement surgery. When the drug is warfarin, the dose is preferably not 1 mg daily, up to 20 days preoperatively.

In certain embodiments, when the cardiac surgery is vein graft CABG, the blood clotting inhibitor is not aspirin administered within 12 hours pre-operatively through seven hours post-operatively. In certain embodiments, when the cardiac surgery is vein graft CABG, the blood clotting inhibitor is not dipyridamole administered within 48 hours pre-operatively through 24 hours post-operatively. See, Goldman, et al, 1988, *Circulation* 77:1324-32; Chesebro, et al, 1982, *NEJM* 307:73-8; Chesebro, et al., 1984, *NEJM* 310:209-14. In certain other embodiments, when the cardiac surgery is vein graft CABG, the blood clotting inhibitor is not ticlopidine or aprotinin. See, *Drug Facts and Comparisons*; updated monthly, September, 2002, Facts and Comparisons, Wolters Kluwer Company, St. Louis, Mo.

Aprotinin is indicated for CABC surgery in one of two dosing regimens, regimen A or regimen B. Regimen A is administration of a 2 million KIU (kallikrein inhibitor units) intravenous loading dose; 2 million KIU into the cardiopulmonary bypass machine (known as pump prime volume) and 500,000 KIU/hr of operation time as a continuous maintenance intravenous infusion. Regimen B is administration of a 1 million KIU intravenous loading dose, 1 million KIU into the pump prime volume and 250,000 KIU/hr of operation time as a continuous maintenance intravenous infusion. Administration of aprotinin begins after anesthetic induction but prior to sternotomy and is continued until surgery is complete and the patient leaves the operating room. *Drug Facts and Comparisons*, updated monthly, September, 2002, Facts and Comparisons, Wolters Kluwer Company, St. Louis, Mo. In certain embodiments when the surgery is vein graft or artery graft CABG, the blood clotting inhibitor is not aprotinin.

The blood clotting inhibitor can be a combination of two or more blood clotting inhibitors. Combinations of blood clotting inhibitors can include blood clotting inhibitors from more than one drug class as described herein. In addition, the combination of blood clotting inhibitors can include different routes of administration for each blood clotting inhibitor. The combination of blood clotting inhibitors can be administered simultaneously or contemporaneously. In addition, the combination of blood clotting inhibitors can be administered separately.

Dosage, Formulation and Administration

The blood clotting inhibitor described herein, can be administered into a patient for the reduction of mortality and morbidity following surgery by any means that produces contact of the blood clotting inhibitor with the blood clotting inhibitor's site of action in the body of the patient. The blood clotting inhibitor can be a pharmaceutical composition that can be administered by any means available. It will be apparent to those of skill in the art that a pharmaceutical composition can be generally administered with a pharmaceutical carrier. The pharmaceutical composition and/or pharmaceutical carrier can be selected on the basis of the chosen route of administration and standard pharmaceutical practice. The pharmaceutical compositions of the invention can be adapted for oral, parenteral or topical administration, and can be in unit dosage form, in a manner well known to those skilled in the pharmaceutical art. Parenteral administration includes, but is not limited to, injection subcutaneously, intravenously, intraperitoneally or intramuscularly. It will be apparent to one of skill in the art that, for example, oral dosage forms can be administered by a number of routes, including, but not limited to rectal and vaginal and via any means to deliver substance to the gastrointestinal tract, such as via a nasogastric tube.

The dose administered will, of course, vary depending upon known factors, such as: the pharmacodynamic characteristics of the particular blood clotting inhibitor and its mode and route of administration; the age, health, height and weight of the patient; the kind of concurrent treatment(s); the frequency of treatment(s); and the effect desired. The dose of the blood clotting inhibitor need not remain constant but can be adjusted according to parameters that are well known to those of skill in the art. In addition, the dose of blood clotting inhibitor can be sub- or supra-therapeutic.

A single dose of active ingredient can be within the normal dosage range appropriate for the individual patient. For instance, aspirin can be used orally at 40 mg-160 mg/day. Dipyridamole can be used at orally at 75 mg-100 mg four times daily. Aspirin and dipyridamole can be given in combination as a single commercially available product at a dose of 25 mg aspirin/200 mg dipyridamole (AGGRENOX®) or the compositions can be given together contemporaneously as individual compositions in the dosage rages described herein. Heparin can be used subcutaneously with an initial dose of 10,000 Units (which can be preceded by an intravenous loading dose of 5,000 units), followed by 8,000 units every 8 hours or 15,000 to 20,000 units ever 12 hours, adjusting for partial thromboplastin time (PTT) to about 1.5 to 2 times normal. Warfarin can be used orally or parenterally at 0.5-30 mg/day. Cilostazol can be used orally at 50-100 mg twice daily. Clopidogrel can be used orally at 75 mg once daily, with or without a 300 mg loading dose. Ticlopidine can be used orally at 250 mg twice daily. Tirofiban can be used parenterally at 0.4 mcg/kg/min over 30 minutes, then continued at 0.1 mcg/kg/min. Eptifibatide can be used parenterally at 180 mcg/kg as an intravenous bolus, followed by 2 mcg/kg/min continuous infusion with a second bolus, given 10 minutes after the initial intravenous bolus. The second parenteral bolus dose can be 180 mcg/kg. Abciximab can be used parenterally at 0.25 mg/kg infused over 10 to 60 minutes as an intravenous bolus, followed by continuous infusion of 0.125 mcg/kg/min, to a maximum of 10 mcg/min, for 12 hours. Anagrelide can be used orally at 0.5 mg four times daily to 1 mg twice daily titrated up to a maximum of 10 mg/day. Dalteparin can be used subcutaneously at 2500-5000 rU once to twice daily. Enoxaparin can be used subcutaneously at 1 mg/kg once to twice daily. Tinzaparin can be used subcutaneously at 175 anti-Xa IU/kg once daily. Danaparoid can be used subcutaneously at 750 anti-Xa units twice daily. Antithrombin III can be used parenterally at a dose based on the pretherapy plasma antithrombin III (AT) level. Dosage can be calculated by:

$$\text{Units required}(IU) = \frac{[\text{desired-baseline}(AT)]}{1.4} \times \text{weight}(kg)$$

or alternatively $$\begin{array}{c}\text{Number of}\\ \text{Factor }IX\\ \text{Required}(IU)\end{array} = \begin{array}{c}\text{body}\\ \text{weight}\\ (kg)\end{array} \times \begin{array}{c}\text{Desired}\\ \text{Factor }IX\\ \text{Increase}\\ (\%\text{ or }IU/dL)\end{array} \times \begin{array}{c}\text{Reciprocal}\\ \text{Of observed}\\ \text{Recovery}\\ (IU/kg\text{ per }IU/dL)\end{array}$$

(See, *Drug Facts and Comparisons*, updated monthly, September, 2002, Facts and Comparisons, Wolters Kluwer Company, St. Louis, Mo.).

Lepirudin can be given parenterally in a bolus dose of 0.4 mg/kg, intravenous push over 15-20 seconds, followed by 0.15 mg/kg continuous intravenous infusion. Argatroban can be given at 2 mcg/kg/min as a continuous infusion. Bivalirudin can be given at 1 mg/kg intravenous bolus followed by a 4 hour intravenous infusion at 2.5 mg/kg/hr. Anisidione can be used orally at 25-300 mg/day. Alteplase can be given intravenously in patients weighing more than 67 kg, at a dose of 100 mg administered as a 15 mg intravenous bolus, followed by 50 mg infused over the next 30 minutes and then 35 mg infused over the next 60 minutes. In patients weighing less than 67 kg, alteplase can be administered intravenously as a 100 mg total dose; a 15 mg intravenous bolus followed by 0.75 mg/kg infused over the next 30 minutes not to exceed 50 mg and then 0.5 mg/kg over the next 60 minutes, not to exceed 35 mg. Reteplase can be used parenterally as a 10 Unit intravenous bolus injection over 2 minutes, followed 30 minutes later by a second 10 Unit intravenous bolus injection over 2 minutes. Tenecteplase can be used parenterally at a dose of 30-50 mg, based on patient weight, and administered as a single bolus over 5 seconds. Drotrecogin can be used parenterally at 24 mcg/kg/hr for a total infusion duration of 96 hours. Anistreplase can be used parenterally at 30 Units administered intravenously over 2 to 5 minutes. Streptokinase can be used parenterally at a dose of 250,000 Units infused over 30 minute. In addition, streptokinase can be used intravenously at 20,000 IU bolus followed by a dose of 2,000 IU/minute for 60 minutes. Urokinase can be used parenterally at a dose of 4400 Units/kg over 10 minutes, followed by continuous infusion of 4400 Units/kg/hr at a rate of 15 ml/hr for 12 hours.

The active ingredient of a blood clotting inhibitor can be administered orally in solid or semi-solid dosage forms, such as hard or soft-gelatin capsules, tablets, or powders, or in liquid dosage forms, such as elixirs, syrups, or suspensions. It can also be administered parenterally, in sterile liquid dosage forms. Other dosage forms are potentially possible such as patches or ointment or transdermal administration.

Parenteral dosage forms can be, for example, injectable preparations including sterile suspensions, solutions or emulsions of the active ingredient in aqueous or oily vehicles. The compositions may also comprise formulating agents, such as suspending, stabilizing and/or dispersing agent. The formulations for injection may be presented in unit dosage form, e.g., in ampules or in multidose containers, and may comprise added preservatives.

An injectable formulation can be in powder form for reconstitution with a suitable vehicle, including but not limited to sterile pyrogen free water, buffer, dextrose solution, etc., before use.

For administration during surgery, the active ingredient can be administered directly into the cardiopulmonary bypass machine, directly into the pericardium or directly into the vessels exposed in the surgical field.

For prolonged delivery, the active ingredient can be formulated as a depot preparation, for administration by implantation; e.g., subcutaneous, intradermal, or intramuscular injection. Thus, for example, the active ingredient may be formulated with suitable polymeric or hydrophobic materials (e.g., as an emulsion in an acceptable oil) or ion exchange resins, or as sparingly soluble derivatives.

Alternatively, transdermal delivery systems manufactured as an adhesive disc or patch that slowly releases the active ingredient for percutaneous absorption may be used. To this end, permeation enhancers may be used to facilitate transdermal penetration of the blood clotting inhibitor.

For oral administration, the pharmaceutical formulations or the blood clotting inhibitor may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid.).

The preparations may also comprise buffer salts, flavoring, coloring and sweetening agents as appropriate. Preparations for oral administration may be suitably formulated to give controlled release of the active compound.

For buccal administration, the compositions may take the form of tablets or lozenges formulated in conventional manner. For rectal and vaginal routes of administration, the active ingredient may be formulated as solutions (for retention enemas) suppositories or ointments.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated comprising a powder mix of the compound and a suitable powder base such as lactose or starch.

The compositions may, if desired, be presented in a pack or dispenser device that may comprise one or more unit dosage forms comprising the active ingredient. The pack may for example comprise metal or plastic foil, such as a blister pack. The pack or dispenser device may be accompanied by instructions for administration.

The blood clotting inhibitor can be administered by any suitable route known to those of skill in the art that ensures bioavailability in the circulation. Administration can be achieved by parenteral routes of administration, including, but not limited to, intravenous (IV), intramuscular (IM), intraderral, subcutaneous (SC), and intraperitoneal (IP) injections. In certain embodiments, administration is by a bypass machine, perfuser, infiltrator or catheter. In certain embodiments, the blood clotting inhibitor is administered by injection, by a subcutaneously implantable pump or by a depot preparation, in doses that achieve a therapeutic effect. Suitable dosage forms are further described in Remington's Pharmaceutical Sciences, 1990, 17$^{th}$ ed., Mack Publishing Company, Easton, Pa., a standard reference text in this field, which is incorporated herein by reference in its entirety.

Administration can be achieved through a variety of different treatment regimens. For example, several oral doses can be administered periodically during a single day, with the cumulative total of blood clotting inhibitor not reaching the daily toxic dose. Alternatively, the blood clotting inhibitor can be administered daily beginning, for example, 48 hours prior to surgery and continuing daily, for example, until 48 hours after surgery.

Intravenous injections can be administered periodically during a single day, with the cumulative total volume of the injections not reaching the daily toxic dose. Alternatively, one intravenous injection can be administered, for example, daily beginning, for example, 48 hours prior to surgery and continuing daily, for example, until 48 hours after surgery. The dose of the blood clotting inhibitor can vary. For example, an escalating dose can be administered. Depending on the needs of the patient, administration can be by slow infusion with a duration of more than one hour, by rapid infusion of one hour or less, or by a single bolus injection.

Other routes of administration may be used. For example, absorption through the gastrointestinal tract can be accomplished by oral routes of administration (including but not limited to ingestion, via nasogastric tube, buccal and sublingual routes). Alternatively, administration via mucosal tissue such as vaginal and rectal modes of administration can be utilized. In yet another alternative, the formulations of the invention can be administered transcutaneously (e.g., transdermally), or by inhalation. It will be appreciated that the preferred route may vary with the condition and age of the recipient.

The actual dose of blood clotting inhibitor will vary with the route of administration. The blood clotting inhibitor will generally be used in an amount effective to achieve the intended purpose. Of course, it is to be understood that the amount used will depend on the particular application.

The effective amount, for example, may vary depending on the type of surgery, condition of the patient, age of the patient, patient's weight, medical history of the patient, the manner of administration and the judgment of the prescribing physician. It will be appreciated by one of skill in the art that the degree of blood anticoagulation can be monitored by laboratory values such as prothrombin time (PT) and partial thromboplastin time (PTT). Determination of an effective amount is well within the capabilities of those skilled in the art, especially in light of the detailed disclosure provided herein.

The administration of a blood clotting inhibitor may be repeated intermittently. The blood clotting inhibitor can be administered alone or in combination with other drugs, for example, other presurgical drugs such as antibiotics or anesthetics.

Blood Clotting Inhibitor and Acadesine Combination

In another aspect of the invention, a method for preventing or reducing adverse effects in a patient undergoing surgery is provided, wherein acadesine, or a prodrug, analog, or salt thereof is first administered and then a blood clotting inhibitor is administered. In one embodiment, the blood clotting inhibitor is administered during the administering of the acadesine, or a prodrug, analog, or salt thereof. In one embodiment, the acadesine, or a prodrug, analog, or salt thereof is administered at a total dose of about 10 mg/kg to about 200 mg/kg. Another aspect provides a method of preventing or reducing adverse effects in a patient undergoing non-vascular surgery, wherein acadesine, or a prodrug, analog, or salt thereof is administered and then a blood clotting inhibitor is administered. The invention can be used on a wide variety of non-vascular surgeries, including, but not limited to, cardiac, abdominal, neurological, gynecological, orthopedic, urological, vascular, and surgery related to otolaryngology. More specifically, non-vascular surgery includes, small and large bowel resection, appendectomy, laparoscopy, paracentesis, transurethral resection of the prostate (TURP), hysterectomy, tuba ligation, vasectomy, salpingo-oophorectomy, Cesarean section, hemorrhoidectomy, tonsillectomy, myringodectomy, placement of myringotomy tubes, removal of polyp(s) from the colon and rectum, repair of rectal prolapse, removal and treatment of neoplasms of the bowel, curettage, thoracentesis, thoracotomy, rhinoplasty, liposuction and the like.

In one embodiment, the blood clotting inhibitor is aspirin. In one embodiment, the patient undergoing surgery or non-vascular surgery has had a past myocardial infarction. In another embodiment, the past myocardial infarction occured within the last 24, 36, or 48 months prior to the surgery.

Another aspect of the invention provides a method of preventing or reducing adverse effects in a patient undergoing CABG surgery by first administering acadesine, or a prodrug, analog, or salt thereof and then administering a blood clotting inhibitor. In one embodiment, the administering of the blood clotting inhibitor occurs during the administering of the acadesine, or a prodrug, analog, or salt thereof. In another embodiment, the acadesine, or a prodrug, analog, or salt thereof is administered at a total dose of about 10 mg/kg to about 200 mg/kg. Another embodiment provides administration of acadesine, or a prodrug, analog, or salt thereof at 0.1 mg/kg/minute. Another embodiment provides administration of acadesine, or a prodrug, analog, or salt thereof over a period of about seven hours. Another embodiment provides administration of aspirin at a dosage of about 400 mg to about 5 g. Another embodiment provides administration of aspirin at least once within 48 hours after surgery.

Another aspect of the invention provides a pharmaceutial formulation comprising acadesine, or a prodrug, analog, or salt thereof, aspirin, and a pharmaceutically acceptable carrier, diluent, or excipient, wherein the formulation provides a patient with a blood plasma concentration between about 1 µg/ml to about 20 µg/ml over a period of about seven hours and aspirin at a dose of about 40 mg to about 5 g. In another embodiment, the invention provides a method of preventing or reducing adverse effects in a patient undergoing surgery by administering the above pharmaceutical formulation within 48 hours of surgery. In another embodiment, the surgery is CABG surgery.

EXAMPLES

The following examples describes specific aspects of the invention to illustrate the invention and provide a description of the methods, compositions, and formulations of the invention. The examples should not be construed as limiting the invention, as the example merely provides specific methodology useful in understanding and practicing the invention.

Example I

AICA Riboside Enhancement of Adenosine Release by Lymphoblasts

With regard to the enhanced in vitro release of adenosine by the claimed method, a human splenic lymphoblast cell line (WI-L2) was used to demonstrate the effect of AICA riboside on adenosine release. The history and properties of the cell line have been described by Hershfield et al. in Science, Vol. 197, p. 1284, 1977. The cell line was maintained in RPMI 1640 cell culture media supplemented with 20% fetal calf serum and 2 mM glutamine and varying concentrations of AICA riboside, and grown for 48 hours in an atmosphere of 5% carbon dioxide in air. Fetal calf serum contains purines and purine metabolizing enzymes, however, and to establish the effect of AICA riboside during 2-deoxyglucose exposure, the WI-L2 cells were incubated in RPMI 1640 medium supplemented with 10% heat-inactivated, dialyzed fetal bovine serum, 2 mM glutamine, and 1 µM deoxycoformycin.

Catabolism of cellular ATP stores was stimulated by adding either 2-deoxyglucose or a calcium ionophore. At various times, the amount of adenosine released by the cells into the supernatant, or the amount of nucleotides remaining in the cells, was determined by mixing 30 µl of chilled 4.4N perchloric acid with 300 µl of supernatants, or by adding 300 µl of chilled 0.4N perchloric acid to the cells collected as pellets and centrifuging the mixtures at 500×G for 10 minutes at 4° C. Each resulting supernatant was neutralized with 660 µl of a solution containing 2.4 grams of tri-n-octylamine (Alamine 336) (General Mills) in 12.5 ml of 1,1,2-trichloro-1,2,2-trifluoroethane (Freon-113) solvent as described by Khym in Clinical Chemistry, Vol. 21, p. 1245, 1975. Following centrifugation at 1500×G for three minutes at 4° C., the aqueous phase is removed and frozen at −20° C. until assayed for adenosine, inosine, or for nucleotides. Adenosine was evaluated isocratically on a C-18 microBondapak reverse phase column equilibrated with 4 millimolar potassium phosphate, (pH 3.4):acetonitrile 60% in water (95:5 v/v) buffer. Adenosine elutes at 8-10 minutes, and its identity was confirmed by its sensitivity to adenosine deaminase and by spiking with adenosine standards. The extracted samples from the cell pellet were analyzed for nucleotides by high pressure liquid chromatography on a Whatman Partisil-10 (SAX) column equilibrated with 10 millimolar potassium phosphate, pH 3.78, and eluted with a linear gradient to a 0.25 molar potassium phosphate, 0.5 molar KCl, pH 3.45. Continuous monitoring was performed by absorbance at 254 and 280 nm. Peaks were quantitated by comparison with high pressure liquid chromatography analysis of suitable standards.

Figure 2:
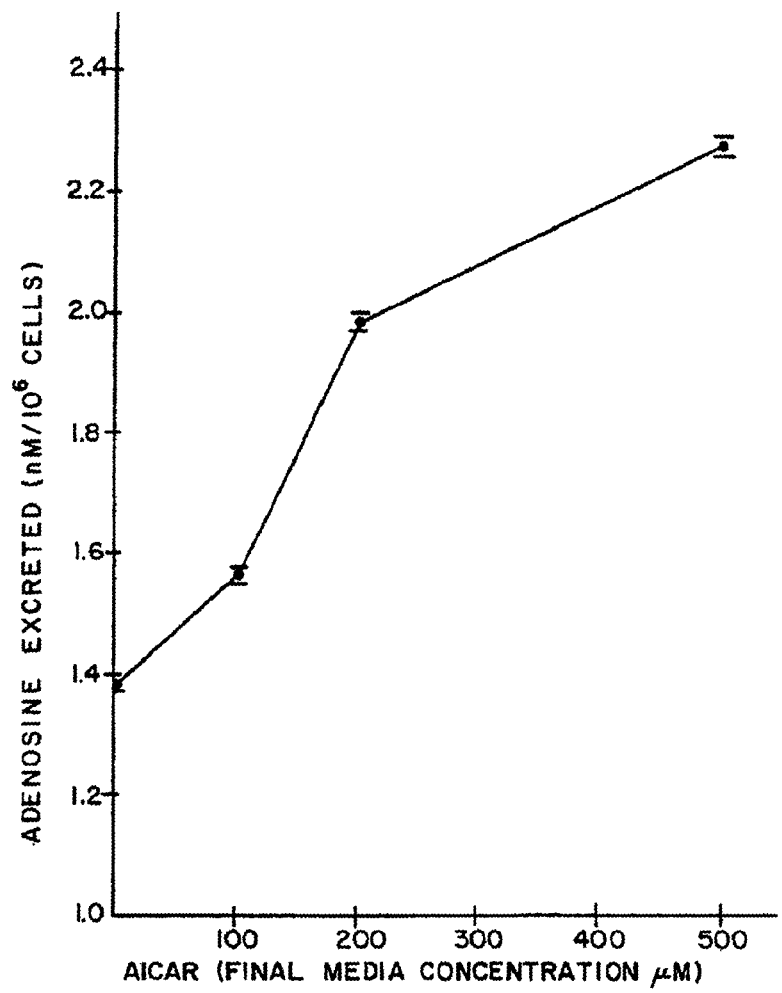
FIG. 2. In vitro effect of 48-hour preincubation with AICA riboside on adenosine excretion by human lymphoblasts during ATP breakdown.
Figure 7:
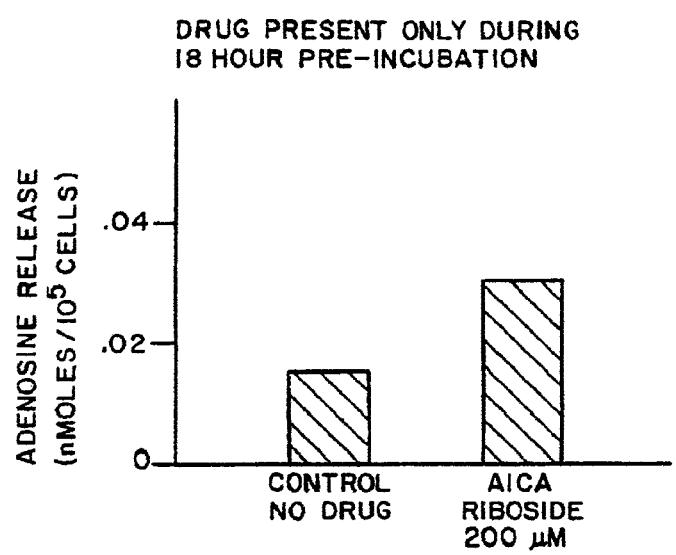
FIG. 7. Effects of 18-hour preincubation with AICA-riboside on adenosine excretion by human lymphoblasts during ATP breakdown.
Figure 8:
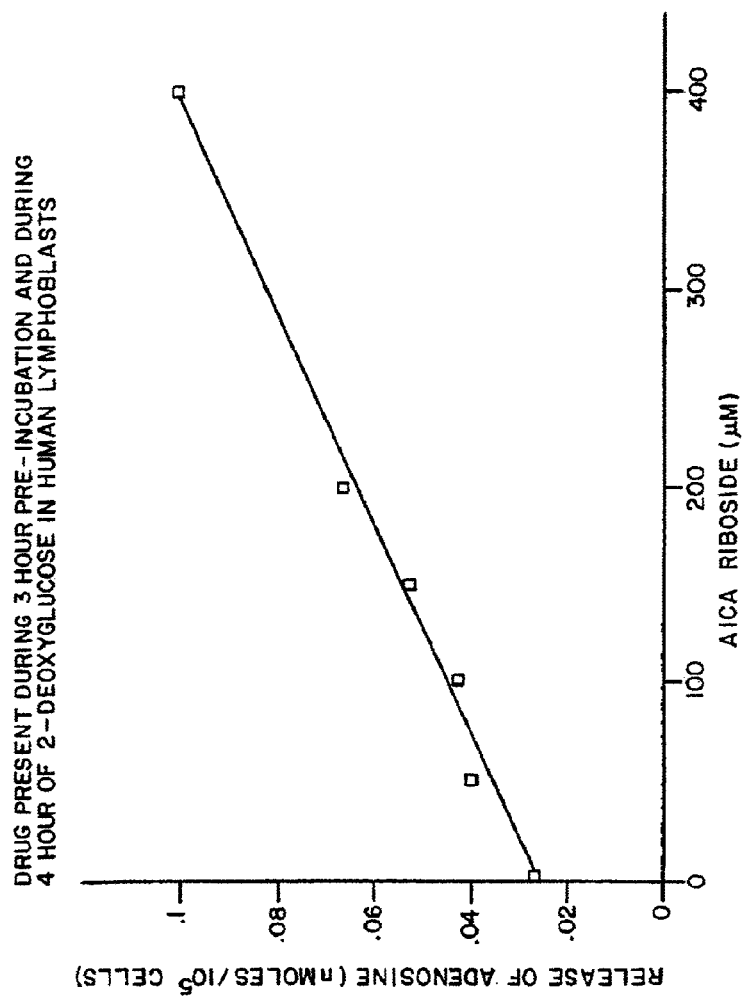
FIG. 8. Effect of three-hour preincubation and four-hour incubation with AICA riboside on in vitro adenosine excretion by human lymphoblasts during ATP breakdown.
Figure 9:
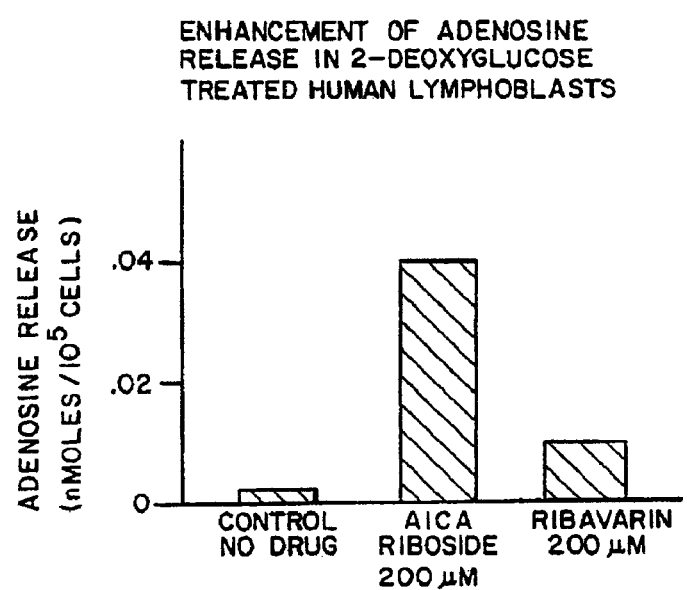
FIG. 9. Increased in vitro adenosine release from human lymphoblasts on treatment with ribavirin.

FIG. 2 shows that 48-hour AICA riboside pretreatment, over the range of 100-500 micromolar, enhances adenosine release from lymphoblasts. About 1.4 nanomoles of adenosine/$10^6$ WI-L2 cells is excreted without the presence of drugs of the invention, and this number was increased to about 2.3 nanomoles at 500 micromolar AICA riboside. When the cells are preincubated with AICA riboside for 18 hours before 2-deoxyglucose exposure, enhanced adenosine release occurs as seen in FIG. 7. Three-hour preincubation and four-hour incubation (during 2-deoxyglucose treatment) with either AICA riboside (FIG. 8) or ribivirin (FIG. 9) also results in increased adenosine release. Cells were grown to about $0.5 \times 10^6$ cells/ml (mid-log phase) in FIG. 2 and to about $1.0 \times 10.\text{sup}.6^6$ cells/ml (early stationary phase) in FIGS. 7-9.

Example II

In Vitro Effect of AICA Riboside on Adenosine Release in Neuroblastoma Cells

There are neuromuscular diseases such as cerebral palsy, autism, schizophrenia, and insomnia where increased adenosine release may be beneficial. Neuroblastoma cell lines were grown in media and under conditions described in Example I. Media was supplemented with 0 or 50 µM AICA riboside. To induce ATP catabolism, the growth medium was replaced by medium containing micromolar amounts of the calcium ionophore A23187 and 1.0 µM deoxycoformycin. Under these conditions it was shown that treated cells secreted at least twofold more adenosine than control cells. Cells deficient in hypoxanthine phosphoribosyl transferase secrete twofold less adenosine than cells with normal enzyme and can be corrected by pretreatment with AICA riboside or ribavirin. The results are shown in Table I below.

TABLE 1

EFFECT OF AICA RIBOSIDE ON ADENOSINE EXCRETION BY STIMULATED HPRT.sup.− AND HPRT.sup.+ NEUROBLASTOMA CELLS

| Cell Line | Concentration of Ionophore (·mu·g/ml) | Concentration of AICA RIBOSIDE (·mu·M) | Concentration of Adenosine (·mu·M) |
|---|---|---|---|
| HPRT.sup.+ | 0 | 0 | <0.01 |
| HPRT.sup.+ | 0 | 50 | <0.01 |
| HPRT.sup.− | 0 | 0 | <0.01 |
| HPRT.sup.− | 0 | 50 | <0.01 |
| HPRT.sup.+ | 10 | 0 | 0.329 |
| HPRT.sup.+ | 10 | 50 | 0.698 |
| HPRT.sup.− | 10 | 0 | 0.124 |
| HPRT.sup.− | 10 | 50 | 0.513 |

Example III

In Vivo Effect of AICA Riboside on Adenosine Levels and Increased Blood Flow in Dogs Experiments were conducted on dogs to test for increased adenosine levels caused by AICA riboside treatment, and the concomitant increase in blood flow resulting therefrom.

Figure 3:
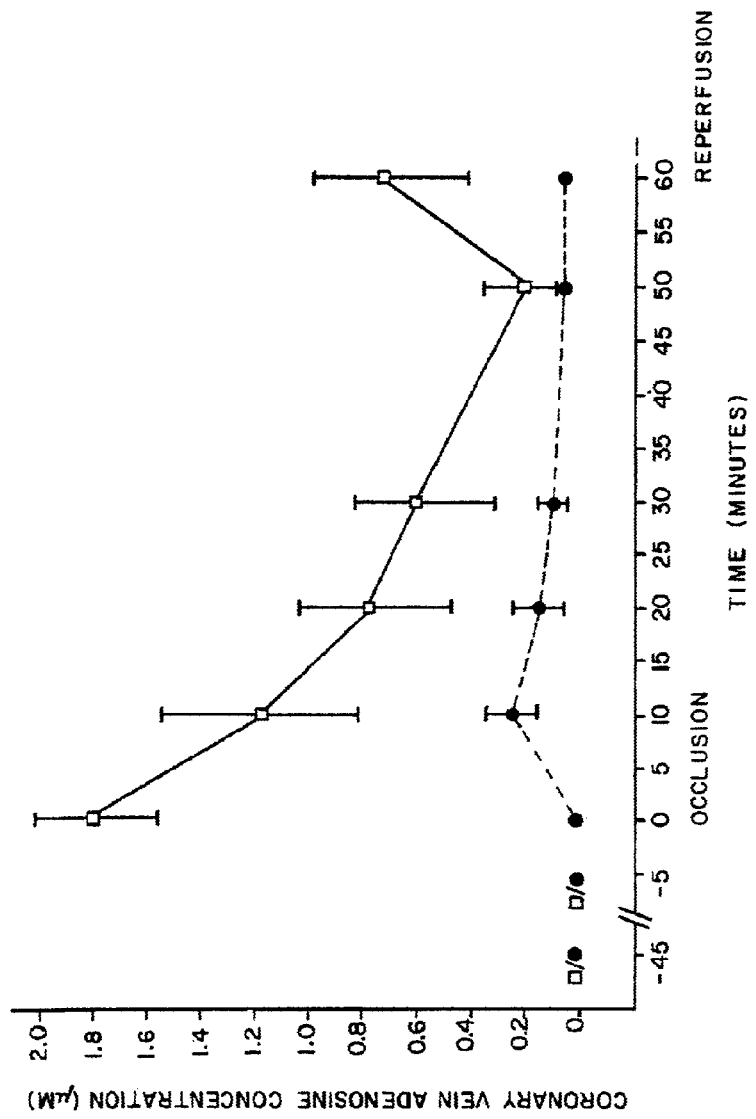
FIG. 3. The effect of AICA riboside treatment on coronary venous adenosine concentrations. Coronary venous blood was collected into chilled 2N perchloric acid at various times before and after coronary artery occlusion. Supernatants from these extracts were neutralized with alamine and freon and evaluated by high performance liquid chromotography. The mean adenosine concentrations+/−standard deviations for the five saline treated (•) and six AICA riboside treated (□) dogs are graph.
Figure 4:
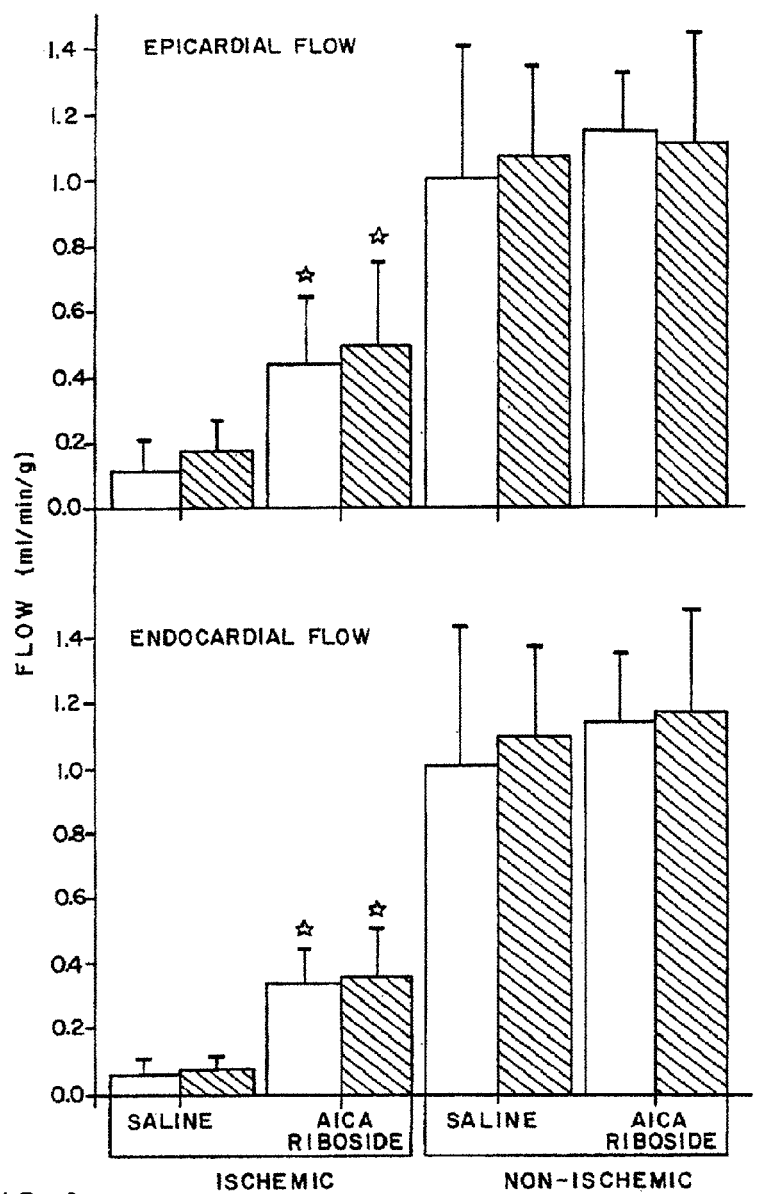
FIG. 4. In vivo effect of AICA riboside on regional myocardial blood flow during coronary artery occlusion in dogs. Regional myocardial blood flow was measured using radiolabelled microspheres infused into the left atrium at 5 minutes (open) and 60 minutes (hatched) of occlusion. The means plus the standard deviations are graphed. The asterisks (*) identify differences from saline-treated dogs that are significant at $p<0.01$.

FIGS. 3 and 4 show the results of a second series of experiments carried out to demonstrate the effects of AICA riboside on adenosine levels in blood and to correlate the increase in adenosine with increased blood flow. Thirteen mongrel dogs were anesthetized with phenobarbital. The anterior coronary vein was cannulated and a blood sample was collected into 2N perchloric acid. Saline or 100 mM AICA riboside in saline was randomly selected for infusion into the femoral vein for 45 minutes prior to coronary artery occlusion at a rate of 1 ml/min. Coronary venous blood was collected and assayed for adenosine in a manner similar to the assay described in Example I at 5 minutes prior to occlusion, and after 1, 10, 20, 30 and 50 minutes of occlusion of the left anterior descending coronary artery, as well as 1 minute after reperfusion. Regional myocardial blood flow was measured within 15 µm radiolabelled spheres infused into the left atzium at 5 and 60 minutes during the ischemic period, as described by Heymann et al. in Prog. C.V. Dis. 20; 55 (1977). The electrocardiogram and arterial pressure were monitored throughout the period of ischemia. Six AICA riboside-treated and five saline-treated dogs survived the procedure. Two of the surviving saline-treated animals fibrillated. The concentration of AICA riboside in AICA riboside-treated dogs immediately before occlusion was 57.4+/−40.2 µM. The range was 4.4 to 100 µM.

FIG. 3 shows that adenosine levels in blood draining ischemic areas are dramatically increased in AICA riboside perfused dogs. Prior to ischemia, none of the dogs had measurable venous adenosine (<0.01 µM) before and during AICA riboside or saline infusion. The saline-treated animals had a peak adenosine level at 10 minutes after occlusion (0.22+/−0.08 µM) which fell to an undetectable level by 60 minutes. In contrast, the AICA riboside-treated animals had a peak adenosine level at 1 minute of ischemia (1.79+/−0.35 µM) which remained elevated at 60 minutes (0.18+/−0.15). Reperfusion resulted in no detectable adenosine washout in saline-treated animals but a significant rise in the AICA riboside-treated animals. Blood obtained from the right atrium (sampling of systemic blood) had no detectable adenosine in saline- and AICA riboside-treated dogs.

FIG. 4 shows that regional myocardial blood flow to the ischemic myocardium was significantly greater in AICA riboside than in saline-treated animals. A similar degree of difference in flow was seen in endocardium and epicardium, and there were no changes between 5 and 60 minutes of ischemia. AICA riboside did not alter flow to normal myocardium, as the non-ischemic tissue flow rates are remarkably similar between the two groups. Systemic arterial pressure and heart rate at 5 and 60 minutes showed no significant differences between the two groups of dogs. Arterial blood gas-content and systemic venous granulocyte counts were not significantly different between the two groups. Thus, AICA riboside is believed to enhance collateral coronary flow to ischemic myocardium, as indicated above, by augmenting localized adenosine release and thus vasodilating vessels in the ischemic region and/or inhibiting granulocyte free radial production and subsequent capillary damage and/or plugging.

Example IV

Effect of AICA Riboside Treatment on Inosine Levels in Dogs

Figure 5:
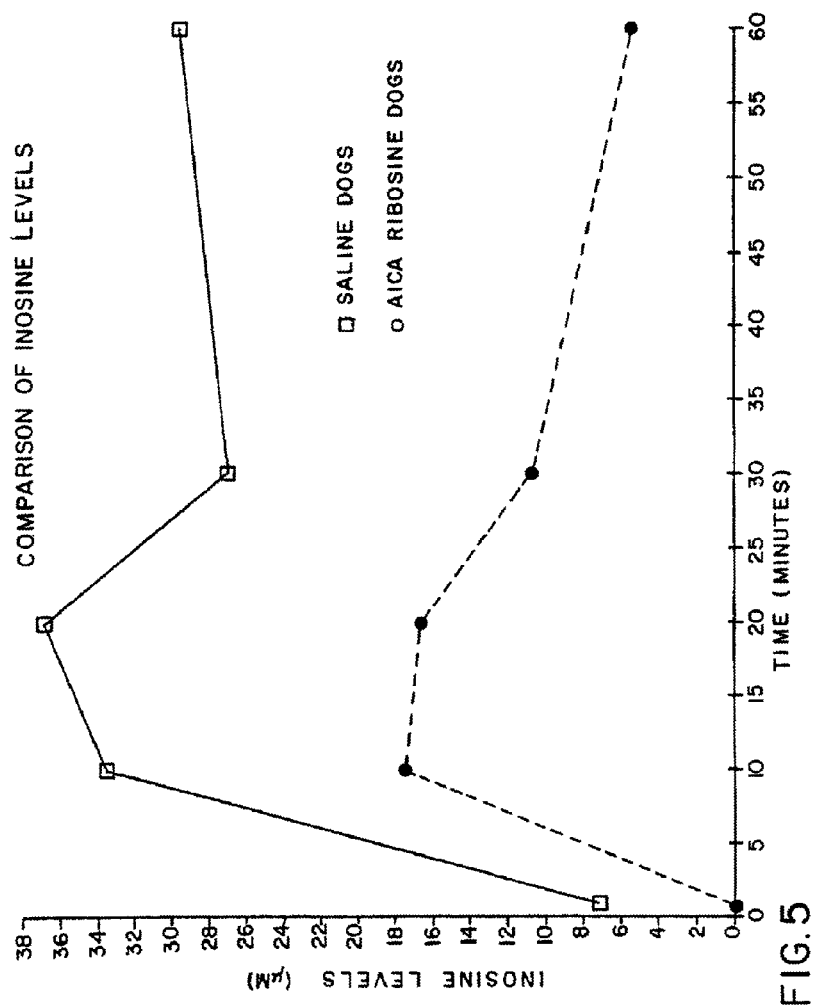
FIG. 5. Comparison of the effects of AICA riboside treatment (•) and control treatment containing only saline (□) on inosine levels in dogs.

That the increase in the levels of adenosine is due, at least in part, to a reduction in the amount of ATP that is converted to inosine was shown by analysis of venous blood from dogs in Example III for inosine levels. FIG. 5 shows a more than twofold decrease in inosine levels over the 60-minute assay period in AICA riboside-treated dogs. These data indicate that the compounds of the invention increase adenosine release by redirecting the catabolism of ATP from the normally more prevalent end product, inosine, to adenosine.

Example V

Effect of AICA Riboside Treatment on Myocardial Infract Size

The effect of AICA riboside treatment on myocardial infarct size was determined in rats given a bolus of either AICA riboside in saline or saline alone, and then inducing restricted blood flow by tying off the left anterior descending coronary artery. The animals were continuously exposed by infusion of either AICA riboside in saline or saline using osmotic mini-pumps well known to those in the art. After three weeks, the rats were sacrificed and infarct size quantitated by planimarizing stained sections of fixed hearts. The results showed that in AICA riboside treated hearts there is a reduction of infarct size of 33% compared to saline-treated controls ($p<0.05$).

Example VI

Effect of AICA Riboside Treatment on Arrhythmias

One consequence of myocardial ischemia is arrhythmia and the frequency of arrhythmias is related to the degree of reduced blood flow. Because adenosine is known to act as an anti-arrhythmic and to supress granulocyte free radical production, which can cause arrhythmia through lipid peroxidation, the prophylactic effect of AICA riboside treatment on arrhythmias was determined. Electrocardiograms recorded during ischemia of Example III were analyzed for the number of premature ventricular depolarizations (PVD) and ventricular tachycardia (VTAC) episodes. Table 2 shows that the saline-treated dogs had 112.2 PVD and 18.2 episodes of VTAC during ischemia, as compared to 37.8 PVD and 4.7 episodes of VTAC for the AICA riboside treated animals ($p<0.01$). The one AICA riboside-treated dog (#3 with frequent arrhythmias had much lower collateral blood flow rates and adenosine concentrations (but an AICA riboside blood concentration of 27.2 µM) compared to the other AICA riboside-treated dogs.

TABLE 2

| TREATMENT GROUP | ARRHYTHMIAS (EPISODES/H) | |
|---|---|---|
| | PVD | VTAC |
| SALINE | | |
| 1 | 101 | 10 |
| 2 | 144 | 23 |
| 3 | 232 | 44 |
| 4 | 57 | 8 |
| 5 | 27 | 6 |
| AVERAGE | 112.2 | 18.2 |

TABLE 2-continued

| | ARRHYTHMIAS (EPISODES/H) | |
|---|---|---|
| TREATMENT GROUP | PVD | VTAC |
| AICA RIBOSIDE | | |
| 1 | 12 | 1 |
| 2 | 10 | 0 |
| 3 | 182 | 27 |
| 4 | 4 | 0 |
| 5 | 13 | 0 |
| 6 | 6 | 0 |
| AVERAGE | 37.8 | 4.7 |

Example VII

Inhibition of AMP Deaminase by Aica Ribotide and Related Molecules

As shown in the experimental results set forth in FIG. 6, the AMP-utilizing enzyme, AMP deaminase, is inhibited by the phosphorylated derivatives of AICA riboside and ribavirin. The phosphorylated forms are referred to as AICA ribotide and ribavirin monophosphate, respectively. Using 200 μM of each ribotide, AMP deaminase was inhibited 38% and 54%, respectively. The enzyme assay is performed by measuring the conversion of $^{14}$C-AMP to $^{14}$C-IMP (adapted from T. J. Wheeler and J. M. Lowerstein, J. Biol. Chem. 254:8994 (1979). The reaction is performed using cytoplasmic lysates from a human lymphoblast line as described by Gruber et al., Biochim. Biophys. Acta 846:135-144, 1985. The substrates and products are separated on thin layer chromatography plates and counted in a liquid scintillation counter. Inhibition of this enzyme leads to an increase in the concentration of AMP, the direct precursor to adenosine, in the cell.

Example VIII

Effect of Adenosine on Granulocyte/Endothelial Cell Interaction

Studies were undertaken to demonstrate whether adenosine reduces the adhesive affinity, or "stickiness" of granulocytes for endothelial cells, an event which should increase blood flow in microvessels. The parameter measured was the fracture stress between the two cell types.

Adenosine decreases fracture stress between granulocytes and endothelial cells (which line the walls of vessels) by a factor of two as measured by a twofold increase in the rolling velocity of granulocytes in microvessels exposed to adenosine by superfusion with a solution of 20 μM, yielding a concentration of approximately 2 μM in the vessel. These studies were performed by intravital microscopy filming of granulocytes in rat mesentary microvessels. The rolling velocity of granulocytes compared to the streaming velocity of red cells was calculated before and after the administration of adenosine.

Example IX

Effect of AICA Riboside on Granulocyte Accumulation in Ischemic Myocardium

AICA riboside decreases the accumulation of $^{111}$indium-labelled granulocytes in ischemic myocardium. In a series of dogs as described in Example III, granulocytes were removed and labelled with $^{111}$indium and re-infused. After one hour of ischemia, the animals were sacrificed and the granulocytes quantitated in myocardial tissue by determining $^{111}$indium content in myocardial biopsies using a gamma counter. Granulocyte content in the ischemic endocardium was significantly less in AICA riboside-treated dogs (1.03+/−0.21× $10^6$ cells/gram) than in saline-treated animals (1.55+/−0.24× $10^6$ cells/gram). Radiolabelled microsphere determination of collateral blood flow yielded essentially identical results to those shown in Example III, i.e., blood flow in the ACA riboside-treated dogs was significantly greater than in saline-treated animals.

Example X

Treatment of Autistic Patients with AICA Riboside

Studies were conducted to determine the beneficial effects of treating autistic individuals with AICA riboside.

Following authorization, therapeutic trials with AICA riboside were started in two patients with adenylosuccinase deficiency (autism). The therapeutic trial was initiated on Day 1 by the oral administration of AICA riboside at the single dose of 5 mg/kg/day. That same day, blood and urine samples were collected at various time intervals and a single lumbar puncture was performed on each patient, respectively, two and three hours after the administration of AICA riboside. In view of the absence of clinical side effects, the same dose of AICA riboside was given during the following days, during which the patients remained in the hospital, and urine collection was continued. Since no adverse effects of the administration of the nucleoside were noticed, the dosage of AICA riboside was increased to 2×5 mg/kg/day and the patients discharged on Day 8, with this therapy. On Day 55, both patients were briefly readmitted for clinical, biochemical and psychiatric evaluation. In the absence of any clinical side effects, the dosage of AICA riboside was increased to 2×10 mg/kg/day from Day 46, on. Treatment was maintained until Day 71, and arrested at that date.

At all dosages used, AICA riboside could not be detected in plasma and CSF with available methodology. The nucleoside is nevertheless reabsorbed in the gut, as evidenced by the finding that during chronic oral administration its triphosphate derivative, AICA riboside triphosphate, was present in the erythrocytes. One hour after intravenous administration, AICA riboside was also undetectable in plasma, but AICA riboside triphosphate had similarly accumulated in the erythrocytes, indicating a rapid cellular uptake and metabolism of AICA riboside. A correct assessment of the renal loss of the nucleoside could not be obtained.

The administration of AICA riboside remained without significant effect on the urinary output of the two abnormal compounds excreted by these patients, succinyladenosine and SAICA riboside, and on that of uric acid. It also did not influence significantly the concentration of ATP and GTP in the erythrocytes. The concentrations of AICA riboside triphosphate reached, following oral as well as intravenous administration of AICA riboside, were of the same magnitude as those of GTP.

Appraisal of the mental development of both patients just prior to the initiation of the therapeutic trial with AICA riboside showed profound psychomotor retardation (mental development around three months on Bayley scales), accompanied by the following autistic features: stereotypic incoordinate movements, absence of reaction to auditory and tactile stimuli, and poor reaction to visual stimuli.

Reassessment of these features, after two months of continuous AICA riboside administration did not show any modification in the older patient. His younger sister; however, displayed a clear-cut improvement: stereotypic movements were less frequent, response to visual stimuli was improved and, most noteworthy, reactions to auditory and tactile stimuli could now be recorded. Two months later, following the six-week interruption of AICA riboside treatment, both patients were described as "more pleasantly active and more easy to handle during therapy" by the father, thereby prompting his request for resumption of the trial.

The following parameters were found normal before and during the trial treatment with AICA riboside: red blood cell count, white blood cell count, platelet and reticulocyte counts; leukocyte differentiations; hematocrit, ionogram, Ca, phosphate, urea, creatinine, uric acid, cholesterol, lipids, SGOT, SGPT, CPK, glucose, lactate and ammonia.

Example XI

Effect of Ribavirin on Mast Cell Degranulation

By preventing mast cell degranulation, it is possible to prevent or control a patient's allergic response. Bone marrow obtained from Balb/C mice femurs was cultured in a 1:1 mixture of Razin media and conditioned media, produced by co-culturing splenocytes from C577Bl/6J and C3H mice in the presence of Concanavalin A as described by Razin et al. in the Proc. Natl. Acad, Sci. USA 28: 2559-2561, 1981. After weekly passaging and at least 15 days in tissue culture, the resulting cells were 90% pure mast cells and 95% viable as assessed by Trypan blue exclusion. Cells exposed to ribavirin in culture were washed three times prior to use in experiments. Parallel cultures of cells grown in media alone were used as controls for pharmacologically manipulated mast cells. Cell growth was assessed by counting cells at particular time points and comparing actual numbers of ribavirin-treated cells to numbers of cells grown in media alone.

β-hexosaminidase was chosen as a representative granule-associated, preformed mast cell mediator because it is easily quantitated, and its release nearly identically parallels that of histamine. Mouse bone marrow-derived mast cells were centrifuged at 200×g for 5 minutes, washed three times in Tyrode's buffer lacking divalent cations, sensitized for 30 minutes at 37° C. with anti-DNP (dinitrophenyl phosphate) IgE (1 μg/$10^6$ cells) and challenged with either DNP-BSA antigen (175 ng/3×$10^5$ cells) or A23187 (10 μg/ml/3×$10^5$ cells) in 400 μl of complete Tyrode's buffer for 10 minutes at 37° C. Reaction mixtures were centrifuged at 200×g for 10 minutes, and supernatant and pellet β-hexosaminidase concentrations were assayed by the hydrolysis of p-nitrophenyl β-D-glucosamide as described in Schwartz et al. in J. Immunol 123, 1445 (1979). Spontaneous β-hexosaminidase release was determined in unchallenged cells. The net % of β-hexosaminidase released is defined as follows: ##EQU1## where [β-hex] is β-hexosaminidase and super is supernatant. When exogenous adenosine was present in reaction mixtures, it was added simultaneously with the secretagogue.

Mouse bone marrow-derived mast cells challenged with A23187 or DNP-BSA antigen released 8-15% of total cell β-hexosaminidase, a preformed, granule-associated mediator. Ribavirin (10 μM) added at the time of mast cell stimulation does not affect β-hexosaminidase release. However, mast cells incubated for three to seven days in 10 μM ribavirin, washed, and challenged with A23187 exhibited a marked attenuation of β-hexosaminidase release compared to parallel cells cultured in media alone (FIG. 10). The asterisks (*) identify data significantly different from control cells ($p<0.05$). Ribavirin exposure did not alter mast cell mediator content (i.e., total cell β-hexosaminidase concentration) nor cell viability, and spontaneous release of β-hexosaminidase was similar in the two cell groups. The dose-response relationship between ribavirin exposure and preformed mediator release is depicted in FIG. 11. Although 1 μM ribavirin for six days inhibits mediator release significantly, maximal inhibition is evidence between 10 μM and 20 μM.

Example XII

Regulation of Mast Cell Activation and Degranulation by AICA Riboside

The activation and degranulation of mast cells play a key role in allergic diseases such as asthma. Thus, a means of preventing activation and degranulation affords a way to control the disease.

A. Mast cell isolation. To demonstrate the prevention of degranulation and activation by the claimed method, the cells were first isolated and cultured as described in Example XI.

B. Effect of AICA riboside on degranulation Inhibition of degranulation by AICA riboside was demonstrated by showing that AICA riboside inhibits degranulation induced by the calcium ionophore, A23187, as reflected in the release of the acid exoglycosidase, β-hexosaminidase. A23187 at 1 μg/ml, with or without AICA riboside, was added to 2-5×$10^6$ mast cells at 37° C. on Tyrode's buffer, and the amount of mast cell β-hexosaminidase released measured. In the presence of 100 micromolar AICA riboside, only 17.6% of hexosaminidase was released, whereas 28.8% was released in its absence. Thus AICA riboside inhibits mast cell degranulation. The percent release of β-hexosaminidase, as well as the method of assaying for the enzyme, was performed as described by Schwartz et al. in the J. of Immun., Vol. 123, October, 1979, p. 1445.

Effect of AICA Riboside on Leukotriene $C_4$ Release.

Cells grown in medium alone or with 100 μM AICA riboside for six days were washed and challenged for 20 minutes with A23187. Supernatant leukotriene $C_4$ concentrations were determined by radioimmune assay and demonstrated to be 51 and 13 nanograms/$10^6$ cells for control and AICA riboside-treated cells, respectively. Leukotriene $C^4$ release was significantly reduced ($p<0.01$) by 75% with AICA riboside pretreatment. Similar results were obtained on four- to six-day pretreatment with 10 μM ribavirin where mast cell activation was accomplished with antigen binding to IgE on the mast cell surface.

Example XIII

Suppression of Pentylene Tetrazol-Induced Seizures

To test the ability of AICA riboside to suppress pentylene tetrazol-induced seizures, rats (10 for each condition) were pretreated (randomly and blinded) with intraperitoneal AICA riboside in saline (0.9%) at 1000 mg/kg or 100 mg/kg, or an equal volume of saline for 30 minutes and 5 minutes before injection of 60 mg/kg pentylene tetrazol. The animals were observed for one hour by two independent seizure experts.

Figure 12:
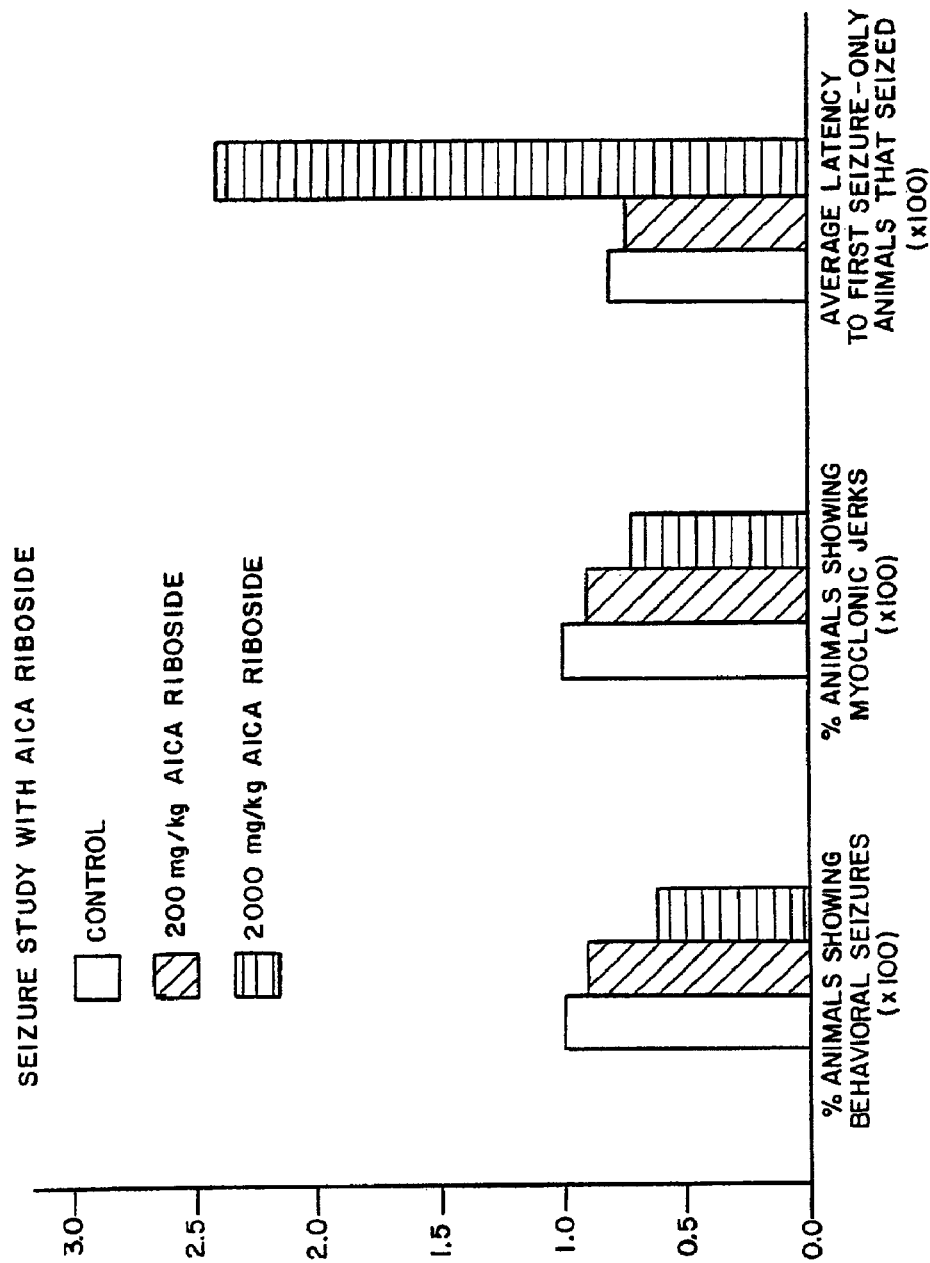
FIG. 12. AICA riboside inhibition of pentylene tetrazol-induced seizures in the rat.

There was a 40% reduction of animals having seizures in the group that received 2000 mg/kg (total dose) and a dramatic prolongation of latency to seizure in this group (FIG. 12).

Example XIV

Suppression of Catecholamine-Induced Arrhythmia

To determine whether AICA riboside would protect the heart from isoproterenol (isuprel)-induced arrhythmias, nine pairs of rats were tested with one animal of each pair injected intraperitoneally with 1000 mg/kg of AICA riboside in water. The other animal of each pair served as a control and was similarly injected with saline (0.9%) in a volume equal to that of the AICA riboside solution.

Five minutes later both animals were anesthetized with 330 mg/kg of chloral hydrate injected intraperitoneally. Then a single EKG lead was attached to each rat for simultaneous recording of the paired rats' electrocardiograms. To produce arrhythmia, each rat was injected subcutaneously with isuprel (1000 mg/kg).

Beginning 30 minutes after isuprel introduction, the electrocardiograph recording paper speed was run (5 cm/sec) for 10 minutes to count the arrhythmic beats of both animals.

Figure 13:
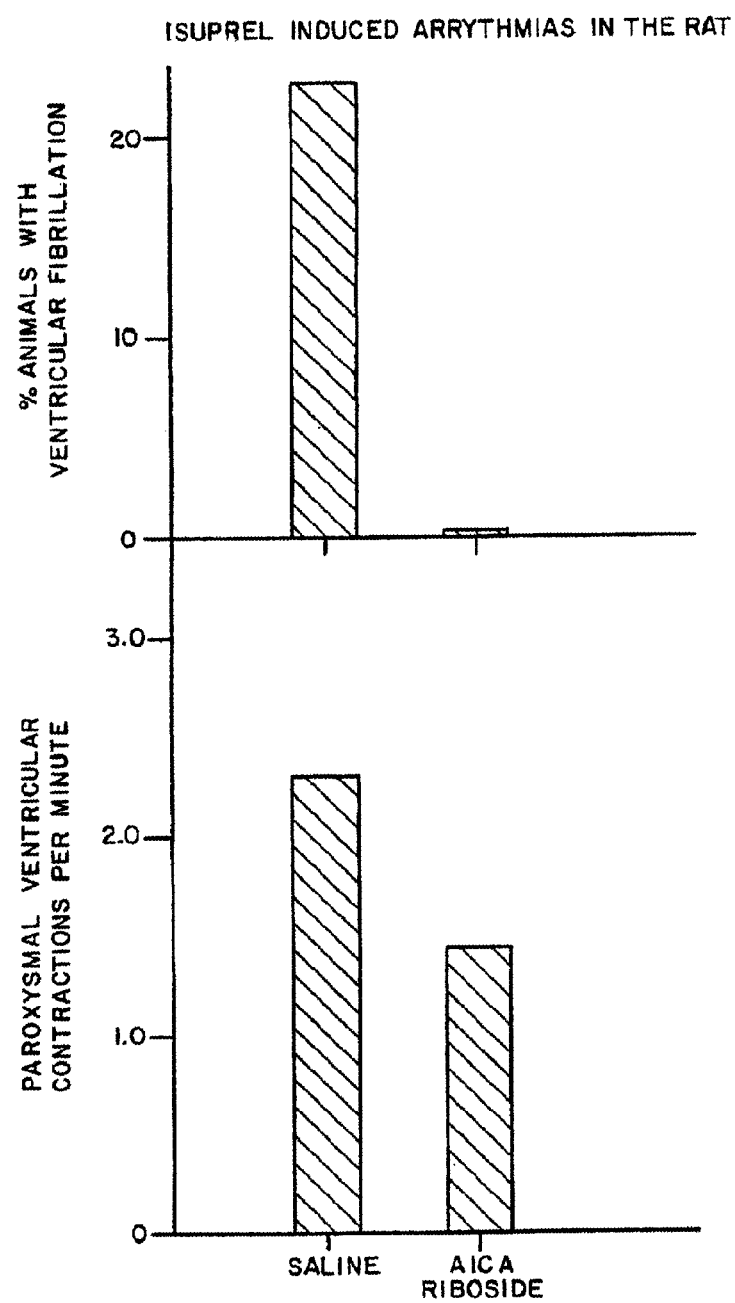
FIG. 13. AICA riboside inhibition of isuprel-induced arrhythmias in the rat.
Figure 14:
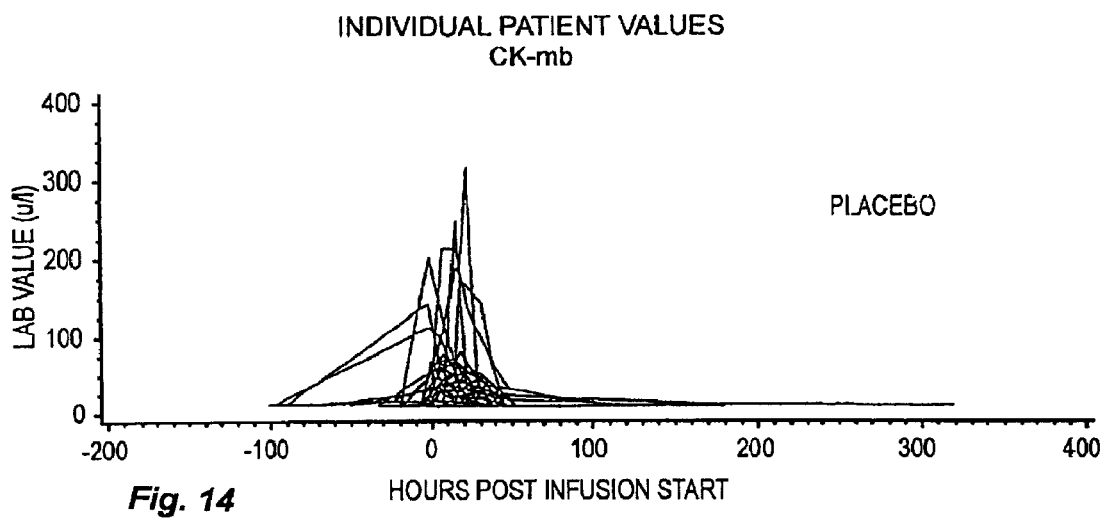
FIG. 14 is a graphical representation of individual patient values of creatinine phosphokinase MB band (CK-MB) levels in placebo patients (n=37) for patients in the study described in Example 1.
Figure 15:
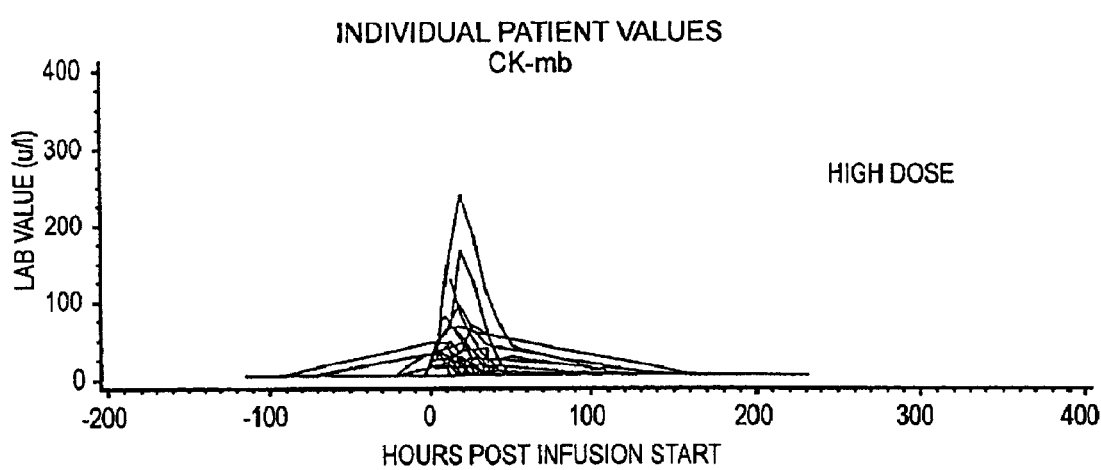
FIG. 15 is a graphical representation of individual patient values of creatinine phosphokinase MB band (CK-MB) levels in high dose (0.01 mh/kg/min.) AICA riboside (n=35) for patients in the study described in Example 1.
Figure 16:
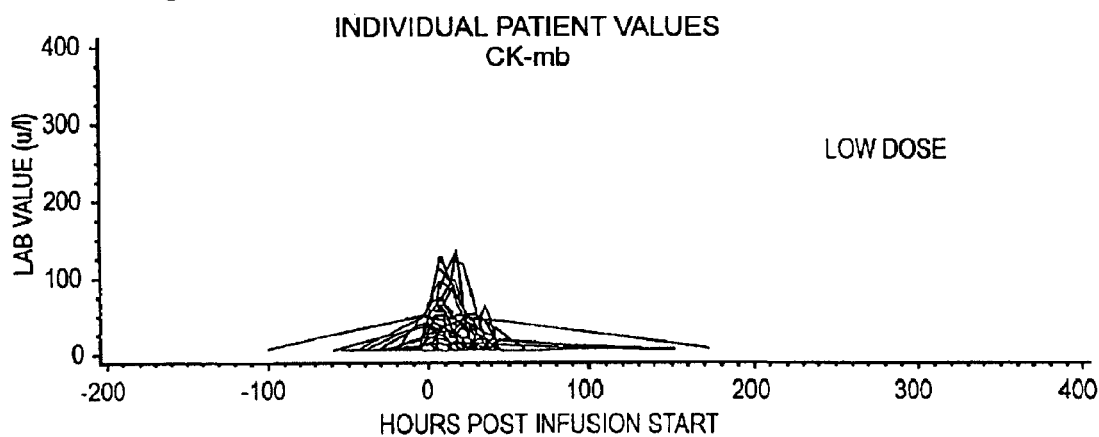
FIG. 16 is a graphical representation of individual patient values of creatinine phosphokinase MB band (CK-MB) levels in low dose (0.05 mg/kg/min.) AICA riboside (n=1) for patients in the study described in Example 1.
Figure 17:
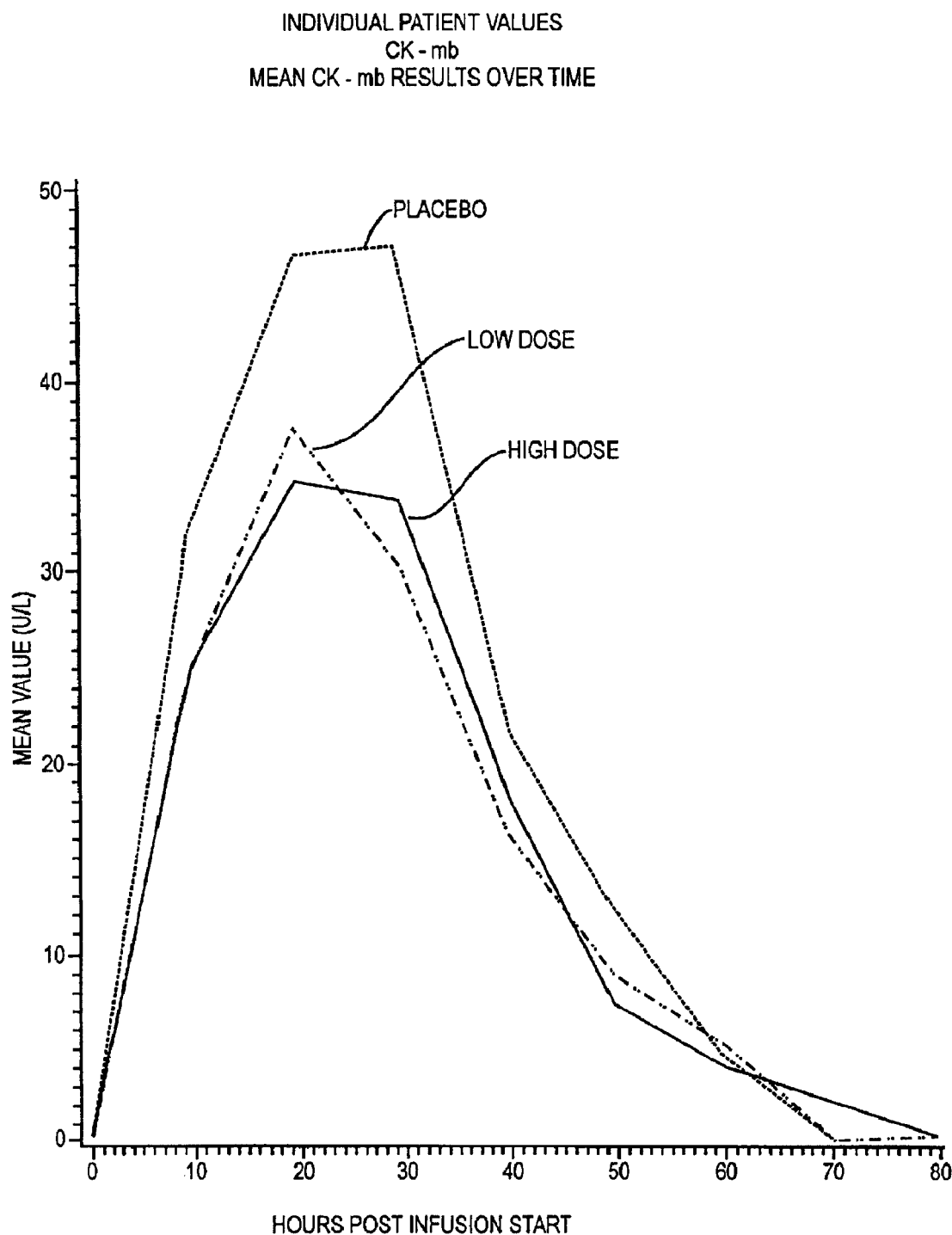
FIG. 17 is a graphical representation of mean creatinine phosphokinase MB band values for each treatment group over time, for the patients in the study described in Example 1.

There was a 39% reduction in paroxysmal ventricular contractions and a complete suppression of ventricular fibrillation in the AICA riboside-treated rats (FIG. 13).

By the following experiments, applicant has determined the concentrations and dosages of AICA riboside which decrease the frequency, duration and severity of ischemic events and which decrease tissue damage, while avoiding side effects such as clinically significant elevated serum and urinary uric acid levels and crystalluria. Applicant has also determined the concentrations and dosages of AICA riboside which prevent or reduce the severity of adverse clinical outcomes, such as adverse cardiovascular and cerebrovascular events.

The following Examples are not limiting to the invention. Those in the art will recognize that administration of AICA riboside in the stated amounts will reduce tissue damage resulting from decreased blood flow, and will reduce the incidence of adverse clinical outcomes, such as adverse cardiovascular and cerebrovascular events, in instances other than CABG surgery, as well.

Example 1

Effects of AICA Riboside in Patients Undergoing Coronary Artery Bypass Graft (CABG) Surgery: Phase 2 Clinical Trials These experiments were undertaken to assess the effects of AICA riboside on the frequency, duration, and severity of cardiac ischemic events and left ventricular function during and following CABG surgery. The effect of AICA riboside treatment on difficulty in weaning from cardiopulmonary bypass was also assessed. In addition, the effect of AICA riboside on the incidence of certain adverse clinic outcomes was evaluated.

Study Design

The study was a multi-center randomized double blind multi-dose placebo controlled parallel group study which evaluated 118 patients in four centers. Patients scheduled for non-emergency CABG surgery were randomly allocated to treatment with one of two doses of AICA riboside, or placebo, by continuous infusion throughout the procedure. Clinical outcomes, hemo-dynamics and the occurrence and severity of ischemia (by continuous electrocardiography (ECG) and transesophageal echocardiography (TEE)) were recorded and compared between treatment groups.

Patients

Included in the study were females not of child-bearing potential and males who were at least 30 years old and who were scheduled to have non-emergency CABG surgery for the treatment of coronary artery disease confirmed by typical changes (at least 50% stenosis of 2 or more major vessels) as shown by coronary angiography carried out within a six-month period prior to surgery. Patients with unstable angina were included, provided that the patient had been stable for at least 24 hours and that myocardial infarction had not occurred within the previous 2 weeks. Excluded from the study were patients undergoing emergency CABG or repeat CABG; those with resting ejection fraction less than 30%, cardiac index less than 1.5 L/min/m$^2$, or with idiopathic cardiomyopathy, significant valvular disease, severe left ventricular hypertrophy, or major intraventricular conduction abnormalities. Also excluded were patients with insulin dependent diabetes mellitus or hypoglycemic states, hepatic or renal disease, uncontrolled gout or a recent history of alcohol or other drug abuse. Thrombolytic therapy was prohibited within the 2 weeks prior to surgery, amiodarone for 60 days and dipyridamole, theophylline and aminophylline for 24 hours before the study. Smoking and ingestion of any methylxanthine-containing foods or drinks were prohibited from 12 hours before drug administration until discharge from the intensive care unit.

Treatment and Methods

Patients scheduled for CABG surgery and selected as described above were randomly allocated to receive an infusion of AICA riboside (0.19 mg/kg/min or 0.38 mg/kg/min initially; 0.05 mg/kg/min or 0.1 mg/kg/min after the first six patients) or placebo commencing shortly before induction of anesthesia and continuing for 7 hours; in all cases this meant that the infusion was not terminated until surgery had been completed and the patient was recovering in the intensive care unit. AICA riboside (20 µM final concentration) or placebo was also added to the crystalloid cardioplegic solution used to perfuse the coronary circulation during the bypass period. No other drugs were added to the crystalloid cardioplegic solution.

During the pre-operative period, a routine history, a physical examination, laboratory determinations, an electrocardiogram (ECG) and a chest x-ray were obtained. A continuous ECG (Holter) recording for a minimum of 8 hours before intubation was obtained. Routine cardiovascular medications were continued up to the morning of surgery as indicated. Immediately before surgery commenced, a catheter was placed in the radial artery for blood pressure measurements and arterial blood sampling. A triple lumen thermodilution catheter was introduced into the pulmonary artery for hemodynamic measurements. After tracheal intubation, an echocardiographic transducer was positioned at the level of the mid-papillary muscles using the transesophageal approach.

During surgery, anesthesia was maintained by continuous infusion of fentanyl and midazolam. Routine clinical parameters were recorded using standard operating room monitoring equipment. Continuous 2-lead Holter ECG and TEE data were recorded. Standard surgical procedures (e.g., aorta cross-clamping, crystalloid cardioplegia, cardiopulmonary bypass, hypothermia) were used. Anastomoses were constructed, aorta cross-clamp removed and patients were discontinued from bypass when body temperature was 37° C. The quality of anastomosis was judged by the surgeon. Difficulty in weaning from bypass was judged by need for one or more of the following: pacemaker, return to bypass, balloon pump or vasopressor administration. Hemodynamic measurements, including heart rate, arterial blood pressure, pulmonary capillary wedge pressure and cardiac output, were recorded before sternotomy, 15 and 30 min after bypass and upon chest closure. Radial artery and pulmonary artery pressures, myocardial and whole body temperature, $O_2$ saturation, end-tidal $CO_2$ and arterial blood gases were measured, and ECG recordings were obtained as clinically indicated. Hemodynamic variables (blood pressure, heart rate, pulmonary capillary wedge pressure) were controlled within 20% of baseline using prescribed regimens.

During the post-operative period through the first post-operative day, morphine and midazolam were used for sedation and analgesia. The cardiovascular medications required were recorded. During this period, continuous ECG monitoring (Holter) was performed for up to 48 hours. Hemodynamic measurements (pulmonary artery pressures and cardiac output) were obtained at 2, 4, 8 and 12 hours (in some cases at 24 and 48 hours) and also whenever clinically indicated.

A twelve-lead ECG was obtained on arrival in the intensive care unit and during post-operative days 1, 2, 3 and at hospital discharge. Creatinine phosphokinase MB band (CK-MB) was obtained every 8 hours for 48 hours and when indicated. Radio-nuclide ventriculography for ejection fraction and wall motion score was done about 14 days post-operation and as close to hospital discharge as possible. Other tests and measurements (e.g., chest x-ray, pulmonary artery wedge pressure (PCWP) were performed when clinically indicated for diagnosis or evaluation of myocardial infarction, or congestive heart failure. Timing and dose of all cardiovascular medications within 48 hours after surgery were recorded. The total dose of all analgesics during the 24-hour post-operative period was recorded. Fluid intake and output (e.g., blood replacement and urine output) were recorded for 48 hours. The type and duration of inotropic support and antiarrhythmic intervention required were recorded through 24 hours after surgery. Two-channel Holter recordings were obtained during 3 periods, the eight hours prior to intabation, from intubation through the end of surgery, and for an additional 24-48 hours after surgery.

Safety Assessment

In addition to the hemodynamic monitoring described above the following tests were performed at screening, on the first post-operative day and at discharge:

1. Hematology included hemoglobin, total white cell count and differential, hematocrit and platelet count.

2. Biochemistry included serum sodium, potassium, chloride, phosphorus, magnesium, urea, creatinine, serum glutamic pyruvic transaminase (SGPT), serum glutamic oxaloacetic transaminase (SGOT), total bilirubin, albumin, total protein, uric acid, alkaline phosphatase, creatine phosphokinase and CPK-MB. CPK-MB was also measured every 8 hours for the 48 hours following chest closure. Blood glucose and uric acid levels were measured before infusion, cardiopulmonary bypass (CPB), after CPB, upon arrival in the intensive care unit (ICU) and at 4 and 8 hours thereafter. The levels were also measured 24 hours post CPB and at discharge.

3. Urinalysis included blood, pH, protein, glucose, ketones, red blood cell, white blood cell casts and crystals. Urine was also collected before treatment, at the end of infusion, and 4 to 8 hours after the end of infusion, for determination of uric acid content.

4. Any adverse events were recorded throughout by the investigator, who assessed their severity and the relationship of these adverse experiences to the treatment.

Efficacy Assessment

One measure of efficacy was the degree to which AICA riboside lowered the incidence, duration and/or severity of ischemic events (by comparison of S-T segment changes on continuous Holter recordings before, during and for 48 hours after the procedure). The efficacy of AICA riboside in reducing the deleterious effects of ischemia on myocardial mechanics (by assessment of regional wall motion on TEE during the pre- and post-bypass periods, and by measurement of ejection fraction pre- and post-operatively), was also determined. The evaluation of Holter tapes and echo videotapes was performed centrally by two independent blinded observers; if there was disagreement between the two, a third observer was used to "break the tie." The same observers were used throughout the study.

The incidence of adverse clinical outcomes, such as cardiac death (death of patient attributable to primarily cardiac causes, non-fatal transmural MI (as measured by the appearance of a new Q-wave on 12-lead ECG plus a CK-MB value of ≥50 units), non-transmural MI (CK-MB value of ≥50 units), congestive heart failure (low cardiac output requiring intra-aortic balloon pump or left ventricular assist device) or life-threatening dysrhythmia (ventricular fibrillation, or ventricular tachycardia requiring cardioversion or drug treatment) was compared between the placebo and treatment groups. For the diagnosis of myocardial infarction, ECG tracings and CK-MB values were assessed centrally by observers blinded to treatment. The difficulty of weaning the patient from bypass, if any, was compared between placebo and treatment groups by noting need for one or more of the following: pacemaker, return to bypass, balloon pump or use of vasopressors.

Statistical Analysis

The results reported herein do not cover all the parameters measured but address the measurements listed below using the methods indicated.

1. Group Comparability. To assess the comparability among the three treatment groups, the following baseline and intra-operative measurements were evaluated using one-way analysis of variance for continuous variables and chi-square tests on contingency tables for discrete variables.

2. Baseline. Age, sex, cardiovascular history (angina, hypertension, prior MI, CHF, arrhythmia), ejection fraction, catheterization data (number of stenosed vessels), number of pre-bypass ischemic events and minutes per hour of ischemia (measured by Holter ECG).

3. Intra-operative. Number of grafted vessels, aortic cross-clamp time, surgery time, bypass time.

4. Clinical Outcome. Outcomes of cardiac death, MI, CHF and life-threatening dysrhythmia were compared. Specific endpoints for analysis were combined into a dichotomous endpoint, i.e., at least one of the four events listed above occurs versus none occurs. Fisher's exact test for small samples was used to compare the rates of clinical outcome between the three treatment groups. The same comparison was done of the combined active treatments vs. placebo.

5. Ischemic Events—TEE. Ischemic event data were evaluated during two time periods—pre-bypass and post-bypass, using the following analysis:

a) The number of patients with ischemic events was compared across the groups using Fisher's exact test. This analysis also included pre-post changes and pre- and post-combined.

b) For patients with events, analysis of the mean duration and severity of ischemia was done. Using only the patients with ischemic events reduced the number included in the analysis, but allowed determination of whether the drug is effective in reducing the magnitude of the events, should they occur. The distribution for duration of ischemia was found to be skewed, so a $\log_{10}$ transformation was used to induce a normal distribution and one-way ANOVA was used to compare the groups. For severity (an ordinary variable, 0-4 scale) and number of events, the nonparametric test was used. The same comparisons were done with the active treatment groups combined.

6. Ischemic Events—ECG. The analysis of ischemic events indicated by ECG was done using the same methods as the echo events. The time periods analyzed were: (a) baseline (Holter start to infusion start), (b) pre-bypass (infusion start to bypass start), (c) post-bypass (sideclamp off to infusion end), and (d) post-treatment (infusion end to Holter end). For patients with events, the following variables were analyzed: mean duration, maximum ST change and area under the curve of significant ST segment deviation. Analysis of variance (ANOVA) was used.

The same comparisons were done with the active treatment groups combined.

7. Ischemia vs. Outcome. The relationships between ischemia (TEE and ECG) detected during the time periods outlined above, and clinical outcomes were analyzed using Fisher's exact test (See J. Leung, et al.: Prognostic Importance of Postbypass Regional Wall-Motion Abnormalities in Patients Undergoing Coronary Artery Bypass Graft Surgery. Anesthesiology 71:16-25, 1989).

8. Difficulty in Weaning. Patients were considered to have difficulty in weaning if they needed one or more of the following interventions: pacemaker, return to bypass, balloon pump or use of vasopressors. The number of patients receiving each of the above interventions was analyzed using a $X^2$ and Fisher's exact test, as was the number of patients classified as having difficulty in weaning. In addition, the time to weaning (defined as time from cross-clamp removal to end of bypass) in the patients experiencing difficulty were compared by a 1-way analysis of variance.

9. Election Fraction. Pre-operative and post-operative ejection fractions were measured using different methodologies; therefore, changes could not be analyzed statistically. Group mean injection fractions and pre- and post-CABG are presented and apparent differences between groups were described.

10. Plasma Levels. AICA riboside plasma levels were measured to check agreement with randomized treatment and to document dose-proportionality and to assess plasma levels achieved. Individual values and group means were tabulated and drug clearance calculated. Dose proportionality was assessed.

11. Adverse Effects. The incidence, severity and drug-relatedness of any adverse effects were tabulated by treatment group by decreasing incidence of such effects in the high dose group. Statistical analysis was not performed.

12. Laboratory Data. For selected parameters of interest, individual values, mean changes and percent changes from baseline were tabulated and plotted over time by treatment group. The following parameters were addressed:

Urine-uric acid, creatinine, uric acid/creatinine ratio, pH, volume, crystals. All values were tabulated as mean±S.E.M.

Blood Chemistry—CPK, CK-MB, uric acid, glucose.

All values were tabulated as mean±S.E.M.

Results

The studies described herein represent the first exposure of prolonged continuous infusion of AICA riboside to patients undergoing anesthesia, heart-lung bypass surgery and hypothermia. Dose levels had been evaluated using results from healthy volunteer subjects or conscious normothermic patients, and there was uncertainty as to the applicability of pharmakinetic studies using short infusion periods in healthy volunteer subjects or conscious normothermic patients.

The first six patients included in the study were given doses of 0.19 mg/kg/min and 0.38 mg/kg/min. When plasma levels of AICA riboside were measured, they were unexpectedly found to be approximately 2-4 times higher than anticipated. While applicant does not wish to be bound by any particular theory, higher AICA riboside levels may have resulted because of reduced drug metabolism due to low liver blood flow and hypothermia. The higher levels may also have been due to the effect of prolonged infusions on clearance rate. The dose levels were reduced from 0.19 and 0.38 mg/kg/min to 0.05 and 0.1 mg/kg/min. This then achieved the steady state plasma concentrations of approximately 2.5 and 5.0 µg/ml in subsequent patients.

Results from these first 6 patients, who were studied at the initial high dose, are summarized below and were included in the overall safety analysis. Except for patient A4 who received placebo, these results were not included in evaluation of efficiency unless expressly stated with respect to such results.

In the initial high dose group there were four patients who received the lower dose (0.19 mg/kg/min), one who received the high dose (0.38 mg/kg/min) and one placebo patient. In general, the drug was well tolerated and there were no serious adverse experiences. As shown in Table 1, blood glucose levels were elevated in all patients at most times; there were no values below the limits of normal. There was significant hyperuricemia and elevated urinary uric acid levels with crystalluria, which necessitated irrigation of the urethral catheter in the five drug-treated patients (Table 1). In these patients, the urine had a clear, green coloration, presumed to be due to high concentrations of AICA riboside and/or its breakdown products. Also, as shown by the data in Table 1, blood glucose levels were not decreased.

Apart from these effects on plasma and urine uric acid levels and crystalluria, there were no adverse events considered to be related to treatment with AICA riboside. At the lower dose (0.19 mg/kg/min), 2 of the 4 patients (A3 and A6) had no other adverse events, 1 patient (A1) had extrasystoles, labile blood pressure and an episode of low blood $PO_2$, which were corrected uneventfully. This patient also had a rectosigmoid carcinoma, clearly not related to drug treatment and for which appropriate therapy was instituted. The fourth low dose patient (A2) had an episode of complete heart block post-bypass, followed by hypertension some 4 hours later. Patient A5, who received 0.38 mg/kg/min, had no events other than S-T segment elevation on the ECG post-bypass.

TABLE 1

LABORATORY DATA - SERUM GLUCOSE AND URIC ACID LISTING BY PATIENT (in mg/dl) FIRST SIX PATIENTS ONLY

| PATIENT | AICA RIBOSIDE TREATMENT GROUP | LAB TEST (NORMAL RANGE) | SCREEN-ING | PRE INF | PRE CPB | POST CPB | ICU + 0 HR | ICU + 4 HR | ICU + 8 HR | 24 HR POST | DIS-CHARGE |
|---|---|---|---|---|---|---|---|---|---|---|---|
| A-01 | 0.19 mg\kg\min | GLUCOSE (65-115 mg/dl) URIC ACID (3.5-8.5 mg/dl) | 80 5.6 | 89 6.2 | 91 7.7 | 254 (H) 9.5 (H) | 140 (H) 10.7 (H) | 171 (H) 9.2 (H) | 117 (H 8.8 (H) | 103 7.7 | 153 (H) 10.7 (H) |
| A-02 | 0.19 mg\kg\min | GLUCOSE (65-115 mg/dl) URIC ACID (3.5-8.5 mg/dl) | 138 (H) 5.8 | 162 (H) 5.1 | 147 (H) 6.9 | 302 (H) 8.5 | 213 (H) 10.7 (H) | 205 (H) 9.8 (H) | 190 (H) 9.2 (H) | 150 (H) 6.4 | 159 (H) 4.8 |
| A-03 | 0.19 mg\kg\min | GLUCOSE (65-115 mg/dl) URIC ACID (3.5-805 mg/dl) | 113 7.2 | 113 7.2 | 91 9.0 (H) | 222 (H) 9.8 (H) | 123 (H) 10.7 (H) | 152 (H) 9.2 (H) | 179 (H) 7.3 | 105 5.5 | 129 (H) 6.7 |
| A-04 | PLACEBO | GLUCOSE (65-115 mg/dl) URIC ACID (3.5-8.5 mg/dl) | 116 (H) 4.3 | 116 (H) 4.3 | 99 4.2 | 260 (H) 3.6 | 135 (H) 3.5 | 115 3.8 | 103 3.8 | 130 (H) 3.9 | 107 4.4 |
| A-05 | 0.38 mg\kg\min | GLUCOSE (65-115 mg/dl) URIC ACID (3.5-8.5 mg/dl) | 124 (H) 7.4 | 111 7.4 | 103 10.7 (H) | 227 (H) 13.5 (H) | 104 18.3 (H) | 144 (H) 16.4 (H) | 143 (H) 15.5 (H) | 137 (H) 12.6 (H) | 108 10.3 (H) |
| A-06 | 0.19 mg\kg\min | GLUCOSE (65-115 mg/dl) URIC ACID (3.5-8.5 mg/dl) | 104 5.7 | 104 5.7 | 97 6.8 | 222 (H) 6.9 | 104 10.0 (H) | 105 8.7 (H) | 103 7.8 | 99 6.0 | 109 8.6 (H) |

PRE INF = pre-infusion with AICA riboside or placebo
PRE CPB = pre-cardiopulmonary bypass
POST CPB = post-cardiopulmonary bypass
ICU + 0 = upon arrival at intensive care unit
ICU + 4 = four hours after arrival at intensive care unit
ICU + 8 = eight hours after arrival at intensive care unit
24 HR POST = 24 hours after cardiopulmonary bypass
(H) Indicates a higher than normal range Patient Characteristics Tables 2 and 3 show clinical and surgical data considered to be of prognostic importance for perioperative morbidity. No significant differences were found in any of the parameters, with the following exceptions: all patients in the placebo and high dose group, but only 83% of the low dose group, had a history of stable angina (p=0.021); there were 3 females in the low dose group, none on the high dose and 1 in the placebo group (p=0.090). It was concluded that overall the groups were well matched in respect of demographics, severity of illness and extent of surgical procedure.

| | | | |
|---|---|---|---|
| Hypertension (%) | 20 (49) | 19 (54) | 25 (68) |
| Hypercholes-terolemia (%) | 18 (45) | 13 (37) | 18 (49) |
| Myocardial Infarction (%) | 17 (41) | 18 (51) | 17 (46) |
| Congestive Heart Failure (%) | 1 (2) | 0 (0) | 0 (0) |
| Cardiac Arrhythmia (%) | 7 (17) | 4 (11) | 4 (11) |
| Carotid Bruit (%) | 6 (15) | 8 (23) | 3 (8) |
| Ejection Fraction (%) | 55.0 ± 2.3 | 58.4 ± 2.4 | 57.6 ± 2.0 |
| LV End Diastolic Pressure- mm Hg | 15.3 ± 1.6 | 15.3 ± 1.7 | 12.8 ± 1.5 |
| Number of Stenosed Vessels | 3.3 ± 0.3 | 3.2 ± 0.2 | 3.9 ± 0.3 |

No differences approach statistical significance.

TABLE 2

PREOPERATIVE CLINICAL DATA

| | 0.05 mg/kg/min | 0.1 mg/kg/min | Placebo |
|---|---|---|---|
| | | Number of Patients | |
| Variable | 41 | 35 | 37 |
| Age in years | 60.4 ± 1.6 | 62.7 ± 1.5 | 63.8 ± 1.5 |
| Males (%) | 34 (83) | 33 (94) | 34 (92) |
| Females (%) | 7 (17) | 2 (6) | 3 (8) |
| Baseline Ischemia by Holter (%) | 3 (15) | 5 (14) | 3 (8) |
| Stable Angina (%) | 33 (80) | 35 (86) | 34 (92) |
| Unstable Angina (%) | 18 (44) | 14 (40) | 15 (41) |
| Valvular Disease (%) | 2 (5) | 0 (0) | 0 (0) |

TABLE 3

SURGICAL DATA

| | 0.05 mg/kg/min | 0.1 mg/kg/min | Placebo |
|---|---|---|---|
| | | Patients (n) | |
| Variable | 41 | 34 | 36 |
| Crossclamp Time (mins) | 54.5 ± 2.5 | 52.4 ± 2.5 | 53.8 ± 2.9 |
| Bypass Time (mins) | 106 ± 4.9 | 99 ± 4.7 | 111 ± 6.7 |
| Surgery Time (mins) | 225 ± 9.3 | 215 ± 7.1 | 235 ± 8.8 |
| Number of Vessels Grafted | 3.2 ± 0.14 | 2.8 ± 0.14 | 3.2 ± 0.16 |

No differences were statistically significant.

Overall Evaluation

Adverse Events

In the setting of CABG surgery, adverse effects are expected to occur frequently. In this study, 29 of 37 placebo patients had one or more adverse events. The numbers of drug-treated patients with events were 30/35 in the high dose group (9.1 mg/kg/min), and 28/41 in the low dose group (0.05 mg/kg/min). There was no evidence that any of these events occurred more frequently in drug-treated patients compared with placebo.

Almost all of these events in all treatment groups were mild or moderate in severity and required no other specific medications. Five other events were categorized as severe; two acute myocardial infarctions (patients A26 and A39), one of whom also had CHF requiring intra-aortic balloon pump assistance, one pulmonary embolus (patient A12), and an arterial embolus to the right leg necessitating amputation (patient A14).

There has been 1 death in the study to date; patient A36, a 67-year-old male in the placebo group, had pre-operative unstable angina, poorly controlled hypertension and high grade left main disease. After an uncomplicated operative course, he developed respiratory distress in the intensive care unit and the ventilator was noted to be malfunctioning. External pacing and eventually internal cardiac massage, along with other resuscitation measures, were unsuccessful.

In virtually all cases (including all the severe events listed above), the events were considered by the investigators to be unrelated to drug, or that the probability that they were due to drug was remote, with the following exceptions: patient A2, who received 0.19 mg/kg/min, developed hyperuricemia and orange granules in urine, and patient A14, at the 0.05 mg/kg/min dose, whose urine developed the same green coloration already described in the initial high dose patients.

Serum Uric Acid and Glucose Levels

After the first six patients, the doses of AICA riboside were reduced, and there were no frtlher clinical elevations in serum uric acid. As shown in Table 4a, mean changes showed a clear trend towards a dose-related increase in serum uric acid in the treated groups. However, clinically relevant hyperuricemia or crystalluria was not seen. During the procedure, infusion containing glucose was given. As shown in Table 4b, plasma glucose levels were elevated in all groups.

TABLE 4a

SERUM URIC ACID-MEAN CHANGES FROM BASELINE (in mg/dl)

| SAMPLE TIME | 0.05 mg\kg\min (n = 41) | 0.10 mg\kg\min (n = 35) | PLACEBO (n = 37) |
|---|---|---|---|
| MEAN BASELINE | 5.9 +/− 0.2 | 5.7 +/− 0.2 | 5.9 +/− 0.3 |
| PRE CPB | −0.1 +/− 0.1 | 0.4 +/− 0.1 | 0.6 +/− 0.1 |
| POST CPB | −0.6 +/− 0.1 | 0.4 +/− 0.1 | −1.6 +/− 0.1 |
| ICU + 0 | −0.3 +/− 0.1 | 1.5 +/− 0.2 | −1.7 +/− 0.1 |
| ICU + 4 HR | −0.1 +/− 0.1 | 1.6 +/− 0.2 | −1.2 +/− 0.3 |
| ICU + 8 HR | −0.0 +/− 0.1 | 1.4 +/− 0.2 | 1.3 +/− 0.1 |
| 24 HR POST | −0.5 +/− 0.2 | 0.3 +/− 0.3 | −1.2 +/− 0.2 |
| DISCHARGE | 0.3 +/− 0.2 | −0.1 +/− 0.2 | −0.2 +/− 0.3 |

TABLE 4b

SERUM GLUCOSE-MEAN CHANGES FROM BASELINE (in mg/dl)

| SAMPLE TIME | 0.05 mg\kg\min (n = 41) | 0.10 mg\kg\min (n = 35) | PLACEBO (n = 37) |
|---|---|---|---|
| MEAN BASELINE | 108.5 + 4.8 | 120.6 + 7.3 | 121.0 + 15.5 |
| PRE CPB | 18.6 + 7.0 | 4.8 + 3.4 | 14.5 + 4.4 |
| POST CPB | 116.5 + 10.7 | 120.6 + 15.9 | 138.0 + 14.7 |
| ICU + 0 | 65.6 + 7.6 | 59.8 + 13.6 | 96.3 + 12.8 |
| ICU + 4 HR | 53.6 + 11.9 | 55.5 + 9.6 | 76.5 + 14.6 |
| ICU + 8 HR | 58.8 + 12.1 | 44.4 + 7.5 | 65.6 + 12.4 |
| 24 HR POST | 44.2 + 7.4 | 27.2 + 7.3 | 45.0 + 6.3 |
| DISCHARGE | 18.7 + 6.3 | 19.2 + 7.0 | 18.6 + 9.0 |

(See Table 1 for explanation of abbreviations)

Clinical Efficacy

1. Transmural Myocardial infarction.

Transmural myocardial infarction, defined as the appearance of a new Q-wave on post-operative 12-lead ECG and CK-MB level ≥50 I.U., occurred in 5 patients in the placebo group, in 2 of the patients receiving low dose AICA riboside, and in 2 of the high dose patient (Table 5). Differences between the groups were not statistically significant by Fisher's exact test, nor was significance achieved when the two treatment groups combined were compared with placebo (p=0.15). However, in view of the small number of subjects per group, these results (64% reduction in the frequency of post-operative myocardial infarctions) show a trend toward a decrease in transmural MI with AICA riboside treatment.

TABLE 5

NUMBER OF PATIENTS IN EACH TREATMENT GROUP
DEVELOPING TRANSMURAL MYOCARDIAL INFARCTION
(NEW Q-WAVE ON POST-OPERATIVE 12-LEAD ECG
AND CK-MB ≥ 50 I.U.)

| | 0.05 mg/kg/min | 0.10 mg/kg/min | Placebo |
|---|---|---|---|
| | | Number of Patients | |
| | 41 | 35 | 37 |
| Myocardial Infarction | 2 (4.9%) | 2 (5.7%) | 5 (13.5%) p = 0.42 |

All of the infarctions were present either on arrival in the intensive care unit or on post-operative day 1. One of the patients who developed myocardial infarction (A39) also required an intra-aortic balloon pump for severe hypotension on weaning from the pump; with this exception, none of the other outcomes being evaluated (CHF requiring intra-aortic balloon pump or left ventricular assist device, cardiac death or life-threatening arrhythmia) occurred in any of the three groups.

2. Non-Transmural Myocardial Infarction. Clinically significant elevation of creatinine phosphokinase MB band (CK-MB) levels, ≥50 I.U., with or without S-T segment elevation, with or without appearance of new Q-waves on 12-lead ECG, was observed in 17 (47%) placebo patients, 13 (13.7%) patients receiving low dose AICA riboside, and 8 (23.5%) in the high dose group (p=0.10, $X^2$ test) (Table 6). For the combined treatment groups versus placebo, the result was statistically significant (p=0.046).

TABLE 6

NUMBER OF PATIENTS IN EACH TREATMENT
GROUP WITH NON-TRANSMURAL MYOCARDIAL
INFARCTION (CK-MB ≥ 50 I.U.)

| | 0.05 mg/kg/min | 0.01 mg/kg/min | Placebo |
|---|---|---|---|
| | | No. of Patients | |
| | 41 | 35 | 37 |
| CK-MB ≥ 50 | 13 (13.7%) | 8 (23.5%) | 17 (47%) |

Across all patients, there was a trend toward a reduction in total CK levels in the treated groups compared with placebo (Table 7a). This same trend was apparent in CK-MB release (Table 7b).

TABLE 7a

CK-MB-MEAN CHANGES FROM BASELINE (in U/L)

| SAMPLE TIME | 0.05 mg/kg/min (n = 41) | 0.10 mg/kg/min (n = 35) | PLACEBO (n = 37) |
|---|---|---|---|
| MEAN BASELINE | 0.2 +/− 0.1 | 0.1 +/− 0.1 | 0.2 +/− 0.1 |
| ICU + 0 | 24.5 +/− 2.7 | 25.2 +/− 2.3 | 33.3 +/− 7.4 |
| ICU + 8 HR | 37.1 +/− 5.1 | 34.3 +/− 6.2 | 44.6 +/− 7.3 |
| ICU + 16 HR | 30.8 +/− 4.9 | 25.9 +/− 6.7 | 44.7 +/− 10.0 |
| ICU + 32 HR | 9.2 +/− 2.5 | 12.8 +/− 4.5 | 20.2 +/− 6.4 |
| ICU + 40 HR | 7.7 +/− 2.2 | 7.1 +/− 3.0 | 11.7 +/− 2.9 |
| ICU + 48 HR | 3.9 +/− 1.5 | 3.5 +/− 2.1 | 3.9 +/− 1.7 |
| 24 HR POST | 23.5 +/− 5.0 | 21.1 +/− 5.3 | 39.7 +/− 11.3 |
| DISCHARGE- | 0.0 +/− 0.1 | 0.4 +/− 0.4 | 0.7 +/− 0.4 |

TABLE 7b

CK-MEAN CHANGES FROM BASELINE (in U/L)

| SAMPLE TIME | 0.05 mg/kg/min (n = 41) | 0.10 mg/kg/min (n = 35) | PLACEBO (n = 37) |
|---|---|---|---|
| MEAN BASELINE | 89.2 +/− 30.9 | 66.6 +/− 11.3 | 118.2 +/− 51.7 |
| ICU + 0 | 346.2 +/− 45.3 | 386.1 +/− 51.8 | 323.3 +/− 46.8 |
| ICU + 8 HR | 839.2 +/− 89.3 | 869.6 +/− 143.7 | 965.6 +/− 140.3 |
| ICU + 16 HR | 1040.6 +/− 120.3 | 891.0 +/− 148.3 | 1136.4 +/− 136.2 |
| ICU + 32 HR | 874.7 +/− 126.3 | 894.0 +/− 142.9 | 1002.9 +/− 143.9 |
| ICU + 40 HR | 806.6 +/− 145.6 | 641.7 +/− 119.7 | 794.0 +/− 110.0 |
| ICU + 48 HR | 784.0 +/− 149.9 | 499.8 +/− 100.5 | 876.7 +/− 202.4 |
| 24 HR POST | 1028.1 +/− 126.4 | 1025.4 +/− 146.8 | 1226.7 +/− 161.8 |
| DISCHARGE | 87.8 +/− 46.6 | 31.9 +/− 22.0 | 34.1 +/− 69.0 |

3. Myocardial Ischemia. Myocardial ischemia was measured with continuous Holter ECG and TEE. Continuous Holter ECG was performed from the day before surgery through postoperative day No. 2. ECG episodes of ischemia were defined as reversible S-T depression 1 mm or greater lasting 1 minute or longer. TEE data were recorded continuously during surgery at the level of the mid-papillary muscles of the left ventricle. The wall motion of each of the four segments was graded from 0-4 (normal to dyskinesis). TEE ischemia was defined by regional wall motion worsening at least 2 grades and lasting 1 minute or longer. There was no difference in the incidence (percent of patients with ischemia) or severity of preoperative (baseline) ECG ischemia in the placebo, low dose and high dose groups (18%, 14% and 14% ischemia, respectively). In the prebypass period, the incidence of ECG ischemia was similar in the placebo, low dose and high dose groups (0%, 3% and 3%, respectively). The incidence of TEE ischemia tended to be lower in the high dose group (6%) versus placebo (19%) and low dose (15%), p=0.22. In the postbypass period, the incidence of TEE ischemia was similar in the placebo, low dose and high dose groups (29%, 27% and 24% ischemia, respectively); p=0.86.

The incidence of ECG ischemia tended to be lower in the high dose group (11%), than in the placebo or low dose groups (18% and 22%, respectively), p=0.42. As shown in Table 8, in those patients who experienced ischemia events, the severity of postbypass ECG ischemic episodes was less severe in the high dose group than in the low dose or placebo groups, judged by mean duration, mean area under the S-T curve (AUC), in millimeter minutes (mm-min), and ischemic minutes per hour (Isch min/h) monitored.

TABLE 8

|  | Placebo | Low Dose | High Dose | p-Value |
|---|---|---|---|---|
| Mean Duration (min) | 175 ± 156 | 125 ± 80 | 36 ± 20 | 0.04 |
| Mean AUC (mm-min) | −258 ± 317 | −172 ± 144 | −52 ± 28 | 0.24 |
| Isch min/h monitored | 35 ± 14 | 40 ± 15 | 27 ± 20 | 0.22 |

These data indicate that AICA riboside limits the extent of postsurgical myocardial ischemia in patients undergoing CABG surgery.

Difficulty in Weaning from Bypass

As noted, patients were determined as being difficult to remove from cardiopulmonary bypass if they required one or more of the following interventions: insertion of a pacemaker, return to bypass, use of a balloon pump or administration of vasopressors, or another intervention which the investigation determines is indicative of difficulty in weaning. There were no significant differences between the groups in respect to need for pacemaker, return to bypass or balloon pump assist. Both the low dose group and the high dose group showed a strong trend towards a reduced need for vasopressor support (p=0.19). See Table 9a. When a combination of the high and low dose groups were compared to placebo (Table 9b), the reduced need for vasopressor support approached statistical significance (p=0.08). As a result of the reduced need for vasopressor support in the high and low drug treated groups, combined with a slight reduction in the need for other support in these patients, there was a strong trend (p=0.17 when compared separately and p=0.06 when combined dose groups were compared with placebo) towards a reduction in weaning difficulty in the drug treated groups. There were no differences in any of the weaning difficulty parameters discussed above between the high and low dose groups (Table 9c).

With respect to weaning time as measured as the time from cross-clamp removal to termination of bypass, there were no statistically significant differences between the groups. If, however, only patients that had difficulty in weaning from bypass (as described above) were evaluated, there was a strong trend toward the reduction in the time seen in the drug treated patients (Table 9d).

TABLE 9a

WEANING DIFFICULTY, BY TYPE OF DIFFICULTY

|  | 0.05 mg/kg/min | 0.10 mg/kg/min | Placebo | |
|---|---|---|---|---|
|  | Patients (n) | | | |
|  | 41 | 35 | 37 | p-value |
| Pacemaker | 4 (9.8%) | 4 (11.4%) | 2 (5.1%) | 0.7 |
| Return to Bypass | 0 | 0 | 1 (2.7%) | 0.6 |
| Vasopressors | 3 (7.3%) | 4 (11.4%) | 8 (21.6%) | 0.19 |
| Balloon Pump | 0 | 0 | 1 (2.7%) | 0.6 |
| Other | 3 (7.3%) | 4 (11.4%) | 5 (13.5%) | 0.7 |

TABLE 9b

VASOPRESSOR WEANING DIFFICULTY
(0.05 + 0.1 mg/kg/min VS PLACEBO)

| 0.05 + 0.10 |  | Placebo | p-value |
|---|---|---|---|
| Vasopressors Required | 7 (9.2%) | 8 (21.6%) | 0.08 |

TABLE 9c

PATIENTS WITH ANY DIFFICULTY WEANING

| 0.05 | 0.10 | Placebo | |
|---|---|---|---|
| Patients (n) | | | |
| 41 | 35 | 37 | p-value |
| 7 (17%) | 8 (23%) | 13 (35%) | 0.17 |

| 0.05 + 0.10 | Placebo | |
|---|---|---|
| Patients (n) | | |
| 76 | 37 | p-value |
| 15 (19.7%) | 13 (35.1%) | 0.06 |

TABLE 9d

WEANING TIME

|  | 0.05 mg/kg/min | 0.1 mg/kg/min | Placebo |
|---|---|---|---|
|  | | Patients (n) | |
| Group | 41 | 34 | 36 |
| All Patients | 20 +/− 2.2 | 17 +/− 1.8 | 23 +/− 2.9 |
| Pts with Difficulty | 20 +/− 4.6 | 20.8 +/− 4.2 | 31.8 +/− 6.3 |
| Pts without Difficulty | 20.4 +/− 2.5 | 16.3 +/− 1.9 | 17.9 +/− 2.2 |

Hemodynamic Efficacy

Results for ejection fraction, measured on all patients preoperatively (by angiography) and at the time of discharge from the intensive care unit (by radionuclide ventriculography) are given in Table 10 below.

TABLE 10

Ejection Fraction (%) Measured Before (by LV Angiography) and After (by Radionuclide Ventriculography) Surgery (p = 1-way ANOVA)

| Period | 0.05 mg/kg/min | 0.10 mg/kg/min | Placebo | |
|---|---|---|---|---|
| Pre-Bypass | 55.0 ± 2.3 | 58.4 ± 2.4 | 57.6 ± 2.0 | p = 0.54 |
| Post-Bypass | 59.0 ± 2.0 | 61.3 ± 1.7 | 56.5 ± 2.3 | p = 0.28 |

At baseline, the groups were reasonably similar in respect to ejection fraction. Post-operatively, although the difference was not statistically significant, the AICA riboside groups had higher mean ejection fractions post-bypass than the placebo group.

Pharmacokinetics

Figure 18:
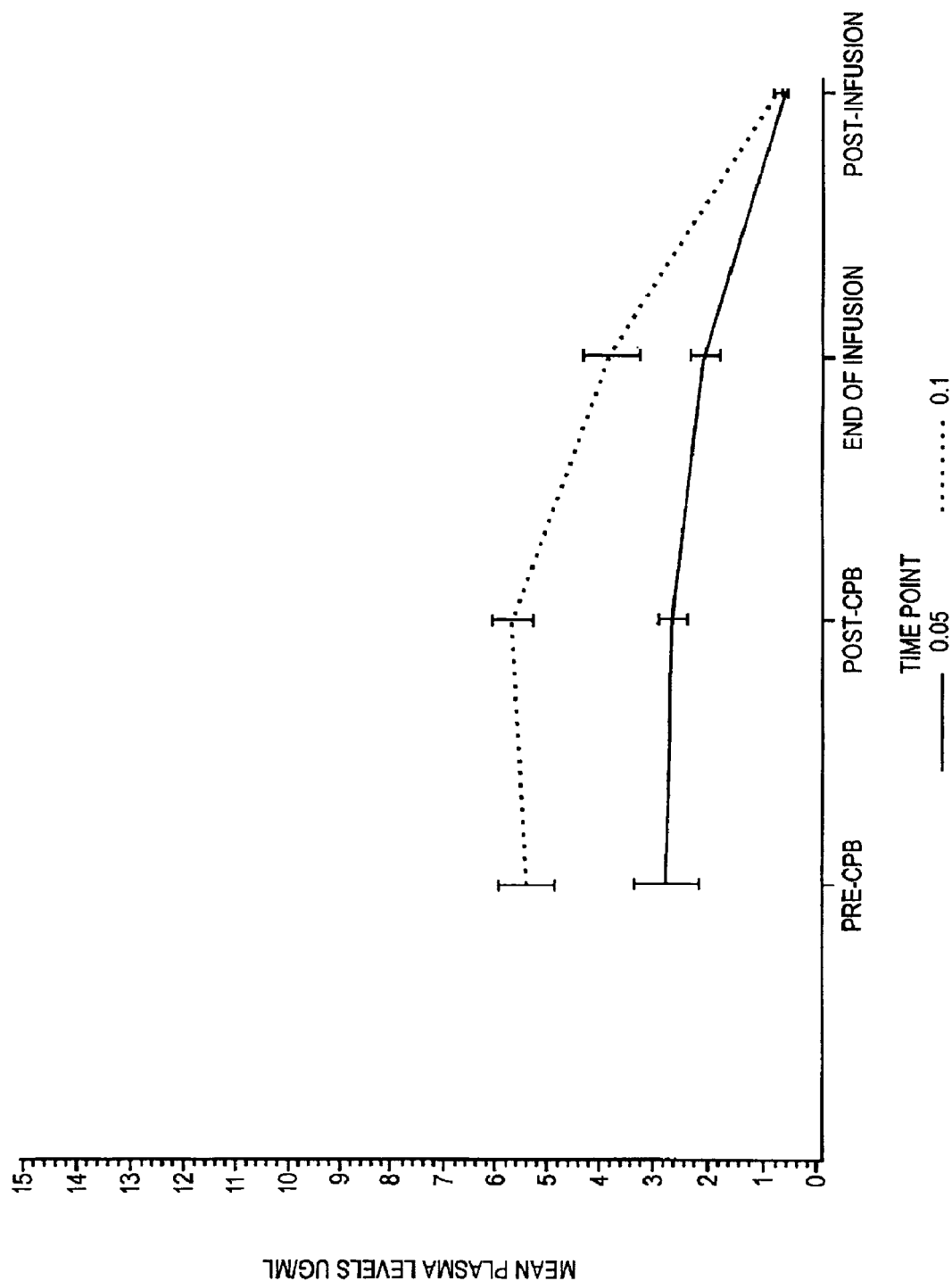
FIG. 18 is a graphical representation showing the mean plasma concentration of AICA riboside (μg/ml) during and following constant infusion of 0.05 or 0.1 mg/kg/min of the drug to patients during CABG surgery, for the patients in the study described in Example 1. The solid line shows 0.05 mg/kg/min and the dotted line shows 0.1 mg/kg/min.

Table 11 below gives the mean plasma AICA riboside concentrations at pre-bypass, post-bypass, end of infusion and 60 minutes post-infusion for 40 patients receiving 0.05 mg/kg/min and 31 patients at the dose of 0.1 mg/kg/min. The data are also presented graphically in FIG. 18.

TABLE 11

Mean (±SEM) plasma AICA riboside concentrations (μg/ml) during and following constant infusion of 0.05 (n = 40) or 0.10 mg/kg/min (n = 31) of AICA riboside to patients undergoing CABG surgery

| Sample Time | 0.05 mg/kg/min | 0.10 in/kg/min |
|---|---|---|
| Pre-Bypass | 2.66 ± 0.30 | 5.11 ± 0.20 |
| Post-Bypass | 2.49 ± 0.13 | 5.47 ± 0.19 |
| End Infusion | 1.83 ± 0.13 | 3.67 ± 0.30 |
| 1 Hour Post-Infusion | 0.32 ± 0.63 | 0.45 ± 0.03 |

Desired steady state plasma concentrations of 2.5 and 5.0 μg/ml for the low and high dose, respectively, were closely approximated at the pre- and post-bypass times, indicating good dose proportionality. Mean estimates of total plasma clearance ($CL_p$) were about the same for the low and high doses at both these times, approximating 1.2 L/hr/kg (range 1.1 to 1.2 L/hr/kg). This indicates that AICA riboside exhibits linear kinetics in patients undergoing CABG surgery at the infusion rates used in this study. These clearance rates are approximately 40-50% of those previously seen in conscious, healthy male subjects. Dixon, R., et al., J. Clin. Pharm. 31:342-347 (1991). While applicant does not wish to be bound by any particular theory, this difference in drug clearance may be a consequence of reduced metabolism due to hypothermia, decreased tissue uptake, lowered liver blood flow during the CABG procedure, or changes in metabolism associated with prolonged infusion. During the post-bypass period, there was a trend for the $CL_p$ to increase, the change coinciding with increase in body temperature and liver blood flow and discontinuation of anesthesia at this time. Once the infusion was terminated, the plasma AICA riboside concentrations declined rapidly to 10% of steady state levels after one hour.

Discussion

Perioperative myocardial infarction (MI) is not an uncommon complication of CABG surgery, with reported incidence of 10 to 50 percent, depending on the criteria used for diagnosis. Recent studies report an adverse effect of perioperative MI on immediate mortality rate, long-term survival or both (See H. Schaff, et al., J. Thorac. Cardiovasc. Surg. 88:972-981 (1984); P. Val. et al., J. Thorac. Cardiovasc. Surg. 86:878-886 (1983); W. Fennell et al., J. Thorac. Cardiovasc. Surg. 78:244-253 (1979); R. Seitelberger, et al., Circulation 83:460-468 (1991).)

The present study shows that AICA riboside protects against the adverse effects of tissue ischemia, prevents irreversible myocardial cell necrosis, and reduces the extent of cardiac functional impairment resulting from ischemic damage when given throughout the perioperative period, including immediately post-surgery (post-operative reperfusion) and by admixture with cardioplegic solution.

The results of the experiments described herein indicate a trend towards a lower incidence of transmural MI, evaluated using both new Q-waves and serum enzyme changes, between placebo (13.5%) and the low and high doses of AICA riboside (4.9% and 5.7%, respectively). This trend is even more apparent in the reduction of non-transmural MI, i.e., CK-MB levels greater than 50 I.U. in the absence of ECG changes (placebo 47.2%, low dose 31.7%, high dose 23.5%).

Although a strong trend (p=0.10) towards reduction of perioperative MIs was seen when the three groups were compared, these results did not reach significance. However, when all patients treated with drug (including the first 5 which received higher doses) are compared to placebo, there is a statistically significant reduction (p<0.05) in the rate of perioperative infarction in the drug treated group.

Applicant has also shown that AICA riboside alters the duration and severity of ischemic events. The mean duration of post-bypass ischemia events in placebo patients was 175 minutes (±156 minutes). Treatment with AICA riboside resulted in a reduction to 125 minutes (.±80 minutes) in the low dose group and a reduction to 36 minutes (±20 minutes) in the high dose group in the average duration of post-bypass ischemia events (p=0.04). In addition, the number of post-bypass ischemic minutes per hour was lower in the high dose group (27±20) than in the placebo (35±14) and low dose (40±15) groups.

The severity of post-bypass ischemia was also lessened by administration of the high dose of AICA riboside. The mean area under the S-T segment was 35±14 and 40±15 in placebo and low dose patients, respectively. But administration of the high dose resulted in a value of 27±20.

AICA riboside also appeared to have an effect on pre-bypass ischemia, at least on the incidence of TEE ischemia (6% for high dose vs. 19% for placebo and 15% for low dose).

The results of this study also demonstrated improvement in the ability to wean patients from bypass. Patients who received AICA riboside were less likely to receive vasopressor assistance in order to regain post-bypass function. In fact, a nearly statistically significant improvement was seen in the reduced use of vasopressors in the drug treated group. This suggests that the patients who receive the drug are less compromised than patients in the placebo group.

Hemodynamic changes are difficult to interpret in the setting of CABG surgery; heart rate and blood pressure are to a large extent controlled by a variety of pharmacologic agents and adjustment of circulating volume, and no effects of treatment with AICA riboside were seen on these parameters. There was, however a trend towards higher ejection fraction in the high dose AICA riboside group immediately before discharge from the intensive care unit, compared with the placebo and the low dose group. Such an improvement in functional cardiac performance would be consistent with the effects on the level of ischemia and the incidence of myocardial infarction.

All of these results show beneficial effects of the administration of AICA riboside, especially in a dosage of about 0.1 mg/kg/min. When combined with the hyperuricemia and crystalluria issues associated with the administration of AICA riboside at a dosage of 0.19 mg/kg/min, and especially at a dosage of 0.38 mg/kg/min, these results show that the particularly therapeutic dosage of AICA riboside is about 0.1 mg/kg/min.

Conclusion

Those of ordinary skill in the art reviewing the above example will recognize that the data indicate that administration of AICA riboside will be safe and effective in the dosages described in preventing tissue damage resulting from undesired decreased blood flow. When administered in the dosages described herein, undesired clinical hyperuricemia and/or crystalluria can be avoided while effectiveness is maintained.

Example 2

Effects of AICA Riboside in Patients Undergoing Coronary Artery Bypass Graft (CABG) Surgery: Phase 3 Clinical Trials Like the experiments described in Example 1, the following experiments were conducted to evaluate the effects of AICA riboside administered to patients undergoing CABG surgery, and to determine effective dosages and concentrations of AICA riboside. Applicant discovered concentrations and dosages at which AICA riboside is effective compared to placebo in preventing adverse clinical outcomes, such as adverse cardiovascular events, including myocardial infarction and cardiac death. Applicant also discovered that AICA riboside is effective compared to placebo in preventing adverse cerebrovascular events, such as cerebrovascular accidents. Applicant has also discovered concentrations and dosages of AICA riboside that are particularly effective to reduce the combined incidence of adverse cardiovascular and cerebrovascular events. These concentrations and dosages of AICA riboside are also believed to be effective in preventing or reducing the incidences of congestive heart failure and life threatening dysrhythmia.

The study described in this Example 2 is a multicenter, placebo control, double blind, study performed in approximately 600 patients at 20 centers in the United States. Patients received the same dosing regimen as was administered in the study described in Example 1: either placebo or one of two AICA riboside doses (0.05 or 0.1 mg/kg/min for 7 hours). In all cases, AICA riboside was also administered in a 5 µg/ml concentration in the cardioplegia solutions of patients who received AICA riboside treatment.

The study described in this Example 2 differs from the study described in Example 1 in patient selection criteria. The study described in Example 1 excluded patients thought to be surgically and medically at highest risk during CABG surgery, that is, repeat CABG patients, emergencies and those who had poor left ventricular function. In the studies described in this Example 2, all patients undergoing CABG procedures were considered suitable to enter the study except that patients with recent or evolving myocardial infarctions were excluded so that new myocardial infarctions could be diagnosed. In addition, in Example 2 a wider selection of cardioplegia solutions was allowed reflecting typical surgical patterns of use.

The following Table 12 depicts a statistical analysis of the incidence of myocardial infarction (as defined by ECG and CK-MB levels, i.e., transmural MI), cerebrovascular accident, cardiac death, congestive heart failure and life-threatening dysrhythmia. As in Example 1, the low dose of AICA riboside is 0.05 mg/kg/min and the high dose is 0.1 mg/kg/min.

TABLE 12

INCIDENCE OF CLINICAL OUTCOMES

|  | Placebo | Low Dose | High Dose | p-value (high dose v. placebo) |
|---|---|---|---|---|
| Myocardial Infarction | 10 (4.7%) n = 211 | 9 (4.4%) n = 205 | 3 (1.5%) n = 203 | <0.05 |
| Cerebrovascular Accident | 9 (4.2%) n = 212 | 2 (0.9%) n = 214 | 1 (0.5%) n = 207 | <0.05 |
| Cardiac Death | 3 (1.4%) n = 212 | 5 (2.3%) n = 214 | 0 (0%) n = 207 | NS* |
| Congestive Heart Failure | 8 (3.8%) n = 212 | 6 (2.8%) n = 214 | 6 (2.9%) n = 207 | NS |
| Life-Threatening Dysrhythmia | 4 (1.9%) n = 212 | 9 (4.2%) n = 214 | 3 (1.4%) n = 207 | NS |
| Combined Clinical Outcomes | 29 (13.7%) n = 212 | 23 (10.7%) n = 214 | 11 (5.3%) n = 207 | <0.05 |

*Not statistically significant.

The MI data shown in Table 12 reflect diagnosis by both ECG and CK-MB. That is, those patients who showed either ECG indication of MI or CK-MB indication of MI (but not both) are excluded. The presence of a new Q-wave (Minnesota Code 1) was used to diagnose MI in ECG testing. CK-MB diagnosis of MI was made if at least one of the following criteria was met:

1. Elevation of CK-MB concentration to ≥100 ng/ml at any time post surgery and with the preceding or following CK-MB sample ≥50% of this peak value;

2. Elevation of CK-MB concentration to ≥70 ng/m at any time after 12 hours post surgery and with the preceding or following CK-MB sample ≥50% of this peak value; or 3. A new elevation of CK-MB release, more than 24 hours after surgery, to a peak of ≥12 ng/ml with another measurement of at least 10 ng/ml immediately preceding or following the peak. If CK-MB levels were previously elevated, the levels must have fallen to below 10 ng/ml before the onset of this second elevation.

Diagnosis of cerebrovascular accident (CVA) was determined by signs and/or symptoms of significant neurologic deficit which persisted for over 24 hours. CVAs were considered study endpoints if there were focal neurological lesions lasting over 24 hours. Patients with non-focal lesions were considered as endpoints only if a neurological consultant diagnosed a CVA or if a CT or MRI scan was reported consistent with a new cerebral infarct or hemorrhage.

Cardiac death is defined as death of the patient from a primary cardiac cause, for example, myocardial infarction, dysrhythmia or ventricle dysfunction. All deaths were reviewed by a group of 3 independent cardiologists who lacked knowledge of the treatment group.

Diagnosis of congestive heart failure (CHF) was made by either: 1) severe worsening of left ventricular functions requiring an intraaortic balloon pump or left ventricular assist device for CI<1.5 l/min/m$^2$; or (2) cariogenic shock with CI<1.5 l/min/m$^2$ and PCWP>20 cm for >1 hour.

Diagnosis of life threatening dysrhythmia was made by either: (1) ventricular dysrhythmia requiring cardioversion; or (2) dysrhythmia requiring insertion of a pacemaker required at hospital discharge.

The combined outcome results in Table 12 show the incidence of the following adverse cardiovascular events: combined MI, CVA, cardiac death, CHF and life-threatening dysrhythmia. There appears to be a trend toward decreased incidence of adverse events in patients treated with the low dose of AICA riboside, however, the low dose appears to show no statistically significant efficacy. Thus, the p-values shown in Table 12 reflect a comparison of high dose (0.1 mg/kg/min) versus placebo.

Table 12 shows a 61% reduction in the incidence of combined outcomes in the high dose group compared to the placebo group (5.3% compared with 13%), with a p-value of <0.05.

The data indicate a 68% decrease in incidence of MI in the high dose group compared to the placebo group (1.5% compared with 4.7%), with a p-value of <0.05, and an 88% decrease in incidence of cerebrovascular accident in the high dose group compared to the placebo group (0.5% compared with 4.2%) (p-value <0.05). The data also show a strong trend toward a decrease in cardiac death (0 compared with 1.4%) in the high dose group compared with the placebo group with non-significant p-value.

For the adverse outcomes actions of congestive heart failure and life-threatening dysrhythmia, there appears to be a trend toward decreased incidence in the high dose group compared to the placebo group (CHF: 2.9% compared with 3.8%; dysrhythmia: 1.4% compared with 1.9%).

The incidence of all deaths tended to be lower in the high dose group than the placebo group (0.5% in the high dose group compared with 3.3% in the placebo group). The incidence of myocardial infarction as determined by either ECG or CK-MB tended to be lower in the high dose group compared to the placebo group (20.8% in the high dose group compared with 24.1% in the placebo group).

The uric acid concentrations of all patients in the study were monitored. While there is a clear dose related increase in uric acid concentrations in the treated patients, the plasma uric acid concentrations generally remained in, or close to, the normal range and there was no clinically significant crystalluria (data not shown).

Table 13 below depicts the incidence of myocardial infarction and combined clinical outcome (MI, CVA, cardiac death, CHF and life-threatening dysrhythmia) according to plasma level of AICA riboside. It is apparent from these data that the most effective plasma level of AICA riboside is in the range of 3-6 µg/ml. The data in Table 13 reflect diagnosis of MI by both ECG and CK-MB (as described above with respect to Table 12).

TABLE 13

INCIDENCE OF MI AND COMBINED CLINICAL OUTCOME BY PLASMA LEVEL OF AICA RIBOSIDE (µg/ml)

| AICA Riboside Plasma Level | Myocardial Infarction MI | Combined Clinical Outcome |
|---|---|---|
| <0.25 | n = 209 | n = 211 |
|  | 9 (4.3%) | 29 (13.7%) |
| 0.25–2.00 | n = 83 | n = 89 |
|  | 2 (2.4%) | 9 (10.1%) |
| 2.00–3.00 | n = 114 | n = 116 |
|  | 5 (4.4%) | 11 (9.5%) |
| 3.00–4.00 | n = 44 | n = 44 |
|  | 1 (2.3%) | 3 (6.8%) |
| 4.00–5.00 | n = 61 | n = 61 |
|  | 0 | 2 (3.3%) |
| 5.00–6.00 | n = 49 | n = 50 |
|  | 2 (4.1%) | 3 (6.0%) |
| >6.00 | n = 44 | n = 46 |
|  | 1 (2.3%) | 4 (8.7%) |

Other Embodiments

Other embodiments are within the following claims. In a preferred embodiment, the AICA riboside (or prodrug) is lyophilized to avoid variable discolorization. Pro-drugs may also be utilized, i.e., thoses which, when introduced to the body, are metabolized to the active forms of AICA riboside. AICA riborise prodrug compound comprise a modified AICA riboside and may have an AICA ribosyl moiety and at least one hydrocarbyloxycarbonyl or hydrocarbylcarbonyl moiety per equivalent weight of AICA ribosyl moiety. Such prodrugs of AICA riboside commonly exhibit one or more of the following improvements over AICA riboside, including: (1) more potent adenosine releasing effects; (2) increased half life; (3) increased brain penetration; (4) increased oral bioavailability; (5) increased myocardial targeting; and (6) in some cases, efficacy improvements over AICA riboside itself.

AICA riboside and prodrugs thereof ("AICA riboside compounds") can be administered in any standard manner using pharmaceutically acceptable buffers. To deliver AICA riboside compounds to patients, it is anticipated that they may be administered intravenously, by intracoronary or intraarterial infusion, by direct intramuscular injection, subcutaneously, orally, topically to the skin or mucous membranes, rectally or by inhalation. AICA riboside compounds may also be introduced into a patient's blood extracorporeally, for example, using a heart-lung machine or dialysis. Compounds acceptable for pharmaceutical use are well known.

Preferably, AICA riboside compounds are administered prophylactically. When such compounds are present in advance of an ischemic event, the net breakdown of ATP can be beneficially directed in larger measure to adenosine rather than inosine, and thus prevent tissue damage. If a drug is introduced into a patient to reach an ischemic region during or after an event causing ischemia, there is less ability to direct ATP to adenosine at that site because the target ATP pools are depleted relatively quickly. With a drug present as a prophylactic agent, there is also the possibility that the process sought to be interrupted can be slowed early enough to prevent the event or any permanent damage.

Other factors make it important to administer the drug before and/or during an ischemic event. If the drug is administered after blockage, it is less able to reach the tissue involved because there is little or no blood flow to the area, unless the ischemic area has undergone corrective reperfusion, such as by tPA adninistration, angioplasty or by-pass surgery. It is also believed that, for example, AICA riboside is metabolized to AICA ribotide and that this is one active form of the molecule. This metabolism is an energy-requiring reaction which utilizes ATP. If ATP is not available because of high metabolic activity and/or increased ATP destruction, then the ATCA riboside cannot be made into this active form.

Example 1

Improved Functional Recovery in Isolated Hearts

The ability of a number of the preferred AICA riboside analogs to improve recovery of post-ischemic cardiac function was examined in an isolated rat heart model.

Isolated rat hearts were cannulated via the ascending aorta and attached to a perfusion apparatus according to the method of Langendorff. The hearts were perfused at a constant pressure of 100 cm of $H_2O$ with a modified Krebs-Henseleit buffer (pH 7.4) at 37° C. As a measure of heart function, left ventricular developed pressure (LVDP) was continuously monitored. Following equilibration of the hearts for a period of 30 min, the hearts were subjected to reduced flow i.e. ischemia, by reducing the pressure to 10 cm of $H_2O$ for 30 min. Flow was then restored by returning the pressure to its original level (100 cm of $H_2O$) for a further 30 min. Each of the AICA riboside analogs together with AICA riboside itself, for comparison, was added to the perfusion buffer to a final concentration of 5 µM or 20 µM. The results are shown in Table I.

TABLE I

| Series | Compound No. | Conc. (µM) | Function Recovery % Baseline LVDP (# of hearts) | P value |
|---|---|---|---|---|
|  | Perfusion Buffer Control (Post Ischemia) | — | 64.9 ± 0.7 (125) | — |
|  | 1 (1-110) | 20 | 79.4 ± 1.3 (34) | .0001 |
|  |  | 5 | 64.2 ± 1.5 (6) | NS[1] |

TABLE I-continued

| Series | Compound No. | Conc. (μM) | Function Recovery % Baseline LVDP (# of hearts) | P value |
|---|---|---|---|---|
| I | 10 (1-186) | 20 | 84.5 ± 3.5 (2) | .0024 |
| | | 5 | 83.7 ± 0.7 (6) | .0001 |
| | 11 (1-226) | 20 | 85.7 ± 6.2 (3) | .0002 |
| | | 5 | 77.2 ± 5.8 (7) | NS[1] |
| | 16 (1-273)[2] | 5 | 83.1 ± 3.2 (5) | .0001 |
| | 23 (1-343) | 1 | 79.0 ± 2.3 (6) | .0002 |
| | 25 (1-360) | 5 | 86.8 ± 2.3 (6) | .0001 |
| | | | 72.4 ± 1.6 (6) | .0289 |
| | 37 (1-270) | 5 | 71.9 ± 3.0 (5) | .0500 |
| | 29 (1-349) | 1 | 76.7 ± 2.9 (7) | .0028 |
| | 40 (1-392)[2] | 20 | 78.5 ± 3.7 (8) | <.005 |
| | 47 (1-450) | 1 | 74.0 ± 2.8 (6) | .0045 |
| | 52 (1-467) | 5 | 86.0 ± 2.5 (5) | .0001 |
| | 53 (1-468) | 5 | 85.6 ± 1.8 (10) | .0001 |
| | 59 (1-506) | 1 | 75.8 ± 2.2 (7) | .0001 |
| | 68 (1-538) | 5 | 75.3 ± 2.2 (4) | .0033 |
| | 69 (1-549) | 5 | 77.0 ± 2.8 (6) | .0002 |
| | 74 (1-572) | 5 | 73.3 ± 3.3 (6) | .0012 |
| II | 27 (1-395) | 5 | 74.6 ± 3.7 (7) | .0060 |
| | 67 (1-535) | 5 | 77.4 ± 5.7 (3) | .0045 |
| III | 19 (1-154) | 20 | 85.5 ± 1.7 (5) | .0001 |
| | 21 (1-227) | 5 | 81.0 ± 3.2 (8) | .0001 |
| | | 1 | 77.0 ± 4.4 (10) | .0007 |
| | 26 (1-332) | 5 | 70.7 ± 4.1 (8) | .0466 |
| | 62 (1-510) | 5 | 75.5 ± 2.3 (4) | .0049 |
| | 63 (1-517) | 5 | 79.7 ± 4.8 (4) | .0001 |
| | 65 (1-522) | 5 | 72.3 ± 5.6 (4) | .0410 |
| | 66 (1-531) | 5 | 88.5 ± 1.8 (5) | .0001 |
| | 76 (1-578) | 5 | 74.0 ± 2.5 (6) | .0016 |

[1]NS = not significant
[2]Known compound

Example 2

Inhibition of Contraction in Isolated Ileum

The ability of the preferred AICA riboside analogs to inhibit stimulated contraction of muscle strips from the isolated ileum has been compared.

Segments (.about.1 cm) of longitudinal muscle were stripped from the guinea pig ileum, connected to isotonic force transducers and suspended in jacketed tissue baths containing Krebs-Ringer Solution aerated with 95% $O_2$/5% $CO_2$ Parallel platinum electrodes were used to deliver electrical current at 1 minute intervals at a voltage adequate to induce contraction of 90% of maximal. Test compounds were added to the tissue baths and the concentrations which inhibited contraction by 50%, ($IC_{50}$) determined. These are detailed in Table II.

TABLE II

| Series | Compound No. | $IC_{50}$ (μM) |
|---|---|---|
| | 1 (1-110) | >1000 |
| I | 11 (1-226) | 200 |
| | 12 (1-232) | 400 |
| | 23 (1-343) | 3 |
| | 24 (1-354) | 400 |
| | 25 (1-360) | 20 |
| | 29 (1-349) | 60 |
| | 35 (1-355) | 60 |
| | 39 (1-390) | 500 |
| | 41 (1-396) | 100 |
| | 42 (1-431) | 6 |
| | 44 (1-434) | 20 |
| | 45 (1-438) | 100 |
| | 47 (1-450) | 10 |
| | 53 (1-468) | 70 |
| | 30 (1-388) | 20 |

TABLE II-continued

| Series | Compound No. | $IC_{50}$ (μM) |
|---|---|---|
| II | 27 (1-395) | 500 |
| | 43 (1-432) | 200 |
| III | 21 (1-227) | 800 |
| | 26 (1-332) | 200 |
| IV | 32 (1-262) | 100 |

Example 3

Effect of AICA Riboside Analogs (Series I) in the Rat Heart Ischemia Model

Series I(N-4) substituted AICA riboside analogs were tested for their ability to enhance tissue adenosine levels in ischemic rat hearts.

Figure 19:
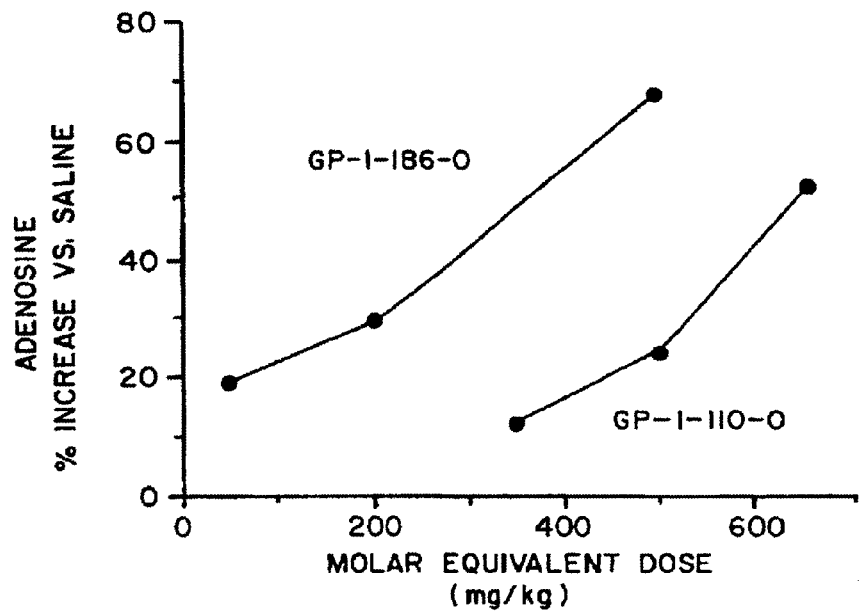
FIG. 19 depicts a comparison of the dose-dependent effects of AICA riboside (Compound No. 1 of Tables XII and XIII (1-110)) and an N-4 (Series I) substituted AICA riboside analog (Compound No. 10 (1-186)) on tissue adenosine levels in a rat heart ischemia model.

Male rats were injected intraperitonealy with either the AICA riboside analog, AICA riboside or saline, as a control. After 60 minutes, the hearts were excised and incubated at 37° C. for a further 60 minutes. Tissue extracts were prepared and analyzed for adenosine by high performance liquid chromatography (HPLC). The ability of this preferred series of AICA riboside analogs to increase tissue adenosine levels compared to AICA riboside is shown in Table III. A more detailed comparison of the dose-dependent effects on tissue adenosine levels of a selected AICA riboside analog in this preferred series (Compound No. 10) compared to AICA riboside (Compound No. 1) is shown in FIG. 19.

TABLE III

| Compound No. | Tissue Adenosine Levels (% Increase vs. Saline) |
|---|---|
| 1 (1-110) | 30 |
| 10 (1-186) (Expt 1) | 79 |
| 10 (1-186) (Expt 2) | 68 |
| 11 (1-226) (Expt 1) | 53 |
| 11 (1-226) (Expt 2) | 45 |
| 12 (1-232) | 29 |
| 36 (1-207) | 34 |

Example 4

Inhibition of Adenosine Utilization by Aica Riboside Analogs (Series I) in Cell Culture Effects of Series I (N-4) substituted AICA riboside analogs on adenosine utilization were compared using coronary endothelial cells in culture. In this assay, endothelial cells were incubated with 5 μM or 50 μM of the test compound together with 1 μM [$^3$H] adenosine for 15 minutes. Inhibition of adenosine utilization was determined by measuring the concentration of extracellular adenosine by scintillation counting following separation by thin layer chromatography (TLC). The results of this evaluation are shown in Table IV.

TABLE IV

| | Inhibition of Adenosine Utilization (%) | |
|---|---|---|
| Compound No. | 5 μM | 50 μM |
| 1 (1-110) | 5 ± 2 | 10 ± 1 |
| 23 (1-343) | 27 ± 4 | 63 ± 2 |

TABLE IV-continued

| Compound No. | Inhibition of Adenosine Utilization (%) | |
|---|---|---|
| | 5 µM | 50 µM |
| 28 (1-348) | 17 ± 3 | 47 ± 2 |
| 29 (1-349) | 41 ± 11 | 67 ± 8 |
| 25 (1-360) | 21 ± 1 | 56 ± 2 |
| 30 (1-388) | 21 ± 1 | 49 ± 4 |
| 38 (1-351)[2] | 16 ± 1 | 44 ± 0 |
| 39 (1-390) | 7 ± 4 | 29 ± 1 |
| 46 (1-445) | 19 ± 4 | 30 ± 9 |
| 47 (1-450) | 17 ± 3 | 19 ± 2 |
| 48 (1-452) | 23 ± 3 | 25 ± 2 |
| 49 (1-453) | 30 ± 4 | 33 ± 8 |
| 51 (1-466) | 27 ± 2 | 65 ± 2 |
| 52 (1-467) | 56 ± 2 | 71 ± 1 |
| 53 (1-468) | 34 ± 4 | 58 ± 2 |
| 56 (1-487) | 55 ± 7 | 65 ± 9 |
| 61 (1-509) | 37 ± 28 | 72 ± 5 |
| 71 (1-562) | 10 ± 3 | 31 ± 11 |
| 73 (1-566) | 16 ± 0 | 33 ± 9 |
| 75 (1-577) | 8 ± 0 | 30 ± 3 |

[2] Known compound

Example 5

Effect of Aica Riboside Analogs (Series I) in [$^3$H]-NBTI Binding Assay

The ability of selected Series I (N-4) substituted AICA riboside analogs to effect the binding of [$^3$H]-nitrobenzylthioinosine (NBTI) to cell membranes was compared. Increasing concentrations of the test compounds were incubated for 30 minutes with 0.5 mg neuronal membrane protein together with 0.5 nM [$^3$H]-NBTI in a Tris buffer (pH 7.4) at room temperature. The assays were quenched and membranes collected by rapid filtration. Filters were then solubilized and radioactivity determined by scintillation counting. The concentration of each test compound which resulted in 50% displacement of bound, [$^3$H]-NBTI, the $ED_{50}$'s, are detailed in Table V.

TABLE V

| Series | Compound No. | $ED_{50}$ (µM) |
|---|---|---|
| | 1 (1-110) | >1000 |
| I | 10 (1-186) | 350 |
| | 24 (1-354) | 300 |
| | 35 (1-355) | 190 |
| | 29 (1-349) | 100 |
| | 25 (1-360) | 72 |
| | 28 (1-348) | 15 |
| | 23 (1-343) | 3 |
| | 30 (1-388) | 225 |
| | 39 (1-390) | 600 |
| | 44 (1-434) | 100 |
| | 45 (1-438) | 90 |
| | 46 (1-445) | 8 |
| | 47 (1-450) | 0.5 |
| | 48 (1-452) | 22 |
| | 49 (1-453) | 7 |
| | 50 (1-459) | 28 |
| | 51 (1-466) | 16 |
| | 52 (1-467) | 80 |
| | 53 (1-468) | about 100 |
| | 55 (1-484) | 60 |
| | 56 (1-487) | 32 |
| | 57 (1-488) | 80 |
| | 58 (1-489) | 80 |
| | 59 (1-506) | 2 |
| | 60 (1-508) | 17 |
| | 61 (1-509) | 32 |
| | 64 (1-519) | 48 |
| II | 27 (1-395) | 344 |
| | 43 (1-432) | 71 |
| III | 54 (1-483) | 28 |

Example 5A

Inhibition of Adenosine Transport in WI-L2 Lymphoblasts

Inhibition of adenosine transport in WI-L2 lymphoblasts in the presence of one of the AICA riboside analogs of the present invention was determined according to the following procedure.

A 200 µl aliquot of WI-L2 lymphoblast cell suspension (0.5×106) was layered on top of 100 µl of a silicone oil:mineral oil mixture (8:2 by volume). Compound No. 53 (1-468) at concentrations of 5.0, 50.0 and 500.0 µM, respectively, was added to the cells and the resulting mixture was incubated for either 1 minute or 1 hour. Then, 5 µl of radio-labelled adenosine (2.5 µCi initial concentration of 1 µM) were added to the cell suspension and the mixture was incubated for 10 seconds. Cells were then centrifuged for 15 seconds at 13,000 rpm and the cell pellets were measured for radioactivity.

Figure 22:
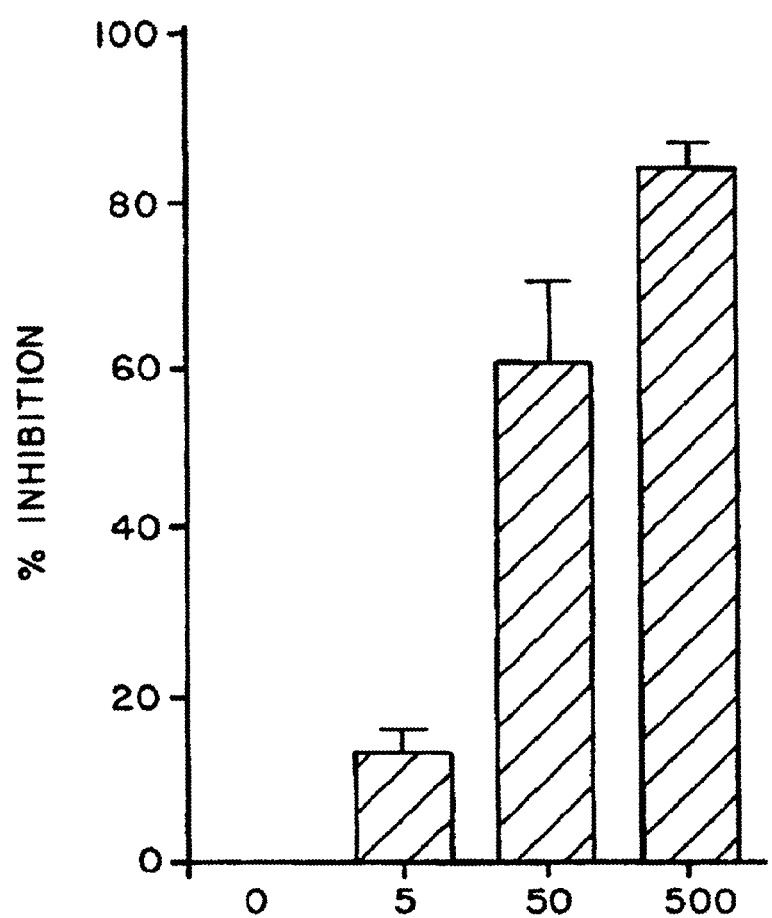
FIG. 22 depicts inhibition of adenosine transport in WI-L2 lymphoblasts after 1 minute preincubation with Compound No. 53 (1-468) at the noted concentrations.
Figure 23:
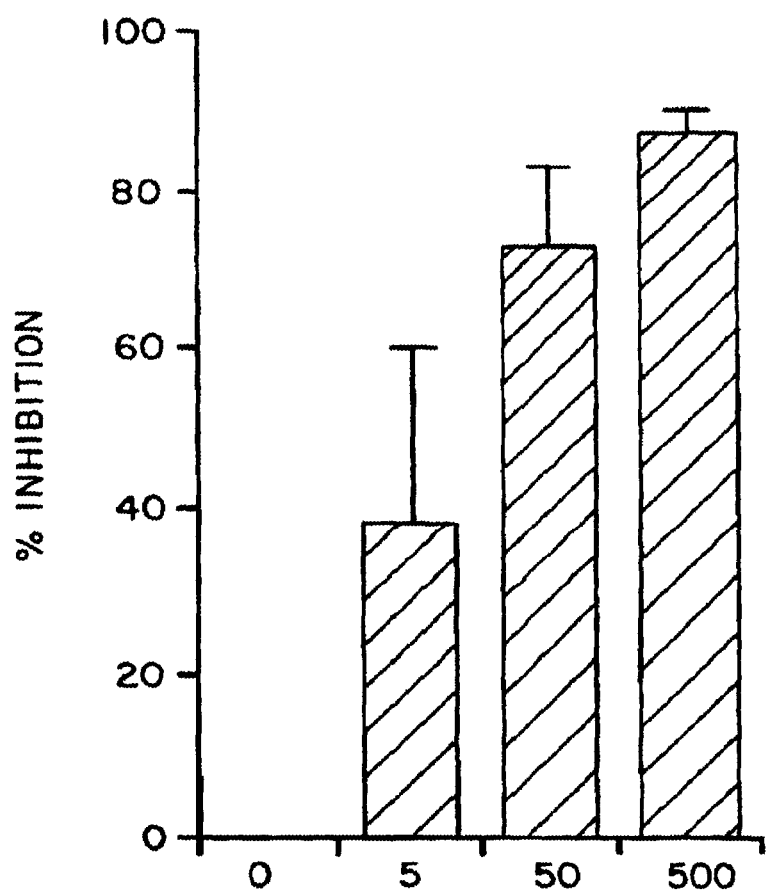
FIG. 23 depicts inhibition of adenosine transport in WI-L2 lymphoblasts after 1 hour preincubation with Compound No. 53 (1-468) at the noted concentrations.

FIG. 22 depicts inhibition of adenosine transport with 1 minute preincubation with compound No. 53 (1-468) and FIG. 23 depicts inhibition of adenosine transport with 1 hour preincubation with compound No. 53 (1-468).

Example 6

Effect of an AICA Riboside Analog (Series III on Adenosine Release from Isolated Cells A Series II (C-2)-substituted AICA riboside analog was compared with AICA riboside itself for its ability to influence adenosine release from coronary endothelial cells. In this experimental model the cells were treated with 50 µM of the test compound and incubated for 16 hours at 37° C. Cells were then washed with phosphate-buffered saline and resuspended in standard culture medium containing no glucose (to inhibit glycolysis), 50 µM antimycin A (to inhibit oxidative phosphorylation) and 20 µM deoxycoformycin (to inhibit adenosine utilization by adenosine deaminase). This treatment was designed to simulate ischemic condition by inducing net ATP breakdown. Media was then processed for HPLC. Adenosine values are given in Table VI.

TABLE VI

| Compound No. | Extracellular Adenosine Levels (µM) | Increase (%) |
|---|---|---|
| Control | 1.42 ± 0.17 | — |
| 1 (1-110) | 1.64 ± 0.12 | 15.5 |
| 13 (1-240) | 2.79 ± 0.19 | 96.5 |

Example 7

Effect of Aica Riboside Analogs (Series II) on Adenosine Kinase Activity

Inhibition of enzyme activity was determined using a 0.1 ml assay mixture containing 50 mM Tris-maleate, pH 7.0, 0.1% (w/v) BSA, 1 mM ATP, 1 mM MgCl$_2$, 0.5 µM [U$^{14}$C] adenosine (500 mCi/mmol) and 0.1 µg of purified pig heart adenosine kinase. Different concentrations of test compound were incubated in the assay mixture for 20 minutes at 37° C. From each reaction mixture, 20 µl portions were removed and spotted on 2$^2$ pieces of Whatman DE81 filter paper. The papers were then washed to remove [$^{14}$C] adenosine in 1 mM ammonium formate followed by deionized water and finally 95% ethanol. The papers were dried, and [$^{14}$C] AMP measured by scintillation counting. Activities were determined from the amount of [$^{14}$C] AMP formed.

The results are shown in Table VII.

TABLE VII

| Compound No. | IC$_{50}$ (µM) |
|---|---|
| 1 (1-110) | >5000 |
| 27 (1-395) | 8 |
| 67 (1-535) | 23 |
| 70 (1-551) | 17 |

Example 8

Figure 20A:
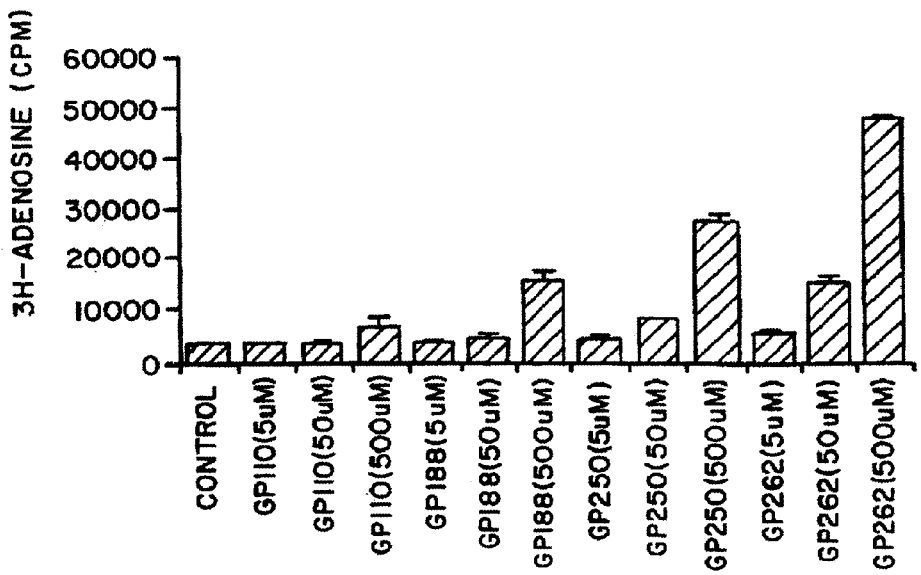
FIGS. 20A-C depicts a comparison of the effect of AICA riboside (Compound No. 1 and a series of 2'-(Series IV) substituted AICA riboside analogs (Compound Nos. 20 (1-188), 34(1-250) and 32 (1-262)) on utilization of adenosine (together with inosine and hypoxanthine) in a cell culture model.

Effect of Aica Riboside Analogs (Series IV) on Adenosine Utilization in Isolated Cells Series IV 2'-substituted AICA riboside analogs were tested for their ability to inhibit adenosine utilization in human B lymphoblasts. In this assay, cells were preincubated with the test compound at a concentration of 5 µM, 50 µM or 500 µM together with [$^3$H]-adenosine (1 µM) for a period of 10 minutes. Inhibition of adenosine utilization was determined from the extracellular concentration of [$^3$H] adenosine measured by scintillation counting following separation of the nucleosides by TLC. Hypoxanthine and inosine levels were also measured. The results from a comparison of 2'-O-methyl (Compound No. 20) 2'-O-ethyl (Compound No. 34) and 2'-O-n-butyl (Compound No. 32) analogs of AICA riboside compared to AICA riboside are shown in FIG. 20A.

Figure 20B:
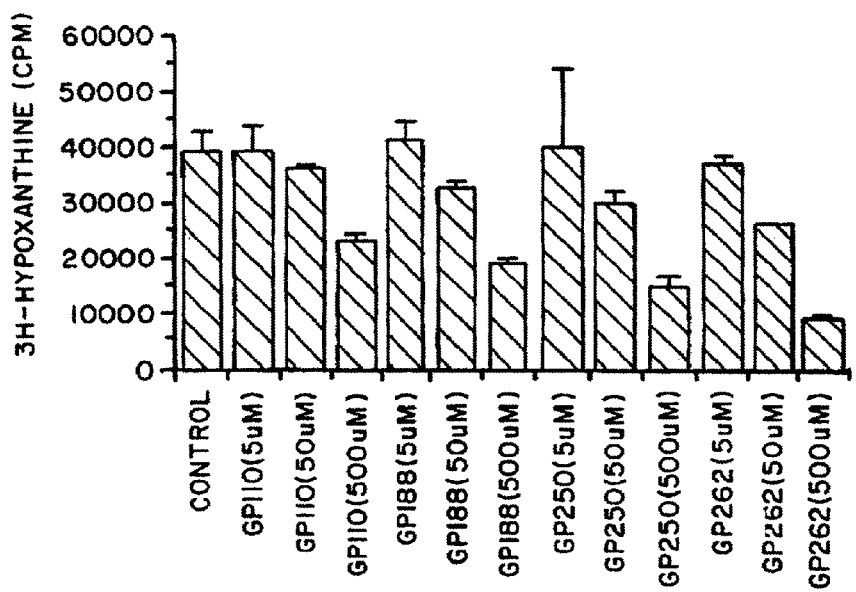
Figure 20C:
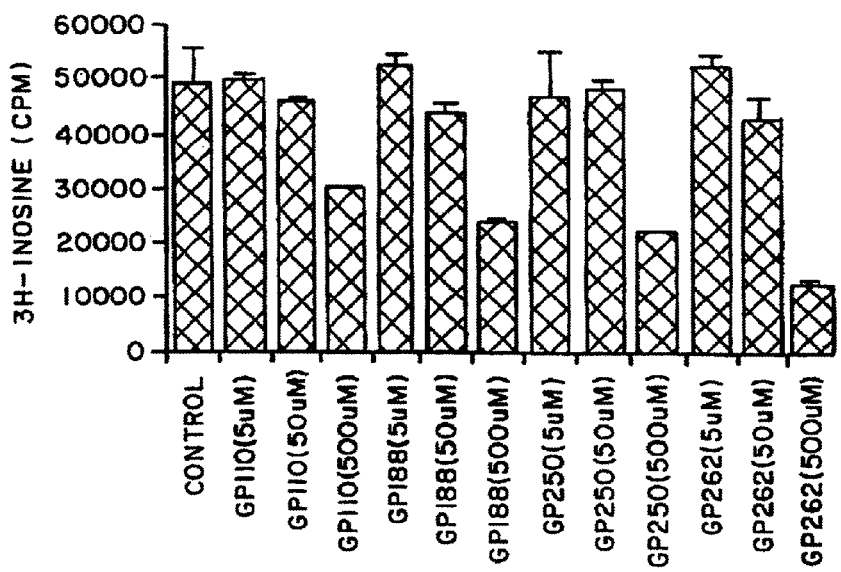

The effects of these AICA riboside analogs on hypoxanthine and inosine levels (shown in FIGS. 20B and 20C, respectively) mirror those effects on adenosine levels suggesting an augmented influence on adenosine utilization mediated by inhibition of adenosine deaminase. This interpretation is supported by direct measurement of the ability of the analogs to inhibit the isolated adenosine deaminase.

Inhibition of adenosine deaminase activity was determined spectrophotometrically using a 1 ml assay mixture containing 50 mM potassium phosphate, pH 7.0, 1 mM alphaketoglutarate, 15 units glutamic dehydrogenase, 0.125 mM NADH, 80 µM adenosine and 0.002 units of calf intestinal musosa adenosine deaminase. Different concentrations of the test compounds were incubated in the assay mixture for 10 minutes at 37° C. The reaction was monitored continuously for oxidation of NADH from the change in absorbance at 340 nm.

The results are shown in Table VIII.

TABLE VIII

| Compound No. | IC$_{50}$ (µM) |
|---|---|
| 1 (1-110) | >5000 |
| 20 (1-188) | 1400 |
| 34 (1-250) | 510 |
| 32 (1-262) | 175 |

Example 9

Effect of AICA Riboside Analogs on Inhibition of Platelet Aggregation in Human Whole Blood The ability of preferred AICA riboside analogs to inhibit platelet aggregation was examined in human whole blood. Whole blood was drawn from healthy donors and collected in 0.1 vol. of sodium citrate to prevent coagulation. Platelet aggregation was measured by the impedance technique using a Whole Blood Aggregometer. The test compounds were incubated in whole blood for 10 minutes at 37° C. and 10 gM adenosine was added 5 minutes before eliciting aggregation. Aggregation was induced by addition of ADP (6-25 µM) at the minimum concentration inducing full aggregation in untreated controls.

The results are shown in Table IX.

TABLE IX

| Series | Compound No. | IC$_{50}$ (µM) |
|---|---|---|
|  | 1 (1-110) | 2700 |
| I | 4 (1-122) | 200 |
|  | 23 (1-343) | 38 |
|  | 28 (1-348) | 180 |
|  | 29 (1-349) | 90 |
|  | 51 (1-466) | 193 |
|  | 52 (1-467) | 480 |
|  | 53 (1-468) | 150 |
|  | 56 (1-487) | 75 |
|  | 59 (1-506) | 70 |
|  | 61 (1-509) | 171 |
|  | 71 (1-562) | 40 |
|  | 72 (1-563) | 300 |
| II | 27 (1-395) | 950 |
|  | 43 (1-432) | 620 |
| IV | 32 (1-262) | 350 |

Example 10

Enhanced Oral Bioavailability and Half-Life of AICA Riboside Analogs

Certain preferred AICA riboside analogs were evaluated for enhanced oral bioavailability in fasted adult beagles. AICA riboside analogs were given as a 10 mg/kg IV bolus via a cephalic leg vein and as a 20 mg/kg solution administered via a stomach tube. Heparinized blood and urine were collected at selected intervals over 24 hours. Each sample was chilled, centrifuged at 4° C. and frozen prior to HPLC analysis.

The results are shown in Table X.

TABLE X

| Series | Compound No. | Absolute Oral Bioavailability % | Half Life (hours) |
|---|---|---|---|
|  | 1 (1-110) | 8 ± 4 (n = 7) | 0.35 |
| I | 53 (1-468) | 32 ± 11 (n = 2) | 5.61 |
| III | 21 (1-227) | 71 ± 13 (n = 2) | 1.30 |

Example 11

Functional Benefits of Compound No. 53(1-468) in a Preclinical Model of Stable Angina The AICA riboside analog (1-468) was evaluated for its ability to prevent cumulative cardiac dysfunction associated with repeated episodes of demand-induced ischemia. Anesthetized male dogs were instrumented to measure regional myocardial wall thickening during right atrial pacing in the presence of a stenosis of the left anterior descending artery (Young & Mullane Am. J. Physiol. in press (1991)). In Table XIA, the effects on wall thickening and arterial pressure of six repeated episodes of pacing in animals treated with a continuous IV infusion of 50 µg/kg/min of the test compound administered post-pace #1 are compared with saline-treated control animals. In Table XIB, the change in heart rate and mean arterial pressure in the post-pace rest period are listed, demonstrating that preservation of wall thickening occurred in the absence of significant hemodynamic effects.

TABLE XIA

% of NON-ISCHEMIC WALL THICKENING

| Pace # | Saline (N = 9) | Compound No. 53 (n = 6) |
|---|---|---|
| 1 | 41.6 ± 2.6 | 49.5 ± 6.5 |
| 2 | 31.7 ± 4.6 | 46.7 ± 7.0 |
| 3 | 25.8 ± 5.6 | 54.2 ± 9.4* |
| 4 | 18.5 ± 5.5 | 48.1 ± 7.6* |
| 5 | 11.8 ± 5.6 | 47.5 ± 8.2* |
| 6 | 12.4 ± 6.0 | 42.1 ± 7.0* |

*P < 0.05 vs. saline

TABLE XIB

Post Pace Rest Period (Change from Baseline)

|  | Baseline | 1 | 2 | 3 | 4 | 5 | 6 |
|---|---|---|---|---|---|---|---|
| Mean Arterial Pressure (mm Hg) | | | | | | | |
| Saline | 86 ± 2 | 0 ± 1 | −2 ± 2 | −1 ± 2 | −3 ± 2 | −2 ± 2 | −2 ± 2 |
| Test Compound | 86 ± 5 | −1 ± 3 | −2 ± 3 | −8 ± 3 | −7 ± 3 | −8 ± 3 | −7 ± 3 |
| Heart Rate (beats/min) | | | | | | | |
| Saline | 113 ± 7 | 2 ± 2 | 4 ± 3 | 8 ± 3 | 9 ± 4 | 11 ± 5 | 13 ± 5 |
| Test Compound | 143 ± 6 | 1 ± 2 | −2 ± 4 | −1 ± 3 | 2 ± 4 | 1 ± 4 | 2 ± 4 |

Example 12

Effect of Aica Riboside Analogs (Series I) in an Experimental Stroke Model

The ability of Series I (N-4) substituted AICA riboside analogs to effect hippocampal pyramidal cell survival in a gerbil stroke model was evaluated. In this test, male Mongolian gerbils were anesthetized with 2-3% halothane in $N_2O:O_2$ and the common carotid arteries exposed. Ischemia was then induced by bilateral occlusion of both common carotid arteries for 5 minutes. Seven days following the ischemic insult, brains were removed and processed for histology. The data presented in FIG. 21 shows the effect of pretreatment of the gerbils with 500 mg/kg of the AICA riboside analogs (Compound Nos. 10 (1-186) or 11 (1-226)) or with saline, as a control.

Example A

Preparation Of 5-Amino-(2,3,5-tri-O-acetyl-beta-D-ribofuranosyl)imidazole-4-carboxamide (Compound No. 2 (1-111))

AICA riboside (50 g) was dissolved in pyridine (450 ml) and then cooled in an ice bath. Acetic anhydride (80 ml) was added and the ice bath removed. The reaction mixture was stirred for 3 hrs. TLC on silica gel, eluting with 9:1 methylene chloride:methanol, showed the reaction to be complete. Methanol (5 ml) was added to neutralize unreacted acetic anhydride. The solvents were removed by evaporation under high vacuum (bath temperature less than 40° C.). The residue was coevaporated with dimethylformamide (3×150 ml). The residue was crystallized from ethanol using seed crystals. The yield of the triacetate 62 g of white solid; melting point 128°-129° C.

NMR (DMSO-$d_6$) Δ ppm 2.05-2.15 (2s, 9H, —$CH_3$), 4.3 (broad s, 3H, 4'-CH, 5'-$CH_2$), 5.3 (m, 1H, 3'-CH) 5.55 (t, 1H, 2'-CH), 5.87 (d, 1H, 1'-CH), 5.9 (broad s, 2H, 5-$NH_2$), 6.7-6.9 (broad d, 2H, 4-$NH_2$), 7.4 (s, 1H, 2-CH).

The preparation this compound is also described in U.S. Pat. No. 3,450,693 to K. Suzuki & I. Kumoshiro (1969); See also Chem. Abs. 71: 816982 (1969).

Example B

Preparation of $N^5$ dimethylaminomethyleneamino-beta-D-ribofuranosylimidazole-4-carboxamide (Compound No. 7 (1-164))

Dissolved 2',3',5'-tri-O-acetyl AICA riboside (10 g) in dimethylformamide (30 ml) and dimethylformamide dimethyl acetal (20 ml). The reaction mixture was allowed to stir overnight. TLC on silica gel, eluting with 9:1 methylene chloride:methanol, showed that the reaction was complete by absence of starting material. The solvent was removed by evaporation under high vacuum (bath temperature less than 40° C.). The residue was dissolved in cyclohexylamine and stirred overnight. The solvent was removed by evaporation under reduced pressure and the residue was crystallized from ethanol. Yield was 4.6 g of white solid, melting point 173°-175° C.

NMR (MeOH-$d_4$), Δ ppm 3.0-3.05 (2s, 6H, N($CH_3$)$_2$), 3.75 (m, 2H, 5'-$CH_2$), 4.0 (g, 1H, 4'-CH), 4.2 (t, 1H, 3'-CH), 4.35 (t, 1H, 2'-CH), 5.8 (d, 1H, 1'-CH), 7.7 (s, 1H, 2-CH), 8.25 (s, 1H, 5-N=CH—N).

Example C

Preparation of 5-Amino-1-beta-D-ribofuranosylimidazole-4-N-(cyclopentyl)carboxamide (Compound No. 10 (1-186))

The literature procedure of P. C. Srivastava, R. W. Mancuso, R. J. Rosseau and R. K. Robins, J. Med. Chem. 17(11), 1207 (1977) was followed to synthesize N-succinimidyl-5-amino-1-(2,3,5-tri-O-acetyl-β-D-ribofuranosyl)imidazole-4-carboxylate ("intermediate No. 4"). Intermediate No. 4 (3.9 g) was dissolved in methylene chloride (60 ml). Cyclopentylamine (0.8 ml) was added and the solution was stirred overnight. TLC on silica, eluting with 9:1 methylene chloride:methanol, showed the reaction was complete by absence of starting material. The solvent mixture was extracted with 5% hydrochloric acid solution (100 ml), saturated sodium bicarbonate solution (100 ml) and water (200 ml). The organic layer was dried over sodium sulfate and evaporated under reduced pressure to give 3.1 g of yellow foam. The acetyl groups were removed by dissolving the 3.1 g of foam in methanol (70 ml) and cooling in an ice bath. Ammonium hydroxide (60 ml) was added and the ice bath was removed. After 2½ hours stirring, TLC on silica gel, eluting with 9:1 methylene chloride:methanol, showed all starting material was gone. The solvent was evaporated under reduced pressure to give a residue which was purified on a silica column, eluting with 9:1 and 6:1 methylene chloride:methanol. Fractions which were alike by TLC were pooled and evaporated under reduced pressure to yield 1.1 g of white foam crystallized from methanol-ethyl acetate, melting point 158°-160° C.

NMR (DMSO-$d_6$), Δ ppm 1.4-1.9 (m, 8H, —CH$_2$—CH$_2$—), 3.6 (m, 2H, 5'-CH$_2$), 3.9 (d, 1H, NH—CH), 4.0-4.35 (m, 3H, 2',3',4'-CH), 5.15-5.4 (m, 3H, 2',3',5'-OH), 5.45 (d, 1H, 1'-CH), 5.9 (broad s, 2H, —NH$_2$), 7.1 (d, 1H, —NH—), 7.3 (s, 1H, 2-CH).

Example D

Preparation of 5-Amino-1-beta-D-ribofuranosylimidazole-4-N-(cyclopropyl)carboxamide (Compound No. 12 (1-232))

This compound was prepared following the procedure described in Example C except cyclopropylamine (0.5 ml) was substituted for cyclopentylamine (0.8 ml). The yield starting with 6.2 g of intermediate No. 4 (the succinate ester) was 2.3 g.

NMR (DMSO-$d_6$) Δ ppm 0.5 (m, 4H, CH$_2$ CH$_2$) 2.7 (m, 1H, N—CH), 3.6 (m, 2H, 5'-CH$_2$), 3.8-4.3 (m, 3H, 2',3',4'-CH), 5.15-5.4 (m, 3H, 2',3',5' OH) 5.45 (d, 1H, 1'-CH), 5.9 (s, 2H, NH$_2$), 7.2 (s, 1H, 2-CH) 7.4 (d, 1H, 4-NH).

Example E

Preparation of 5-Amino-1-beta-D-ribofuranosylimidazole-4-N-(benzyl)carboxamide (Compound No. 11 (1-226))

Inosine (10 g) was suspended in dimethylformamide (100 ml) and dimethylformamidedibenzylacetal (25 ml). The resulting mixture was stirred at 70° C. overnight. TLC on silica, eluting with 6:1 methylene chloride:methanol, showed completion of reaction. Solvent was removed by evaporation at reduced pressure. The remainder was dissolved in ammonium hydroxide (130 ml). The mixture was stirred overnight, then evaporated under reduced pressure. Ethanol (80 ml) was added to the residue and the resulting mixture was warmed. The solid was collected by filtration. Yield of 1-benzylinosine was 10.5 g which was characterized by NMR.

The intermediate, 1-benzylinosine (10.5 g), was dissolved in ethanol (1.0 L) and 3M sodium hydroxide solution (140 ml). This solution was refluxed for 3 hours. TLC on silica showed the reaction was complete. The solvent was removed by evaporation under reduced pressure. The residue was chromatographed on a silica gel column, eluting with 6:1 methylene chloride:methanol. Fractions were collected which were similar by TLC and concentrated until crystals appeared. Yield was 7.4 g of the above-identified compound as a white solid, melting point 178°-179° C.

NMR (DMSO-$d_6$) Δ ppm 3.6 (m, 2H, 5'-CH$_2$) 3.85-4.35 (m, 3H, 2',1',3',4'-CH), 4.4 (d, 2H, N—CH$_2$), 5.15-5.4 (m, 3H, 2',3',5'-OH), 5.5 (d, 1H, 1'-CH), 5.9 (broad s, 2H, 5-NH$_2$), 7.2-7.4 (m, 6H, 2-CH, C$_6$H$_5$) 7.95 (t, 1H, NH). See also E. Shaw, J.A.C.S. 80: 3899 (1958).

Example F

Preparation of 5-Amino-1-β-D-ribofuranosylimidazole-4-carboxylic acid methyl ester (Compound No. 14 (1-260))

5-amino-1-(2,3,5-tri-O-acetyl-β-D-ribofuranosyl)-imidazole-4-carboxylic acid (3.85 g, 10 mmol) was dissolved in 40 ml tetrahydrofuran and cooled to 0° C. An excess of diazomethane in ether was added and the mixture warmed to room temperature. Acetic acid was added to destroy excess diazomethane and the mixture was evaporated to dryness. The residue was purified by chromatography on silica gel, eluting with 7:3 ethyl acetate:hexane. The major product fractions, judged by silica thin layer chromatography (TLC) using the above system, were combined and evaporated to yield 1.2 g of a white foam. This was dissolved in 40 ml of methanol containing 20 mg of sodium methoxide and stirred for 30 minutes. Silica TLC, eluting with 6:1 methylene chloride:methanol, showed no remaining starting material and a new slower-moving product spot. The reaction was neutralized with Dowex 50 (H$^+$) resin and evaporated to yield 0.64 g of the desired product as a white foam. IR (KBr): 1725 cm$^{-1}$ (—CO—OCH$_3$).

NMR (DMSO-$d_6$): Δ ppm, 3.65 (s, 3H, CH$_3$), 3.8 (m, 3H, 4'-CH and 5'-CH$_2$), 4.1 (m, 1H, 3'-CH), 4.2 (m, 1H, 2'-CH), 5.5 (d, 1H, 1'-CH), 8.0 (s, 1H, 2-CH).

Example G

Preparation of 5-Amino-5'-sulfamoyl-1-β-D-ribofuranosyl-imidazole-4-carboxamide (Compound No. 15 (1-261))

A. Preparation of 5-Amino-2',3'-isopropylidene-1-β-D-ribofuranosyl-5-sulfamoylimidazole-4-carboxamide To a solution of 2',3'-isopropylidene-AICA-riboside (2.98 g, 10 mmol) in dry N,N-dimethylformamide (25 ml), sodium hydride (300 mg, 80% dispersion in oil) was added over a period of 10 min. After the evolution of hydrogen gas had ceased, the flask was immersed in an ice bath and the mixture was stirred for 30 min. A solution of sulfamoyl chloride (1.3 g, 11 mmol) in dry tetrahydrofuran (20 ml) was added slowly. TLC of the reaction mixture (silica gel, solvent 9:1 methylene chloride:methanol) indicated presence of some starting material. An additional 200 mg of sulfamoyl chloride in tetrahydrofuran (10 ml) was added and the resulting mixture stirred for one hour. Methanol (1 ml) was added and solvent was evaporated under high vacuum. The residue chromatographed over silica gel, eluting with a mixture of methylene chloride:methanol (9:1). Several fractions were collected. Fractions showing identical TLC patterns were pooled and evaporated to a glassy product. Yield was 1.5 g.

$^1$H-NMR (DMSO-$d_6$) Δ ppm, 1.25 and 1.55 (2s, 6H, C(CH$_3$)$_2$), 4.1 (d, 2H, 5'-CH$_2$), 4.25-4.35 (m, 1H, 4'-CH), 4.8-4.9 and 5.1-5.2 (2m, 2H, T-CH and 3'-CH), 5.8 (d, 1H, 1'-CH), 5.9 (s, 2H, 5-NH$_2$), 6.65-6.95 (broad d, 2H, CONH$_2$), 7.35 (s, 1H, 2-CH), 7.7 (s, 2H, SO$_2$ NH). The NMR data conformed to the structure of 5-amino-2',3'-isopropylidene-1-β-ribofuranosyl-5'-sulfamoylimidazole-4-carboxamide. This intermediate product was used in the following deblocking step without further purification or isolation.

B. Preparation of 5-Amino-5'-sulfamoyl-1-β-D-ribofuranosyl-imidazole-4-carboxamide Compound No. 15 (1-261)

The compound from the preceeding preparation was dissolved in 60% formic acid (20 ml) and the resulting solution was stirred at room temperature for 48 hours. The solvent was removed by evaporation under high vacuum. The residue was coevaporated with water. The product was crystallized from aqueous ethanol. Yield was 1.0 g of the above-identified product, melting point 174°-175° C.

$^1$H-NMR (DMSO-d$_6$) Δ ppm 3.9-4.3 (m, 5H, 2'-CH, 3'-CH, 4'-CH and 5'-CH$_2$), 5.4 and 5.5 (2d, 2H, 2'-OH and 3'-OH), 5.5 (d, 1H, 1'-CH), 5.8 (broad-s, 2H, 5-NH$_2$), 6.6-6.9 (broad-d, 2H, CONH$_2$), 7.3 (s, 1H, 2-CH) and 7.6 (s, 2H, SO$_2$ NH$_2$).

Example H

Preparation of 5'-Amino-5'-deoxy-AICA-riboside (Compound No. 21 (1-227))

A. Preparation of 5'-Azido-5'-deoxy-AICA-riboside

A mixture 5'-deoxy-5'-iodo-2',3'-isopropylidene-AICA riboside (8.0 g) (Ref: P. C. Srivastava, A. R. Newman, T. R. Mathews, and R. K. Robins, J. Med. Chem. 18 1237 (1975)), lithium azide (4.0 g), and N,N-dimethylformamide was heated at 80°-90° C. for 5 hours. The mixture was evaporated to dryness and the residue was chromatographed over silica gel column eluting with methylene chloride. The fast moving product-containing fractions were pooled and evaporated to obtain 7.2 g of a product which was subjected to deblocking with 60% formic acid (100 ml) at room temperature for 48 hours. Excess formic acid was removed by evaporation under high vacuum. The residue was coevaporated with water (3×25 ml) to obtain a semi-solid product. This product was crystallized from aqueous ethanol. Yield was 5.0 g, of the above-identified product, melting point 138°-139° C. $^1$H NMR (DMSO-d$_6$) Δ ppm 3.55 (d, 2H, 5'-CH$_2$), 3.95 (broad-s, 2H, 3'-CH and 4'-CH), 4.2-4.4 (m, 1H, 2'-CH), 5.35 and 5.50 (2d, 2H, 2'-OH and 3'-OH), 5.55 (d, 1H, 1'-CH), 5.75-5.9 (broad s, 2H, 5-NH$_2$), 6.6-6.9 (broad d, 2H, CONH$_2$) and 7.35 (s, 1H, 2-CH). IR (KBr) cm$^{-1}$: 3400-3000 (broad-NH$_2$, CONH$_2$, OH, etc.), 2150 (S, N$_3$) 1640 (CONH$_2$).

B. Preparation of 5'-Amino-5'-deoxy-AICA-riboside

A solution of 5'-azido-5'-deoxy-AICA-riboside (800 mg) (the product of step (A)) in methanol (40 ml) was hydrogenated in a Parr apparatus with palladium on carbon (5%) (100 mg) as the hydrogenation catalyst at 40 psi for 60 min. The catalyst was removed by filtration of the reaction mixture through a celite pad. The clear filtrate was evaporated to dryness. The product was crystallized from boiling ethanol. Yield was 650 mg of the above-identified product, melting point 188°-189° C. $^1$H-NMR (D$_2$O) Δ ppm, 2.7 (d, 2H, 5'-CH$_2$), 3.8-4.4 (3m, 3H, 2'-CH, 3'-CH and 4'-CH), 5.4 (d, 1H, 1'-CH) and 7.3 (s, 1H, 2-CH). IR (KBr) cm$^1$: 3500-3000 (broad OH, NH$_2$, CONH$_2$, etc.), 1640-1645 (broad-s. CONH$_2$).

Example I

Preparation of 5-Amino-1-(2-O-methyl-β-D-ribofuranosyl)-imidazole-4-carboxamide (Compound No. 20 (1-188)) and 5-Amino-1-(3-O-methyl-β-D-ribofuranosyl)imidazole-4-carboxamide (Compound No. 22 (1-243))

5-Amino-1-β-D-ribofuranosylimidazole-4-carboxamide (5.2 g, 20 mmol) was dissolved in 40 ml hot dimethylformamide and diluted with 70 ml methanol containing 35 mg tin(II) chloride dihydrate. A solution of 0.1 mol of diazomethane in 200 ml of ether was added in portions over 45 min. After each addition, 20 mg of tin(II) chloride dihydrate was added. The resulting mixture was filtered and evaporated to give a syrup. The syrup was dissolved in 25 ml of methanol and upon cooling yielded crystalline 5-amino-1-(2-O-methyl-β-D-ribofuranosyl)imidazole-4-carboxamide which was collected by filtration and dried. Yield was 1.2 g, melting point 114°-117° C. $^1$H NMR (DMSO-d$_6$) (for Compound 20) Δ ppm, 3.3 (s, 3H, CH$_3$), 3.6 (m, 2H, 5'-CH$_2$), 3.9 (m, 1H, 4'-CH), 4.1 (m, 1H, 2'-CH), 4.2 (in, 1H, 3'-CH), 5.2 (d, 1H, 3'-OH), 5.3 (t, 1H, 5'-OH), 5.6 (d, 1H, 1'-CH), 6.0 (broad s, 2H, 5-NH$_2$), 6.7 (broad-d, 2H, 4-CONH$_2$), 7.3 (s, 1H, 2-CH).

The supernatant from the above crystallization was concentrated and applied to a 200 ml column of silica gel. The column was eluted with 10:1 methylene chloride:methanol (1 L), 8:1 methylene chloride:methanol (500 ml) and 5:1 methylene chloride:methanol (500 nil). The 5:1 eluate contained a major product and was evaporated and residue dissolved in 10 ml of methanol. Upon cooling this yielded crystals which were collected and dried. Yield was 1.4 grams. By NMR decoupling and exchange experiments the product was shown to be 5-amino-1-(3-O-methyl-β-D-ribofuranosyl)imidazole-4-carboxamide. $^1$H NMR (DMSO-d$_6$) (for Compound 18) Δ ppm: 3.3 (s, 3H, CH$_3$), 3.6 (m, 2H, 5'-CH$_2$), 3.7 (m, 1H, 4'-CH), 4.0 (m, 1H, 3'-CH), 4.4 (m, 1H, 2'-CH), 5.3 (t, 1H, 5'-OH), 5.4 (2d, 2H, 2'-CH and 1'-CH), 5.9 (broad-s, 2H, 5-NH$_2$), 6.7 (broad-d, 2H, CO NH$_2$), 7.7 (s, 1H, 2-CH).

Example J

Preparation of 5-Amino-1-β-D-ribofuranosyl-imidazole-4-N-[(4-nitrophenyl)methyl]carboxamide (Compound No. 23 (1-343))

N-Succinimidyl-5-amino-1-(2,3,5-tri-O-acetyl-β-D-ribofuranosyl-imidazole-4-carboxylate[3] (0.50 g), 4-nitrobenzylamine hydrochloride (210 mg) and triethylamine (0.16 ml) were stirred in chloroform (30 ml) at room temperature overnight. The solution was washed with saturated sodium bicarbonate solution and water, then evaporated under reduced pressure. The resulting yellow tar was chromatographed on silica gel, eluting with 9:1 methylene chloride:methanol. The collected fractions were monitored by TLC. The like fractions were combined and concentrated under reduced pressure to afford a yellow foam (0.38 g). The foam was dissolved in methanol (20 ml) and methanolic sodium methoxide solution was added (0.3 ml of 0.25M solution). The solution was stirred under an argon atmosphere for 15 min. TLC indicated the reaction was complete. The solution was neutralized to pH 6 with ion exchange resin. The resin was filtered and the solution concentrated under high vacuum to yield a yellow foam (0.23 g). [3]Srivastava, P. C., J. Med. Chem. 17: 1207 (1974). $^1$H NMR (DMSO-$d_6$) Δ ppm, 3.6 (m, 2H, 5'-$CH_2$) 3.9-4.3 (m, 3H, 2'-CH, 3'-CH, 4'-CH), 4.5 (d, 2H, —$CH_2$ $C_6$ $H_4$—$NO_2$), 5.2-5.4 (broad, 3H, 2'-OH, 3'-OH, 5'-OH), 5.5 (d, 1H, 1'-CH), 6.10 (broad s, 2H, 5-$NH_2$, 7.3 (s, 1H, 2-CH), 7.4-8.2 ($AB_q$, 4H, —$C_6$ $H_4$—$NO_2$), 8.3 (t, 1H, 4-CONH).

Example K

Preparation of 5-Amino-1-α-D-ribofuranosylimidazole-4-N-[(3-chlorophenyl)methyl]carboxamide (Compound No. 24 (1-354))

This compound was prepared according to the procedures described in Example J for the 4-p-nitrobenzyl derivative, substituting 2-chlorobenzylamine for 4-nitrobenzylamine hydrochloride. $^1$H NMR (DMSO-$d_6$) Δ ppm, 3.6 (m, 2H, 5'-$CH_2$), 3.9-4.3 (m, 3H, 2'-CH, 3'-CH, 4'-CH), 4.4 (d, 2H, —$CH_2$—O—Cl), 5.1-5.4 (broad, 3H, 2'-OH, 3'-OH, 5'-OH), 5.5 (d, 1H, 1'-CH), 6.0 (broad s., 2H, 5-$NH_2$), 7.2-7.4 (m, 4H, —$C_6$ $H_4$—Cl), 8.0 (t, 1H, 4-CONH).

Example L

Preparation of 5-amino-1-β-D-ribofuranosylimidazole-4-N-[(2,4-dichlorophenyl)methyl]carboxamide (Compound No. 25 (1-360))

This compound was prepared according to the procedures described in Example J for the 4-p-nitrobenzyl derivative, substituting 2,4-dichlorobenzylamine for 4-nitrobenzylamine hydrochloride. $^1$H NMR (DMSO-$d_6$), Δ ppm, 3.6 (m, 2H, 5'-$CH_2$), 3.9-4.3 (m, 3H, 2'-CH, 3'-CH, 4'-CH), 4.4 (d, 2H, —$CH_2$—$C_6$ $H_3$—$Cl_2$), 5.2-5.4 (m, 3H, 2'-OH, 3'-OH, 5'-OH), 5.5 (d, 1H, 1'-CH), 6.0 (broad s, 2H, 5-NH2), 7.2-7.6 (m, 3H, —$C_6$ $H_3$—$Cl_2$), 8.1 (t, 1H, 4-CONH—).

Example M

Preparation of 5-amino-2-thio-1-β-D-ribofuranosyl imidazole-4-carboxamide (Compound No. 27 (1-395-0))

To 10 ml of 80% formic acid was added 400 mg of 5-amino-2-thio-1-(2,3-O-isopropylidene-β-D-ribofuranosyl)-imidazole-4-carboxamide[4]. The resulting mixture was stirred for 1 hour at room temperature. Silica TLC, eluting with 4:1 methylene chloride:methanol, showed conversion of staring material to one major product. The mixture was evaporated to dryness, dissolved in 5 ml of methanol and applied to a 50 ml column of silica gel. The column was eluted with methylene chloride:methanol (5:1). The major product, as determined by TLC, was collected and evaporated to dryness. The residue was dissolved in 3 ml of hot methanol and crystallized upon cooling. Yield was 150 mg of the above-identified product, melting point 205°-208° C.[4] Preparation described in T. Miyoshi, S. Suzaki, A. Yamazaki, Chem. Pharm. Bull., 24 (9): 2089-2093 (1976).

$^1$H NMR (DMSO-$d_6$), Δ ppm 3.6 (m, 2H, 5'-$CH_2$), 3.8 (m, 1H, 4'-CH), 4.1 (m, 1H, 3'-CH), 4.5 (n, 1H, 2'-CH), 5.1 (d, 1H, 2' or 3'-OH), 5.2 (d, 1H, 2' or 3'-OH), 5.7 (t, 1H, 5'-OH), 6.3 (d, 1H, 1'-CH), 6.4 (broad s, 2H, 5-$NH_2$), 6.9 (broad s, 2H, 4-$CONH_2$), 11.1 (broad s, 1H, 5'-SH).

Preparation of 5-amino-1-(5-chloro-5-deoxy-β-D-ribofuranosyl)imidazole-4-carboxamide (Compound No. 26 (1-332))

Example N

Preparation of 5-amino-1-(5-chloro-5-deoxy-.beta.-D-ribofuranosyl)imidazole-4-carboxamide (Compound No. 26(1-332))

AICA riboside (1.00 g), triphenylphosphine (3.05 g) and carbon tetrachloride (1.15 ml) were stirred in dimethyl formamide (38 ml) at room temperature for 3 hours. The solution was diluted with methanol (15 ml), then concentrated under reduced pressure. The resulting yellow tar was chromatographed on silica gel, eluting with 4:1 methylene chloride:methanol. The like fractions were combined and concentrated under reduced pressure to afford a purple foam. The presence of triphenylphosphine oxide, as determined by $^1$H NMR, necessitated a second chromatographic step as above. Yield was 0.43 g of a white foam.

[1]NMR (DMSO-$d_6$), Δ ppm 3.7-3.9 (m, 2H, 5'-$CH_2$), 4.0-4.4 (m, 3H, 2'-CH, 3'-CH, 4'-CH), 5.4-5.5 (m, 2H, 2'-OH, 3'-OH), 5.6 (d, 1H, 1'-CH), 5.9 (broad s, 2H, 5-$NH_2$), 6.7-6.9 (broad d, 2H, 4-$CONH_2$), 7.3 (s, 1H, 2-CH).

Example O

Preparation of 5-amino-1-(2-O-ethyl-β-D-ribofuranosyl)-4-imidazole carboxamide (Compound No. 34 (1-250)) and 5-amino-1-(3-O-ethyl-β-D-ribofuranosyl)-4-imidazole carboxamide (Compound No. 31 (1-251))

A solution of approximately 30 mmol diazoethane in 40 ml of ether was prepared by slow addition of 7 g (44 mmol) of 1-ethyl-3-nitro-1-nitrosoguanidine to a mixture of 8 g of potassium hydroxide, 9 ml water and 60 ml of ether followed by distillation. This was slowly added to a solution of 3.2 g (12 mmol) of 5-amino-1-β-D-ribofuranosylimidazole-4-carboxamide (AICA riboside) in 35 ml dimethylformamide containing 50 mg of tin(II) chloride dihydrate. During the addition approximately 20 ml of methanol was added to maintain solubility. The reaction was filtered to remove a trace precipitate and evaporated to a yellow syrup. Thin layer chromatography on silica gel using methylene chloride/methanol (3:1) showed a major product spot moving faster than AICA riboside. The syrup was chromatographed on silica gel using methylene chloride/methanol (8:1) collecting the major product as determined by TLC. The appropriate fractions were evaporated to a white foam. This was dissolved in 7 ml of methanol. Upon cooling to 4° C. the mixture crystallized to yield 160 mg of 5-amino-1-(2-O-ethyl-β-D-ribofuranosyl) imidazole-4-carboxamide (Compound No. 34 (1-250)) confirmed by NMR decoupling and exchange experiments.

$^1$H NMR (DMSO-$d_6$) (for Compound No. 34) Δ ppm, 1.05 (t, 3H, $CH_3$), 3.3-3.6 (m, 4H, 2'-$OCH_2$, 5'-$CH_2$), 3.9 (m, 1H, 4'-CH), 4.1-4.3 (m, 2H, 2'-CH, 3'-CH), 5.15 (d, 1H, 3-OH), 5.25 (t, 1H, 5'-OH), 5.55 (d, 1H, 1'-CH), 6.0 (broad s, 2H, 5-$NH_2$), 6.6-6.9 (broad d, 2H, 4-$CONH_2$), 7.3 (S, 1H, 7-CH).

The supernatant from the above crystallization was cooled overnight at −12° C. yielding a second crop of crystals, 0.58 g, which by NMR decoupling and exchange experiments was shown to be mostly 5-amino-1-(3-O-ethyl-β-D-ribofuranosyl) imidazole-4-carboxamide (Compound No. 31 (1-251))

$^1$H NMR (DMSO-$d_6$) (for Compound No. 31) Δ ppm, 1.1 (t, 3H, $CH_3$), 3.4-3.7 (m, 4H 3'-$OCH_2$—, 5'-$CH_2$), 3.85 (m, 1H, 4'-CH), 4.0 (m, 1H, 3'-CH) 4.4 (q, 1H, 2-CH), 5.25 (t, 1H, 5'-OH), 5.35 (d, 1H, 2'-OH), 5.45 (d, 1H, 1'-CH), 5.9 (broad s, 2H, 5-NH$_2$), 6.6-6.9 (broad d, 2H, 4-CONH$_2$), 7.3 (s, 1H, 1-CH). The major impurity was identified as the 2'-O-ethyl isomer.

Example P

Preparation of 5-amino-1-(2-O-n-butyl-β-D-ribofuranosyl)imidazole-4-carboxamide and 5-amino-1-(3-O-n-butyl-β-D-ribofuranosyl) imidazole-4-carboxamide (Compound Nos. 32 (1-262) and 33 (1-263))

5-Amino-1-β-D-ribofuranosylimidazole-4-carboxamide (2.50 g, 10.0 mmol) and tin(II) chloride hydrate (35 mg) were dissolved in dimethylformamide (40 ml) and methanol (30 ml). A solution of 0.1 ml of diazobutane[5] in 150 ml of ether was added in portions. Halfway through the addition, more tin (II) chloride hydrate was added (35 mg). Methanol was added, as needed, to ensure the starting material stayed in solution. The mixture was stirred for 1 hr, then concentrated under reduced pressure to give an oil. Analysis of the oil by $^1$H NMR showed mostly N-butylethylcarbamate. The oil was stirred with hexane and decanted to remove the N-butylethylcarbamate. The resulting tar was chromatographed on silica gel using 6:1 methylene chloride:methanol as eluting solvent. The appropriate fractions were combined and concentrated under reduced pressure to give a pink foam. $^1$H NMR analysis showed a mixture of 2' and 3' butyl ethers. HPLC analysis showed a 56:28 mixture. The solid was dissolved in isopropanol (2 ml) and cooled. The resulting solid was filtered and dried to give 63 mg. HPLC analysis showed a 77/18 mixture. $^1$H NMR decoupling and exchange experiments showed the major product to be the 2'-O-n-butyl ether.

[5]Diazobutane was prepared by treatment of 16.5 g of N-nitroso-N-n-butylmethane [Wilds, A. L. and Meeder, A. L., SOC 13 (1948)] in ethyl ether (100 ml) with potassium hydroxide (55 g) in water (60 ml). The ethereal diazobutane was used without distillation.

$^1$H NMR (DMSO-d$_6$) (for Compound No. 32) Δ ppm, 0.8-1.5 (m, 7H, —CH$_2$ CH$_2$ CH$_3$), 3.3-4.2 (m, 7H, 2'-OCH$_2$, 2'-CH, 3'-CH, 4'-CH, 5'-CH$_2$), 5.1 (d, 1H, 3'-OH), 5.3 (t, 1H, 5'-OH), 5.6 (d, 1H, 1'-CH), 6.0 (broad s, 2H, 5-NH$_2$), 7.6-7.8 (broad d, 2N, 4-CONH$_2$), 7.3 (s, 1H, 2-CH).

The supernatant from the above crystallization was concentrated under reduced pressure to give 125 mg of a pink foam. HPL analysis showed a 14/71 mixture. $^1$H NMR decoupling and exchange experiments showed the major product to be the 3'-O-n-butyl ether.

$^1$H NMR (DMSO-d$_6$) (for Compound No. 33) Δ ppm, 0.8-1.6 (m, 7H, —CH$_2$ CH$_2$ CH$_3$), 3.4-4.4 (m, 7H, 3'-OCH$_2$—, 2'-CH, 3'-CH, 4'-CH, 5'-CH$_2$), 5.2 (t, 1H, 5'-OH), 5.3 (d, 1H, 2'-OH), 5.4 (d, 1H, 1'-CH), 5.9 (broad s, 2H, 5-NH$_2$), 6.6-6.8 (broad d., 2H, 4-CONH$_2$), 7.3 (s, 1N, 7-CH).

Example O

Preparation of 5-amino-1-β-D-ribofuranosylimidazole-4-N-[(3-nitrophenyl)methyl]carboxamide (Compound No. 28 (1-348))

This compound was prepared according to the procedures described in example J for the 4-p-nitrobenzyl derivative, substituting 3-nitrobenzylamine hydrochloride for 4-nitrobenzylamine hydrochloride.

$^1$H NMR (DMSO-d$_6$) Δ ppm, 3.6 (m, 2H, 5'-CH$_2$), 3.9-4.3 (m, 3H, 2'-CH, 3'-CH, 4'-CH), 4.4 (d, 2H, —CH$_2$—NO$_2$), 5.2-5.4 (broad, 3H, 2'-OH, 3'-OH, 5'-O), 5.5 (d, 1H, 1'-CH), 6.0 (broad s., 2H, 5-NH$_2$), 7.4 (s, 1H, 7-CH), 7.6-8.2 (m, 4H, —C$_6$H$_4$Cl), 8.3 (t, 1H, 4-CONH).

Example R

Preparation of 5-amino-1-β-D-ribofuranosylimidazole-4-N-[(4-Chlorophenyl)methyl]carboxamide (Compound No. 29 (1-349)), This compound was prepared according to the procedures described in Example J for the 4-p-nitrobenzyl derivative, substituting 4-chlorobenzene amide for 4-nitrobenzylamine hydrochloride.

$^1$H NMR (DMSO-d$_6$) Δ ppm, 3.6 (m, 2H, 5'-CH$_2$), 3.9-4.3 (m, 3H, 2'-CH, 3'-CH, 4'-CH), 4.4 (d, 2H, —CH$_2$—C$_6$H$_4$—Cl), 5.2-5.4 (broad, 3H, 2'-OH, 3'-OH, 5'-OH), 515 (d, 1H, 1'-CH) 5.9 (broad s., 2H, 5-NH$_2$), 7.3-7.4 (m, 5N, —C$_6$H$_4$C$_1$), 7-CH), 8.1 (t, 1H, 4-CONH).

Example S

Preparation of 5-amino-1-β-D-ribofuranosylimidazole-4-N-[(4-methylphenyl)methyl]carboxamide (Compound No. 30 (1-388))

This compound was prepared according to the procedures described in Example J for the 4-p-nitrobenzyl derivative, substituting 4-methylbenzylamine for 4-nitrobenzylamine hydrochloride.

$^1$H NMR (DMSO-d$_6$) Δ ppm, 2.2 (s, 3H, —C$_6$H$_4$—CH$_3$), 3.6 (m, 2H, 5'-CH$_2$), 3.9-4.3 (m, 5H, 2'-CH, 3'-CH, 4'-CH, —CH$_2$—C$_6$H$_4$—CH$_3$), 5.2-5.4 (broad, 3H, 2'-OH, 3'-OH, 5'-OH), 5.5 (d, 1H, 1'-CH), 5.9 (broad s., 2H, 5-NH$_2$), 7.1-7.2 (M, 4H, —C$_6$H$_4$—CH$_3$), 7.3 (s, 1H, 7-CH), 7.9 (t, 1H, 4-CONH).

Example T

Preparation of 5-amino-1-β-D-ribofuranosyl-imidazole-4-N[(3-chlorophenyl)methyl]carboxamide (Compound No. 35 (1-355))

This compound was prepared according to the procedures described in Example J for the 4-p-nitrobenzyl derivative, substituting 3-chlorobenzylamine for 4-nitrobenzylamine hydrochloride.

$^1$H NMR (DMSO-d$_6$) Δ ppm, 3.6 (m, 2H, 5'-CH$_2$), 3.9-4.3 (m, 3H, 2'-CH, 3'-CH, 4'-CH), 4.3 (d, 2H, —CH$_2$—H$_4$—Cl), 5.1-5.4 (broad, 3H, 2'-OH, 3'-OH, 5'-OH), 5.5 (d, 1H, 1'-CH), 6.0 (broad s., 2H, 5-NH$_2$), 7.2-7.4 (m, 4H, —C$_6$H$_4$—Cl), 7.4 (s, 1H, 7-CH), 8.1 (t, 1H, 4-CONH).

Example U

Preparation of 5-amino-4-(1-piperidinocarbamoyl)-1-β-D-ribofuranosylimidazole (Compound No. 36 (1-207))

This compound in Example J for the 4-p-nitrobenzyl derivative, substituting piperidine for 4-nitrobenzylamine hydrochloride. The product was crystallized from ethanol to give the above-identified product, m.p. 190°-192° C.

$^1$H NMR (DMSO-d$_6$) Δ ppm, 1.4-1.7 (M, GH, 3, 4, 5-CH$_2$ groups of piperidine ring), 3.55 (m, 2H, 5'-CH$_2$), 3.8-3.95 (m, 5H, 2- and 6-CH$_2$ groups of piperidine ring, and 4'-CH), 4.0-4.1 (m, 1H, 3'-CH), 4.25-4.35 (m, 7H, 2-CH) 5.15 (d, 1H, 2' or 3'-OH), 5.2 (t, 1H, 5'-OH).

Example V

Preparation of 5-Amino-1-β-D-ribofuranosyl-imidazole-4-N-[p-methoxybenzyl]carboxamide (Compound No. 39 (1-390))

A mixture of the activated succinate ester (0.5 g) (prepared according to Example J), 4-methoxybenzylamine (0:15 ml) and methylene chloride (20 ml) was stirred overnight. TLC indicated completion of the reaction. The solvent was evaporated and the residue was chromatographed over a short silica gel column using a mixture of methylene chloride:methanol (9:1). The fractions containing the product were pooled and evaporated. The residue thus obtained was dissolved in methanol (20 ml) and the pH was adjusted to about 10 by adding a sodium methoxide solution. After stirring the reaction mixture for 45 minutes at room temperature, the solution was neutralized with Dowex 50 H+-resin (pH about 6.0). The resin was filtered off, washed with methanol (2×2 ml). The combined filtrate and the washings was evaporated and the residue was crystallized from ethanol. Yield was 100 mg, with amp of 187°-188° C.

$^1$H NMR (DMSO-d$_6$): Δ ppm, 3.55 (m, 2H, 5'-CH$_2$), 37 (s, 3H, —OCH$_3$), 3.7-4.1 (m, 3H, 2'-CH, 3'-CH, and 4'-CH), 4.35-4.2 (dd, 2H, —CH$_2$—N—), 5.1-5.4 (3, m, 3H, 2'-OH, 3'-OH, and 5'-OH), 5.45 (d, 1H, 1-CH), 5.9 (broad 2H, NH$_2$), 6.8-7.2 (m, 4H, aromatic-phenyl), 7.3 (s, 17H, C$_2$—H), and 7.85 (t, 1H, C—NH).

Example W

Preparation of 5-Amino-1-β-D-ribofuranosylimidazole-4-N(4-dimethylaminobenzyl)-carboxamide hydrochloride (Compound No. 41 (1-396-3))

To a suspension of 4-dimethylaminobenzylamine hydrochloride (245 mg, 2 mmol) in methylene chloride (25 ml), triethylamine (222 mg, 2 mmol) was added and the resulting mixture stirred 45 minutes to it was added the activated succinate ester prepared according to example J (500 mg); the resulting mixture was stirred at room temperature overnight. TLC indicated completion of the reaction. The reaction mixture was evaporated and the residue was chromatographed through a short silica gel column using a mixture of methylene chloride-methanol (9:1). Fractions showing the major product were pooled and evaporated to dryness. The residue was dissolved in methanol (15 ml) and the pH was adjusted to about 10 using a sodium methoxide solution. After stirring at room temperature for 45 minutes, the solution was neutralized with Dowex 50-resin. The resin was filtered off and washed with methanol (2×5 ml). The combined filtrate and the washings were evaporated to dryness. The residue which was in the form of a foam was dissolved in absolute ethanol (10 ml). The pH of the solution was adjusted to about 5 with an ethanolic-HCl solution. Solvent was evaporated to dryness and the residue was treated with anhydrous ether. The amorphous solid that separated was collected by filtration and washed with ether (2×10 ml), and dried under high vacuum to yield 250 mg. The compound obtained was highly hygroscopic; no melting point could be obtained.

$^1$H NMR (D$_2$O) Δ ppm, 3.05 (s, 6H, N(CH$_3$)$_2$), 3.6 (m, 2H, 5'-CH), 3.8-4.3 (3m, 3H, 2'-CH, 3'-CH, and 4'-CH), 4.4 (s, 2H, CH$_2$—N—), 5.5 (d, 1H, 1'-CH), 7.3-7.4 (m, 4H, phenyl), and 7.9 (s, 1H, 2-CH).

Example X

Preparation of (R)-5-Amino-1-β-D-ribofuranosylimidazole-4-N-[2-hydroxy-2-(3,4-dihydroxyphenyl)ethyl]carboxamide (Compound 42 (1-431))

This compound was prepared according to the procedure described in Example J substituting (R)-norepinephrine for 4-nitrobenzylamine hydrochloride and dimethylformamide in place of chloroform as the reaction solvent.

$^1$H NMR (DMSO-d$_6$): Δ ppm, 3.1-3.3 (m, 2H, —CH$_2$—N), 3.5-3.6 (m, 2H, 5'-CH$_2$), 3.8-3.9 (m, 1H, 4'-CH) 4.0-4.1 (m, 1H, 3'-CH) 4.2-4.3 (m, 1H, 2'-CH), 4.4-4.5 (m, 1H, phenyl-CH—OH), 5.2-5.2 (m, 1H, 2' or 3'-OH), 5.2-5.3 (t, 1H, 5'-OH) 5.3-5.4 (m, 1H, 2' or 3'-OH), 5.4-5.5 (d, 1H, 1'-CH), 5.9 (broad s, 2H, 5-NH$_2$), 6.5-6.8 (m, 3H, aryl of catechol), 7.1 (t, 1H, 4-CONH), 7.3 (s, 1H, 2-CH), 7.2-7.8 (broad s, 2H, catechol-OH).

Example Y

Preparation of 5-Amino-2-thiophenyl-1-β-D-ribofuranosylimidazole-4-carboxamide (Compound No. 43 (1-432))

5-Amino-2-bromo-1-(2,3-O-isopropylidene-β-D-ribofuranosyl)imidazole-4-carboxamide[1] (1.1 g), thiophenol (1.3 g) and triethylamine (0.61 g) were refluxed in a mixture of 25 ml methanol and 3 ml of 1N sodium hydroxide for 18 hours. The reaction mixture was concentrated and the residue mixed with 40 ml of methylene chloride. The methylene chloride mixture was washed with water and saturated sodium bicarbonate and dried over magnesium sulfate. The methylene chloride was evaporated and the residue purified by chromatography on 200 ml of silica gel using a mixture of methylene chloride and methanol (95:5), yielding 0.5 g of 5-amino-2-thiophenyl-1-(2,3-O-isopropylidene-β-D-ribofuranosyl)imidazole-4-carboxamide. Treatment of that compound with 80% formic acid for 3 hours at room temperature to remove the isopropylidene group followed by evaporation and purification by silica chromatography using methylene chloride:methanol (9:1) yielded 250 mg of the title compound as a white foam.

[1]Miyosi T., Chem. Pharm. Bull. 24: 2089 (1976).

$^1$H NMR (DMSO-d$_6$) Δ ppm, 3.3-3.5 (m, 2H, 5'-CH$_2$), 3.8-3.9 (m, 1H, 4'-CH) 4.0-4.1 (m, 1H, 3'-CH), 4.5 (q, 1H, 2'-CH) 5.1 (d, 1H, 2'- or 3'-OH), 5.3 (d, 1H, 2'- or 3'-OH), 5.7 (t, 1H, 5'-OH), 5.9 (d, 1H, 1'-CH) 7.5 (broad s, 2H, 4-NH$_2$), 6.7 and 7.1 (br s, 2H, CONH$_2$) 7.1-7.5 (m, 5H, phenyl).

Example Z

Preparation of 5-Amino-1-β-D-ribofuranosylimidazole-4-N-(2-endo-norbornyl)carboxamide) (Compound No. 45 (1-438))

A mixture of (±) endo-2-aminonorbornane hydrochloride (240 mg), triethylamine (160 mg) and methylene chloride was stirred at room temperature for 45 minutes under argon. To it was added activated succinate ester (See Example J) (750 mg) and stirred overnight. TLC indicated completion of the reaction. Solvent was evaporated and the residue chromatographed over silica gel column using a mixture of methylene chloride.methanol (9:1). Fractions containing the product were pooled and evaporated. The residue was dissolved in methanol (25 ml) and the pH was adjusted to about 10 with a sodium methoxide solution. After stirring for 45 minutes at room temperature the solution was neutralized with H+resin (pH approximately 6). The resin was filtered off and washed with methanol. The combined washings and the filtrate was evaporated and the residue kept under high vacuum to obtain a solid glossy product. Yield was 280 mg.

$^1$H NMR (DMSO-d$_6$) Δ ppm, 1.1-2.4 (m, 10H, norbonyl), 3.6 (broad M, 2H, 5'-CH$_2$), 3.9 (m, 1H, —N—CH), 4-4.4 (2 m, 3H, 2'-CH, 3'-CH and 4'-CH), 5.05, and 5.35 (2-d, 2H, 2'-OH and 3'-OH), 5.25 (t, 1H, 5'-OH), 5.5 (d, 1H, 1'-CH), 5.9 (broad 2H, NH$_2$) 6.8 (d, 1H, —NH—CO), 7.25 (S, 1H, 2-CH).

Example AA

Preparation of 5-Amino 1-β-D-ribofuranosyl-imidazole-4-N-[(3-iodophenyl)methyl]carboxamide (Compound No. 44 (1-434))

This compound was prepared according to the procedures described in Example J for the 4-p-nitrobenzyl derivative, substituting 3-iodobenzylamine hydrochloride for 4-nitrobenzylamine hydrochloride.

$^1$H NMR (DMSO-d$_6$) Δ ppm, 3.6 (m, 2H, 5'-CH$_2$), 3.9-4.3 (m, 3H, 2'-CH, 3'-CH, 4'-CH), 4.3 (d, 2H, —CH$_2$—C$_6$H$_4$—I), 5.2-5.4 (m, 3H, 2'-OH, 3'-OH, 5'-OH), 5.5 (d, 1H, 1'-CH), 5.9 (broad s., 2H, 5-NH$_2$), 7.1-7.7 (m, 4H, —C$_6$H$_4$), 7.3 (s, 1H, 2-CH), 8.1 (t, 1H, 4-CONH—)

Example AB

Preparation of 5-Amino-1-(5-iodo-5-deoxy-β-D-ribofuranosyl)imidazole-4-N-[(4-nitrophenyl)methyl]carboxamide (Compound No. 46(1-44)

The compound used in this procedure, 5-amino-1-(5-iodo-5-deoxy-2,3-isopropylidene-β-D-ribofuranosyl)imidazole-4-N-[(4-nitrophenyl)methyl]carboxamide, was prepared by the same reaction sequence (stopping at step B) described in Example AH for compound 53 (1-468), substituting the 4-N-p-nitrobenzylamide (compound 23 (1-343)) for the 4-N-p-chlorobenzylamide (compound 29 (1-349)).

5-Amino-1-(5-iodo-5-deoxy-2,3-O-isopropylidene-β-D-ribofuranosyl)imidazole-4-N-[(4-nitrophenyl)methyl]carboxamide (200 mg) was dissolved in 10 ml of 80% formic acid. The solution was stirred at 45° C. for 2 hours. The solvents were evaporated under reduced pressure and the resulting residue co-evaporated twice with water and twice with methanol. The residue was chromatographed on silica gel, using 6/1 methylene chloride/methanol as eluting solvent. The appropriate fractions were combined and concentrated under reduced pressure to yield 60 mg of the above-identified compound as a yellow foam.

$^1$H NMR (DMSO-d$_6$) Δ ppm, 3.3-3.6 (m, 2H, 5'-CH$_2$), 3.8-4.4 (m, 3H, 2'-CH, 3'-CH,4'—CH), 4.5 (d, 2H, CH$_2$—C$_6$H$_4$NO$_2$), 5.4-5.5 (m, 2H, 2'-OH, 3'-OH), 5.6 (d, 2H, 1'-CH), 5.9 (broad s., 2H, 5-NH$_2$), 7.4 (S, 1H, 2-CH), 7.5-8.2 (m, 4H, C$_6$H$_4$—NO$_2$, 8.3 (4, 1H, 4-CONH—).

Example AC

Preparation of 5-Amino-1-β-D-ribofuranosylimidazole-4-carboxylic Acid, p-Nitrobenzylthio Ester (Compound No. 47 (1-450))

5-Amino-1(2,3,5-tri-O-acetyl-β-D-ribofuranosyl)imidazole-4-carboxylic acid$^1$ (1.0 g) was dissolved in 8 ml of thionyl chloride under argon with stirring for 10 minutes. The mixture was evaporated under vacuum and the residue was dissolved in 15 ml of tetrahydrofuran containing 2.0 g of p-nitrobenzyl mercaptan. Triethylamine (1.5 ml) was added and the mixture stirred under argon for 20 minutes. The reaction is evaporated to a gum and the residue mixed with 50 ml of methylene chloride and washed with 2×25 ml of water. The methylene chloride phase was dried over magnesium sulfate and evaporated to a syrup which was purified by chromatography on silica gel using a mixture of ethyl acetate and methylene chloride (1:1) yielding 500 mg of 5-amino-1-(2,3,5-tri-O-acetyl-β-D-ribofuranosyl)imidazole-4-carboxylic acid, p-nitrobenzylthio ester. Treatment with sodium methoxide in 30 ml of dry methanol such that a slightly basic pH was maintained until deacetylation was complete (as determined by thin layer chromatography), followed by neutralization with Dowex 50 (H+) and evaporation yielded the desired compound contaminated with a product presumed to be the methyl ester. Purification by chromatography on silica using a mixture of methylene chloride and methanol (9:1) gave 38 mg of the desired compound as a yellow foam.

$^1$Srivastava, P. C., J. Med. Chem. 17: 1207 (1974).

$^1$H NMR (DMSO-d$_6$) Δ ppm, 3.5-3.7 (m, 2H, 5'-CH$_2$), 3.9-4.0 (m, 1H, 4'-CH), 4.2-4.4 (m, 2H, 2'- and 3'-CH), 5.2 (d, 1H, 2'- or 3'-OH), 5.3-5.5 (m, 2H, 5' and 2'- or 3'-OH), 5.6 (d, 1H, 1'-CH), 6.9 (broad s, 2H, 5-NH$_2$), 7.4 (s, 1 h, 2-CH), 7.6 and 8.2 (d, 2H, phenyl).

Example AD

Preparation of 5-Amino-1-β-D-ribofuranosyl-imidazole-4-N-indolinylcarboxamide (Compound No. 48 (1-452))

This compound was prepared according to the procedures described in Example J for the 4-p-nitrobenzyl derivative, substituting indoline for 4-nitrobenzylamine hydrochloride.

$^1$H NMR (DMSO-d$_6$) Δ ppm, 3.1 (t, 2H, indolinyl-CH$_2$), 3.6 (m, 2H, 5'-CH$_2$—), 5.2-5.4 (m, 3H, 2'-OH, 3'-OH, 5'-OH), 5.5 (d, 1H, 1'-CH), 6.4 (broad s., 2H, 5-NH$_2$), 6.9-8.1 (m, 4H, indolinyl aromatics). 7.4 (S, 1H, 2-CH).

Example AE

Preparation of (R)-5-Amino-1-β-D-ribofuranosylimidazole 4-N-[1-4-nitrophenyl)ethyl]carboxamide (Compound No. 49(1-453))

This compound was prepared according to the procedures described in Example J for the 4-p-nitrobenzyl derivative, substituting (R)-4-nitro-α-methylbenzylamine hydrochloride for 4-nitrobenzylamine hydrochloride.

$^1$H NMR (DMSO-d$_6$) Δ ppm, 1.5 (d, 3H, α-methyl on N4-benzyl carboxamide), 3.6 (m, 2H, 5'-CH$_2$), 3.9-4.3 (m, 3H, 2'-CH, 3'-CH, 4'-CH), 5.1 (m, 1H, methine proton on N4-benzylcarboxamide), 5.1-5.4 (m, 3H, 2'-OH 3'-OH, 5'-OH), 5.5 (d, 1H, 1'-CH), 7.3 (s, 1H, 2-CH), 7.6-8.2 (m, 4H, C$_6$H$_4$—NO$_2$), 8.0 (d, 1H, 4-CONH—).

Example AF

Preparation of (S)-5-Amino-1-β-D-ribofuranosylimidazole-4-N-[(4-nitrophenyl)ethyl]carboxamide (Compound No. 50(1-459))

This compound was prepared according to the procedures described in Example) for the 4-p-nitrobenzyl derivative, substituting (S)-4-nitro-α-methylbenzylamine hydrochloride for 4-nitrobenzylamine hydrochloride.

$^1$H NMR (DMSO-d$_6$) Δ ppm, 1.5 (d, 3H, α-methyl on N4-benzyl carboxamide), 3.6 (m, 2H, 5'-CH$_2$), 3.9-4.3 (m, 3H, 2'-CH, 3'-CH, 4'-CH), 5.1 (m, 1H, methine proton on N4-benzylcarboxamide), 5.1-5.4 (m, 3H, 2'-OH, 3'-OH, 5'-OH), 5.5 (d, 1H, 1'-CH' 5.9 (broad s., 2H, 5-NH$_2$), 7.4 (s, 1H, 2-CH), 7.6-8.2 (m, 4H, C$_6$ H$_4$ NO$_2$) 8.0 (d, 1H, 4-CONH—).

Example AG

Preparation of 5-Amino-1-(5-chloro-5-deoxy-β-D-ribofuranosyl) imidazole-4-N-[4-nitrophenyl)methylethyl]carboxamide (Compound No. 51(1-466))

5-amino-1-β-D-ribofuranosylimidazole-N-[(4-nitrophenyl)methyl]carboxamide, Compound 23 (1-343) (0.5 g), triphenylphosphine (1.00 g), carbon tetrachloride (0.37 ml), and THF (25 ml) were combined and stirred at ambient temperature, under argon, overnight. A white precipitate formed. Dimethylformamide (8 ml) was added and the solution was stirred at ambient temperature, under argon, overnight. The solvent was evaporated under reduced pressure and the resulting oil co-evaporated with methanol (3×20 ml). The resulting viscous oil was chromatographed on silica gel, using 7:1 methylene chloride:methanol as eluting solvent. The appropriate fractions were combined and concentrated in vacuo to give a yellow foam (0.28 g). The foam was crystallized from cold methanol to give yellow crystals (200 mg), mp=174°-176° C.

$^1$H NMR (DMSO-d$_6$) Δ ppm 3.7-3.9 (m, 2H, 5'-CH$_2$), 4.0-4.4 (m, 3H, 2'-CH, 3'-CH, 4'-CH), 4.5 (d, 2H, —CH$_2$—C$_6$H$_4$ NO$_2$), 5.4-5.6 (m, 2H, 2'-OH, 3'-OH), 5.6 (d, 1H, 1'-CH), 5.9 (broad s., 2H, 5-NH$_2$), 7.4 (s, 1H, 2-CH), 7.5-8.2 (m, 4H, —C$_6$ H$_4$ NO$_2$), 8.3 (t, 1H, 4-CONH—).

Example AH

Preparation of 5-Amino-1-(5-azido-5-deoxy-β-D-ribofuranosyl)imidazole-4-N-[4-chloro phenyl)methyl]carboxamide (compound 52 (1-467)) and 5-Amino-1-(5-amino-5-deoxy-β-D-ribofuranosyl) imidazole-4-N-[(4-chlorophenyl)methyl]carboxamide Hydrochloride (Compound No. 53 (1-468))

A. Preparation of 5-Amino-1-(2,3-O-isopropylidene-β-D-ribofuranosyl)imidazole-4-N-[(4-chlorophenyl)methyl]carboxamide Compound 29 (1-349), (6.8 g, 17.8 mmole), was dissolved in a mixture of 100 ml DMF, 15 ml acetone and 15 ml 2,2-dimethoxypropane. Hydrogen chloride gas (approximately 1.0 g) was added and the mixture stirred under argon for 4 hours. The mixture was poured into 50 ml of saturated sodium bicarbonate and evaporated under vacuum at 45° C. The residue dissolved in a mixture of 100 ml ethyl acetate and 25 ml water. The ethyl acetate phase was separated and washed with 25 ml of water, dried over magnesium sulfate and concentrated to a foam. TLC (silica gel, 9:1 methylene chloride:methanol) showed a significant faster moving impurity in the product which was identified as the 5'-(2-methoxypropane) mixed ketal of the above-identified compound. This was converted to the above-identified compound by dissolving the foam in 100 ml of methanol and adjusting the pH to 2.5 with ethanolic hydrogen chloride. After 30 minutes the mixture was neutralized with saturated sodium bicarbonate and concentrated to a slurry. This was dissolved in 100 ml of methylene chloride, washed with 25 ml of water. The methylene chloride phase was dried over magnesium sulfate and concentrated to a foam. Drying under vacuum at 40° C. for 18 hours yielded 7.2 g (96%) of the above-identified compound.

B. Preparation of 5-Amino-1-(5-iodo-5-deoxy-2,3-isopropylidene-β-D-ribofuranosyl)imidazole-4-N-[(4-chlorophenyl)methyl]carboxamide A mixture of the product of Step A (25 g, 59 mmole) and methyltriphenoxyphosphonium iodide (76 g, 166 mmole) in 500 ml of methylene chloride was stirred for 30 minutes at room temperature under argon. The resulting solution was extracted with 150 ml of water, 150 ml of 5% sodium thiosulfate, 150 ml of 1N sodium hydroxide, 100 ml of water and dried over magnesium sulfate. The solvent was removed under vacuum and the resulting oil applied to a 1.31 column of flash grade silica gel prepared in 2:1 hexane:ethyl actetate. The column was eluted with the same solvent to remove impurities then 1:1 hexane:ethyl acetate was used to elute the desired product. Appropriate fractions were combined and evaporated to yield 24.4 g of the above-identified compound as a gummy solid. Impure fractions were again subjected to chromatography to yield an additional 2.3 g of the above-identified product. Total yield was 26.7 g (85%).

C. Preparation of 5-amino-1-(5-azido-5-deoxy-2,3-O-isopropylidene-β-D-ribofuranosyl)imidazole-4-N-[(4-chlorophenyl)methyl]carboxamide A mixture of the product of Step B (26.7 g, 50 mmole), lithium azide (14 g, 285 mmole) and 100 mg of 18-crown-6 in 350 ml of DMF was stirred for 8 hours at room temperature under argon. The slurry was concentrated to remove solvent and the residue dissolved in a mixture of 500 ml of ethyl acetate and 100 ml of water. The ethyl acetate phase was separated, washed with water and saturated sodium chloride, and then dried over magnesium sulfate. Evaporation of the solvent yielded 25 g of the above-identified compound as a yellow gum which still contained solvent. This was used in the next step without further purification.

D. Preparation of 5-Amino-1-(5-azido-5-deoxy-β-D-ribofuranosyl)imidazole-4-N-[(4-chloro phenyl)methyl]carboxamide. (Compound No. 52 (1-467))

The product of Step C, as obtained, was dissolved in 150 ml of 80% trifluoracetic acid and warmed to 50° C. for 30 minutes. The solution was evaporated to a syrup at 40° C. under vacuum and the residue evaporated twice from 25 ml of water. The syrupy residue was dissolved in 100 ml of ethyl acetate and gently stirred over 100 ml of saturated sodium bicarbonate. Crystallization began in the ethyl acetate phase and after 1 hour crystals were collected by filtration. These crystals were combined with two additional crops or crystals obtained by concentration of the ethyl acetate phase to yield 15.7 g (77% yield based on the product of Step B). Melting point of an analytical sample was 182°-183° C.

$^1$H NMR (DMSO-d$_6$) Δ ppm, 3.6 (M, 2H, 5'-CH$_2$), 4.0-4.3 (m, 311, 2'-CH, 3'-CH, 4'-CH), 4.3 (d, 2H, —CH$_2$ C$_6$ H$_4$ C$_1$), 5.4-5.5 (m, 2H, 2'-OH, 3'-OH), 5.5 (d, 1H, 1'-CH), 5.9 (broad s., 2H, 5-NH$_2$), 7.3-7.4 (m, 4H, C$_6$ H$_4$ Cl), 7.4 (s, 1H, 2-CH), 8.1 (t, 1H, 4-CONH—). IR (KBr) cm$^1$, 2110.

E. Preparation of 5-Amino-1-(5-amino-5-deoxy-β-D-ribofuranosyl)imidazole-4-N-[(4-chlorophenyl)methyl]carboxamide Compound 52 (1-467) (6.5 g, 159 mmole) was dissolved in 500 ml of boiling ethanol. After cooling to 40° C. the solution was saturated with argon and 0.5 g of 10% palladium on carbon added. The mixture was stirred under a hydrogen atmosphere for 8 hours. The mixture was saturated with argon and filtered through Celite 505 and concentrated to a syrup which was used in the next step without further purification.

F. Preparation of 5-Amino-1-(5-amino-5-deoxy-β-D-ribofuranosyl)imidazole-4-N-[(4-chlorophenyl)methyl]carboxamide Hydrochloride (Compound No. 53 (1-468))

The product of Step E (theoretically 159 mmole) was dissolved in 100 ml of ethanol and 3.5 ml of 6N hydrochloric acid added (pH to wet pH paper approximately 3). The solution was evaporated to a hard syrup. This syrup was dissolved in 50 ml of hot ethanol and diluted with 150 ml of ethyl ether. The resulting gummy precipitate was stirred sealed for 12 hours and the resulting white precipitate collected by filtration and washed with ether. Drying under vacuum at 40° C. yielded 6.0 g of the above-identified compound (90% yield based on the compound from Step D).

$^1$H NMR (DMSO $d_6$) Δ ppm, 3.0-3.2 (m, 2H, 5'-$CH_2$), 4.0-4.4 (M, 3H, 2'-CH, 3'-CH, 4'-CH), 4.4 (d, 2H, —$CH_2$—$C_6H_4$Cl), 5.8-6.2 (broad, 2H, 2'-OH, 3'-OH), 7.2-7.4 (m, 4H, $C_6H_4$Cl), 7.8 (s, 1H, 2-CH), 8.3 (broad, 3H, $NH_2$, HCl).

Example AI

Preparation of 5-Amino-1-(5-amino-5-deoxy-β-D-ribofuranosyl)imidazole-4-N-(cyclopentyl)carboxamide Hydrochloride ((Compound No. 37) 1-270))

This compound was prepared by the same reaction sequence described in Example AH for compound 53 (1-468), substituting the 4-N-cyclopentylamide, compound 10 (1-186), of Table XII for the 4-N-p-chlorobenzylamide compound 29 (1-349) of Table XII.

$^1$H NMR (DMSO-$d_6$) Δ ppm, 1.4-1.9 (m, 9H, cyclopentyl aliphatic protons), 3.0-3.2 (m, 2H, 5'-$CH_2$), 4.0-4.3 (m, 3H, 2'-CH, 3'-CH, 4'-CH), 5.5 (d, 1H, 1'-CH), 5.9 (broad s, 2H, 5-$NH_2$), 7.1 (d, 1H, 4-CONH—), 7.4 (s, 1H, 2-CH).

Example AJ

Preparation of 5-Amino-1-(5-deoxy-5-methylthio-β-D-ribofuranosyl)imidazole-4-carboxamide (Compound No. 54 (1-483))

The intermediate, 5-amino-1-(5-chloro-5-deoxy-β-D-ribofuranosyl)imidazole-4-carboxamide, was prepared according to the procedures described in Example AI for compound $5^1$ (1-466), substituting 5-amino-1-β-D-ribofuranosylimidazole-4-carboxamide for 5-amino-1-D-ribofuranosylimidazole-4-N-[(4-nitrophenylmethyl]carboxamide.

To a 0.1N sodium methoxide/methanol solution, at 0° under argon, was bubbled methyl mercaptan. To the resulting 0.1 N sodium methylthiolate/methanol solution was added 5-amino-1-(5-chloro-5-deoxy-β-D-ribofuranosyl) imidazole-4-carboxamide (0.40 g). The solution was heated of reflux overnight. The solution was cooled and neutralized with Dowex 50 strongly acidic ion exchange resin. The mixture was filtered and concentrated under reduced pressure. The resulting residue was chromatographed on silica gel, using 4:1 methylene chloride:methanol as the eluting solvent. The appropriate fractions were combined, concentrated under reduced pressure, and vacuum dried to give the above-identified compound as a white foam (0.28 g).

$^1$H NMR (DMSO-$d_6$) Δ ppm, 2.1 (s, 3H, —S—$CH_3$), 3.7-3.9 (m, 2H, 5'-$CH_2$), 3.9-4.4 (m, 3H, 2'-CH, 3'-CH, 4'-CH), 5.3-5.4 (m, 2H, 2'-OH, 3'-OH), 5.5 (d, 1H, 1'-CH), 5.8 (broad s., 2H, 5-$NH_2$), 6.6-6.9 (broad m, 2H, 4-$CONH_2$), 7.3 (s, 1H, 2-CH).

Example AK

Preparation 5-Amino-1-β-D-ribofuranosylimidazole-4-N-(4-bromophenyl)carboxamide (Compound No. 55 (1-484))

5-Amino-1-(2,3,5-tri-O-acetyl-βD-ribofuranosyl)imidazole-4-carboxylic acid (Srivastava, P. C., et al., J. Med. Chem. 17 1207, (1974), (0.75 g) and thionyl chloride (7 ml) were stirred at ambient temperature under a drying tube, for 15 minutes. The excess thionyl chloride was evaporated under reduced pressure and the resulting residue co-evaporated with methylene chloride (3×20 ml). The resulting yellow foam was dissolved in methylene chloride (40 ml) and 4-bromoaniline (0.35 g) was added. Triethylamine (approximately 0.75 ml) was added until the solution was basic. The solution was stirred at ambient temperature under a drying tube for 2 hours. The solution was washed with water, dried with magnesium sulfate, and concentrated under reduced pressure to give a yellow foam. The foam was dissolved in methanol (35 ml). A sodium methoxide methanol solution (approximately 0.75 ml of a 0.5N solution) was added and the resulting solution stirred at ambient temperature under a drying tube, for 30 minutes. The solution was neutralized with methanol-washed Dowex 50 (strongly acidic ion-exchange resin). The mixture was filtered and concentrated under reduced pressure to give a pale yellow residue. The residue was crystallized from methanol (15 ml)/methylene chloride (10 ml) to give tan crystals (0.23 g). The crystals were recrystallized to give off-white crystals (90 mg). Mp: 214°-216° C. (decomp).

$^1$H NMR (DMSO-$d_6$) Δ ppm, 3.6 (m, 2H, 5'-$CH_2$), 3.9-4.3 (m, 3H, 1'-CH, 3'-CH, 4'-CH), 5.2-5.4 (m, 3H, 2'-OH, 3'-OH, 5'-OH), 5.5 (d, 1H, 1'-CH), 6.2 (broad s., 2H, 5-$NH_2$), 7.4-7.8 (m, 4H, $C_6H_4$Br), 7.4 (s, 1H, 2-CH), 9.5 (s, 7H, 4-CONH).

Example AL

Preparation of 5-Amino 1-β-D-ribofuranosyl-imidazole-4-N-[(4-bromophenyl)methyl]carboxamide (Compound No. 56 (1-487))

This compound was prepared according to the procedures described in Example J for the 4-p-nitrobenzyl derivative, substituting 4-bromobenzylamine hydrochloride for 4-nitrobenzylamine hydrochloride.

$^1$H NMR (DMSO-$d_6$) Δ ppm, 3.5-3.6 (m, 2H, 5'-$CH_2$), 3.9-4.3 (m, 3H, 2'-CH, 3'-CH, 4'-CH), 4.3 (d, 2H, $CH_2$ $C_6H_4$ Br), 5.1-5.4 (m, 3H, 2'-OH, 3'-OH, 5'-OH), 5.5 (d, 1H, 1'-CH), 5.9 (broad s, 2H, 5-$NH_2$), 7.2-7.5 (m, 4H, $C_6H_4$ Br), 7.3 (s, 4H, 2-CH), 8.0 (t, 1H, 4-CONH—).

Example AM

Preparation of 5-Amino-1-β-D-ribofuranosyl-imidazole-4-N-(4-iodophenyl) carboxamide (Compound No. 57 (1-488))

This compound was prepared according to the procedures described in Example AK for the 4-p-bromophenyl derivative, substituting 4-iodoaniline for 4-bromoaniline. The final product was recrystallized from ethanol. Mp: 227°-229° C. H NMR (DMSO-$d_6$) Δ ppm, 3.5-3.6 (m, 2H, 5'-$CH_2$), 3.9-4.4 (m, 3H, 2'-CH, 3'-CH, 4'-CH), 5.2-5.4 (m, 3H, 2'-OH, 3'-OH, 5'-OH), 5.5 (d, 1H, 1'-CH), 6.2 (broad s., 2H, 5-$NH_2$), 7.4 (s, 1H, 2-CH), 7.6-7.7 (m, 4H, $C_6H_4$ I), 9.5 (s, 1H, 4-CONH).

Example AN

Preparation of 5-Amino-1-β-D-ribofuranosylimidazole-4-N-(4-nitrophenyl)carboxamide (Compound No. 58 (1-489))

This compound was prepared according to the procedures described in Example AK for the 4-p-bromophenyl derivative, substituting 4-nitroaniline for 4-bromoaniline. The final product was recrystallized from methanol to give a yellow powder.

$^1$H NMR (DMSO-$d_6$) Δ ppm, 3.5-3.6 (m, 2H, 5'-$CH_2$), 3.9-4.4 (m, 3H, 2'-CH, 3'-CH, 4'-CH), 5.2-5.4 (m, 3H, 2'-OH, 3'-OH, 5'-OH), 5.6 (d, 1H, 1'-CH), 6.4 (broad s., 2H, 5-$NH_2$), 7.5 (s, 1H, 2-CH), 8.1-8.3 (m, 4H, $C_6H_4$ $NO_2$), 10.1 (s, 1H, 4-CONH).

Example AO

Preparation of 5-Amino-1-β-D-ribofuranosyl-imidazole-4-N→2-(4-nitrophenyl)ethyl carboxamide (Compound No. 59 (1-506))

This compound was prepared according to the procedures described in Example J for the 4-p-nitrobenzyl derivative, substituting 4-nitrophenethylamine hydrochloride for 4-nitrobenzylamine hydrochloride.

$^1$H NMR (DMSO-$d_6$) Δ ppm, 2.9-3.0 (t, 2H, —$CH_2$—$C_2H_4$—$NO_2$), 3.4-3.6 (m, 2H, 5'-$CH_2$), 3.9-4.3 (m, 3H, T-CH, 3'-CH, 4'-CH), 4.8-5.4 (broad, 3H, 2'-OH, 3'-OH, 5'-OH), 5.5 (d, 1H, 1'-CH), 5.9-6.2 (broad, 2H, 5-$NH_2$), 7.5-8.2 (m, 4H, $C_6H_4$ $NO_2$), 7.6 (s, 1H, 2-CH), 7.7 (t, 1H, 4-CONH).

Example AP

Preparation of 5-Amino-4-[1-[4-(4-nitrophenyl)] piperazinocarbamoyl]-1-1-β-D-ribofurano sylimidazole (Compound No. 60 (1-508))

This compound was prepared according to the procedures described in Example J for the 4-nitrobenzyl derivative, but substituting 1-(4-nitrophenyl)piperazine for 4-nitrobenzylamine hydrochloride. The product as recrystallized from cold methanol and had a mp of 199°-200° C.

$^1$H NMR (DMSO-$d_6$) Δ ppm, 3.4-3.6 (m, 10H, 3'-$CH_2$, piperazonyl methylenes), 3.9-4.3 (m, 3H, 2'-CH, 3'-CH, 4'-CH), 5.2-5.4 (m, 3H, 2'-OH, 3'-OH, 5'-OH), 5.5 (d, 1H, 1'-CH), 6.3 (broad s., 2H, 5-$NH_2$), 7.0-8.1 (m, 4H, —$C_6H_4$ $NO_2$), 7.3 (s, 1H, 2-CH).

Example AQ

Preparation of 5-Amino-1-(5-deoxy-β-D-ribofuranosyl)imidazole-4N-[(4-chlorophenyl)methyl]carboxamide (Compound No. 61 (1-509))

5-Amino-1-(5-iodo-5-deoxy-2,3-isopropylidene-βD-ribofuranosyl)imidazole-4-N-[(4-chlorophenyl)methyl]carboxamide (see procedures described in Example AH for preparation of Compound 53 (1-468), step 13) (0.64 g) was stirred in 30 ml of 50% formic acid overnight. The excess solvent was evaporated under reduced pressure. The resulting residue was co-evaporated with water (25 ml) and methanol (25 ml). The resulting yellow foam was chromatographed on silica gel, using 9:1 methylene chloride:methanol as eluting solvent. The appropriate fractions were combined and concentrated under reduced pressure to give 0.47 g of 5-amino-1-(5-iodo-5-deoxy-β-D-ribofuranosyl)imidazole-4-N-[(4-chlorophenyl)methyl]carboxamide.

5-Amino-1-(5-iodo-5-deoxy-β-O-ribofuranosyl)imidazole-4-N-[(4-chlorophenyl)methyl]carboxamide (0.04 g), palladium on carbon 10% (20 mg), and ethanol (20 ml) were charged to a Parr bottle. The bottle and contents were charged with 45 p.s.i. hydrogen. The reaction progress was monitored by HPLC (Waters C18, 55% methanol/45% 0.1N acetic acid, 260 nm, 1.0 ml/min). After 24 hour, there was 34% starting material. Fresh catalyst was added (20 mg) and the mixture re-charged with hydrogen (45 p.s.i.). The mixture was shaken for an additional 48 hours. The reaction mixture contained 30% starting material. The mixture was filtered through Celite, and concentrated under reduced pressure. The resulting residue was chromatographed on silica gel, using ethyl acetate (400 ml) and 5% methanol in ethyl acetate (200 ml) as the eluting solvent. The appropriate fractions were combined and concentrated under reduced pressure to yield 70 mg of a white foam. HPLC indicated 9% starting material. The material was rechromatographed on silica gel, using ethyl acetate as eluting solvent. All fractions containing less than 3% starting material were combined and concentrated under reduced pressure to yield 36 mg of the above-identified compound as a pink foam.

$^1$H NMR (DMSO-$d_6$) Δ ppm, 1.2-1.3 (d, 3H, 5'-$CH_3$), 3.7-4.3 (m, 3H, 2'-CH, 3'-$CH_2$ 4'-CH), 4.3 (d, 2H, $CH_2$—$C_6H_4$ Cl), 5.1-5.4 (m, 3H, 2'-OH, 3'-OH, 1'-CH), 5.8 (broad s., 2H, 5-$NH_2$), 7.2-7.4 (m, 5H, $C_6H_4$ Cl, 2-CH), 8.1 (t, 1H, 4-CONH).

Example AR

Preparation of 5-Amino-1-(5-deoxy-5-methylsulfinyl-β-D-ribofuranosyl)imidazole-4-carboxyamide (Compound No. 62 (1-510))

5-Amino-1-(5-deoxy-5-methylthio-β-D-ribofuranosyl)imidazole-4-carboxamide (compound 54 (1-483)) of Example AK (0.40 g) was dissolved in water (20 ml). Hydrogen peroxide, 30 weight percent, (0.42 ml), was added and the solution stirred for 30 minutes. TLC (6/1, methylene chloride/methanol) indicated some starting material present. An additional 1.0 ml of hydrogen peroxide was added and the solution stirred for 15 minutes. TLC indicated no starting material. The solvent was evaporated under reduced pressure to give a yellow foam. The foam was chromatographed on silica gel, using 3/1, methylene chloride/methanol, as eluting solvent. The appropriate fractions were combined and concentrated in vacuo to give 75 mg of the above-identified compound as a yellow foam.

HPLC (Waters C18, 100% 0.1N acetic acid, 1.0 ml/minutes, 260 nm) indicated 2 equimolar products. This is consistent with oxidation of the product to a diasteromeric mixture of sulfoxides.

$^1$H NMR (DMSO-$d_6$) Δ ppm, 2.6 (s, 3H, $CH_3$ S(O)—), 3.0-3.2 (m, 2H, 5'-$CH_2$), 4.0-4.4 (m, 3H, 2'-CH, 3'-CH, 4'-CH) 5.4-5.6 (m, 3H, 2'-OH, 3'-OH, 1'-CH), 5.9 (broad s., 2H, 5-$NH_2$), 6.6-6.9 (broad, 2H, 4-$CONH_6$), 7.3 (s, 1H, 2-CH).

Example AS

Preparation of 5-Amino-1-β-D-(5-deoxy-5-methylaminoribofuranosyl)imidazole-4-carboxamide (Compound No. 63 (1-517)

5'-Deoxy-5'-iodo-2',3'-O-isopropylidene-AICA riboside (1.00 g) (ref: P. C. Srivastava, A. R. Newman, T. R. Mathews, and T. R. Mathews, and R. K. Robins, J. Med. Chem., 18, 1237 (1975)), methylamine 40% weight in water (3 ml), and methanol (30 ml) were combined and heated at reflux for 18 hours. The reaction gave a mixture of products. The solution was cooled and the solvents evaporated under reduced pressure. The resulting residue was chromatographed on silica gel, using 6/1 methylene chloride/methanol (400 ml) and 3/1 methylene chloride/methanol (300 ml) as the eluting solvent. The fractions containing the slow-eluting component which was desired product were combined and evaporated under reduced pressure to give 0.13 g of 5'-deoxy-5'-methylamino-2',3'-isopropylidene-AICA riboside.

5'-deoxy-5'-methylamine-2',3'-isopropylidene AICA riboside (0.13 g) was heated at 60° C. in 75% formic acid (20 ml) for 1.5 hour. The solution was cooled and the solvent evaporated under reduced pressure to yield a white foam. The foam was dissolved in water (5 ml) and applied to a short column of Dowex 50 strongly acidic ion-exchange resin. The column was washed with water then eluted with 1M $NH_4$ OH in 20% methanol/water. The solvent was evaporated under reduced pressure and the resulting residue co-evaporated with methanol ($3\times20$ ml) to yield 75 mg of the above-identified product as an off-white foam.

$^1$H NMR ($D_6$-DMSO-$d_6$) Δ ppm, 2.3 (s, 3H, $CH_3$ N), 2.5-2.7 (m, 2H, 5'-$CH_2$), 3.3-3.4 (broad, 1H, MENH), 3.9-4.3 (m, 3H, 2'-CH, 3'-CH, 4'-CH), 5.1-5.4 (m, 2H, 2'-OH, 3'-OH), 5.4 (d, 1H, 1'-CH), 6.2 (broad s., 2H, 5-$NH_2$), 6.6-6.8 (broad, 2H, 4-$CONH$), 7.2 (s, 1H, 2-CH).

Example AT

Preparation of 5-Amino-1-β-D-ribofuranosylimidazole-4-N-(2-chlorophenyl)carboxamide (Compound No. 64 (1-519))

This compound was prepared according to the procedures described in Examples for compound 55 (1-484) for the 4-p-bromophenyl derivative, substituting 2-chloroaniline for 4-bromaniline. The final product was recrystallized from methylene chloride (20 ml)/methanol (1 ml) to yield 0.25 g of the above-identified product. Mp=131°-135° C.

$^1$H NMR (DMSO-$d_6$) Δ ppm, 3.5-3.6 (m, 2H, 5'-$CH_2$), 3.9-4.3 (m, 3H, 2'-CH, 3'-CH, 4'-CH), 5.2-5.4 (m, 3H, 2'-OH, 3'-OH, 5'-OH), 5.5 (d, 1H, 1'-CH), 6.2 (broad s., 2H, 5-$NH_2$), 7.0-8.4 (m, 5H, $C_6 H_4$ Br, 2'-CH), 9.1 (s, 1H, 4-CONH).

Example AU

Preparation of 5-Amino-1-β-D-(5 benzylamino-5-deoxyribofuranosyl)imidazole-4-carboxamide (Compound No. 66(1-5311)

5'-deoxy-5'-iodo-2',3'-isopropylidene AICA riboside (1.00 g) (ref: P. C. Srivastava, A. R. Newman, T. R. Mathews, and R. K. Robins, J. Med. Chem. 18: 1237 (1975)), benzylamine (2.0 ml), and methanol (40 ml) were combined and heated at reflux for 24 hours. Then, the procedures described in Example AS for Compound 63 (1-517) were followed to give the above-identified compound.

$^1$H NMR (DMSO-$d_6$) Δ ppm, 2.7 (d, 2H, —$CH_2$—$C_6 H_5$), 3.3-3.4 (broad, 1H, —NH—$CH_2$ $C_6$ $H_5$), 3.9-4.3 (m, 3H, 2'-CH, 3'-CH, 4'-CH), 5.1-5.4 (m, 2H, 2'-OH, 3'-OH), 5.4 (d, 1H, 1-CH), 6.1 (broad s., 2H, 5-$NH_2$), 6.6-6.8 (broad, 2H, 4-$CONH_2$), 7.2-7.4 (m, 6H, —$C_6 H_5$, 2-CH).

Example AV

Preparation of 5-Amino-2-thio-1-βD-(5 deoxyribofuranosyl)imidazole-4-carboxamide (Compound No. 67 (1-535))

A. Preparation of 5'-Deoxy-2',3'-isopropylidene-2-bromo-AICA Riboside

To a solution of 5'-deoxy-2',3'-isopropylidene-AICA riboside (2.90 g) (ref: P. C. Srivastava, A. R. Newman, T. R. Mathews, and R. K. Robins, J. Med. Chem., 18: 1237 (1975)) in chloroform (100 ml), was added N-bromosuccinimide in small portions over 20 minutes. The solution was stirred at ambient temperature for 30 minutes. The solution was washed with water, twice with brine, and then dried over magnesium sulfate. The solvent was evaporated in vacuo to yield a dark foam. The foam was passed through a column of silca gel, eluting with 9:1 methylene chloride:methanol. The fractions containing product were combined and concentrated under reduced pressure to yield 2.02 g of reddish-brown foam.

B. Preparation of 5'-Deoxy-2-,3'-O-isopropylidene-2-thio AICA Riboside

Potassium sulfate (3.7 g) was heated at reflux in ethanol (20 ml) for 15 minutes. The mixture was filtered. To the filtrate was added 5'-deoxy-2,3'-isopropylidene-2-bromo AICA riboside (from step A). The mixture was heated at 100° C. in a steel bomb for 5.5 hours. The mixture was cooled and filtered. The pH of the filtrate was adjusted to about 5-6 with acetic acid, and the solvent evaporated under reduced pressure. The resulting residue was passed through a column of silica gel, eluting with 7/1, methylene chloride/methanol. The fractions containing the product were combined and concentrated under reduced pressure to give a dark brown foam. The foam was stirred in methylene chloride (50 ml), then filtered to yield a pale purple powder. The powder was stirred in cold methanol, then filtered and vacuum dried to yield 0.52 g of a pale yellow solid. Mp=211-214 (decomposition).

C. Preparation of 5-Amino-2-thio-1-(deoxy-β-D-ribofuranosyl)imidazole-4-carboxamide (Compound 67 (1-535))

5'-deoxy-2',3'-isopropylidene-2-thiol AICA riboside (0.45 g) (from step B) was stirred in 50% formic acid (30 ml) at 50° C. for 1 hour. The solvent was evaporated under reduced pressure. The resulting residue was co-evaporated with methanol ($2\times20$ ml). The resulting solid was warmed in methanol (25 ml), then stirred at room temperature overnight. The mixture was filtered and the filtrate concentrated under reduced pressure to yield a greenish foam. The foam was chromatographed on silica gel, using 5/1, methylene chloride/methanol, as the eluting solvent. The appropriate fractions were combined and concentrated under reduced pressure to give a yellow foam. The foam was crystallized from cold methanol to yield 69 mg. of the above-identified compound mp=201°-203° C., (decomposition).

¹H NMR (DMSO-d₆) Δ ppm 1.3 (d, 3H, 5'-CH₃), 3.6-4.5 (m, 3H, 2'-CH, 3'-CH, 4'-CH), 5.0-5.2 (m, 2H, 2'-OH, 3'-OH), 5.6 (broad s., 2H, 5-NH₂), 6.0 (d, 1H, 1'-CH), 7.0 (broad, 2H, 4-CONH), 12.0 (broad s., 1H, —SH).

Example AW

Preparation of N,N'-bis-(5-amino-1-β-D-ribofuranosyl imidazole-4-carbonyl)-1,6-diaminohexane (Compound No. 68 (1-538))

N-succinimidyl-5-amino-1-(2,3,5-tri-O-acetyl-βD-ribofuranosyl-imidazole-4-carboxylate (2.50 g) (ref: Srivastava, P. C., et al., J. Med. Chem. 17: 1207 (1974)), 1,6-hexane diamine (0.300 g), triethylamine (0.5 ml), and methylene chloride (35 ml) were combined and stirred at room temperature for 18 hours. The title compound was prepared according to the procedures described in Example J. The final product was crystallized from methanol to yield 0.32 g of the above-identified compound. Mp –181°-185° C.
¹H NMR data reported as for half the symmetrical dimer.
¹H NMR (DMSO-d₆) Δ ppm, 1.2-1.5 (m, 4H, β- and Δ methylenes of N-hexyldicarboxamide), 3.0-3.2 (m, 2H, α methylene of N-hexyl dicarboxamide), 3.5-3.6 (m, 2H, 5'-CH₂), 3.8-4.3 (m, 3H, 2'-H, 3'-CH, 4'-CH), 5.1-5.4 (m, 3H, 2'-OH, 3'-OH, 5'-OH), 5.5 (d, 1H, 1'-CHI), 5.9 (broad s., 2H, 5-NH₂), 7.3 (s, 1H, 2-Ch), 7.4 (t, 1H, 4-CONH).

Example AX

Preparation of N N'-Bis-(5-Amino-1-β-D-ribofuranosylimidazole-4-carbonyl)-1,4-diaminocyclohexane (Compound No. 69 (1-549))

This compound was prepared according to the procedures described in Example AW for compound 68 (1-538), substituting 1,4-diaminocyclohexane for 1,6-hexanediamine.
¹H NMR data are reported as for half the symmetrical dimer. ¹H NMR (DMSO-d₆) Δ ppm 1.3-1.8 (m, 4H, cyclohexane methylene protons), 3.5-3.7 (m, 3H, 5'-CH₂, cyclohexane methine), 3.8-4.3 (m, 3H, 2'-CH, 3'-CH, 4'-CH), 5.1-5.4 (m, 3H, 2'-OH, 3'-OH, 5'-OH), 5.5 (d, 1H, 1'-CH), 5.9 (broad s., 2H, 5-NH₂), 7.1 (d, 1H, 4-CONH) 7.3 (s, 1H, 2-CH).

Example AY

Preparation of 5-Amino-2-thio-1-(5-amino-5-deoxy-β-D-ribofuranosyl)imidazole-4-carboxamide (Compound No. 70(1-551))

A. Preparation of 5-Deoxy-5'-iodo-2-bromo-2',3'-isopropylidene AICA Riboside

2-Bromo-2'3'-isopropylidene AICA riboside (4.50 g) (ref: T. Miyoshi, S. Suzaki, A. Yamazaki, Chem. Pharm. Bull. 29, 9: 2089, (1976) methyltriphenoxyphosphonium iodide (16.2 g), and methylene chloride (125 ml) were combined and stirred at room temperature for 16 hours. The mixture was washed with water, 0.5M NAOH (100 ml), 5% NaS₂O₃ (150 ml), and brine, then dried over magnesium sulfate. The solvent was evaporated under reduced pressure to give an orange oil. The oil was triturated in cold diethylether. The resulting mixture was filtered to give 3.53 g of a grey powder. The mother liquor was concentrated under reduced pressure to give an orange oil. The oil was applied to a short column of silica gel. The column was washed with methylene chloride, then the product eluted with 9/1, methylene chloride/methanol (250 ml). The appropriate fractions were combined and concentrated under reduced pressure to give an orange tar. The tar was triturated with cold diethyl ether. The mixture was filtered to yield an additional 0.94 g of a gray powder. The combined powder (4.47 g) was chromatographed on silica gel, using 2/1, ethylacetate/hexane, as eluting solvent. The appropriate fractions were combined and concentrated under reduced pressure to yield a yellow foam (4.02 g).

B. Preparation of 5'-Azido-5' deoxy-2-bromo-2',3'-isopropylidene AICA Riboside

5'-deoxy-5'-iodo-2-bromo-2',3'-isopropylidene AICA riboside (4.02 g) lithium azide (1.82 g), and DMF (65 ml) were combined and stirred at ambient temperature for 2 hours. The solvent was evaporated under reduced pressure to give a yellow oil. The oil was dissolved in ethyl acetate (200 ml), washed with water and brine, then dried over magnesium sulfate. The solvent was evaporated under reduced pressure to give a yellow foam (3.01 g).

C. Preparation of 5'-Amino-5'-deoxy-2-bromo-2',3'-isopropylidene AICA Riboside

5'-azido-5'-deoxy-2-bromo-2',3'-isopropylidene AICA riboside (2.00 g), triphenylphosphine (1.83 g), and THF (100 g) were combined and stirred at room temperature for 16 hours. Concentrated NH₄OH (15 ml) was added and the solution heated at reflux for 6 hours. The solution was cooled and the solvent evaporated under reduced pressure. The resulting residue was coevaporated with methanol (2×30 ml). The resulting residue was stirred in cold methanol (25 ml) for 30 minutes. The mixture was filtered to give an off-white powder. The solid was recrystallized from methanol to give a white powder (0.73 g).

D. Preparation of 5-Amino-2-thio-1-(5-amino-5-deoxy-β-D-ribofuranosyl)imidazole-4-carboxamide (Compound No. 70 (1-551))

Potassium sulfide (1.0 g) was heated at reflux in ethanol (10 ml) for 15 minutes. The mixture was filtered and to the filtrate was added 5'-amino-5'-deoxy-2-bromo-2',3'-isopropylidene AICA riboside (0.50 g). The mixture was heated in a steel bomb at 110° C. for 5 hours. The mixture was cooled and filtered. The filtrate was again filtered, then concentrated under reduced pressure to give a yellow tar. The tar was chromatographed on silica gel, using 3/1, methylene chloride/methanol, as eluting solvent. The appropriate fractions were combined and concentrated under reduced pressure to give a yellow glass (0.12 g). The glass was dissolved in 80% of trifluoroacetic acid (8 ml) and stirred at room temperature for 1 hour. The solvent was evaporated under reduced pressure to give a yellow solid. The solid was stirred in diethylether/ethanol (10 ml of 95/5), then filtered and dried to yield a yellow solid (55 mg).
¹H NMR (DMSO-d₆+D₂O) Δ ppm, 2.6-2.9 (m, 2H, 5'-CH₂), 3.8-4.5 (m, 3H, 2'-CH, 3'-CH, 4'-CH), 6.2 (d, 1H, 1'-CH).

Example AZ

Preparation of 5-Amino-1-(5-azido-5-deoxy-β-D-ribofuranosyl)imidazole-4-N→(4-nitrophenyl)methyl]carboxamide (Compound No. 71 (1-562))

This compound was prepared according to the procedures described in example AH for compound 52 (1-467), substituting compound 23 (1-343) (p-nitrobenzyl derivative), for compound 29 (1-349) (p-chlorobenzyl derivative).

$^1$H NMR (DMSO-$d_6$). Δ ppm, 3.5-3.7 (m, 2H, 5'-$CH_2$), 3.9-4.4 (m, 3H, 2'-CH, 3'-CH, 4'-CH), 4.4-4.5 (d, 2H, —$CH_2$-PhNO$_2$), 5.4-5.5 (m, 2H, 2'-OH, 3'-OH), 5.5 (d, 1H, 1'-CH), 5.9 (broad s., 2H, 5-$NH_2$), 7.4 (s, 1H, 2-CH), 6.5-8.2 (m, 4H, —$C_6H_4NO_2$), 8.3 (4, 1H, CONH—).

Example BA

Preparation of 5-Amino-1-(5-amino-5-deoxy-β-D-ribofuranosyl)imidazole-4-N-[4-nitrophenyl)methyl]carboxamide (Compound No. 72 (1-563))

This compound was prepared according to the procedures described in Example AH for compared 53 (1-468), substituting the p-nitrobenzyl amide derivative (compound 23 (1-343)) for the p-chlorobenzyl amide derivative (compound 29 (1-349)).

$^1$H NMR (DMSO+$D_2$O) Δ ppm 2.6-2.8 (m, 2H, 5'-$CH_2$), 3.8-4.3 (m, 3H, 2'-CH, 3'-CH, 4'-CH), 4.4-4.5 (m, 2H, —$CH_2$—$C_6H_4NO_2$), 5.4 (d, 1H, 1'-CH), 7.3 (s, 1H, 2-CH), 7.5-8.3 (m, 5H, $CH_2C_6H_4NO_2$, 4-CONH).

Example BB

Preparation of 5-Amino-1-β-D-ribofuranosyl-imidazole-4-N-[(4-(trifluoromethylphenyl)methyl]carboxamide (Compound No. 74 (1-572))

This compound was prepared according to the procedures described in Example J for the p-nitrobenzyl derivative substituting 4-(trifluoromethyl)benzylamine for 4-nitrobenzyl amine hydrochloride. The final product was recrystallized from methylene chloride/methanol. Mp=137-140.

$^1$H NMR (DMSO-$d_6$) Δ ppm 3.5-3.7 (m, 2H, 5'-$CH_2$), 3.9-4.4 (m, 3H, 2'-CH, 3'-CH, 4'-CH), 4.4-4.5 (d, 2H, —$CH_2$-PhCF$_3$), 5.2-5.5 (m, 3H, 2'-OH, 3'-OH, 5'-OH), 5.5 (d, 1H, 1'-CH), 5.9 (broad s., 2H, 5-$NH_2$), 7.3 (S, 1H, 2-CH), 7.4-7.7 (m, 4H, —$C_6H_4CF_3$), 8.2 (t, 1H, 4-CONH).

Example BC

Preparation of 5-Amino-1-β-D-ribofuranosylimidazole-4-N-[(4-sulfamoylphenyl)methyl]carboxamide (Compound No. 75 (1-577))

This compound was prepared according to the procedures described in Example J for the p-nitrobenzyl derivative, substituting 4-(aminomethyl)benzene sulfonamide hydrochloride for 4-nitrobenzylamine hydrochloride.

$^1$H NMR (DMSO-$d_6$) Δ ppm, 3.5-3.7 (m, 2H, 5'-$CH_2$—), 3.9-4.4 (m, 3H, 2'-CH, 3'-CH, 4'-CH), 4.4-4.5 (d, 2H, —$CH_2$—$C_6H_4SO_2$), 5.2-5.4 (m, 3H, 2'-OH, 3'-OH, 5'-OH), 5.5 (d, 1H, 1'-CH), 6.0 (broad s., 2H, 5-$NH_2$), 7.3 (broad s., 2H, —$SO_2NH_2$), 7.4 (s, 1H, 2-CH), 7.4-7.8 (m, 4H, —$C_6H_4$), 8.2 (t, 1H, 4-CONH—).

Example BD

Preparation of 5-Amino-1-(5-(4-chlorobenzyl-amino)-5-deoxy-β-D-ribofuranosyl)imidazole-4-carboxamide (Compound No. 76 (1-578))

5'-amino-5'-deoxy-AICA-riboside (0.50 g) (compound No. 21 (1-227)) of Table VIII, 4-chlorobenzyl iodide (0.50 g), potassium carbonate (0.26 g), and DMF (15 ml) were combined and stirred at room temperature for 16 hours. The solvent was evaporated under reduced pressure and the resulting residue stirred in warm ethanol (35 ml). The insolubles were removed by filtration and the filtrate concentrated under reduced pressure. The resulting residue was chromatographed on silica gel, using 3:1, methylene chloride:methanol, as eluting solvent. The fractions containing the slower moving of the two products were combined and concentrated under reduced pressure to yield a tan foam (0.21 g)

$^1$H NMR (DMSO-$d_6$+$D_2$) Δ ppm 2.9-3.0 (m, 2H, 5'-$CH_2$—), 3.9 (s, 2H, —$CH_2$—$C_6H_4$), 3.9-4.3 (m, 3H, 2'-CH, 3'-CH, 4'-CH), 5.5 (d, 1H, 1'-CH), 7.3 (s, 1H, 2-CH), 7.4 (m, 4H, —$CH_4Cl$).

Example BE

Preparation of 5-Amino-1-(5-deoxy β-D-ribofuranosyl)imidazole; (Compound No. 77 (1-588))

5'-deoxy AICA riboside (1.00 g) (ref: P. C. Srivastava, A. R. Newman, T. R. Mathews, and R. F. Robins, J. Med. Chem. 18: 1237 (1975) was heated at reflux in N potassium hydroxide (4.0 ml) for 5 hours. The solvent was evaporated under reduced pressure and the resulting residue co-evaporated with ethanol (4×10 ml). The resulting residue was diluted with ethanol (15 ml) and a fine precipitate was filtered. Upon setting for several days, the filtrate gave an additional precipitate. The microscopic solid was collected, and the combined solid material was dissolved in water (20 ml) and neutralized with Dowex 50W strongly acidic ion exchange resin. The solvent was evaporated under reduced pressure to give a dark tar. The tar was dissolved in 80% acetic acid (20 ml) and gently heated (60° C.). The solvent was evaporated under reduced pressure to give a dark tar. The tar was co-evaporated with methanol (2×15 ml). The resulting residue was chromatographed on silica gel, using 3/1, methylene chloride/methanol, as eluting solvent. The appropriate fractions were combined and concentrated under reduced pressure to yield a dark tar. The tar was co-evaporated with toluene (3×20 ml), then vacuum dried to yield a dark brown, hygroscopic foam (110 mg).

$^1$H NMR ($D_2$) Δ ppm, 1.3 (d, 3H, 5'-$CH_3$), 4.0-4.5 (m, 3H, 2'-CH, 3'-CH, 4'-CH), 5.6 (d, 1H, 1'-CH), 6.4 (s, 1H, 4-CH), 7.7 (s, 1H, 2-CH).

Example BF

Preparation of 5-Amino-1-(5-deoxy-5-diethylaminoribo-β,D-furanosyl)imidazole-4-carboxamide (Compound No. 65 (1-522)

5-deoxy-5'-iodo-2',3'-isopropylidene AICA riboside (1.00 g) (ref.: P. C. Srivastava, A. R. Newman, T. R. Mathews, and R. K. Robins, J. Med. Chem. 18: 1237, (1975)), diethylamine (2.5 ml of 40 wt % in water), and methanol (30 ml) were combined and heated at reflux for 18 hours. The procedures described in Example AS for compound 63 (1-519) were followed to give the above-identified compound.

$^1$H NMR (DMSO-$d_6$) Δ ppm 0.9 (t, 6H, methyl groups on 5'-diethylamine), 2.4-2.7 (m, 6H, 5'-$CH_2$, methylene groups on 5'-diethylamine), 3.3-4.2 (m, 3H, 2'-CH, 3'-CH, 4'-CH), 5.2 (broad, 2H, 2'-OH, 3'-OH), 5.4 (d, 1H, 1'-CH), 5.9 (broad s., 2H, 5-$NH_2$), 5.7-5.9 (broad, 2H, 4-$CONH_2$), 7.3 (s, 1H, 2-CH).

Example BG

Preparation of 5-Amino 1-β-D-ribofuranosylimidazole-4-N[3-4-nitrophenyl)propyl]carboxamide (Compound No. 73 (1-566))

This compound was prepared according to the procedures described in Example J for the p-nitrophenyl derivative, substituting 3-(4-nitrophenyl)propylamine (ref: G. W. Hardy, et al., J. Med. Chem. 32: 1108, (1989)) for p-nitrobenzylamine hydrochloride.

$^1$H NMR (DMSO-$d_6$) Δ ppm 1.7-3.2 (m, 6H, —$CH_2$ $CH_2$—), 3.5-3.6 (m, 2H, 5'-$CH_2$), 3.9-4.3 (m, 3H, 2'-CH, 3'-CH, 4'-CH), 5.2-5.4 (m, 3H, 2'-OH, 3'-OH, 5'-OH), 5.5 (d, 2H, 1'-CH), 5.9 (broad s., 2H, 5-$NH_2$), 7.3 (s, 1H, 2-CH), 7.5-8.2 (m, 5H, —$C_6 H_4 NO_2$, 4-CONH—).

Example BH

Preparation of 5-Amino-1-(5-amino-5-deoxy-2,3-di-O-acetyl-β-D-ribofuranosyl)imidazole-4-N-[(4-chlorophenyl)methyl]carboxamide, (Compound No. 78 (1-599))

A. Preparation of 5-amino-1-(5-azido-5-deoxy-2,3-di-O-acetyl-β-D-ribofuranosyl)imidazole-4-N-[4-chlorophenyl)methyl]carboxamide Compound 52 (example AH), 2.4 g (5.8 mmol), was dissolved in a mixture of 20 ml of diemthylformamide and 20 ml of pyridine. The solution was cooled to 30° C. under argon, and acetic anhydride, 1.5 g, (14 mmol), was added. The mixture was allowed to warm to room temperature over 18 hours and then concentrated to a syrup. The syrup was dissolved in 25 ml of methylene chloride and washed with 3×15 ml of water, dried over magnesium sulfate and evaporated to yield 3.0 grams of a white foam. This was further purified by chromatography on 200 ml of silica gel using a mixture of methylene chloride and methanol (95:5), yielding 2.5 grams of the desired product as a white foam.

B. Preparation of 5-amino-(5-amino-5-deoxy-2,3-di-O-acetyl-β-D-ribofuranosyl)imidazole-4-N-[(4-chlorophenyl)methyl]carboxamide (Compound No. 78 (1-599))

The product of step A, 400 mg, was dissolved in 10 ml of ethanol and 50 mg of 10% Pd on carbon was added. The mixture was stirred under a hydrogen atmosphere for 30 minutes, filtered and the filtrate evaporated to yield 300 mg of the desired product as a white foam.

$^1$H NMR (DMSO-$d_6$) A 2.0 (s, 3H, $CH_3$ CO—), 2.1 (s, 3H, $CH_3$ CO—), 2.9 (m, 2H, 5'-$CH_2$), 4.1 (m, 1H, 4'-CH), 3.4 (broad s, 2H, 5'-$NH_2$) 4.4 (d, 2H, —$CH_2$—$C_6 H_4$—Cl), 5.3 (m, 1H, 3'-CH) 5.6 (m, 1H, 3'-CH), 5.8 (d, 1H, 1'-CH), 6.4 (broad s, 2H, 5-$NH_2$), 7.3 (m, 4H, —$C_6 H_4$—Cl), 7.4 (s, 1H, 2-CH), 8.1 (t, 1H, 4-CONH—).

Example BI

Prodrugs of the invention can also be prepared and administered under appropriate conditions. In a preferred embodiment, the prodrugs of the invention enhance oral bioavailability, and include in particular the carboxylic acid esters of 2' and 3' hydroxyls.

Prodrug esters of the invention can be made by standard acetylation procedures, which may involve protection and deprotection steps. For example, the 5' group of Series III compounds may require protection (e.g., the 5'-benzylamino of Compound 66 can be protected with a benzyloxycarbonyl group.)

Preparation of 5-Amino-1-(5-N-benzylamino-2,3,-di-O-pivaloyl-5-deoxy-β-D-ribofuranosyl)imidazole-4-carboxamide (Prodrug of Compound 66)

1-(5-N-benzylamino-5-deoxy-β-D-ribofuranosyl)imidazole-4-carboxamide tartrate salt (8.8 g, 16.77 mmol) in water (60 mL), potassium carbonate (8.5 g), and tetrahydrofuran (120 mL) was taken in a three-necked round bottom flask fitted with a mechanical stirrer, an addition funnel, and a nitrogen inlet. The flask was cooled in an ice water bath. A solution of benzyl chloroformate (3.4 mL, 20 mmol) in THF (15 mL) was added over a period of 1 5 minutes. The cooling bath was removed and stirring was continued for two hours, at which time t.l.c. ($SiO_2$, 6:1 $CH_2 Cl_2$-Methanol) indicated complete consumption of the starting material. The reaction mixture was transferred to a separatory funnel and the organic layer was separated. The aqueous layer was washed with ethyl acetate (3×30 ml). The organic layers were combined, dried over anhydrous $MgSO_4$ and evaporated to obtain a syrupy residue. The product was further purified by column chromatography using 9:1 $CH_2 Cl_2$-Methanol as the eluting system. Fractions containing the product were pooled and evaporated to obtain, A. 5-amino-1-(5-N-benzylamino-N-benyoxycarbonyl-5-deoxy-β-D-ribofuranosy 1)imidazole-4-carboxamide as a glassy solid. Yield: 5.5 g. Rf=0.5 $SiO_2$, 6:1 $CH_2 Cl_2$-Methanol.

A solution of compound A (2.0 g, 4.15 mmol) and 4-N,N-dimethylaminopyridine (100 mg) in dry pyridine (20 mL) was cooled in an ice water bath and treated with pivalic anhydride (3.3 mL). The ice bath was removed and the reaction mixture was stirred at room temperature for 16 hours. The t.l.c. ($SiO_2$, 9:1 $CH_2 Cl_2$-Methanol) indicated complete consumption of the starting material. Methanol (1.5 mL) was added and stirred for an additional half-hour, and the volatiles were evaporated under reduced pressure. The residue was dissolved in ethyl acetate (50 mL) and extracted with water (1×50 mL) and sodium bicarbonate solution (1×20 mL). The organic layer was dried over anhydrous $MgSO_4$ and evaporated to obtain a syrupy residue. The product was further purified by column chromatography using 19:1 $CH_2 Cl_2$-Methanol as the eluting system. Fractions containing the product were pooled and evaporated to obtain, B. 5-amino-1-(5-N-benzylamino-N-benyoxycarbonyl-2,3-di-O-pivaloyl-5-deoxy-β-D ribofuranosyl)imidazole-4-carboxamide as a glassy solid. Yield: 5.5 g. Rf=0.6 $SiO_2$, 9:1 $CH_2 Cl_2$-Methanol. HNMR, DMSC-$d_6$ Δ ppm.

To a solution of compound B (1.1 g) in ethyl acetate (30.0 mL) and acetic acid (6.0 mL) the catalyst Pd(OH)$_2$ on carbon (100 mg) was added and purged with nitrogen. Hydrogenation was carried out using a balloon of hydrogen. Completion of the reaction was evidenced by the absence of starting material on t.l.c. ($SiO_2$, 9:1 $CH_2Cl_2$-Methanol). The catalyst was removed by filtration through a celite pad and washed with ethyl acetate. The filtrate was evaporated under reduced pressure and the residue was redissolved in ethyl acetate (50 mL) and extracted with saturated sodium bicarbonate solution (1×20 mL). The organic layer was dried over anhydrous $MgSO_4$ and evaporated to obtain a residue which was further purified over a silica gel column using 19:1 $CH_2Cl_2$-Methanol as the eluting system. Fractions containing the product were pooled and evaporated to obtain.

C. 5-amino-1-(5-N-benzylamino-N-benylamino-2,3-di-O-pivaloyl-5-deoxy-β-D-ribofuranosyl)imidazole-4-carboxamide as a glassy solid. Yield: 800 mg. Rf=0.55 $SiO_2$, 9:1 $CH_2Cl_2$-Methanol.

To obtain the corresponding hydrochloride salt of the title compound, the above free base (200 mg) was dissolved in methanol and diluted with 1N aqueous HCL solution. The resulting solution was evaporated under reduced pressure (bath temperature, 30 C.). The residue was dissolved in double distilled water (15 mL) and filtered through a 45µ membrane filter. The filtrate was frozen in a lyophilizing jar and lyophilized repeatedly until a constant weight was obtained. The final product 5-amino-1-(5-N-benzylamino-N-benylamino-2,3-di-O-pivaloyl-5-deoxy-β-D-ribofuranosyl)imidazole-4-carboxamide hydrochloride was obtained as a white solid was dried under high vacuum and stored in the freezer. Yield: 180 mg, m.p. 172°-175° C.

The following prodrugs can be made in a similar manner:
5-amino-1-(5-N-benzylamino-2,3-di-O-acetyl-5-deoxy-β-D-ribofuranosyl)imidazole-4-carboxamide.
5-amino-1-(5-N-benzylamino-2,3-di-O-propionyl-5-deoxy-β-D-ribofuranosyl)imidazole-4-carboxamide.
5-amino-1-(5-N-benzylamino-2,3-di-O-butyryl-5-deoxy-β-D-ribofuranosyl) imidazole-4-carboxamide.
5-amino-1-(5-N-benzylamino-2,3-di-O-isobutyryl-5-deoxy-β-D-ribofuranosyl)imidazole-4-carboxamide.
5-amino-1-(5-N-benzylamino-2,3-di-O-pentanoyl-5-deoxy-β-D-ribofuranosy 1)imidazole-4-carboxamide.
5-amino-1-(5-N-benzylamino-2,3-di-O-benzoyl-5-deoxy-β-D-ribofuranosyl) imidazole-4-carboxamide.
5-amino-1-(5-N-benzylamino-2,3-di-O-(4-methylbenzoyl)-5-deoxy-β-D-ribofuranosyl)imidazole-4-carboxamide.
5-amino-1-(5-N-benzylamino-2,3-di-O-phenylacetyl-5-deoxy-β-D-ribofuranosyl)imidazole-4-carboxamide.
5-amino-1-(5-N-benzylamino-2,3-di-O-palmitoyl-5-deoxy-β-D-ribofuranosy 1)imidazole-4-carboxamide.
5-amino-1-(5-N-benzylamino-2,3-di-O-oleyl-5-deoxy-β-D-ribofuranosyl)imidazole-4-carboxamide.
5-amino-1-(5-N-benzylamino-5-deoxy-β-D-ribofuranosyl) imidazole-4-carboxamide-2',3'-cyclic carbonate.

Example BJ

The oral bioavailability of Compound 66 (1-531) and one of its prodrugs (Example BH) was studied, based on urinary excretion of Compound 66 following its administration, and administration of the prodrug. An IV bolus of Compound 66 was used as the 100% bioavailable control.

Four rats were used for each drug and each route of administration. Food was removed for two hours prior to and two hours after dosing; water was allowed. The first group of rats received an aqueous solution of Compound 66 as a tartate salt (20 mg/kg equivalents of free base) as a bolus via the tail vein. The second group received an aqueous solution of Compound 66 as a tartrate salt (20 mg/kg equivalents of free base) by oral gavage. The third group of rats received a solution of the prodrug, 5-Amino-1-(5-N-benzylamino-2,3,-di-O-pivaloyl-5-deoxy-β-D-ribofuranosyl)imidazole-4-carboxamide (20 mg/kg equivalents of Compound 66 as a free base) by oral gavage.

The rats were kept in metabolic cages, and urine was collected over the following intervals: −15-0 (control), 0-24, and 24-48 hours. The volume of each collection was recorded and a 5 mL aliquot was frozen at −20° C. The urinary concentrations of Compound 66 were then determined for these IV and oral administrations.

The samples were assayed for intact Compound 66 by HPLC. Each sample was diluted 1:10 with water prior to HPLC analysis, which was performed on a Beckman Ultrasphere $C_{18}$ reverse phase column (4.6×150 mm, 5 micron) eluted isocratically at ambient temperature with a mobile phase of 40% methanol and 20 mM heptane sulfonic acid (sodium salt) at a flow rate of 1.5 ml/min. The eluant was monitored by UV absorbance at 259 nm.

TABLE XII

COMPOUNDS OF THE FORMULA

| Compound No. | R$_1$ | R$_2$ | R$_3$ | X | R$_4$ | R$_5$ | R$_6$ |
|---|---|---|---|---|---|---|---|
| 10(1-110) | —NH$_2$ | —C(=O)NH$_2$ | —H | —O— | —H | —H | —OH |
| 2(1-111) | —NH$_2$ | —C(=O)NH$_2$ | —H | —O— | —H | —H | —O—C(=O)CH$_3$ |
| 3(1-115) | —NH$_2$ | —CN | —H | —O— | —C(=O)CH$_3$ | —C(=O)CH$_3$ | —OH |
| 4(1-122) | —NH$_2$ | —C(NH$_2$)=NOH | —OH | —H | —H | —OH | —OH |
| 5(1-145) | —NH$_2$ | —C(=O)NH$_2$ | —H | —CH$_2$— | —H | —H | —OH |
| 6(1-155) | —NH$_2$ | —C(NH)OCH$_2$CH$_3$ | —H | —O— | —H | —H | —OH |
| 7(1-164) | —N=CHN(CH$_2$)$_2$ | —C(=O)NH$_2$ | —H | —O— | —H | —H | —OH |

TABLE XII-continued
COMPOUNDS OF THE FORMULA
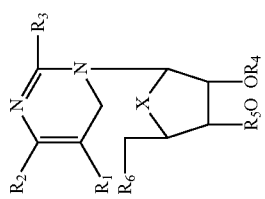
| Compound No. | R$_1$ | R$_2$ | R$_3$ | X | R$_4$ | R$_5$ | R$_6$ |
|---|---|---|---|---|---|---|---|
| 8(1-172) | —NH$_2$ | —C(O)NH$_2$ | —H | —O— | —H | —H | —OP(O)(OH)(OH) |
| 9(1-177) | —NHC(O)CH$_3$ | —C(O)NH$_2$ | —H | —O— | —C(O)CH$_3$ | —C(O)CH$_3$ | —OC(O)CH$_3$ |
| 10(1-186) | —NH | —C(O)NH-cyclopentyl | —H | —O— | —H | —H | —OH |
| 11(1-126) | —NH$_2$ | —C(O)NH-CH$_2$-phenyl | —H | —O— | —H | —H | —OH |
| 12(1-232) | —NH$_2$ | —C(O)NH-cyclopropyl | —H | —O— | —H | — | —OH |
| 13(1-240) | —NH$_2$ | —C(O)NH$_2$ | —Br | —O— | —H | —H | —OH |
| 14(1-260) | —NH$_2$ | —C(O)CH$_3$ | —H | —O— | —H | —H | —OH |

TABLE XII-continued
COMPOUNDS OF THE FORMULA
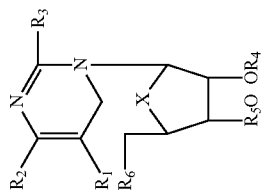
| Compound No. | R₁ | R₂ | R₃ | X | R₄ | R₅ | R₆ |
|---|---|---|---|---|---|---|---|
| 15(1-261) | —NH₂ | O=CNH₂ | —H | —O— | —H | —H | —OS(O)₂NH₂ |
| 16(1-273) | —NH₂ | —H | —H | —O— | —H | —H | —OH |
| 17(1-295) | —NHCCH₃ (O=) | —H | —H | —O— | —H | —H | —OH |
| 18(1-335) | —NH₂ | C(=NOCH₃)NH₂ | —H | —O— | —H | —H | —OH |
| 19(1-154) | —NH₂ | O=CNH₂ | —H | —O— | —H | —H | —H |
| 20(1-188) | —NH₂ | O=CNH₂ | —H | —O— | —H | —H | —OH |
| 21(1-127) | —NH₂ | O=CNH₂ | —H | —O— | —H | —H | —NH₂ |
| 22(1-243) | —NH₂ | O=CNH₂ | —H | —O— | —H | —CH₃ | —OH |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 23(1-343) | —NH₂ | —C(=O)NHCH₂-(4-NO₂-C₆H₄) | —H | —O— | —H | —H | —OH |
| 24(1-354) | —NH₂ | —C(=O)NHCH₂-(2-Cl-C₆H₄) | —H | —O— | —H | —H | —OH |
| 25(1-360) | —NH₂ | —C(=O)NHCH₂-(2,4-Cl₂-C₆H₃) | —H | —O— | —H | —H | —OH |
| 26(1-332) | —NH₂ | —C(=O)NH₂ | —H | —O— | —H | —H | —Cl |
| 27(1-395) | —NH₂ | —C(=O)NH₂ | —SH | —O— | —H | —H | —OH |
| 28(1-348) | —NH₂ | —C(=O)NHCH₂-(3-NO₂-C₆H₄) | —H | —O— | —H | —H | —OH |

TABLE XII-continued

COMPOUNDS OF THE FORMULA

| Compound No. | $R_1$ | $R_2$ | $R_3$ | X | $R_4$ | $R_5$ | $R_6$ |
|---|---|---|---|---|---|---|---|
| 29(1-349) | —NH$_2$ | —C(O)NHCH$_2$-(4-Cl-C$_6$H$_4$) | —H | —O— | —H | —H | —OH |
| 30(1-388) | —NH$_2$ | —C(O)NHCH$_2$-(4-CH$_3$-C$_6$H$_4$) | —H | —O— | —H | —H | —OH |
| 31(1-251) | —NH$_2$ | —C(O)NH$_2$ | —H | —O— | —H | —CH$_2$CH$_3$ | —OH |
| 32(1-262) | —NH$_2$ | —C(O)NH$_2$ | —H | —O— | —CH$_2$)$_3$CH$_3$ | —H | —OH |
| 33(1-263) | —NH$_2$ | —C(O)NH$_2$ | —H | —O— | —H | —(CH$_2$)$_3$CH$_3$ | —OH |
| 34(1-250) | —NH$_2$ | —C(O)NH$_2$ | H | —O— | —CH$_2$CH$_3$ | —H | —OH |
| 35(1-355) | —NH$_2$ | —C(O)NH$_2$—CH$_2$-(3-Cl-C$_6$H$_4$) | —H | —O— | —H | —H | —OH |

TABLE XII-continued
COMPOUNDS OF THE FORMULA
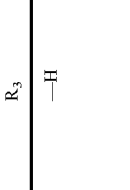
| Compound No. | R₁ | R₂ | R₃ | X | R₄ | R₅ | R₆ |
|---|---|---|---|---|---|---|---|
| 36(1-207) | —NH₂ | 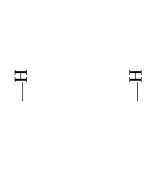 | —H | —O— | —H | —H | —OH |
| 37(1-270) | —NH₂ |  | —H | —O— | —H | —H | —NH₂ |
| 38(1-351) | —NH₂ | 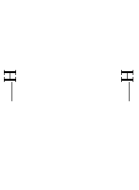 | —H | —O— | —H | —H | —OH |
| 39(1-390) | —NH₂ |  | —H | —O— | —H | —H | —OH |
| 40(1-392) | —NH₂ |  | —H | —O— | —H | —H | —OH |
| 41(1-396-3) | —NH₂ |  | —H | —O— | —H | —H | —OH |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 42(1-431) | —NH₂ | —C(O)—NH—CH₂—CH(OH)—(3,4-dihydroxyphenyl) | —H | —O— | —H | —H | —OH |
| 43(1432) | —NH₂ | —C(O)—NH₂ | —S—phenyl | —O— | —H | —H | —OH |
| 44(1-434) | —NH₂ | —C(O)—NH—CH₂—(3-iodophenyl) | —H | —O— | —H | —H | —OH |
| 45(1-438) | —NH₂ | —C(O)—NH—CH₂-norbornyl | —H | —O— | —H | —H | —OH |
| 46(1-445) | —NH₂ | —C(O)—NH—CH₂—(4-nitrophenyl) | —H | —O— | —H | —H | —I |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 47(1-450) | —NH₂ | —C(O)—S—CH₂—(4-NO₂-C₆H₄) | —H | —O— | —H | —H | —OH |
| 48(1-452) | —NH₂ | —C(O)—(indolin-1-yl) | —H | —O— | —H | —H | —OH |
| 49(1-453) | —NH₂ | —C(O)—NH—CH(CH₃)—(4-NO₂-C₆H₄) | —H | —O— | —H | —H | —OH |
| 50(1-459) | —NH₂ | —C(O)—NH—CH(CH₃)—(4-NO₂-C₆H₄) | —H | —O— | —H | —H | —OH |
| 511(1-466) | —NH₂ | —C(O)—NH—CH₂—(4-NO₂-C₆H₄) | —H | —O— | —H | —H | —Cl |
| 52(1-459) | —NH₂ | —C(O)—NH—CH₂—(4-Cl-C₆H₄) | —H | —O— | —H | —H | —N₃ |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 53(1-468) | $-NH_2$ | $-C(=O)-NH-CH_2-C_6H_4-Cl$ | $-H$ | $-O-$ | $-H$ | $-H$ | $-NH_3+Cl-$ |
| 54(1-483) | $-NH_2$ | $-C(=O)-NH_2$ | $-H$ | $-O-$ | $-H$ | $-H$ | $-S-CH_3$ |
| 55(1-484) | $-NH_2$ | $-C(=O)-NH-C_6H_4-Br$ | $-H$ | $-O-$ | $-H$ | $-H$ | $-OH$ |
| 56(1-487) | $-NH_2$ | $-C(=O)-NH-CH_2-C_6H_4-Br$ | $-H$ | $-O-$ | $-H$ | $-H$ | $-OH$ |
| 57(1-488) | $-H_2$ | $-C(=O)-NH-C_6H_4-I$ | $-H$ | $-O-$ | $-H$ | $-H$ | $-OH$ |
| 58(1-489) | $-NH_2$ | $-C(=O)-NH-C_6H_4-NO_2$ | $-H$ | $-O-$ | $-H$ | $-H$ | $-OH$ |
| 59(1-506) | $-NH_2$ | $-C(=O)-NH-CH_2-CH_2-C_6H_4-NO_2$ | $-H$ | $-O-$ | $-H$ | $-H$ | $-OH$ |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 60(1-509) | —NH₂ | —C(=O)—N(piperazine)-C₆H₄-NO₂ | —H | —O— | —H | —H | —OH |
| 61(1-509) | —NH₂ | —C(=O)—NH—CH₂-C₆H₄-Cl | —H | —O— | —H | —H | —OH |
| 62(1-510) | —NH₂ | —C(=O)—NH₂ | H | —O— | —H | —H | —S(=O)—CH₂—CH₃ |
| 63(1-517) | —NH₂ | —C(=O)—NH₂ | H | —O— | —H | —H | —NH—CH₃ |
| 62(1-519) | —NH₂ | —C(=O)—NH-C₆H₄-Cl | —H | —O— | —H | —H | —OH |
| 63(1-522) | —NH₂ | —C(=O)—NH₂ | —H | —O— | —H | —H | —N(CH₂—CH₃)(CH₂—CH₃) |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 64(1-531) | —NH₂ | —C(=O)—NH₂ | —H | —O— | —H | —H | —NH—CH₂—C₆H₅ |
| 67(1-535) | —NH₂ | —C(=O)—NH₂ | —SH | —O— | —H | —H | —H |
| 68(1-538) | —NH₂ | —C(=O)—NH—(CH₂)₄NH—C(=O)— [pyrrolidine-ribose moiety] | —H | —O— | —H | —H | —OH |
| 69(1-549) | —NH₂ | —C(=O)—NH—(CH₂)₄NH—C(=O)— [pyrrolidine-ribose moiety] | —H | —O— | —H | —H | —OH |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 70(1-551) | $-NH_2$ | $-C(O)-NH_2$ | $-SH$ | $-O-$ | $-H$ | $-H$ | $-NH_2$ |
| 71(1-562) | $-NH_2$ | $-C(O)-NH-CH_2-$(4-$NO_2$-phenyl) | $-H$ | $-O-$ | $-H$ | $-H$ | $N_3$ |
| 72(1-563) | $-NH_2$ | $-C(O)-NH-CH_2-$(4-$NO_2$-phenyl) | $-H$ | $-O-$ | $-H$ | $-H$ | $-NH_2$ |
| 73(1-566) | $-NH_2$ | $-C(O)-NH-(CH_2)_3-$(4-$NO_2$-phenyl) | $-H$ | $-O-$ | $-H$ | $-H$ | $-OH$ |
| 74(1-572) | $-NH_2$ | $-C(O)-NH-CH_2-$(4-$CF_3$-phenyl) | $-H$ | $-O-$ | $-H$ | $-H$ | $-OH$ |
| 75(1-577) | $-NH_2$ | $-C(O)-NH-CH_2-$(4-$S(O)_2-NH_2$-phenyl) | $-H$ | $-O-$ | $-H$ | $-H$ | $-OH$ |
| 76(1-578) | $-NH_2$ | $-C(O)-NH_2$ | $-H$ | $-O-$ | $-H$ | $-H$ | $-NH-CH_2-$(4-Cl-phenyl) |

TABLE XII-continued

COMPOUNDS OF THE FORMULA

| Compound No. | R₁ | R₂ | R₃ | X | R₄ | R₅ | R₆ |
|---|---|---|---|---|---|---|---|
| 77(1-588) | —NH₂ | —H | —H | —O— | —H | —H | —OH |
| 78(1-599) | —NH₂ | —C(O)NHCH₂-(4-Cl-C₆H₄) | —H | —O— | —C(O)—CH₃ | —C(O)—CH₃ | —OH |
| 79(1-607) | —NH₂ | —C(O)—NH₂ | —H | —O— | —H | —H | —OH |

Example

Administration of Aspirin Reduces Morbidity and Mortality Following Cardiac Surgery The following example describes specific aspects of the invention to illustrate the invention and provide a description of the methods used to reduce morbidity and mortality following cardiac surgery. The example should not be construed as limiting the invention, as the example merely provides specific methodology useful in understanding and practicing the invention.

1. Materials and Methods
   a. Patient Population and Methods

A prospective, longitudinal study enrolled 5,436 patients. Eligible patients included those with medically-refractory coronary artery disease and scheduled for coronary artery bypass surgery at 70 medical institutions among 17 countries in North and South America, Europe, the Middle East and Asia. At each institution, 100 patients were to be prospectively enrolled according to a systematic sampling scheme that allowed a random sampling of patients at each institution among all patients undergoing surgery at that institution.

Of the 5,436 patients enrolled, 5,065 patients completed the study and were included in the final analysis. Of the 371 patients excluded, 32 were excluded due to patient withdrawal, 2 due to death prior to surgery, 97 due to cancellation or rescheduling of surgery, 132 patients due to change in procedure, 11 due to inadvertent enrollment in another study, 86 due to incomplete data and 11 due to incomplete blood sampling, shipping or storage.

Aspirin was administered in doses of 160 mg to 650 mg to 3,001 patients within 48 hours of revascularization. All potential side-effects associated with aspirin use were recorded daily by blinded investigators. Independent investigators coded all medications received-including pro- and anti-thrombotic and pro- and anti-coagulant medications, and blood products—by day throughout hospitalization, as well as at admission and at discharge, or until death.

b. Study Data

For each enrolled patient, approximately 7,500 fields of data were collected throughout the patient's index hospitalization, from admission until discharge, by independent investigators; treated physicians were blinded to all research data. Data included demographic, historical, clinical, laboratory, eloectrocardiographic, specialized testing, resource utilization, and adverse outcomes. Following last patient enrollment, all data fields for each patient were queried centrally for completeness and accuracy, with all changes documented prior to database closure.

c. Outcome Measurements

All outcomes were prespecified, defined by protocol, and discerned by investigators blinded to treatment group. Fatal and non-fatal outcomes were classified as cardiac (myocardial infarction, congestive heart failure and cardiac death), cerebral (stroke, encephalopathy and cerebral death), renal (dysfunction, failure and renal death), gastrointestinal (ischemia, infarction and GI death), or other (such as infectious, pulmonary). The diagnosis of myocardial infarction required either: the development of new Q waves (as defined by Minnesota Code 1-1-1I or 1I-2-7); or new persistent S T-segment or T-wave changes (Minnesota Code 4-1, 4-2, 5-1 or 5-2) associated with an elevation of CK-MB isoenzyme values; or autopsy evidence of acute myocardial infarction. The diagnosis of heart failure required either: the use of a ventricular assist device; or the use of continuous inotropic support for at least 24 hours; or autopsy evidence of heart failure. Cerebral outcomes were classified as: clinically diagnosed stroke or encephalopathy; or CT, MRI or autopsy evidence of a focal or global defect. Renal dysfunction was defined as: a serum creatinine ≥177 μmol/L accompanied by a ≥62 μmol/L rise over baseline; and renal failure was defined as dysfunction requiring dialysis, or autopsy evidence of renal failure. Gastrointestinal ischemia was defined as abdominal pain diagnosed as intestinal ischemia, or detected at exploration; infarction required bowel resection, or autopsy evidence of intestinal infarction.

d. Statistical Analysis

The risk of death for aspirin taking versus control populations were compared using the Chi-Square test. Individual ischemic outcomes involving the heart, brain, kidney and gastrointestinal tract, and combined ischemic outcomes were compared using Fisher's Exact Test or the Chi-Square test as appropriate. Odds ratios and the 95% confidence intervals are presented with associated P values. All predictor variables significant at two-tailed nominal P values <0.15 in univariate analyses were then entered into a multivariate logistic model. Stepwise logistic regress was performed, retaining variables significant at two-tailed nominal P values <0.05. All statistical analysis were performed with SAS Version 8.12 software. (SAS Institute, Cary, N.C.)

e. Results

Small differences existed between study groups, notably patients receiving aspirin were more likely to have unstable angina, prior PTCA and be treated with beta-blockers, calcium channel blockers and antiplatelet therapy and less likely to have a history of heart failure and be treated with ACE inhibitor (Table 1). No other important differences existed for any medical or surgical characteristic. Most cardiac medications were continued up to the time of surgery, however, anti-platelet medications were discontinued prior to surgery in 50% of patients that had been receiving anti-platelet treatment at hospital admission.

Figure 24:
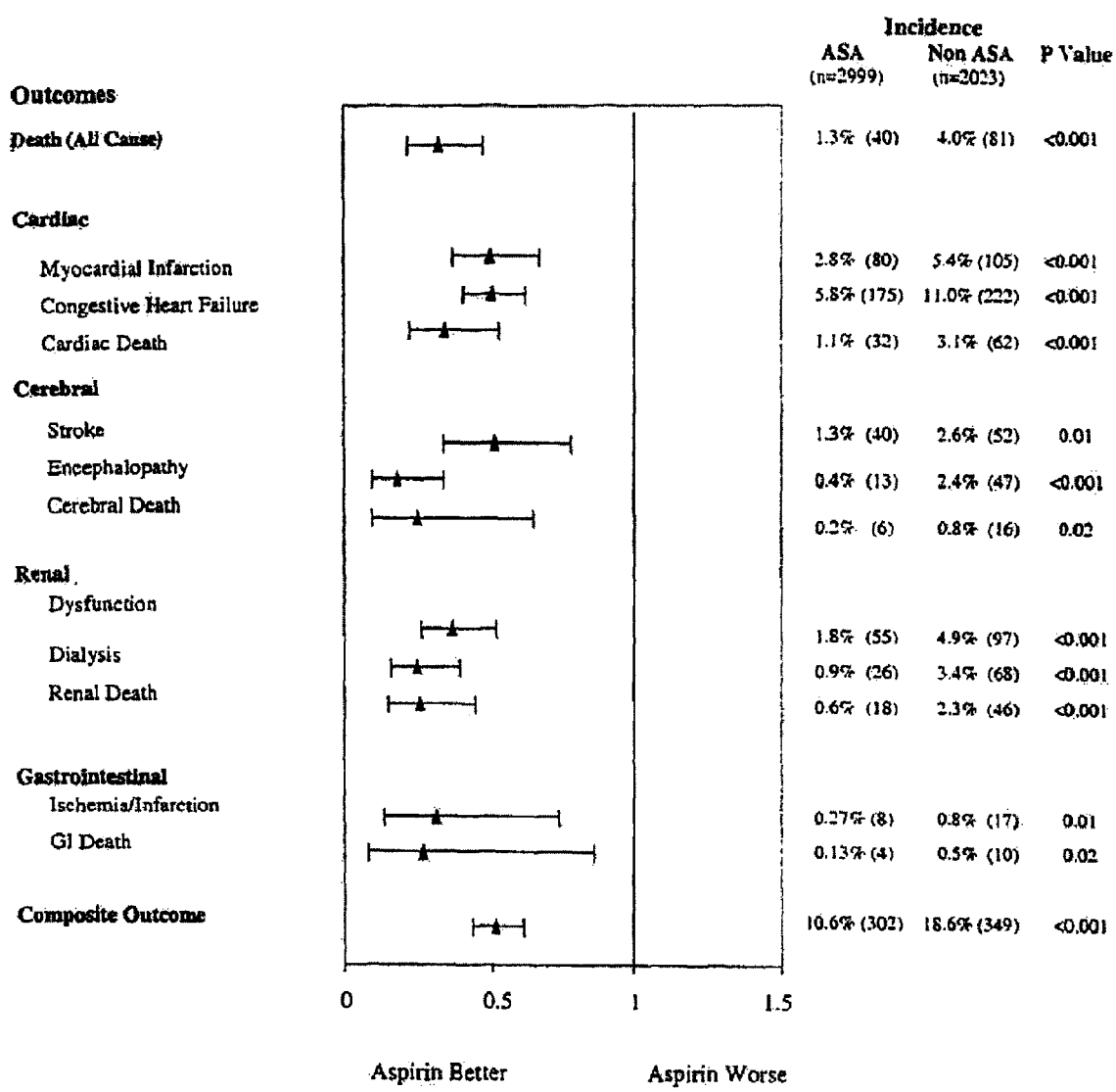
FIG. 24 Aspirin, Death and Surgery. This provides fatal (N=164) and non-fatal (N=748) ischemic outcomes among the aspirin and non-aspirin groups. The population at risk varies among individual outcomes since respective outcomes occuring within 48 hours were excluded. Odds Ratio and its 95% Confidence Interval.
Figure 25:
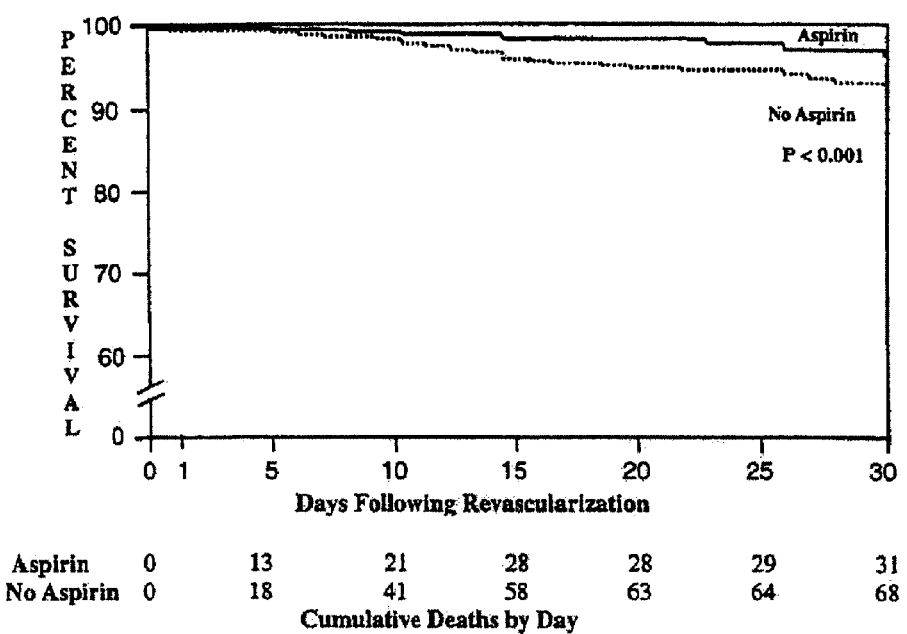
FIG. 25 Aspirin, Death and Surgery. This provides in-hospital survival by aspirin use among the 5022 study patients who survived the first 48 hours post CABG Surgery. It provides thirty-day survival by aspirin use among the 5065 study patients. Kaplan-Meier analysis of survival according to aspirin use.

Patients receiving aspirin within 48 hours of revascularization had one-fourth the risk of dying during hospitalization (1.4% v. 5.9%; P<0.0001). Patients receiving aspirin also had one-half the risk of non-fatal ischemic complications associated with the heart, brain kidney or gastrointestinal tract (13.6% v. 24.5%; P<0.0001). FIG. 24. Of those receiving aspirin, none died within 12 hours of surgery (versus 25 patients in the control group) and one died within 48 hours of surgery (versus 42 patients from the control group). FIG. 25.

Figure 26:
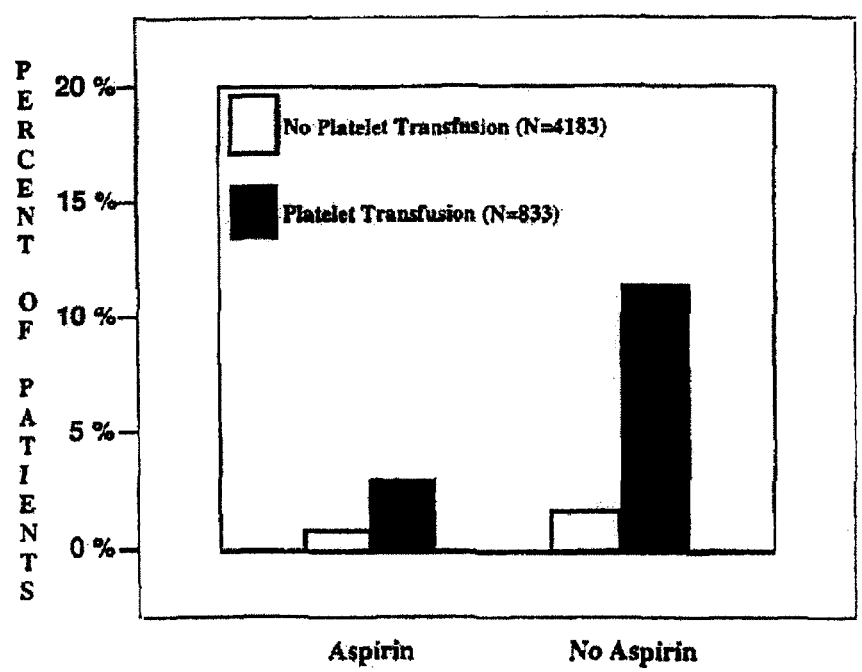
FIG. 26 Aspirin, Death and Surgery. It provides mortality associated with platelet transfusion among the aspirin and non-aspirin groups. All comparisons are significant. For the aspirin group, platelet transfusion versus no platelet transfusion (P<0.001), for the no aspirin group, platelet transfusion versus no platelet transfusion (P<0.001), for the platelet transfusion group, aspirin versus no aspirin (P<0.001), for the no platelet transfusion group, aspirin versus no aspirin (P<0.001).
Figure 27:
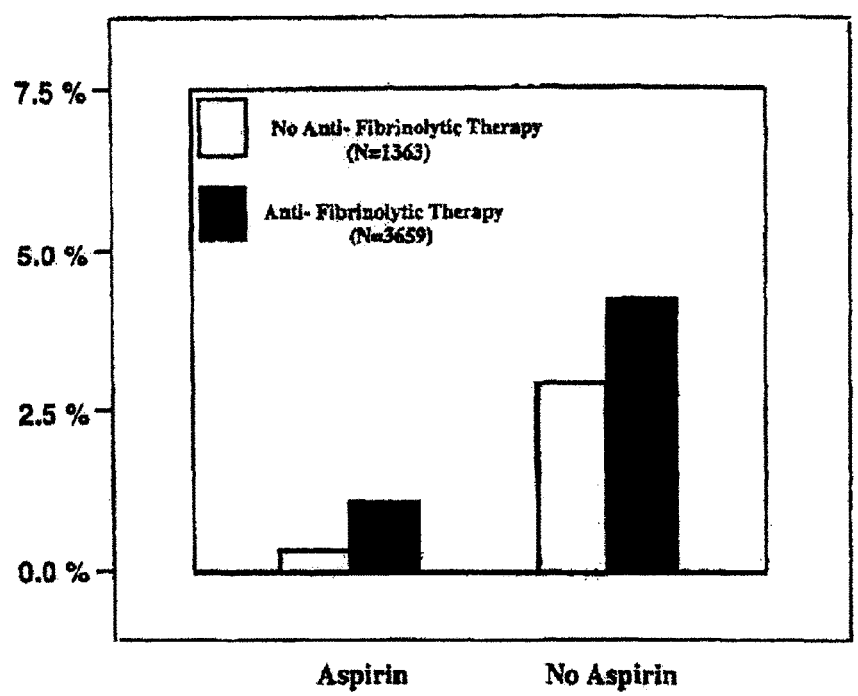
FIG. 27 Aspirin, Death and Surgery. It provides mortality associated with use of anti-fibinolytic therapy among the aspirin and non-aspirin groups. This includes 3659 patients receiving either aprotinin (1578 patients), epsilon aminocaproic acid (1258 patients), tranexaminic acid (951 patients), or desmopressin (61 patients). All comparisons are significant. For the aspirin group, anti-fibrinolytic therapy versus no anti-fibrinolytic therapy (P=0.04); for the aspirin group, anti-fibrinolytic therapy versus no anti-fibrinolytic therapy (P=0.31), for the anti-fibrinolytic therapy group, aspirin versus no aspirin (P<0.001), for the no anti-fibrinolytic therapy group, aspirin versus no aspirin (P<0.001).
Figure 28:
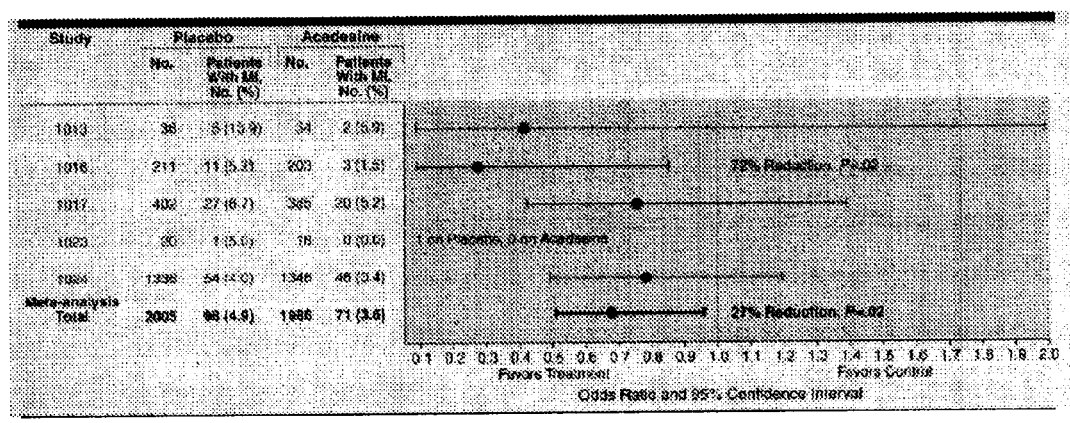
FIG. 28. Myocardial infarction (MI) results for individual trials and meta-analysis by patient. The bars indicate 95% confidence intervals for the odds ratios.
Figure 29:
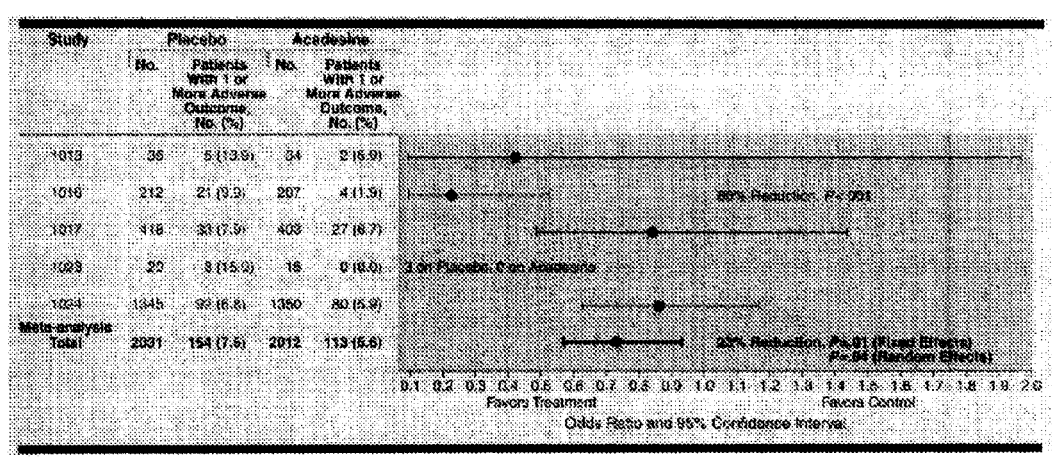
FIG. 29. Combined adverse cardiac outcomes (myocardial infarction, cardiac death, or stroke/cerebrovascular accident) for individual trials and meta-analysis by patient. The error bars indicate 95% confidence intervals for the odds ratios.
Figure 30:
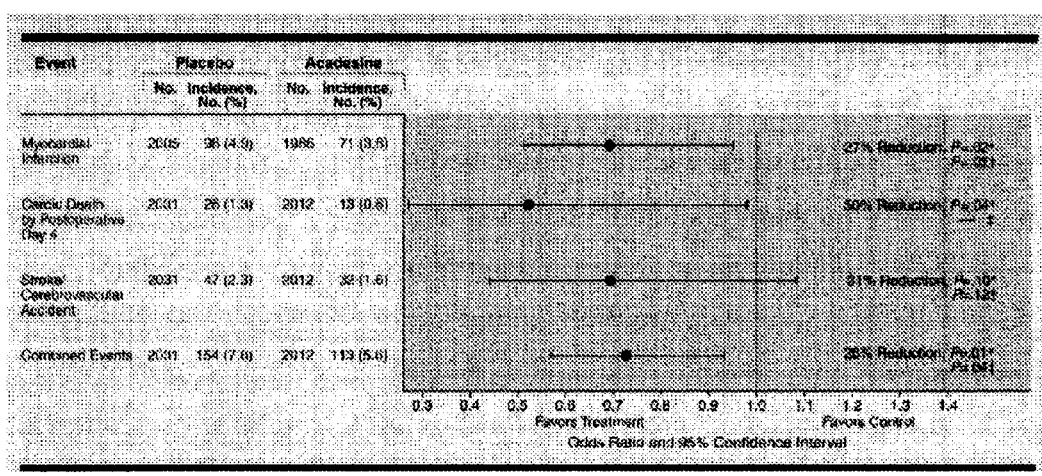
FIG. 30. Summary of protocol-specified events for meta-analysis by patient. The bars indicate 95% confidence intervals for the odds ratio. The asterisk indicates the P values were calculated using a fixed effects model; the dagger, the P values were calculated using a random effects model; and the double dagger, the between-study variance estimate is negative for cardiac death; thus, the test statistic for the random effects model cannot be estimated. Combined means occurrence of any of the events (myocardial infarction, cardiac death, or stroke/cerebrovascular accident), appearing singly or in any combination.
Figure 31:
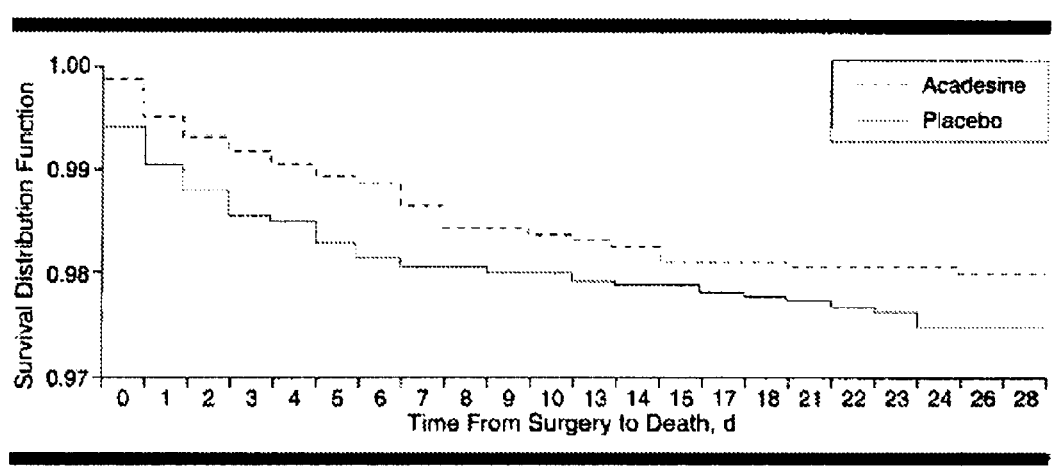
FIG. 31. Survival analysis comparing acadesine-treated patients with placebo-receiving patients.

Improved survival over the first 30 postsurgical days was associated only with early aspirin use, as opposed to other reversible factors. (FIG. 25). A first use of aspirin 48 hours after surgery was not associated with a significant reduction in mortality (15%; P=0.534). The beneficial effect of aspirin on fatal outcomes was significant over all subsets including gender, age, geographical region and type of insurance. Length of hospitalization was decreased in those receiving aspirin (9.57±7.14 versus 11.32±9.44; P<0.0001). The risks associated with platelet transfusion after reperfusion and prophylactic anti-fibrinolytics were associated with increased risk of dying and ischemic complications. Aspirin use substantially reduced, but did not eliminate these risks. FIG. 26. In addition to the unexpected benefits of aspirin use according to the methods, aspirin use was also safe. Table 2.

Various embodiments of the invention have been described. The descriptions and examples are intended to be illustrative of the invention and not limiting. Indeed, it will be apparent to those of skill in the art that modifications may be made to the various embodiments of the invention described without departing from the spirit of the invention or scope of the appended claims set forth below.

TABLE 1

Baseline Demographic and Medical Characteristics Among the 5065 Study Patients

| | | All Patients (N = 5605) | Aspirin Group (N = 3001) | Non-Aspirin Group (N = 2064) | P Value |
|---|---|---|---|---|---|
| Age (years) | | | | | |
| | Mean (±SD) | 64.1 (±9.76) | 63.6 (±9.71) | 64.7 (±9.8) | <0.0001 |
| | Median | 64.8 | 64.3 | 65.5 | <0.0001 |
| Body Surface Area < 1.93$^2$ | | 49.2% (2478) | 52.6% (1573) | 44.0% (905) | <0.001 |
| Female Gender | | 20.5% (1038) | 19.3% (579) | 22.2% (459) | 0.0107 |
| Race* | | 8.2% (413) | 7.4% (221) | 9.3% (192) | 0.0141 |
| Cardiac History | | | | | |
| Diabetes | | 30.1% (1525) | 29.2% (877) | 31.4% (648) | 0.0941 |
| Hypertension | | 67.3% (3407) | 66.6% (1993) | 68.9% (1414) | 0.0839 |
| Smoking | | 69.2% (3506) | 71.1% (2132) | 66.7% (1374) | 0.0007 |
| Hypercholesterolemia | | 70.6% (3575) | 74.5% (2183) | 69.3% (1392) | <0.0001 |
| Unstable angina | | 50.3% (2550) | 52.1% (1564) | 47.8% (986) | <0.0001 |
| Myocardial infarction | | 51.4% (2603) | 52.5% (1558) | 51.2% (1045) | 0.3498 |
| Congestive heart failure | | 34.7 (1758) | 41.7% (853) | 30.3% (905) | <0.0001 |
| PTCA | | 15.1% (767) | 16.2% (484) | 13.8% (283) | 0.0184 |
| CABG | | 6.0% (306) | 5.9% (177) | 6.3% (129) | 0.6054 |
| Medications | | | | | |
| At hospital admission/prior to surgery | | | | | |
| ACE inhibitor | | 40.9%/38.0% | 38.0%/34.9% | 45.0%/42.5% | <0.0001 |
| Beta-blockers | | 62.3%/63.9% | 65.6%/67.9% | 57.6%/58.1% | <0.0001 |
| Calcium channel blockers | | 33.4%/31.8% | 35.7%/33.9% | 30.1%/28.7% | <0.0001 |
| Anti-platelet therapy | | 48.9%/23.8% | 53.4%/26.8% | 42.1%/19.2% | <0.0001 |
| Aspirin | | 46.8%/22.4% | 52.0%/25.9% | 39.2%/17.3% | <0.0001 |
| Dipyridamole | | 0.4%/0.2% | 0.3%/0.1% | 0.5%/0.3% | 0.1938/0.1133 |
| Other | | 4.0%/2.4% | 3.1%/1.8% | 5.2%/3.2% | <0.0001/0.0013 |

*Includes patients with the stated race of African American, American Indian or Hispanic.

TABLE 2

Aspirin Use and Adverse Safety Events Among 5065 Study Patients

| EVENT Hemorrhage | Aspirin % (N) | No aspirin % (N) | P value |
|---|---|---|---|
| Gastrointestinal tract bleeding | 1.1% (34) | 2.0% (42) | 0.0099 |
| Other source bleeding | 1.7% (50) | 3.4% (70) | <0.001 |
| Return to operating room for bleeding | 1.9% (57) | 5.3% (109) | <0.0001 |
| Gastritis | 0.33% (10) | 0.15% (3) | 0.1941 |
| Infection | 8.4% (253) | 12.8% (265) | <0.0001 |
| Impaired Wound Healing | 4.5% (134) | 4.5% (92) | >0.9813 |

TABLE 3A

Multivariate Analyses for Mortality

| Variable | Odds Ratio | 95% Confidence Interval | P value |
|---|---|---|---|
| Aspirin use following revascularization | 0.27 | 0.19-0.40 | <0.0001 |
| Previous CABG | 3.07 | 1.91-4.93 | <0.0001 |
| Creatinine > 1.3 μmol (admission) | 2.76 | 1.94-3.92 | <0.0001 |
| Prior hospitalization for heart failure | 2.14 | 1.42-3.22 | <0.001 |
| Heart failure (admission) | 1.99 | 1.40-2.83 | <0.001 |
| Unstable angina (admission) | 1.71 | 1.20-2.43 | 0.003 |
| Race* | 2.02 | 1.24-3.29 | 0.005 |
| Warfarin/coumadin** | 2.00 | 1.23-3.25 | 0.005 |

TABLE 3A-continued

Multivariate Analyses for Mortality

| Variable | Odds Ratio | 95% Confidence Interval | P value |
|---|---|---|---|
| Heart block (admission) | 1.57 | 1.06-2.32 | 0.025 |
| Age > 70 years | 1.48 | 1.05-2.09 | 0.026 |
| BSA < 1.93 m2 | 1.46 | 1.02-2.07 | 0.038 |

*Includes African-American, American Indian or Hispanic.

**Over the week prior to revascularization.

TABLE 3B

Multivariate Analyses for Mortality

| Variable | Odds Ratio | 95% Confidence Interval | P value |
|---|---|---|---|
| Aspirin use (admission) | 1.46 | 0.41-5.15 | 0.557 |
| Aspirin use (prior to surgery) | 0.77 | 1.23-2.64 | 0.681 |
| Discontinuation of aspirin use | 1.04 | 0.28-3.91 | 0.949 |
| Anti-platelet use (admission) | 1.35 | 0.13-14.01 | 0.800 |
| Anti-platelet use (prior to surgery) | 0.74 | 0.09-6.04 | 0.780 |
| Discontinuation of anti-platelet use | 1.00 | 0.08-12.25 | 0.999 |

Meta Study

Example

Effects of Acadesine on Myocardial Infarction. Stroke, and Death Following Surgery Objective.

To determine the effects of a purine nucleoside, acadesine, on the incidence of fatal and nonfatal cardiovascular and cerebrovascular complications following coronary artery bypass graft (CABG) surgery.

Data Sources.

Individual patient data from 5 randomized, placebo-controlled, double-blind clinical trials, including 81 international medical centers of the United States, Canada, and Europe.

Study Selection.

All patients from all clinical trials were included: a total of 4043 patients undergoing CABG surgery, evaluable for efficacy, and randomized to receive either placebo (n=2031) or acadesine (0.1 mg-kg$^{-1}$-min$^{-1}$; n=2012) by intravenous infusion for 7 continuous hours and via the cardioplegia solution.

Data Extraction.

Individual patient data were collected prospectively using standardized forms and methods and double-data entry. A general parametric approach and analysis-by-patient meta-analysis were used, including both fixed effects and random effects models. Inclusion and exclusion criteria, general methodology, and outcome assessment techniques were similar for all trials.

Data Synthesis.

Acadesine decreased the incidence of the primary outcome, perioperative myocardial infarction (MI) by 27% (odds ratio [OR], 0.69; 95% confidence interval [CI], 0.51-0.95; P=0.02), decreased the incidence of cardiac death through postoperative day 4 by 50% (OR, 0.52; 95% CI, 0.27-0.98; P=0.04), and decreased the incidence of combined outcome (MI, stroke, or cardiac death) by 26% (OR, 0.73; 95% CI, 0.57-0.93; P=0.01). The random effects models for these outcomes also yielded significant results. The incidence of cerebrovascular accident was not significantly reduced by acadesine (OR, 0.69; 95% CI, 0.44-1.08; P=. 10). A secondary analysis of cardiac death following MI through postoperative day 4 demonstrated that acadesine decreased by 89% the number of deaths from 13.3% (13 deaths/98 Mls) in the placebo group to 1.4% (1 death/71 Mls) in acadesine-treated patients (P=0.003). Acadesine also reduced the use of ventricular-assistance devices for severe postoperative heart failure by approximately one third (P=0.05). Finally, regarding safety, the incidence of adverse events was similar in the acadesine vs placebo groups, with the exception of a transient increase in serum uric acid in the acadesine group.

Conclusions.

The results of this meta-analysis indicate that in patients undergoing CABG surgery, treatment with acadesine before and during surgery can reduce early cardiac death, MI, and combined adverse cardiovascular outcomes. *JAMA* 1996; 277:325-332

The number of patients undergoing coronary artery bypass graft (CABG) surgery worldwide has increased dramatically over the last 2 decades to more than 800,000 patients annually, with associated health care expenditures exceeding $20 billion. Mortality currently ranges from less than 1% to more than 8% and morbidity from 1% to 28%—incidences that are likely to worsen given the continued aging of the population and the selection of higher risk patients for this procedure. Thus, it is expected that the costs of such adverse cardiovascular outcome, currently estimated at $4 billion annually, will continue to escalate.

Although several therapeutic approaches to reduce adverse outcome following cardiac surgery have been suggested, only 1 agent has been studied in large-scale clinical trials—acadesine, a purine nucleoside analogue that selectively raises tissue adenosine levels during ischemic conditions. At 81 international centers, 5 multicenter trials using reasonably similar methods have been conducted in more than 4000 CABG patients in the United States, Canada, and Europe, investigating the safety and efficacy of acadesine using myocardial infarction (MI), cardiac death, and stroke as outcomes. However, the true magnitude of acadesine's effect in CABG patients was difficult to assess from the results of any 1 of the 5 trials, since trials were powered to detect only effect sizes of 50% or more. Less of an effect, although potentially therapeutic, could not be discerned by design. Accordingly, we (the Ischemia Research and Education Foundation [IREF] and the Multicenter Study of Perioperative Ischemia [McSPI]) decided to combine the data from all 5 trials and apply an analysis-by-patient meta-analytic approach, using well-described standards and methods, to achieve the appropriate power to detect true effect size and report reliably on the efficacy and safety of acadesine. That is, we used the entire clinical experience of acadesine in more than 4000 CABG patients to determine the effects of this agunlon prespecified perioperative outcomes of MI, stroke, and cardiac death.

TABLE 1

Study Designs*

| Study (Dates) | Centers (No. of Patients) | Study Arms (Patients, No.) | Agent | Entity Criteria | Primary Efficiency Outcomes |
|---|---|---|---|---|---|
| 1013 (July 1990-May 1991) | 4 United States (116) | Placebo (36) LD (41) HD (34) VHD (5) | 7 h continuous intravenous 5 pg/mL cardioplegia solution | Low or moderate-risk patients | Myocardial ischemia |
| 1016 (June 1991-April 1992) | 20 United States (633) | Placebo (212) LD (214) HD (207) | 7 h continuous intravenous + 5 p.g./mL cardioplegia solution | Low-, moderate-, or high-risk patients | MI, combined§ |
| 1017 (June 1991-June 1992) | 27 Europe/Canada (821) | Placebo (418) HD (403 | 7 h continuous intravenous + 5 p.g./mL cardioplegia solution | Low-, moderate-, or high-risk patients | MI, combined§ |
| 1023 (June 1991-June 1992) | 1 Europe (38) | Placebo (20) HD (18) | 7-h continuous intravenous | Low-, moderate-, or high-risk patients | MI, combined§ |

TABLE 1-continued

Study Designs*

| Study (Dates) | Centers (No. of Patients) | Study Arms (Patients, No.) | Agent | Entity Criteria | Primary Efficiency Outcomes |
|---|---|---|---|---|---|
| 1024 (March 1993-September 1994) | 54 United States/ Canada | Placebo (1346) HD (1352) | 7 h continuous intravenous + 5 p.g./mL cardioplagia solution | Low-, moderate-, or high risk patients | MI |

*Trials were all randomized, placebo-controlled, and double-blind. All patients underwent coronary artery bypass graft (CABG) surgery.

+ LD indicates low dose (0.05 mg-kg$^{-1}$ of acadesine); HD, high dose (0.01 mg-kg$^1$ · min$^1$ of acadesine); VHD, very high dose (0.19-0.38 mg · kg$^{-1}$ · min$^{-1}$ of acadesine);

± Excluded patients with repeat CABG, acute percutaneous transluminal coronary angioplasty failure, unstable angina, and poor left ventricular function.

§Combined outcomes include MI, cardiac death, stroke, severe congestive heart failure, and life-threatening dysrhythmias.

1. Methods a. General Structure of the Individual Trials

Meta-analysis included all patients undergoing CABG surgery in the United States, Canada, and Europe who had received acadesine at a dose of 0.1 mg-kg$^1$min$^1$. No patients satisfying these criteria were excluded. All 5 studies were randomized, placebo controlled, double blinded, and performed with approval from the 81 participating McSPI institutions and with patient informed consent. Inclusion and exclusion criteria, general methods, and outcome assessment techniques were similar for all trials; with several exceptions (Table 1). Noteworthy was that the phase 2 trial 1013 and phase 3 trial 1016 included 3 test groups, placebo, low-dose acadesine (0.05 mg-kg$^{-1}$min$^{-1}$), and high-dose acadesine (0.1 mg-kg$^{-1}$ min$^{-1}$), but the results demonstrated that, although safe, low-dose acadesine appeared ineffective in reducing outcome, and we excluded low-dose data (n=41 in trial 1013; n=214 in trial 1016) from meta-analysis. For all patients, blinded study drug (acadesine or placebo) was administered intravenously, starting approximately 15 minutes before induction of anesthesia and continuing for a total of 7 hours to include the intraoperative (prebypass and postbypass) and immunediate postoperative (into the intensive care unit) periods. For all studies (except trial 1023 [n=38], which did not use cardioplegia), the cardioplegia solution used for myocardial protection during cardiopulmonary bypass contained acadesine at a concentration of 5 p.g./mL for patients randomized to receive acadesine or placebo (sterile water for injection) for those randomized to receive placebo.

b. Study Protocol

Prior to surgery, investigators ascertained cardiac history and recorded cardiac catheterization information. The use of agents potentially affecting endogenous adenosine concentration (which could complicate the analysis of efficacy) was restricted, including dipyridamole, theophylline, adenosine, and pentoxifylline. All chronic cardiovascular medications, including nitrates, β-blockers, and calcium channel blockers, were continued until the time of surgery. During surgery, but prior to bypass, the usual monitors wore applied, anesthetic techniques were standardized, and hemodynamic variables (blood pressure, heart rate) were to be maintained within specific boundaries for trials 1013, 1016, and 1023; for trials 1023 and 1017, guidelines for anesthetic use and hemodynamic control were recommended. For all studies, prophylactic use of cardiovascular agents having potential anti-ischemic properties (nitrates, calcium channel Mockers) was specifically excluded to avoid confounding data interpretation. During cardiopulmonary bypass, neither the surgical technique nor bypass procedures (including cardioplegia administration) were controlled for the phase 3 trials, and bypass typically was conducted using a membrane oxygenator and arterial filter with hemodilution and moderate systemic hypothermia. Following bypass, the use of inotropic and vasodilating agents (excluding the prophylactic use of anti-ischemic medications) and treatment of clinically detected ischemia were not controlled; all medications administered were recorded.

c. Outcomes

For all studies, the primary outcome, MI, and other secondary outcomes were ascertained and validated by IREF Coordinating Center investigators who were blinded to patient identity and group assignment. Secondary outcomes included cardiac death, stroke, life-threatening dysrhythmia, and severe heart failure (Table 1). For MI, repeated electrocardiograms (ECGs) were coded centrally by core investigators using Minnesota Code criteria. Creatine kinase-MB (CK-M13) concentrations were sampled approximately 18 times during the first 4 postoperative days and, for phase 3 studies, were analyzed centrally using an immunoenzymetric assay (Hybritech Tandem-E CK-MB II, SmithKline Beecham, Van Nuys, Calif.). The presence of infarction at autopsy was based on pathologic data from the respective institution and confirmed centrally by the Endpoint Committee. Cerebrovascular accident (CVA) was diagnosed by the neurologist at the respective institution and required that signs and symptoms of a significant focal defect persisted for more than 24 hours post-operatively. Diagnosis of CVA in the presence of nonfocal clinical signs required computed tomographic scan or magnetic resonance imaging results consistent with a new cerebral infarct. Outcomes of cardiac death and CVA were validated by 2 independent IREF investigators blinded to patient group assignment, with conflicts resolved by a third investigator, the majority opinion prevailing. An independent safety and data monitoring panel reviewed all safety data on an ongoing basis for each of the phase 3 trials and oversaw the prespecified stopping rules for each trial.

TABLE 2

Patient Characteristics*

| Demographics | Study 1013 Placebo (n = 36) | Study 1013 Acadesine (n = 34) | Study 1016 Placebo (n = 212) | Study 1016 Acadesine (n = 207) | Study 1017 Placebo (n = 418) | Study 1017 Acadesine (n = 403) | Study 1023 Placebo (n = 20) | Study 1023 Acadesine (n = 18) | Study 1024 Placebo (n = 1346) | Study 1024 Acadesine (n = 1352) |
|---|---|---|---|---|---|---|---|---|---|---|
| Mean age, y | 64 | 62 | 63 | 63 | 61 | 61 | 65 | 65 | 63 | 63 |
| Female, % | 8 | 6 | 19 | 18 | 17 | 16 | 30 | 44 | 21 | 19 |
| Medical history Unstable angina, % | 41 | 40 | 40 | 42 | 31 | 30 | 100 | 100 | 31 | 31 |
| Hypertension, % | 68 | 54 | 61 | 59 | 43 | 41 | 35 | 50 | 59 | 58 |
| Prior MI, % | 46 | 51 | 51 | 51 | 56 | 56 | 25 | 39 | 54 | 54 |
| CHF, % | 0 | 0 | 10 | 13 | 3 | 5 | 5 | 0 | 12 | 9 |
| Arrhythmias, % | 11 | 11 | 15 | 17 | 12 | 12 | 15 | 22 | 17 | 17 |
| Carotid bruit, % | 8 | 23 | 10 | 13 | 5 | 4 | 25 | 22 | ... | ... |
| Previous CABG, % | 0 | 0 | 11 | 8 | 3 | 4 | 0 | 0 | 8 | 7 |
| Previous PTCA, % | 0 | 0 | 12 | 14 | 8 | 7 | 5 | 17 | 13 | 14 |
| Catheterization EF, mean ± SD, % | 58 ± 11 | 60 ± 13 | 56 ± 15 | 56 ± 15 | 56 ± 16 | 57 ± 15 | 63 ± 13 | 65 ± 12 | ... | ... |
| % Left main > 50%† | 22 | 26 | 17 | 19 | 18 | 16 | 25 | 28 | 22 | 21 |
| % >2, >70%‡ | ... | ... | 92 | 93 | 93 | 94 | 90 | 94 | 94 | 94 |
| Stenosed vessels, No. | 4.1 ± 1.7 | 3.5 ± 1.0 | 6.0 ± 2.9 | 5.9 ± 2.9 | 5.9 ± 2.8 | 5.8 ± 2.7 | 8.8 ± 2.6 | 8.6 ± 2.7 | ... | ... |
| Cardioplegia type Containing crystalloid, % | 100 | 100 | 97 | 97 | 75 | 76 | ... | ... | ... | ... |
| Containing blood, % | 0 | 3 | 70 | 69 | 27 | 25 | ... | ... | 85 | 85 |
| Containing colloid, % | 0 | 0 | 3 | 5 | 0 | 0 | ... | ... | ... | ... |
| Blood alone, % | 0 | 0 | 2 | 3 | 17 | 15 | ... | ... | ... | ... |
| Acadesine infusion duration, mean ± SD, h | 6.6 ± 1.2 | 6.7 ± 1.2 | 7.0 ± 0.7 | 7.0 ± 0.4 | 7.1 ± 0.6 | 7.1 ± 0.6 | 7.0 ± 0.0 | 7.0 ± 0.0 | 7.0 ± 0.6 | 7.0 ± 0.5 |

*MI indicates myocardial infarction; CHF, coronary heart failure; CABG, coronary artery bypass graft; PTCA, percutaneous transluminal coronary angioplasty; ellipses, data not available; and EF, ejection fraction.
†Percentage of patients with left main artery stenosed 50% or more.
‡Percentage of patients with 2 vessels or more stenosed 70% or more.

d. Data and Statistical Analyses

The endpoint for meta-analysis were prospectively defined prior to analysis with the primary outcome being MI and with secondary outcomes being cardiac death, stroke, and the combined adverse cardiovascular outcome set of MI, cardiac death, or stroke. For each trial, MI was diagnosed based on the presence of either a new Q wave on EGG and satisfying protocol-specified CK-MB criteria, or the presence of autopsy evidence of infarction.[11,13-16] Creatine kinase-MB criteria for the trials generally were (1) CK-MB concentration of 100 ng/mL or more anytime with a bordering value of 50% or more; (2) CK-MB concentration of 70 ng/mL or more anytime after 12 hours postoperatively with a bordering value of 50% or more; or (3) CK-MB concentration of 12 ng/mL or more after 24 hours with a bordering value of 10 ng/mL or more (for trial 1013, the criterion was CK-MB exceeding 50 U/L[11]; arid for trial 1024,[15] the third condition was not used). A series of other prespecified outcomes also were evaluated, including cardiac death following MI, late cardiac death (through postoperative day 28), all cause mortality (through postoperative day 4 and through postoperative day 28), and combined endpoints using late cardiac death and all-cause mortality.

Of the 4311 patients in the 5 clinical trials, 265 were excluded from meta-analysis: 255 had received low-dose acadesine (0.05 mg·kg$^{-1}$·min$^{-1}$) in trials 1013 and 1016, 5 had received very high-dose acadesine (0.19-0.38 mg·kg$^{-1}$·min$^{-1}$) in trial 1013, and 5 were nonevaluable for MI in trial 1016 (1 placebo patient and 4 high-dose acadesine patients) (Table 1). Meta-analysis by patient was performed using the methods described in Whitehead and Whitehead[19] and Yusuf et al.[20] An estimate of the log odds ratio comparing the outcome event rate in the acadesine group with that in the placebo group was calculated for each study, taking into account each individual patient's information on risk group and treatment center. The weighted average of the log odds ratios was then computed using the inverses of the estimated variances. For all cases, a fixed effects model was used, with the addition of a random effects model when heterogeneity between studies was significant. Because trial 1024 used a sequential design for analyzing MI, the estimate of the log odds ratio was biased, requiring that we calculate (using the PEST 3.0 software package[21]) an adjusted estimate that accounted for the stopping procedure. The homogeneity of treatment effect across studies was tested using the Q statistic described in Whitehead and Whitehead,[19] in which a finding of a significant P value indicates that treatment effect is not constant across studies. When this occurred, we applied a random effects model to derive an estimate of the between-study component of variance using the method of moments.[19] For the survival data analyses, the Kaplan-Meier product-limit method[22] was used to compare the 2 (acadesine vs placebo) survival distributions.

2. Results

A total of 4043 patients were included in the meta-analysis with 2031 receiving placebo and 2012 receiving acadesine (0.1 mg·kg$^{-1}$·min$^{-1}$). Patients in the placebo and acadesine groups had similar cardiac medical histories, preoperative cardiac catheterization findings, cardioplegia types, and mean durations of placebo and acadesine infusions (Table 2).

a. Efficacy

Myocardial Infarction.

Myocardial infarction, the primary efficacy outcome, was determined by the presence of a new Q wave and CK-MB concentrations exceeding protocol-defined limits, or autopsy evidence of MI. In each of the 5 clinical trials, the incidence of MI was lower in the acadesine than the placebo group (FIG. 1), but this difference was significant only in the phase 3 trial 1016.[14] The test for homogeneity across studies revealed no significant heterogeneity (P0.39), resulting in the use of only the fixed effects model to analyze combined MI results. Acadesine reduced the incidence of infarction by 27% from 4.9% to 3.6% (odds ratio [OR], 0.69; 95% confidence interval [CI], 0.51-0.95; P=0.02), as noted in FIG. 1, with the CIs based on the by-patient analysis (not on the combined data). Also, the incidence of autopsy-defined MT was lower in acadesine-treated patients (16/19 placebo patients vs 2/11 acadesine patients, P=0.001).

Cardiac Death.

The incidence of cardiac death through postoperative day 4 was lower in acadesine-treated patients in each study (except phase 2 trial 1013, which had no cardiac deaths) and decreased by 50% in the overall population, from 26 to 13 deaths (OR, 0.52; 95% CI, 0.27-0.98; P=0.04). The test for homogeneity was not significant (P=0.76), resulting in the use of only the fixed effects model.

Stroke (CVA). The number of patients with CVA was lower in the acadesine group than the placebo group for each trial, except trial 1013, which did not report any strokes. The tests for homogeneity between studies yielded marginal findings (P=0.18); therefore, the results were analyzed using both the random and fixed effects models. The incidence of CVA was 2.3% (47/2031) in the placebo group vs 1.6% (32/2012) in the acadesine group, which was not statistically significant using either the fixed effects model (P=0.10) or the random effects model (P=0.12).

Combined Adverse Cardiovascular Outcomes (MI, CVA, or Cardiac Death).

The number of patients with 1 or more adverse cardiovascular outcomes through postoperative day 4 was consistently lower in the acadesine group than the placebo group in each trial (FIG. 2). The test for homogeneity was statistically significant (P=0.02), and both fixed and random effects models were used as prespecified by study design and protocol. Acadesine treatment decreased, by 26%, the incidence of combined outcome from 7.6% to 5.6% (fixed effects model, P=0.01; random effects model, P=0.04), as shown in FIG. 2. Meta-analysis results for the primary and secondary outcome variables are summarized in FIG. 3.

b. Other Outcomes

Death Following MI.

Myocardial infarction occurred in 71 patients given acadesine vs 98 given placebo (Table 3). Of the 71 patients with MI in the acadesine group, 1 patient (1.4%) had a cardiac death in the first 4 days following surgery, vs 13 patients (13.3%) in the placebo group (89% reduction; P=0.003). The incidence of cardiac death in the first 4 days after surgery was similar in patients without MI, or not evaluable for MI, in both groups: 0.6% in acadesine-treated vs 0.7% in placebo-treated patients.

Survival.

Patients in the acadesine group had increased survival throughout the observation period (FIG. 4), with the Irajority of deaths in both treatment groups occurring in the first 4 days following surgery. The primary survival effect of acadesine appears to be on death following MI (13 placebo patients vs 1 acadesine patient) and on cardiac death within the first 4 days following surgery (26 placebo patients vs 13 acadesine patients). Cardiac death at 28 days also was reduced (34 placebo patients vs 20 acadesine patients); acadesine had no effect on noncardiac death.

Safety.

The incidence of serious adverse events generally was similar for the acadesine and placebo groups in both individual studies and across all studies, ie, 9.1% (n=184/2014) in the acadesine group and 9.0% (n=182/2032) in the placebo group. (Note that there were 3 more patients included in the safety analysis [a total of 4046 patients] vs 4043 patients evaluable for efficacy.) However, cardiac failure, which was immediately life-threatening or prolonged hospitalization, was reduced by approximately one third (placebo, 3.2% [66/2032]; acadesine, 2.1% percent [43/2014]; P=03), and the use of an intraaortic balloon pump was reduced from 3.5% (70/2025 evaluable for this endpoint) in placebo-treated patients to 2.4% (48/2006) in acadesine-treated patients (P=0.049).

3. Comment

Our meta-analysis of the total clinical experience to date with acadesine in patients undergoing CABG surgery supports the hypothesis that acadesine reduces the incidence of perioperative MI, early cardiac death, and combined adverse cardiovascular outcomes (MI, cardiac death, stroke). Specifically, acadesine treatment significantly decreased MI by 27%, combined outcomes by 26%, and cardiac death by 50%. These results demonstrate for the first time that severe myocardial injury associated with bypass surgery and coronary reperfusion can be prevented and, in addition, a novel pharmacological approach is suggested—modulation of the natural nucleoside acadesine.

a. Significance of the Question and Individual Trial Results

Despite advances in surgical and anesthetic technique, morbidity and mortality associated with CABG surgery continue to increase due to changes in patient demographics, ie, patients are now older and sicker, often having had prior CABG surgery or acutely failed angioplasty.[1-7,26-28] Reported perioperative MI rates range from 1% to 15% or more, cardiac death rates from 0.5% to 8.0%, and stroke rates from 2% to 6%.[12-7,26-28] Pharmacological interventions aimed at mitigating adverse outcomes associated with CABG surgery have been investigated in a series of smaller trials, focusing primarily on surrogates of these outcomes as the primary endpoints. Nitrates, β-blockers, and calcium channel blockers have been recommended, but not widely accepted

TABLE 3

Death Following Myocardial Infarction

|  | Placebo (n = 98), No. (%) | Acadesine (n = 71), No. (%) | Reduction, % | Odds Ratio | 95% Confidence Interval | P Value* |
|---|---|---|---|---|---|---|
| Cardiac death by postoperative day 4 | 13 (13) | 1 (1) | 89 | 0.185 | 0.061-0.556 | .003 |
| Cardiac death by postoperative day 28 | 20 (20) | 3 (4) | 79 | 0.240 | 0.098-0.585 | .002 |
| Death by postoperative day 4 | 13 (13) | 2 (3) | 79 | 0.243 | 0.084-0.708 | .009 |
| Death by postoperative day 28 | 21 (21) | 4 (6) | 74 | 0.272 | 0.115-0.644 | .003 |

*P values determined using the Cochran-Mantel-Haenszel test because preliminary findings could not be confirmed.[1,7,8] Various techniques of myocardial preservation also have been suggested to reduce outcomes; however, findings are based on relatively small physiologic studies,[29-31] without confirmation in large-scale outcome trials.

The interest in adenosine[32] and adenosine-regulating agents (acadesine)[9-11,13-15,38,35] for mitigating ischemia, combined with findings of acadesine's efficacy in animals treated under bypass conditions,[36-37] led to our developing a phase 2 and phase 3 clinical trial series. In composite, this meta-analysis involved 4043 patients, 2031 of whom received placebo and 2012 of whom received high-dose acadesine (0.1 mg·kg$^{-1}$min$^{-1}$). To date, this program constitutes the largest set of trials—aimed at reducing cardiovascular morbidity and mortality following cardiac surgery.

Individual Trials.

The phase 2 trial 1013 demonstrated that acadesine reduced incidence and severity of markers for perioperative ischemia, and, based on these findings, we developed 2 phase 3 trials (1016 and 1017) to investigate the efficacy of high-dose acadesine in preventing perioperative MI.[13,14] Both studies were designed to detect an effect size of 50% (based on the effect size indicated by phase 2 trial 1013) with 80% power (b=0.2) and a level of significance of 0.05, adjusted for multiple comparisons. Although neither trial demonstrated that acadesine significantly reduced the incidence of protocol-defined MI, the trials provided unique insight into biochemical markers for non-Q-wave infarction, finding substantial release of CK-MB in these patients (17% of patients had CK-MB concentrations exceeding 100 ng/mL following surgery[13,14,27]), perhaps representing mechanical and other injury associated with surgery, rather than irreversible ischemic injury. Accordingly, choosing a more specific and conservative definition of MI would reduce the contribution of "CK-MB noise." Developed post hoc for trial 1016, the definition of MI mandated the presence of both an electrocardio-graphic Q wave and CK-MB release of prespecified limits or autopsy evidence of infarction.[14] With this definition, analysis revealed a significantly lower infarction rate (1.5%) in patients given acadesine than those given placebo (5.2%; P=0.02), as well as lower rates for stroke (0.5% vs 4.2%; P=0.02) and combined adverse cardiovascular outcome (MI, CVA or cardiac death) (1.9% vs 9.9%; P=0.004). Finally, a small study (trial 1023) was conducted in 38 CABG patients and demonstrated that acadesine improved ventricular function following bypass.[16] Consequently, we developed a larger third phase 3 trial (1024) which was conducted in 2698 patients from 54 centers. Based on effect size findings in trial 1016, trial 1024 was statistically powered to detect a 50% effect size with 95% power at a level of significance of 0.05.[15] Results revealed that acadesine reduced, but not significantly, the rate of MI, stroke, cardiac death, and combined outcomes (FIGS. 1, 2).

Rationale for the Meta-Analysis.

The findings of the phase 3 trials convincingly demonstrated that the initial study design that mandated a 50% effect size, though based on prior smaller trials, overestimated effect size. Given effect sizes for MI of 73% for trial 1016 (n=414),[14] 23% for trial 1017 (n=821),[13] and 22% for trial 1024 (n=2698),[15] a more reasonable estimate of effect size might be 20% to 25%. For example, despite enrollment of 2698 patients, trial 1024 had little power (β>0.4) to detect an effect size below 35%,[38] and to detect a 25% effect in that trial would have required approximately 3 times the number of enrolled patients (8757 patients).[21] Review of the 3 major phase 3 trials (1016, 1017, 1024) revealed another important finding: of the 3 outcome variables (MI, CVA, death) assessed over the 3 trials, the incidence of these 9 individual outcomes was uniformly lower (11%-89%) in acadesine-treated patients with statistical significance achieved for most of these comparisons despite limited sample size.

b. Meta-Analysis Findings

Myocardial Infarction.

Several previous studies have addressed the efficacy of anti-ischemic agents and myocardial preservation techniques; however, most studies included only a limited number of patients and measured only surrogates of outcome.[1,7,8,20,31] No previous set of trials has been large enough to examine effects on MI, rendering the present set unique. Additionally, the positive findings of this meta-analysis, and supportive data in the individual trials;[11,13-16] demonstrate that pharmacological intervention may prevent MI associated with CABG surgery. This finding is important, because injury and infarction are induced during CABG by a profound ischemic insult (complete occlusion of coronary flow) lasting 45 minutes or longer, and the possibility that pharmacologic therapy can mitigate the effects of such a dramatic mechanical insult allows further exploration of new approaches to such injury.[8] These results also suggest not only that a specific agent, acadesine, may mitigate injury, but also that a class of agents which preserve adenosine in ischemic tissue may have specific advantages in this important clinical setting.[32] These findings are consistent with laboratory and animal data, suggesting beneficial effects on postreperfusion ventricular function,[39,40] ventricular dysrhythmia,[9,41] platelet adherence,[42,48] granulocyte accumulation,[9,44] and other phenomena.[36,37,45] However, the present results do not allow us to discern which, if any, of these mechanisms are applicable in man. Finally, it should be recognized that the definition of MI in this program was quite specific, mandating both the presence of Q wave and substantial CK-MR release. Given that such infarctions following CABG surgery may be associated with a poorer long term prognosis (ie, increased death and re current MI),[46,47] then one may hypothesize that acadesine could have a beneficial long-term effect, mandating further study.

Mortality.

Survival was improved in acadesine-treated results (FIG. 4), with the predominant effect on early (≤4 days) cardiac death (26 vs 13 patients). Furthermore, the results of the secondary analysis to determine the effect of acadesine on post-MI death demonstrated a 74% reduction in such deaths (4/71 acadesine-treated patients vs 21/98 in the placebo group; P=0.003), supporting the premise that acadesine reduces the incidence of death following MI. This suggests that acadesine reduces not only the incidence, but also the extent, of infarction and perhaps the impact of post-bypass myocardial stunning, as measured by either biochemical markers (CK-MB release) or post-MI mortality. Finally, acadesine did not appear to have a substantial effect on non-cardiac death.

Combined Cardiovascular Outcomes.

Meta-analysis demonstrated that acadesine decreased the incidence of combined cardiovascular outcomes of MI, cardiac death, and stroke by 26%: that is, 41 fewer patients in the acadesine group suffered an adverse outcome (Table 3). This reduction in combined outcomes from 7.6% to 5.6% suggests that the use of acadesine would prevent adverse outcomes in approximately 20 of every 1000 patients undergoing CABG surgery, or 16000 patients per year, thereby also reducing resource utilization and associated hospital costs. 17

Other Findings.

Based on the safety data, administration of acadesine at a dose of 0.1 mg·kg$^{-1}$ min$^{-1}$ for 7 hours to patients undergoing CABG surgery is safe, with the exception of a transient hyperuricemia that peaks at the end of infusion, but resolves during hospital stay without clinical sequelae.[14] Unlike adenosine,[32] acadesine does not affect blood pressure or cardiac electrical conduction. Another safety finding was the lower incidence of intra-aortic balloon pump usage and serious heart failure with acadesine that is consistent with recent findings demonstrating improved left ventricular function in the immediate post-bypass period in acadesine-treated patients.[16] Improved ventricular function following bypass may be the mechanism by which acadesine improves survival following MI. Finally, we also found that infusion of low-dose acadesine (0.05 mg-kg$^{-1}$ min$^{-1}$), although safe, had no significant effect on any outcome measure.

Meta-Analysis Strengths and Limitations.

Results of 5 individual trials of more than 4000 patients suggested a true effect of acadesine on MI, cardiac death, and stroke. Our decision to combine the data from all trials and apply a meta-analytic approach to evaluate the anti-ischemic or myocardial preservative effects of acadesine in CABG patients was based on the observed results and the subsequent need to overcome the specification of criteria requiring 50% effect sizes in all of the phase 3 study designs. Factors supporting valid use of meta-analysis included homogeneity across studies, such as patient populations, inclusion and exclusion criteria, clinical designs, drug infusion techniques, outcome variable measurements, and time periods of study.[19,48-50] Moreover, data were available from every patient undergoing CABG surgery who had ever received acadesine (0.1 mg-kg$^{-1}$ min$^{-1}$); thus, all trials, whether positive or negative, could be included. Also, analysis by individual patient could be, and was, performed, and such analysis is believed to be more precise.[17,18] Finally, all studies were completed over a relatively brief 4-year period of time.

A number of limitations, however, may be associated with meta-analysis.[19,20,48,54] First is nonrandom selection of studies[19,49,52] which not relevant to the present analysis because we included all patients who had received acadesine and underwent CAB& surgery. Second is multiple tests of the same data,[19,52] which does apply because we analyzed the data from each of the 5 trials individually, then again using meta-analysis, but the standard parametric statistics we used appear to be sufficiently robust to overcome this limitation. Third is selection bias,[53] precluded here because we included all patients. Fourth is variability or inhomogeneity across studies,[19,49,52] which is pertinent to the present analysis (Table 1). However, it is not clear that any of these differences affected the observed results. The potential confounding effect of factors, such as anesthetic technique or cardioplegia, on analysis was found to be minimal; formal statistical investigation of homogeneity of outcome across these trials revealed inhomogeneity only for combined adverse outcome, and, in this case, both the random and fixed effects models yielded similar results.

4. Conclusions

We examined the entire clinical experience of acadesine in CABG surgery, consisting of 5 multicenter trials having reasonably similar methods. The results of this meta-analysis of more than 4000 patients indicate that treatment with acadesine (0.01 mg-kg$^{-1}$ min$^{-1}$ given intravenously prior to and during surgery along with a fixed concentration of 5 µg/mL in cardioplegia solution) can reduce perioperative MI, cardiac death, and combined adverse cardiovascular outcomes.

Continued study of adenosine-related compounds is necessary to define those subgroups of patients undergoing myocardial revascularization who may specifically benefit from these therapies, thereby allowing appropriate health care expenditure; investigations in other clinical settings of reperfusion injury also may be warranted.

Grant support for this meta-analysis and the associated publications was provided by the Ischemia Research and Education Foundation (IREF) and Gensia Pharmaceuticals, Inc. There were no other financial relationships between the investigators, the central analysis unit (IREF), and Gensia Pharmaceuticals, Inc. The results of this meta-analysis and their interpretation are solely those of the investigators and IREF, and the results are without interpretation or approval by Gensia Pharmaceuticals, Inc.

The Multicenter Study of Perioperative Ischemia (McSPI) Research group is a consortium of investigators from approximately 150 worldwide medical centers, focusing on the problems of perioperative myocardial infarction, stroke, renal dysfunction, as well as other organ dysfunction and the implications of such diseases for health economics. The Ischemia Research and Education Foundation is a nonprofit foundation dedicated to multicenter research in these areas and is closely affiliated with the McSPI investigators and their institutions.

For the 5 individual trials, the coordinating and analysis groups and the policy and data monitoring boards have been cited previously.[11,16]

REFERENCES

1. Mangano D T. Perioperative cardiac morbidity. Anesthesiology. 1990; 72:153-184.
2. US Public Health Service. Mortality, part A. Vital Health Stat 2. 1985; 2:10-17, 67-68, 100-101.
3. Kouchoukos N T, Ebert P A, Grover F L. Lindesmith G G. Report of the ad hoc committee on risk factors for coronary artery bypass surgery. Ann Thorac Surg. 1988; 45:348-349.
4. CASS Principal Investigators and Their Associates. Myocardial infarction and mortality in the Coronary Artery Surgery Study (CASS) randomized trial. N Engl J. Med. 1984; 310:750-758.
5. Murphy M L, Hultgren H N, Detre K, Thomsen J, Takaro T, for the Participants of the Veterans Administration Cooperative Study. Treatment of chronic stable angina: a preliminary report of survival data of the randomized Veterans Administration Cooperative Study. N Engl J. Med. 1977; 297:621-627.
6. Varnauskas E. European coronary surgery study. Z Kardiol. 1985; 6:73-78.
7. Mangano D T. Perioperative cardiac morbidity: epidemiology, costs, problems, and solutions. West J. Med. 1994; 161:87-89.
8. Mangano D T. Myocardial stunning: an overview. J Cardiac Surg. 1993; 8:204-213.
9. Gruber H E, Hoffer M E, McAllister D R, et al. Increased adenosine concentration in blood from ischemic myocardium by AICA riboside: effects on flow, granulocytes, and injury. Circulation. 1989; 80:1400-1411.
10. Mullane K. The prototype adenosine regulating agent for reducing myocardial ischemic injury. Cardiovasc Res. 1993; 27:43-47.
11. Leung J L, Stanley T, Mathew J, for the McSpi Research Group. Initial multicenter randomized controlled trial on the safety and efficacy of acadesine in patients undergoing CABG surgery. Anesth Analg. 1994; 78:420-434.

12. Mangano D T, Browner W S, Hollenberg M, London M J, Tubau J F, Tateo I M, for the McSPI Research Group. Association of perioperative myocardial ischemia with cardiac morbidity and mortality in men undergoing noncardiac surgery. N Engl J. Med. 1990; 323:1781-1788.
13. Menasché P, Jamieson WRE, Flameng K, Davies M, on behalf of the Multinational Acadesine Study Group. Acadesine: a new drug that may improve myocardial protection in coronary artery bypass graft surgery: results of the first international multicenter study. J Thorac Cardiovasc Surg. 1995; 110: 1096-1106.
14. The Multicenter Study of Perioperative Ischemia (McSPI) Research Group. Effects of acadesine on morbidity and mortality following coronary artery bypass graft surgery. Anesthesiology. 1995; 88:658-673.
15. Mangano D T, for the McSPI Research Group. Effects of acadesine on myocardial infarction, stroke, and death following surgery. Anesth Analg. 1996; 82:SCA42.
16. Demeyere R H, Van Kerrebroeck C J, Flameng W J. Cardioprotective effects of acadesine in patients with unstable angina undergoing aortocoronary bypass surgery. Circulation. 1994; 90(4, pt 2):I-370.
17. Oxman A D, Clarke M J, Stewart L A. From science to practice: meta-analyses using individual patient data are needed. JAMA, 1995; 274:845-846.
18. Jeng G T, Scott J R, Burmeister L F. A comparison of meta-analytic results using literature vs individual patient data: paternal cell immunization for recurrent miscarriage. JAMA. 1995; 274:830-836.
19. Whitehead A, Whitehead J. A general parametric approach to the meta-analysis of randomized clinical trials. StatMed. 1991; 10:1665-1677.
20. Yusuf S, Peto R, Lewis J, Collins R, Sleight P. Beta blockade during and after myocardial infarction: an overview of the randomized trials. Prog Cardiovasc Dis. 1985; 27:335-371.
21. Department of Applied Statistics. PEST 3.0: Planning and Evaluation Sequential Trials. Reading, United Kingdom: University of Reading; 1993.
22. Kalbfleisch J D, Prentice R L. The Statistical Analysis of Failure Time Data. New York, N.Y.: John Wiley & Sons Inc; 1980.
23. Jones E L, Weintraub W S, Craver J M, Guyton R A, Cohen C L. Coronary bypass surgery: is the operation different today? J Thorac Cardiovasc Surg. 1991; 101: 108-115.
24. Haraphongse M, Na-Ayudhya R K, Teo K K, et al. The changing clinical profile of coronary artery bypass graft patients, 1970-1989. Can J Cardiol. 1994; 10:71-86.
25. Clark R E. Calculating risk and outcome: the Society of Thoracic Surgeons database. Ann Thorac Surg. 1996; 62:S2-5.
26. Jain U, Zhang A, Sears R J, Titov V, Titov T, for the McSPI Research Group. Incidence of Q wave myocardial infarction during coronary artery bypass graft surgery in the 24-center McSPI population. Anesthesiology. 1994; 81:A157.
27. Aggarwal A, Jain U, Ramsay J G, Wilson R, Comunale M E, for the McSPI Research Group. CK-MB release after coronary artery bypass graft surgery in a multicenter population. Anesthesiology. 1994; 81: A1291.
28. Mora C T, Murkin J M. The central nervous system: responses to cardiopulnonary bypass. In: Mora C T, ed. Cardiopulmonary Bypass: Principles and Techniques of Extracorporeal Circulation. New York, N.Y.: Springer-Verlag NY Inc; 1995:114-146.
29. The Warm Heart Investigators. Randomized trial of normothermic versus hypothermic coronary bypass surgery, Lancet, 1994; 343:559-563.
30. Martin T C, Craver J M, Gott J P, et al. Prospective, randomized trial of retrograde warm-blood cardioplegia: myocardial benefit and neurologic threat. Ann Thorac Surg. 1994; 57:298-304.
31. Rashid A, Fabri B M, Fabri B M, et al. A prospective randomized study of continuous warm versus intermittent cold blood cardioplegia for coronary artery surgery: prelirminary report. Eur J Cardiothorac Surg. 1994; 8:265-269.
32. Ely S W, Beme R M. Protective effects of adenosine in myocardial ischemia. Circulation. 1992; 85:893-904.
33. Mullane K, Young M. Acadesine: prototype adenosine regulating agent for treating myocardial ischemia-reperfusion injury. Drug Dev Res. 1993; 28:336-343.
34. Ambrosio G, Jacobus W, Mitchell M, Litt M, Becker L. Effects of ATP precursors on ATP and free ADP content and functional recovery of post-ischemic hearts. Am J. Physiol. 1989; 256:H560-H566.
35. Mentzer R, Ely S, Lasley R, Beme R. The acute effects of AICAR on purine nucleotide metabolism and postischemic cardiac function. J Thorac Cardiovas Surg. 1988; 95:286-293.
36. Vinten-Johansen J, Nakanishi K, Zhao Z Q, Mc-Gee D S, Tan P. Acadesine improves surgical myocardial protection with blood cardioplegia in ischemically injured canine hearts. Circulation. 1993; 88:350-358.
37. Galinanes M. Rullough D, Mullane K M, Hearse D J. Sustained protection by acadesine against ischemia and reperfusion-induced injury: studies in the transplanted rat heart. Circulation. 1992; 86:589-597.
38. Lachin J. Sample size determination for rxc comparative trials. Biometrics. 1977; 331:315-324.
39. Young M, Mullane K. Progressive cardiac dysfunction with repeated pacing-induced ischemia: protection by AICA-riboside. Am J. Physiol. 1991; 261:H1570-H1577.
40. Mazur C, Mullane K, Young M A. Acadesine preserves cardiac function and enhances coronary blood flow in isolated, blood perfused rabbit hearts with repeated ischemia and reperfusion. J Mol Cell Cardial. 1991; 23:S45.
41. Molina-Viamonte V, Rosen M R. AICA-riboside suppresses arrhythrnias induced by coronary artery occlusion and reperfusion. Circulation. 1990; 82:645.
42. Henry C, Young M, Zhang C, Bullough D, Mullane K. Adenosine release from red cells mediates inhibition of platelet aggregation by acadesine and delays post-thrombolytic reocclusion in dogs. Circ Suppl. 1991; 84:247.
43. Young M, Montag A, Zhang C, Bullough D, Mullane K. Inhibition of intracoronary thrombosis by acadesine: an adenosine-mediated, erythrocyte-dependent activity. Eur Heart J. 1993; 31:14.
44. Cronstein B N, Eberle M A, Gruber H E, Levin R I. Methotrexate inhibits neutrophil function by stimulating adenosine release from connective tissue cells. Proc Natl Acad Sci USA. 1991; 88:2441-2445.
45. Galinianes M, Mullane K M, Bullough D, Hearse D J. Acadesine and myocardial protection: studies of time of administration and dose-response relations in the rat. Circulation. 1992; 86:598-608.
46. Val P G, Pelletier L C, Hernandez M G, et al. Diagnostic criteria and prognosis of perioperative myocardial infarction following coronary bypass. J Thorac Cardiovas Surg. 1983; 86:878 886.
47. Schaff H V, Gersh B J, Fisher L D, et al. Detrimental effect of perioperative myocardial infarction on late survival after coronary artery bypass: report from the Coronary Artery Surgery Study (CASS). J Thorac Cardiovasc Surg. 1984; 88:972-981.
48. Thacker S B. Meta-analysis: a quantitative approach to research integration. JAMA. 1988; 259:1685-1689.
49. DerSimonian R, Laird N. Meta-analysis in clinical trials. Control Clin Trials. 1986; 7:177-188.
50. Lau J, Antman E M, Jiminez-Silva J, Kupelnick B, Mosteller F, Chalmvers T C. Cumulative meta-analysis of therapeutic trials for myocardial infarction. N Engl J. Med. 1992; 327:248-254.
51. Egger M, Smith G D. Misleading meta-analysis: lessons from an effective, safe, simple intervention that wasn't. BMJ. 1995; 310:752-754.
52. Antman E M, Lau J, Kupeinick B, Mosteller F, Chalmers T C. A comparison of results of meta-analyses of randomized control trials and recommendations of clinical experts: treatments for myocardial infarction. JAMA. 1992; 268:240-248.
53. Gotzsche P C. Reference bias in reports of drug trials. BMJ. 1987; 295:654-656.
54. Yusuf S, Flather M. Magnesium in acute myocardial infarction. BMJ. 1995; 310:751-752.

All references cited herein are hereby incorporated by reference in their entireties.

It should be noted that where the terms "AICA riboside" or "acadesine" appear throughout, each may be interpreted to mean acadesine, a prodrug, analog, or salt thereof.

The above examples are in no way intended to limit the scope of the instant invention. Further, it can be appreciated to one of ordinary skill in the art that many changes and modifications can be made thereto without departing from the spirit or scope of the appended claims, and such changes and modifications are contemplated within the scope of the instant invention.

The invention claimed is:

1. A method of reducing the incidence of mortality in a patient comprising administering to a patient in need thereof an effective amount of 5-amino-1-β-D-(5-benzylamino-5-deoxy-1-β-D-ribofuranosyl)imidazole-4-carboxamide, 5-amino-1-(5-amino-5-deoxy-β-D-ribofuranosyl) imidazole-4-N-[(4-chlorophenyl)methyl]carboxamide, or a salt thereof,
    wherein, prior to initial administration, said patient has decreased left ventricular function as measured by an ejection fraction that is less than 30%, and
    wherein, following the administration, the patient has improved left ventricular function.

2. A method of treating a patient with decreased left ventricular function having an ejection fraction that is less than 30% comprising administering to said patient in need thereof an effective amount of 5-amino-1-β-D-(5-benzylamino-5-deoxy-1-β-D-ribofuranosyl)imidazole-4-carboxamide, 5-amino-1-(5-amino-5-deoxy-β-D-ribofuranosyl) imidazole-4-N-[(4-chlorophenyl)methyl]carboxamide or a salt thereof,
    wherein, prior to initial administration, said patient has decreased left ventricular function having an ejection fraction that is less than 30%, and
    wherein, following the administration, the patient has improved left ventricular function.

3. The method of claim 1 or claim 2 wherein administration of 5-amino-1-β-D-(5-benzylamino-5-deoxy-1-β-D-ribofuranosyl)imidazole-4-carboxamide 5-amino-1-(5-amino-5-deoxy-β-D-ribofuranosyl) imidazole-4-N-[(4-chlorophenyl)methyl]carboxamide or a salt thereof provides a blood plasma concentration between about 1 µg/mL about 20 µg/mL.

4. The method of claim 1 or claim 2 wherein 5-amino-1-β-D-(5-benzylamino-5-deoxy-1-β-D-ribofuranosyl) imidazole-4-carboxamide is administered.

5. The method of claim 1 or claim 2 wherein 5-amino-1-(5-amino-5-deoxy-β-D-ribofuranosyl) imidazole-4-N-[(4-chlorophenyl)methyl]-carboxamide is administered.

6. The method of claim 1 or claim 2 wherein 5-amino-1-β-D-(5-benzylamino-5-deoxy-1-β-D-ribofuranosyl)imidazole-4-carboxamide, 5-amino-1-(5-amino-5-deoxy-β-D-ribofuranosyl) imidazole-4-N-[(4-chlorophenyl)methyl] carboxamide or a salt thereof is administered at 0.1 mg/kg/minute.

7. The method of claim 1 wherein said mortality is caused by a cardiovascular event.

8. The method of claim 7, wherein said cardiovascular event is a myocardial infarction, dysrhythmia or ventricle dysfunction.

9. The method of claim 1 or 2, wherein prior to administration, the patient has had a myocardial infarction.

10. The method of claim 1 or 2, wherein the patient has had congestive heart failure.

11. The method of claim 9, wherein the patient has had congestive heart failure.

* * * * *